United States Patent
Kwon et al.

(10) Patent No.: US 12,383,624 B2
(45) Date of Patent: *Aug. 12, 2025

(54) CARGO DELIVERY SYSTEM AND COMPOSITION COMPRISING THE SAME

(71) Applicants: SEOUL NATIONAL UNIVERSITY R&DB FOUNDATION, Seoul (KR); AUTOTAC INC., Seoul (KR)

(72) Inventors: Yong Tae Kwon, Seoul (KR); Chang Hoon Ji, Seoul (KR); Srinivasrao Ganipisetti, Seoul (KR); Hee Yeon Kim, Seoul (KR); Su Ran Mun, Seoul (KR); Chan Hoon Jung, Seoul (KR); Eui Jung Jung, Seoul (KR); Ki Woon Sung, Seoul (KR); Hyun Tae Kim, Seoul (KR); Jeong Eun Na, Seoul (KR); Eun Hye Jeong, Seoul (KR); Ji Eun Lee, Seoul (KR); Min Ju Lee, Seoul (KR); Chang Min Park, Seoul (KR); Su Jin Kim, Seoul (KR)

(73) Assignees: SEOUL NATIONAL UNIVERSITY R&DB FOUNDATION, Seoul (KR); AUTOTAC INC., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 18/169,734

(22) Filed: Feb. 15, 2023

(65) Prior Publication Data

US 2023/0190938 A1    Jun. 22, 2023

Related U.S. Application Data

(63) Continuation-in-part of application No. 17/262,157, filed as application No. PCT/KR2019/009205 on Jul. 24, 2019, now Pat. No. 12,129,218.
(Continued)

(51) Int. Cl.
A61K 47/55    (2017.01)
A61K 47/54    (2017.01)

(52) U.S. Cl.
CPC ............ *A61K 47/545* (2017.08); *A61K 47/55* (2017.08)

(58) Field of Classification Search
CPC ....... A61K 47/545; A61K 47/55; A61K 47/54
See application file for complete search history.

(56) References Cited

U.S. PATENT DOCUMENTS 4,167,581 A    9/1979 Smith
4,471,116 A    9/1984 Davidson et al.
(Continued)

FOREIGN PATENT DOCUMENTS

CN    102229602    11/2011
CN    107848932    3/2018
(Continued)

OTHER PUBLICATIONS

Office Action issued Feb. 2, 2023 in U.S. Appl. No. 17/262,129.
(Continued)

*Primary Examiner* — Rayna Rodriguez
(74) *Attorney, Agent, or Firm* — Sughrue Mion, PLLC

(57) ABSTRACT

One aspect of the disclosure relates to a cargo delivery system comprising an autophagy targeting ligand and a target-binding ligand. In one aspect of the disclosure, by comprising an autophagy targeting ligand, cargo, which is a target-binding ligand that specifically binds to a target, is delivered to the p62 protein and autophagy is activated, so that depending on the type of target-binding ligand used, a target to be degraded can be selectively and directly removed. Accordingly, the cargo delivery system according to an aspect of the disclosure may be used in pharmaceutical
(Continued)

compositions or food compositions for preventing, alimerating, and treating various diseases.

8 Claims, 31 Drawing Sheets

Related U.S. Application Data

(60) Provisional application No. 62/702,473, filed on Jul. 24, 2018.

(56) References Cited

U.S. PATENT DOCUMENTS

| | | | |
|---|---|---|---|
| 4,857,522 | A | 8/1989 | DiPietro et al. |
| 2004/0009932 | A1 | 1/2004 | Phelan et al. |
| 2015/0175607 | A1 | 6/2015 | Xie et al. |
| 2016/0031799 | A1 | 2/2016 | Xie et al. |
| 2018/0243244 | A1 | 8/2018 | Kwon et al. |
| 2018/0265452 | A1 | 9/2018 | Xie |
| 2021/0024454 | A1 | 1/2021 | Kwon et al. |
| 2021/0163399 | A1 | 6/2021 | Kwon et al. |
| 2021/0347749 | A1 | 11/2021 | Kwon et al. |

FOREIGN PATENT DOCUMENTS

| | | |
|---|---|---|
| CN | 112105598 A | 12/2020 |
| EP | 3338787 | 6/2018 |
| KR | 10-2015-0039894 | 4/2015 |
| KR | 10-2017-0021525 | 2/2017 |
| KR | 10-2017-0023045 | 3/2017 |
| KR | 10-2149539 B1 | 8/2020 |
| KR | 10-2154294 B1 | 9/2020 |
| WO | 2013022919 | 2/2013 |
| WO | 2015031710 | 3/2015 |
| WO | 2016200827 | 12/2016 |
| WO | 2017030292 | 2/2017 |
| WO | 2017079267 | 5/2017 |

OTHER PUBLICATIONS

Office Action issued Jul. 21, 2023 in Chinese Application No. 201980047607.6.
Office Action dated Oct. 19, 2023 in U.S. Appl. No. 17/262,129.
Ciechanover, A. & Kwon, Y.T., Exp Mol Med 47, e147 (2015).
Dikic, I. & Elazar, Z., Nat Rev Mol Cell Biol 19, 349-364 (2018).
Caccamo, A., Majumder, S., Richardson, A., Strong, R. & Oddo, S., J Biol Chem 285, 13107-20 (2010).
Ji, C.H. & Kwon, Y.T., Mol Cells 40, 441-449 (2017).
Jung, C. H., Ro, S. H., Cao, J., Otto, N. M. & Kim, D. H., Fees Lett 584, 1287-95 (2010).
Ravikumar, B., Duden, R. & Rubinsztein, D.C., Hum Mol Genet 11,1107-17 (2002).
Rodriguez-Navarro, J. A. et al., Neurobiol Dis 39, 423-38 (2010).
Sriram, S.M. & Kwon, Y.T., Nat Struct Mol Biol 17, 1164-5 (2010).
Sriram, S.M., Kim, B.Y. & Kwon, Y.T., Nat Rev Mol Cell Biol 12, 735-47 (2011).
Tasaki, T. et al., Mol Cell Biol 25, 7120-36 (2005).
Webb, J.L., Ravikumar, B., Atkins, J., Skepper, J.N. & Rubinsztein, D.C., J Biol Chem 278,25009-13 (2003).
Puissant et al., Cancer Res., Feb. 1, 2010, vol. 70, No. 3, pp. 1042-1052.
AUTOTAC (Autophagy-targeting chimera) Technology, Nov. 29, 2018, pp. 6-7.
Bondeson et al., Cell Chem Biol 25, 78-87.e5 (2019).
Xiong J Cell Physiol. 2019;1-9.
Lei et al., Leukemia & Lymphoma, Dec. 4, 2017, pp. 1-8.
AN and FU, EBioMedicine 36, 553-562 (2018).
Ji et al., "The AUTOTAC chemical biology platform for targeted protein degradation via the autophagy-lysosome system", Nature Communications, (2022)13:904 | https://doi.org/10.1038/s41467-022-28520-4.
International Search Report and Written Opinion of the International Searching Authority issued Nov. 11, 2019 in International Application No. PCT/KR2019/009204.
Barlow et al., "β-Adrenoceptor Stimulant Properties of Amidoalkylamino-Substituted 1-Aryl-2-ethanols and 1-(Aryloxy)-2-propanols", J. Med. Chem., 1981, vol. 24, pp. 315-322.
International Search Report and Written Opinion of the International Searching Authority issued Nov. 11, 2019 in International Application No. PCT/KR2019/009203.
Puissant et al., "Resveratrol Promotes Autophagic Cell Death in Chronic Myelogenous Leukemia Cells via JNK-Mediated p62/SQSTM1 Expression and AMPK Activation", Cancer Research, 2010, vol. 70, No. 3, pp. 1042-1052.
Teramachi et al., "Blocking the ZZ domain of sequestosome1/p62 suppresses myeloma growth and osteoclast formation in vitro and induces dramatic bone formation in myeloma-bearing bones in vivo", Leukemia, 2016, vol. 30, pp. 390-398.
Office Action issued Feb. 1, 2022 in Japanese Application No. 2021-503886.
Registry(STN) [online], Nov. 16, 1984, CAS Registration No. 51169-99-4 (1 page total).
Registry(STN) [online], Nov. 16, 1984, CAS Registration No. 47689-63-4 (1 page total).
Registry(STN) [online], Jul. 27, 2004, CAS Registration No. 717091-45-7 (1 page total).
Kaiser, C. et al., "Adrenergic agents. 4. Substituted phenoxypropanolamine derivatives as potential β-adrenergic agonists," Journal of Medicinal Chemistry, 1977, vol. 20, No. 5, pp. 687-692 (6 pages total).
Yadav, J. S. et al., "An efficient protocol for regioselective ring opening of epoxides using samarium triflate: Synthesis of propranolol, atenolol and RO363," Journal of Molecular Catalysis A: Chemical, 2007, vol. 261, No. 2, pp. 207-212 (6 pages total).
Nelson, W. L. et al., "The 3, 4-Catechol derivative of propranolol, a minor dihydroxylated metabolite," Journal of Medicinal Chemistry, 1984, vol. 27, No. 7, pp. 857-861 (5 pages total).
Office Action issued Mar. 8, 2022 in Japanese Application No. 2021-503891.
Australian Office Action dated Aug. 29, 2022 in Australian (AU) Application No. 2019312065.
John W.A. Findlay et al., "Relationships between Immunogen Structure and Antisera Specificity in the Narcotic Alkaloid Series", Clinical Chemistry, 1981, vol. 27, No. 9, pp. 1524-1535 (12 pages total).
Maciej J. Stefanko et al., "Synthesis of functionalised polyethylene glycol derivatives of naproxen for biomedical applications", Tetrahedron, 2008, vol. 64, No. 44, pp. 10132-10139 (8 pages total).
Nicolai Stuhr-Hansen et al., "Synthesis of Symmetrical and Non-Symmetrical Bivalent Neurotransmitter Ligands", ChemistrySelect, 2016, vol. 1, No. 3, pp. 407-413 (7 pages total).
"CAS RN1181561-56-7", STN Registry Database, 2009 (3 pages total).
"CAS RN1181561-57-8", STN Registry Database, 2009 (4 pages total).
"CAS RN1217054-95-9", STN Registry Database, 2010 (3 pages total).
"CAS RN1869641-58-6", STN Registry Database, 2016 (4 pages total).
"CAS RN1874579-12-0", STN Registry Database, 2016 (3 pages total).
"CAS RN774192-20-0", STN Registry Database, 2004, (14 pages total).
"CAS RN87265-43-8", STN Registry Database, 1984 (5 pages total).
"CAS RN892571-80-1", STN Registry Database, 2006 (3 pages total).
"CAS RN892573-08-9", STN Registry Database, 2006 (4 pages total).
Keith D. Green et al., "Identification and Characterization of Inhibitors of the Aminoglycoside Resistance Acetyltransferase Eis from Mycobacterium tuberculosis", ChemMedChem, 2012, vol. 7, pp. 73-77 (5 pages total).

(56) References Cited

OTHER PUBLICATIONS

Communication dated Feb. 20, 2023, issued in Korean Application No. 10-2020-0092536.
Communication dated Feb. 20, 2023, issued in Korean Application No. 10-2020-0101379.
CAS Registry No. 562847-32-9, 2003, 1 page.
CAS Registry No. 99396-44-8, 1985, 2 pages.
CAS Registry No. 99342-74-2, 1985, 1 page.
CAS Registry No. 86955-68-2, 1984, 2 pages.
CAS Registry No. 77209-47-3, 1984, 1 page.
CAS Registry No. 76420-86-5, 1984, 2 pages.
CAS Registry No. 76420-85-4, 1984, 1 page.
CAS Registry No. 74867-70-2, 1984, 2 pages.
CAS Registry No. 58165-85-8, 1984, 1 page.
Office Action issued Dec. 18, 2023 by the United States Patent and Trademark Office in U.S. Appl. No. 17/262,157.
Bondeson et al., "Catalytic in vivo protein knockdown by small-molecule PROTACs", Nature Chemical Biology, 2015, vol. 11, pp. 611-617 (9 pages total).
Lu et al., "Hijacking the E3 Ubiquitin Ligase Cereblon to Efficiently Target BRD4", Chemistry & Biology, 2015, vol. 22, No. 6, pp. 755-763 (10 pages total).
Winter et al., "Phthalimide conjugation as a strategy for in vivo target protein degradation", Science, 2015, vol. 348, Issue. 6241, pp. 1376-1381 (7 pages total).
Islam et al., "Autophagic Regulation of p62 is Critical for Cancer Therapy" Int. J. Mol. Sci. 2018, vol. 19, No. 1405, pp. 1-15 (15 pages total).

CARGO DELIVERY SYSTEM AND COMPOSITION COMPRISING THE SAME

CROSS REFERENCE TO RELATED APPLICATION

This application is a Continuation-In-Part application of U.S. Non-provisional patent application Ser. No. 17/262,157, filed Jan. 21, 2021, which is a National Stage Application of International Patent Application No. PCT/KR2019/009205, filed Jul. 24, 2019, which claims the benefit of priority to a U.S. Provisional Patent Application No. 62/702,473, filed Jul. 24, 2018, the disclosures of all of which are hereby incorporated by reference in their entireties. The International Application was published on Jan. 30, 2020 as WO2020/022785. To the extent appropriate, a claim of priority is made to each of the above disclosed applications.

DESCRIPTION OF GOVERNMENT-SPONSORED RESEARCH AND DEVELOPMENT

This research is acknowledged as Korea Health Technology R&D Project through the Korea Health Industry Development Institute and Korea Dementia Research Center, funded by the MSIP (HI20C1234). This research is sponsored by Ministry of Health and Welfare under the management of Korea Dementia Research Center. Project name is Development of Alzheimer & Apoptosis Disease Therapeutics using novel target degrading platform technology (Project Serial No.: HU21C0201) and Business name is Anti-dementia Research.

PARTIES TO A JOINT RESEARCH AGREEMENT

The subject matter disclosed in U.S. application Ser. No. 17/262,157 (issued as U.S. Pat. No. 12,129,218) and the claimed invention were made by or on the behalf of parties to a joint research agreement that was in effect on or before the effective filing date the claimed invention, and the claimed invention was made as a result of activities undertaken within the scope of the joint research agreement. The parties to the joint research agreement are SEOUL NATIONAL UNIVERSITY R&DB FOUNDATION and AUTOTAC INC.

BACKGROUND

Field

The present disclosure relates to a novel cargo delivery system and composition comprising the same.

Description of the Related Art

Traditional drugs vary such as small molecule synthetic compounds, antibodies, proteins, peptides, etc., but the basic principle is to bind to an active site of a particular protein to inhibit the activity of disease-causing proteins, thereby exhibiting drug efficacies. These traditional drug development methods have some limitations. First, high concentrations of drugs are required, which can cause side effects of the drugs. Since drug-protein binding is not a stable covalent bond, it can be separated. That is, when the drug binds to the target protein, it exhibits drug efficacy, but when the drug is separated from the target protein, it does not exhibit drug efficacy. Therefore, in order to maintain the drug efficacy, a high drug concentration must be maintained throughout the body. However, increasing the drug concentration for drug efficacy allows the drug to bind to other unexpected proteins, and this situation can lead to drug side effects. Second, drug target proteins are limited. Until now, approximately 400 types of drug target proteins have been approved by the US Food and Drug Administration (FDA). Over 90% of these are enzymes, transmitter proteins, channel/membrane proteins, etc. Because these drug target proteins have an active site and a binding site, it can be relatively easily found with relatively traditional drug development process. However, there are an estimated 3,000 proteins associated with disease, and currently, only about 13% of approved drugs are used for the target. Therefore, a paradigm shift in development of new drugs is necessary.

The N-end rule pathway is a proteolytic system where a specific N-terminal residue of a protein acts as a degradation signal. The N-end rule degradation signal is exemplified by type I basic residues including N-terminal arginine (Nt-Arg), lysine (Nt-Lys) and histidine (Nt-His); and type II hydrophobic residues including phenylalanine (Nt-Phe), leucine (Nt-Leu), tryptophan (Nt-Trp), tyrosine (Nt-Tyr) and isoleucine (Nt-Ile). These N-terminal residues bind to specific N-recognins (hereinafter referred to as N-ligands). The present inventors have first discovered or cloned previously known N-recognins, namely UBR1, UBR2, UBR4, and UBR5, and found that they utilize the UBR box as a substrate recognition domain (Tasaki, T. et al., Mol Cell Biol 25, 7120-36 (2005)). The present inventors have also found that the UBR box binds to type-I N-end rule ligands (Nt-Arg, Nt-Lys, Nt-His) such as N-terminal arginine residue to recognize a substrate and to link a ubiquitin chain to the substrate. It has further been found that UBR1 and UBR2 have an N-domain which plays an important role in the binding of type-2 N-end rule ligands (Nt-Trp, Nt-Phe, Nt-Tyr, Nt-Leu, and Nt-Ile) (Sriram, S. M., Kim, B. Y. & Kwon, Y. T., Nat Rev Mol Cell Biol 12, 735-47 (2011)). The ubiquitinized substrate produced from the binding between N-recognins and N-end rule ligands is delivered to proteasome where it is degraded into a short peptide. In this process, specific N-terminal residues (Nt-Arg, Nt-His, Nt-Lys, Nt-Trp, Nt-Phe, Nt-Tyr, Nt-Leu, Nt-Leu) are the essential determinants of binding since N-recognins provide most of the hydrogen bonds needed to target the N-end rule substrate (Sriram, S. M. & Kwon, Y. T., Nat Struct Mol Biol 17, 1164-5 (2010)).

Intracellular protein degradation is mainly performed by the ubiquitin-proteasome system (UPS) and the autophagy-lysosome system. In general, UPS regulates the intracellular concentrations of regulators with normal folding, or degrades proteins that have been misfolded and have lost their functions. At this time, the substrate is directly or indirectly recognized and ubiquitinated by estimated about 500-1,000 E3 ligases, and then unfolded into polypeptide helices and degraded by proteasomes (Ji and Kwon, Mol Cells 40, 441-449 (2017)). In normal cells, the process of the ubiquitin-proteasome system is smooth, but disease-related proteins become misfolded proteins that are incorrectly folded, or aggregates resulting from the accumulation of misfolded proteins block proteasome functions, or proteasome function declines during aging, or the degradation of proteins associated with diseases are not smoothly performed due to the reprogramming of protein transcription and translation (Ciechanover, A. & Kwon, Y. T., Exp Mol Med 47, e147 (2015)). In a representative example, the respective major pathological proteins of proteinopathies (Alzheimer's disease, Huntington's disease, Parkinson's disease, human mad cow disease, Lou Gehrig's disease/amyotrophic lateral sclerosis, alpha-1 antitrypsin deficiency, keratopathy, type 2 diabetes, etc.) are misfolded, ubiquitinated and accumulated, and these surplus protein wastes are converted back into aggregates (Aguzzi and O'Connor, Nat Rev Drug Discov 9, 237-48 (2010)). Such specific mutant proteins have a strong property of being transformed into aggregates, and thus are not degraded into the proteasome described above. The reason is that since proteasome has a narrow inner diameter of about 13 Angstroms, the misfolded protein must be unfolded, and when the proteins are aggregated, they will not be unfolded. In another representative example, cancer cells are known to increase transcription and translation of oncoproteins and simultaneously inhibit the degradation by reprogramming intracellul7ar transcription and translation (Xiong et al., J Cell Physiol 234, 14031-14039 (2019)). In addition, subunit proteins and transmembrane proteins that form a complex also have limited degradation due to the ubiquitin-proteasome system.

Autophagy is a major intracellular protein degradation system along with UPS (ubiquitin-proteasome system). Autophagy is a protein degradation process essential to maintain cell homeostasis and genetic stability by degrading aged or impaired cellular organelles or damaged or abnormally folded proteins and their aggregates (Ji and Kwon, Mol Cells 40, 441-449 (2017)). In particular, when pathological proteins and their aggregates are accumulated in a cytoplasm, they can become cytotoxic substances, and thus, should be received and degraded by autophagy. The mechanism for autophagy is largely divided into macroautophagy, microautophagy and chaperone-mediated autophagy, and it is divided into bulk autophagy and selective autophagy, depending on the purpose of degrading the intracellular substrate (Dikic, I. & Elazar, Z., Nat Rev Mol Cell Biol 19, 349-364 (2018)). Of these, selective autophagy and chaperone-mediated autophagy cause selective degradation of unwanted intracellular proteins and dysfunctional organelles. By inducing selective autophagy, the development of new therapies for diseases based on the accumulation of pathologically misfolded proteins and dysfunctional organelles is currently building a new paradigm. p62/SQSTM1/Sequestosome-1 protein is important for initiating the formation of autophagosome which is a mediator in the mechanism for selective autophagy, and delivering the contents. At this time, p62 proteins bind to pathological proteins and their aggregates, which are then delivered to autophagosome. P62 undergoes self-oligomerization as a key process when delivering pathological proteins to autophagosomes (Dikic, I. & Elazar, Z., Nat Rev Mol Cell Biol 19, 349-364 (2018)). At this time, the pathological proteins are concentrated together to reduce the volume, thus facilitating degradation by autophagy. PB1 domain mediates the self-oligomerization of p62, but the regulatory mechanism thereof is not well known. The misfolded protein-p62 conjugate delivered to autophagosome can be degraded by lysosomal enzymes as the autophagosome binds to a lysosome.

Through the mechanisms described above, autophagy is important for maintaining cell homeostasis by regulating intracellular changes in damaged proteins and cellular organelles. When autophagic function is weakened, it leads to the accumulation and aggregation of the misfolded proteins, which results in proteinopathies or cancer. Studies on the activation of bulk autophagy to treat these diseases have been actively conducted (Ciechanover, A. & Kwon, Y. T., Exp Mol Med 47, e147 (2015)). A regulator that normally inhibits bulk autophagy is mTOR. A method of activating autophagy using mTOR inhibitors is most widely used (Jung, C. H., Ro, S. H., Cao, J., Otto, N. M. & Kim, D. H., FEBS Lett 584, 1287-95 (2010)). Specifically, by using rapamycin treatment, amyloid beta (Ab) and tau were eliminated and simultaneously cognitive ability was improved in an AD animal model over-expressing APP (Caccamo, A., Majumder, S., Richardson, A., Strong, R. & Oddo, S., J Biol Chem 285, 13107-20 (2010)); tau was eliminated in an AD animal model over-expressing tau (Rodriguez-Navarro, J. A. et al., Neurobiol Dis 39, 423-38 (2010)); and the overexpressed mutant alpha-synuclein protein aggregate was eliminated in a PD mouse model (Webb, J. L., Ravikumar, B., Atkins, J., Skepper, J. N. & Rubinsztein, D. C., J Biol Chem 278, 25009-13 (2003)). It was confirmed that in a HD mouse, CCI-779, a rapamycin-like substance, is used to efficiently eliminate huntingtin aggregates and also to improve animal behavior and cognitive ability (Ravikumar, B., Duden, R. & Rubinsztein, D. C., Hum Mol Genet 11, 1107-17 (2002)). However, mTOR plays a very important role in various intracellular pathways including NF-kB. Therefore, although it exhibits excellent activity to eliminate misfolded protein aggregates of proteinopathies, there is a limitation in that these bulk autophagy activators, which are known that mTOR is a drug target, are used as therapeutic agents. In addition, there are no effective autophagosome-targeted therapies and therapeutic agents to target disease-inducing proteins.

In central dogma, genetic information stored in DNA is transcribed into RNA and translated into proteins to regulate cell functions. In the case of DNA, target cleavage can occur using DNA editing technology such as CRISPR; and in the case of RNA, target degradation can occur using siRNA. However, in the case of proteins, targeted degradation techniques are relatively limited. If it can be degraded by targeting disease-inducing proteins, it may be used as a platform technology for drug development in the pharmaceutical industry. PROTAC (PROteolysis Targeting Chimera) is a technology developed to effect intracellular degradation of target proteins. PROTAC uses a chimeric compound of a ligand that recognizes a target protein and a ligand that recognizes an E3 ubiquitin enzyme (An and Fu, EBioMedicine 36, 553-562 (2018)). When the target binder binds to disease-inducing protein and brings it closer to E3, E3 recognizes as a substrate and performs ubiquitination to induce proteasomal degradation. Since the existing disease treatment paradigm is protein enzyme inhibition, the development of new therapies for proteins that cannot be targeted with the existing therapeutic agent is of a great importance. From these viewpoints, PROTAC is an attractive new therapeutic development method by enabling selective degradation under ubiquitin-proteasome system with respect to proteins that cannot be targeted by a conventional enzyme inhibition method. However, PROTAC induces proteasomal degradation by utilizing only ligands that recognize the E3 ubiquitin enzyme, and therefore, when the target protein is misfolded to form an aggregate, or to form a complex, or to bind to a membrane structure, it is difficult to degrade (Bondeson et al., Cell Chem Biol 25, 78-87.e5 (2019)). In addition, PROTAC is unable to degrade intracellular organelles such as endoplasmic reticulum and mitochondria, and pathogens such as viruses and bacteria. Therefore, there is a need for the development of a method to target pathological proteins, organelles and aggregates and deliver them to selective autophagy.

In order to regulate cell functions, a method of indirectly regulating protein activity and concentration by editing DNA or by degrading RNA is widely used. In particular, RNA enables target degradation using siRNA, but has low cell permeability of siRNA, and is delivered into cells using transfection reagents, etc. Therefore, the process is complicated and expensive. Moreover, if the target protein is stable, it is difficult to lower the protein concentration even if RNA is degraded. Therefore, it is necessary to develop a method or a substance, i.e., a protein degrader, that directly degrades by targeting specific proteins.

SUMMARY

In one aspect, the disclosure is to provide a cargo delivery system capable of delivering cargo to p62 protein and activating autophagy.

In one aspect, the disclosure is to provide a pharmaceutical composition comprising the cargo delivery system as an active ingredient.

In one aspect: the disclosure is to provide a food composition comprising the system as an active ingredient.

In one aspect, the disclosure is to provide a method for activating autophagy of a target, comprising administering to a subject a composition comprising the cargo delivery system in an effective amount.

An embodiment of the disclosure provides a cargo delivery system which comprises an autophagy targeting ligand; and a target-binding ligand, which is cargo, carried by the autophagy targeting ligand, wherein the autophagy targeting ligand is a compound having a structure of the following Chemical Formula 1, or a pharmaceutically acceptable salt, stereoisomer, solvate or hydrate thereof:

[Chemical Formula 1]

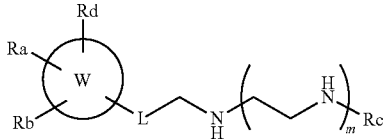

wherein,
W is C6-C10 aryl;
L is —(CH$_2$)$_{n1}$— or —O—(CH$_2$)$_{n2}$—CH(OH)—, provided that —O— in the —O—(CH$_2$)$_{n2}$—CH(OH)— is bonded to any one of carbones of W, where n1 is an integer of 1 to 4;
n2 is an integer of 1 to 4;
m is an integer of 0 to 2;
R$_a$ is R$_1$ or —OR$_1$,
where R$_1$ is hydrogen or —(CH$_2$)$_{n3}$—R'$_1$,
R'$_1$ is phenyl which is unsubstituted or substituted by hydroxy, halogen, C$_{1-4}$ alkyl, C$_{1-4}$ alkoxy, nitro, amino, (C$_{1-4}$ alkyl)amino, or di (C$_{1-4}$ alkyl)amino,
n3 is an integer of 1 to 6;
R$_b$ is —OR$_2$,
where R$_2$ is hydrogen or —(CH$_2$)$_{n4}$—R'$_2$,
R'$_2$ is phenyl which is unsubstituted or substituted by hydroxy, halogen, C$_{1-4}$ alkyl, C$_{1-4}$ alkoxy, nitro, amino, (C$_{1-4}$ alkyl)amino, or di (C$_{1-4}$ alkyl)amino,
n4 is an integer of 1 to 6;
R$_c$ is —(CH$_2$)$_{n5}$—OH, —(CH$_2$)$_{n5}$—NH—C(=NH)NH$_2$, —C(=NH)NH$_2$, —CH(R$_3$)—COOH, —CH(COO—R$_4$)—CH$_2$CH$_2$CH$_2$—NH—C(=NH)NH$_2$, —(CH$_2$)$_{n5}$—O—(CH$_2$)$_{n5}$—OH, —CONH(CH$_2$)$_{n5}$—OH, —CO(CH$_2$)$_{n6}$—OH, —(CH$_2$)$_{n6}$—CH(NH$_2$)—COOH, or —(CH$_2$)$_{n6}$—CONH$_2$, n5 is an integer of 2 to 4,
n6 is an integer of 1 to 4,
R$_3$ is hydrogen or C$_{1-4}$ alkyl,
R$_4$ is C$_{1-4}$ alkyl, and
R$_d$ is hydrogen, halogen, C$_{1-4}$ alkoxy or C$_{1-4}$ alkyl.

One embodiment of the disclosure provides a pharmaceutical composition comprising the cargo delivery system as an active ingredient.

One embodiment of the disclosure provides a food composition comprising the cargo delivery system as an active ingredient.

One embodiment of the disclosure provides a method for activating autophagy of a target, comprising administering to a subject a composition comprising the cargo delivery system in an effective amount.

The disclosure provides a novel platform technology capable of selectively and directly removing various targets to be degraded according to the type of cargo, target-binding ligands, through autophagy. Since the autophagy targeting ligand comprised in the cargo delivery system of the disclosure delivers the target-binding ligand, which is cargo, to the p62 protein and activates autophagy, the target, which specifically binds to the target-binding ligand, is also degraded, and removed by the system through an autophagy mechanism when administered in the body. According to the disclosure, because it can degrade transcription factors, proteins involved in signal transduction through protein binding, and aggregated and accumulated proteins such as tau, it is possible to degrade and remove undruggable proteins that are difficult to target with conventional drugs. Further, it is possible to overcome the phenomenon in which the target protein is overexpressed and overactivated or tolerated by conventional drugs, or the drug efficacy may be reduced by activation of other signal transduction systems. Accordingly, the disclosure may be applied to prevention, amelioration, and treatment of various diseases. Still further, since the cargo delivery system according to the disclosure targets autophagy, it can be administered at a low dose, and since a specified time is required to degrade and reproduce the target protein, the administration cycle is increased and the economy is high.

Immunoblotting shows representative results from three or more independent experiments.

Figure 2A:
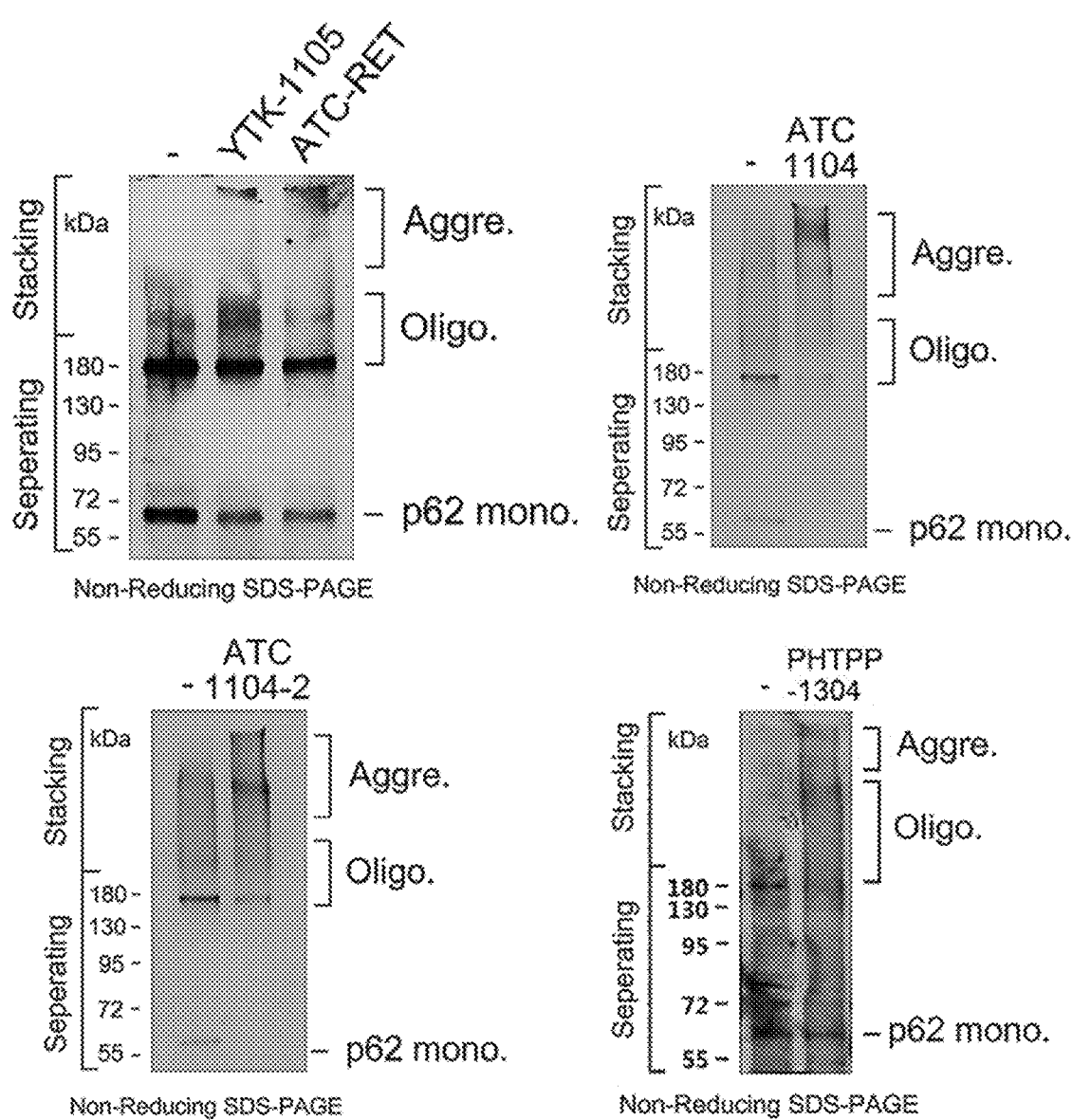
FIG. 2A is an immunoblot assay result showing the oligomerization and high molecular weight aggregation efficacy of a p62 protein according to a cargo delivery system of an embodiment of the disclosure. This shows that the oligomerization and high molecular weight aggregation of the p62 protein increase according to the treatment with the cargo delivery system of an embodiment of the disclosure. Immunoblotting shows representative results from three or more independent experiments.
Figure 2B:
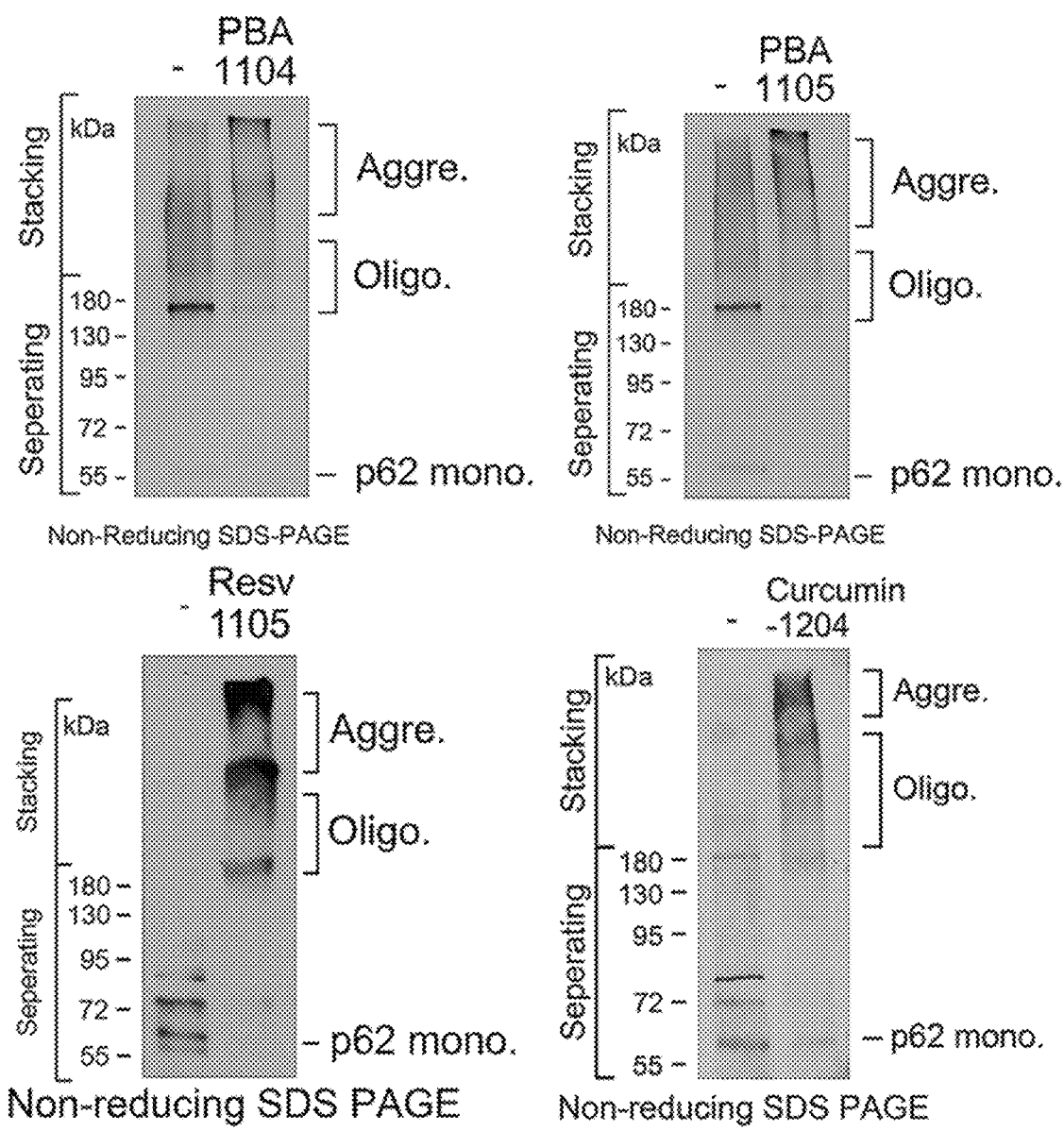
FIG. 2B is an immunoblot assay result showing the oligomerization and high molecular weight aggregation efficacy of a p62 protein according to a cargo delivery system of an embodiment of the disclosure. This shows that the oligomerization and high molecular weight aggregation of the p62 protein increase according to the treatment with the cargo delivery system of an embodiment of the disclosure.
Figure 2C:
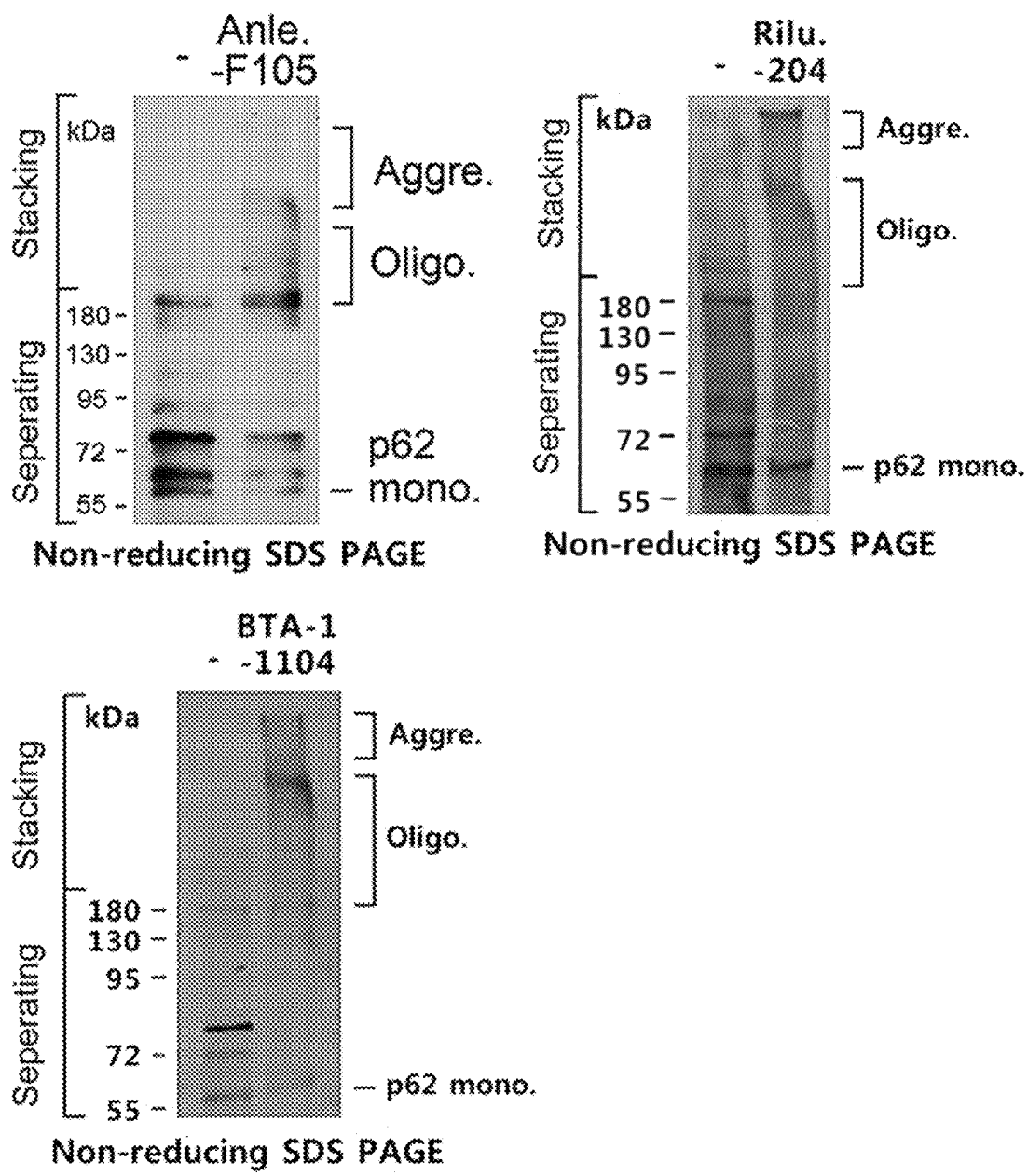

FIG. 2C is an immunoblot assay result showing the oligomerization and high molecular weight aggregation efficacy of a p62 protein according to a cargo delivery system of an embodiment of the disclosure. This shows that the oligomerization and high molecular weight aggregation of the p62 protein increase according to the treatment with the cargo delivery system of an embodiment of the disclosure. Immunoblotting shows representative results from three or more independent experiments.

Figure 3A:
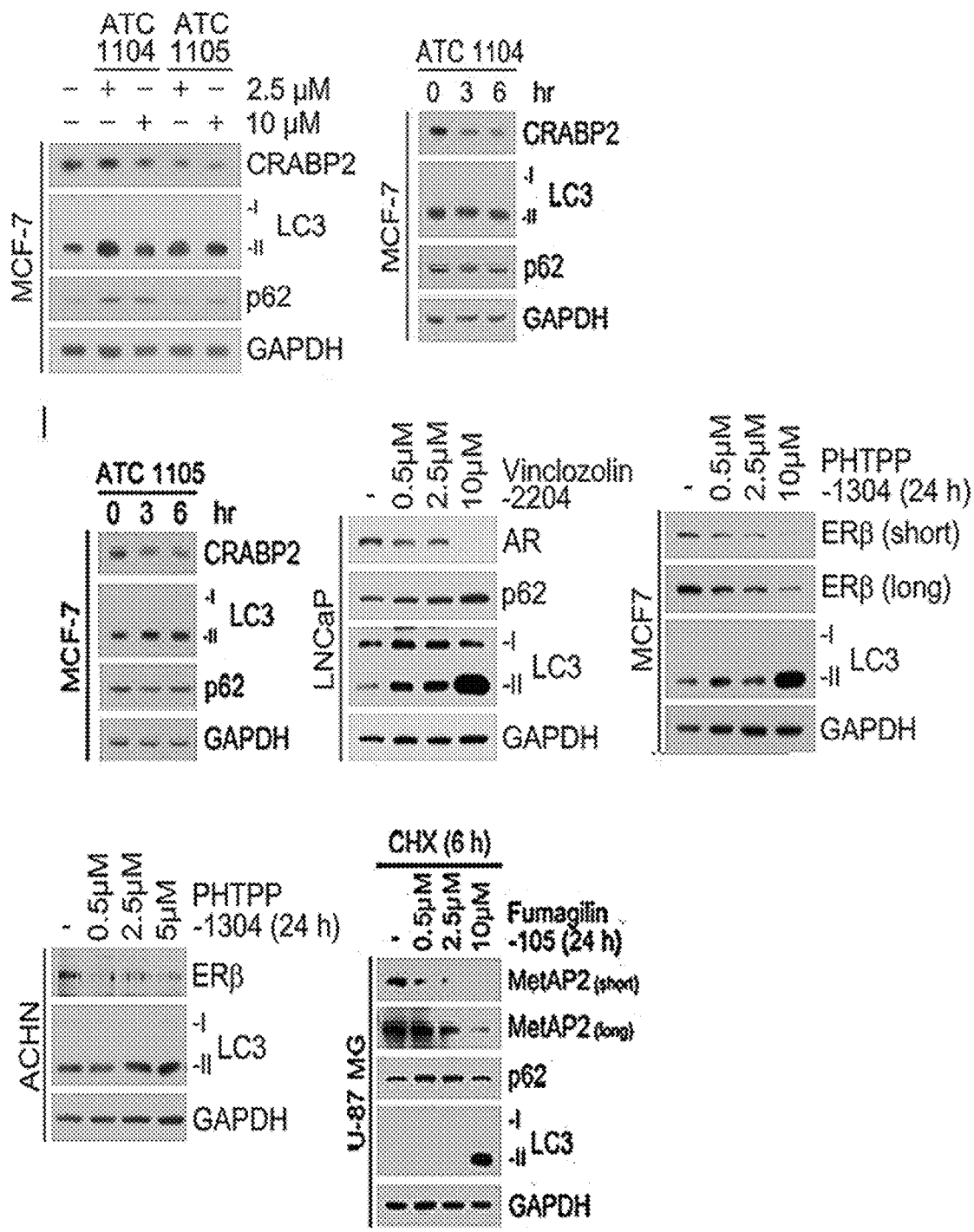

FIG. 3A is an immunoblot assay result showing the degradation efficacy of a target protein according to a cargo delivery system of an embodiment of the disclosure. This shows that an amount of the target protein decreases according to the treatment with the cargo delivery system of an embodiment of the disclosure. Immunoblotting shows representative results from three or more independent experiments.

Figure 3B:
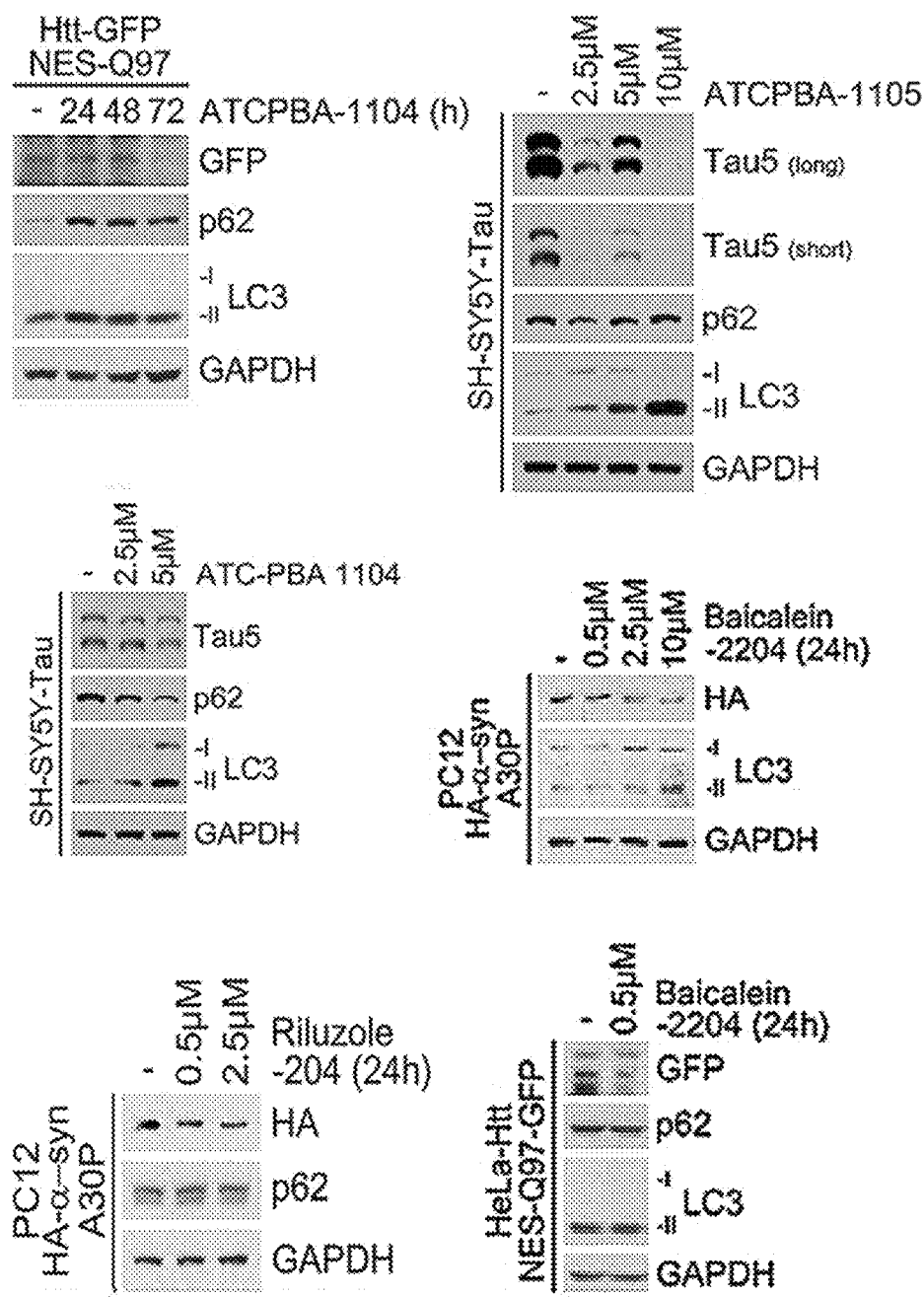

FIG. 3B is an immunoblot assay result showing the degradation efficacy of a target protein according to a cargo delivery system of an embodiment of the disclosure. This shows that an amount of the target protein decreases according to the treatment with the cargo delivery system of an embodiment of the disclosure. Immunoblotting shows representative results from three or more independent experiments.

Figure 3C:
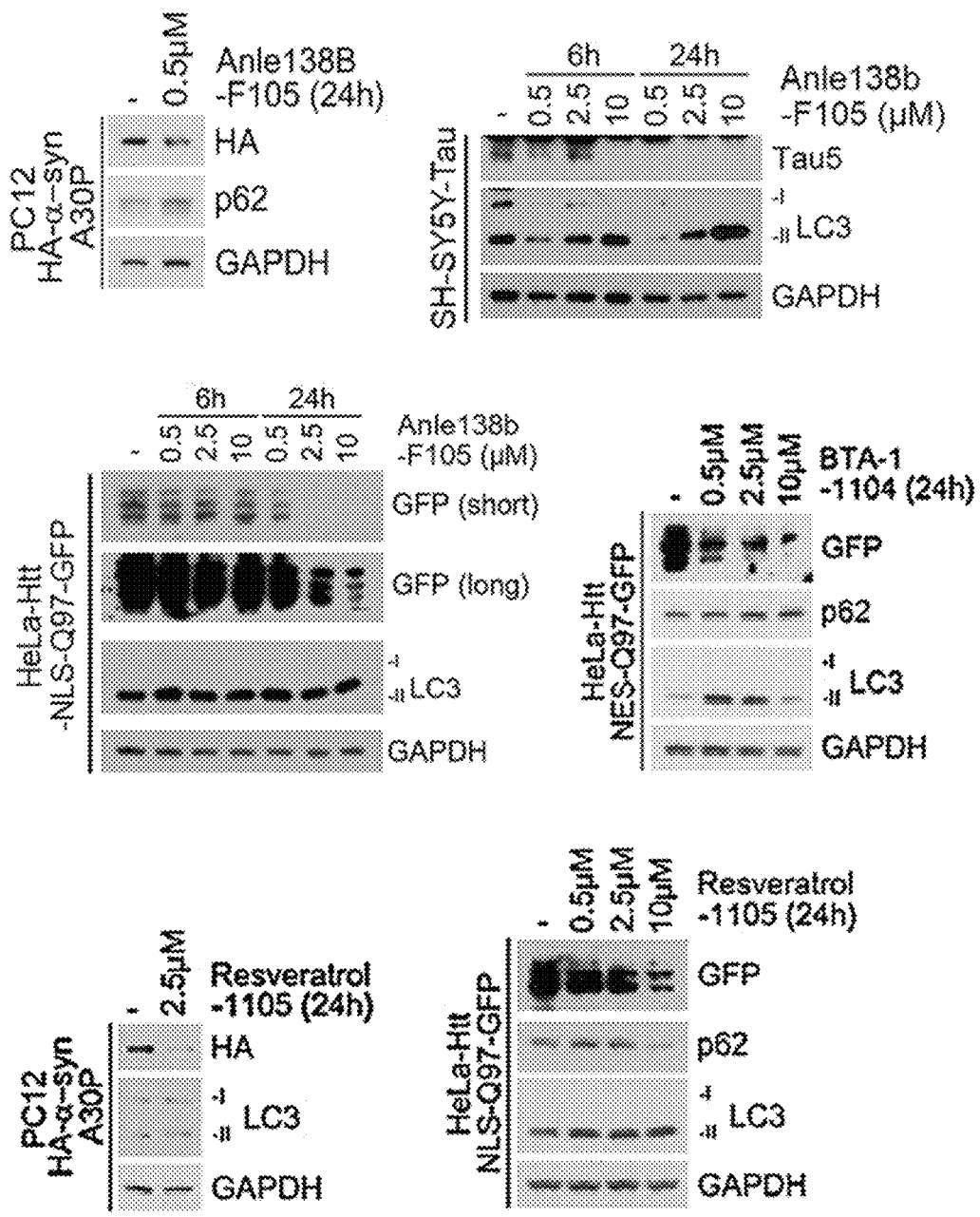

FIG. 3C is an immunoblot assay result showing the degradation efficacy of a target protein according to a cargo delivery system of an embodiment of the disclosure. This shows that an amount of the target protein decreases according to the treatment with the cargo delivery system of an embodiment of the disclosure. Immunoblotting shows representative results from three or more independent experiments.

Figure 4A:
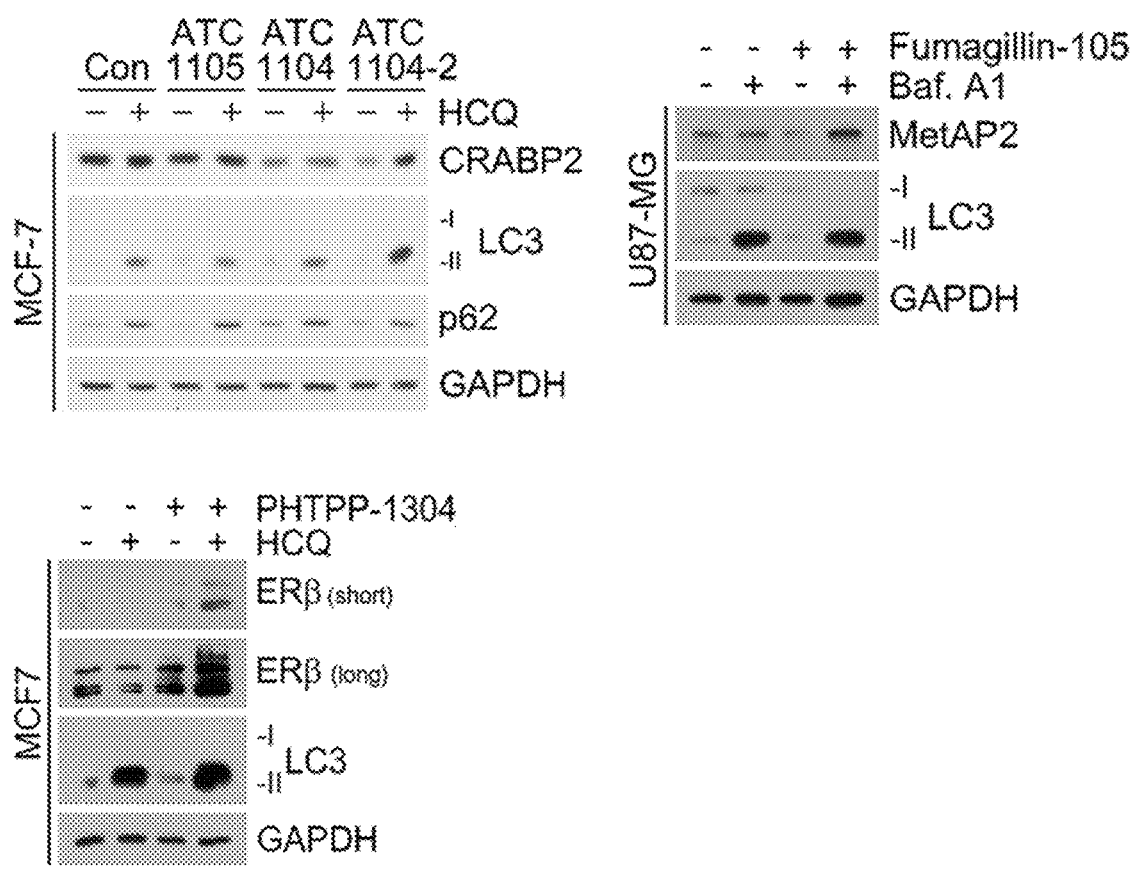

FIG. 4A is an immunoblot assay result showing that a degradation efficacy mechanism of a target protein according to a cargo delivery system of an embodiment of the disclosure is mediated through an autophagy-lysosome pathway. This shows that an amount of the target protein is decreased according to the treatment with the cargo delivery system of an embodiment of the disclosure, and an amount of the target protein increases again when treated with hydroxychloroquine (HCQ) which is an autophagy-lysosome pathway inhibitor. Immunoblotting shows representative results from three or more independent experiments.

Figure 4B:
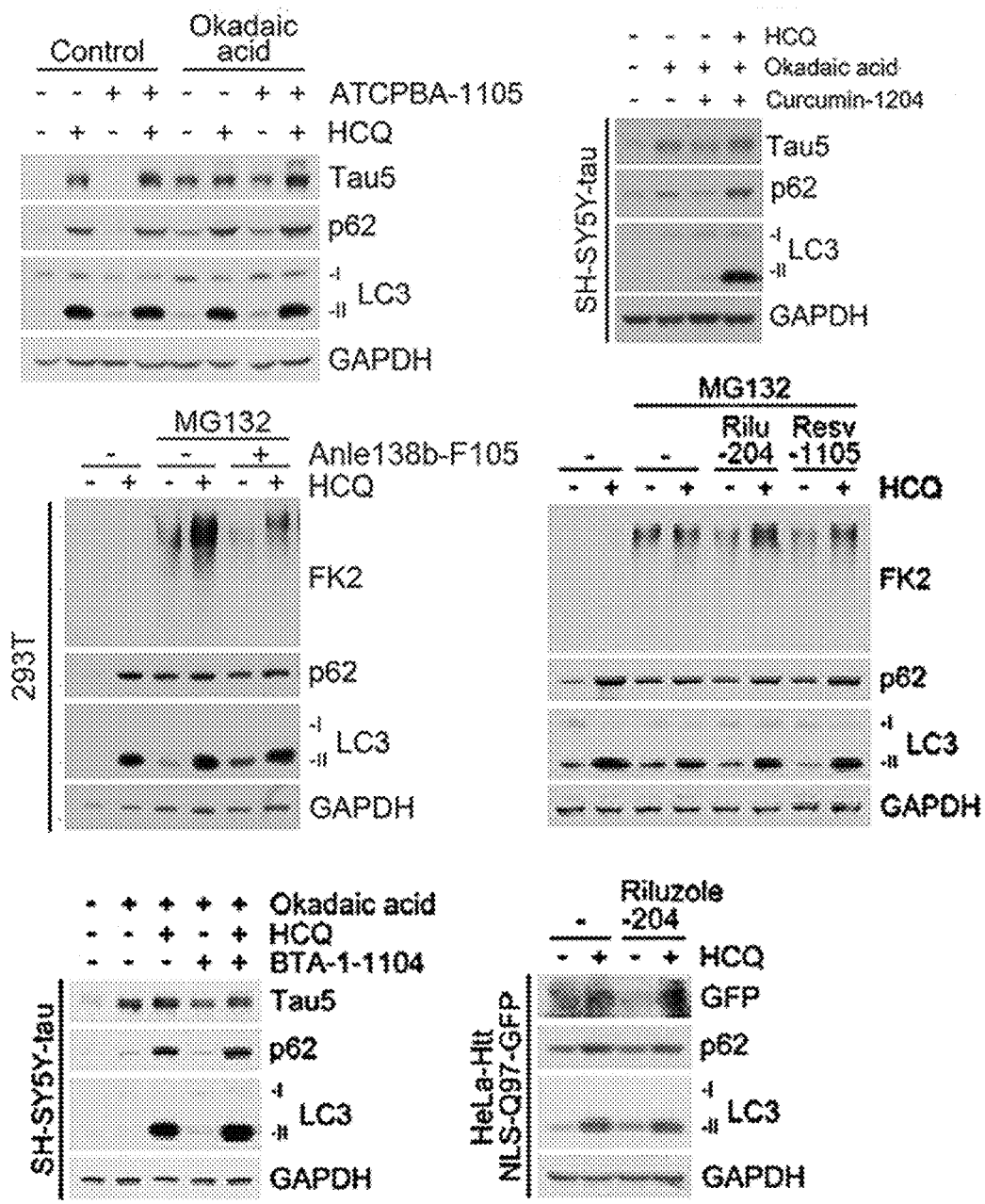

FIG. 4B is an immunoblot assay result showing that a degradation efficacy mechanism of a target protein according to a cargo delivery system of an embodiment of the disclosure is mediated through an autophagy-lysosome pathway. This shows that an amount of the target protein is decreased according to the treatment with the cargo delivery system of an embodiment of the disclosure, and an amount of the target protein increases again when treated with hydroxychloroquine (HCQ) which is an autophagy-lysosome pathway inhibitor. Immunoblotting shows representative results from three or more independent experiments.

Figure 5A:
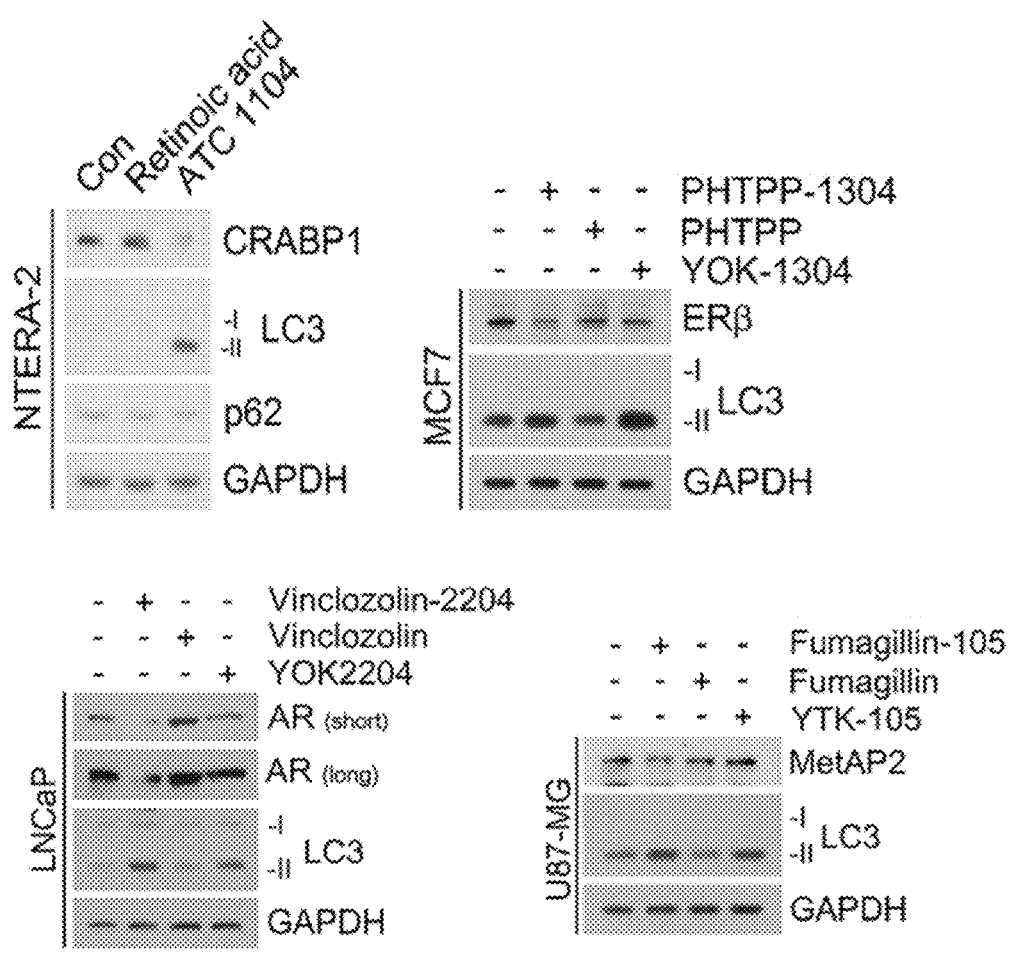

FIG. 5A is an immunoblot assay result showing that the target protein degradation efficacy of a cargo delivery system of an embodiment of the disclosure is superior to the target protein degradation efficacy of an autophagy targeting ligand alone or a target-binding ligand, respectively. This shows that an amount of the target protein after treatment with the cargo delivery system of an embodiment of the disclosure is significantly decreased as compared with that after treatment with the autophagy targeting ligand or the target-binding ligand. Immunoblotting shows representative results from three or more independent experiments.

Figure 5B:
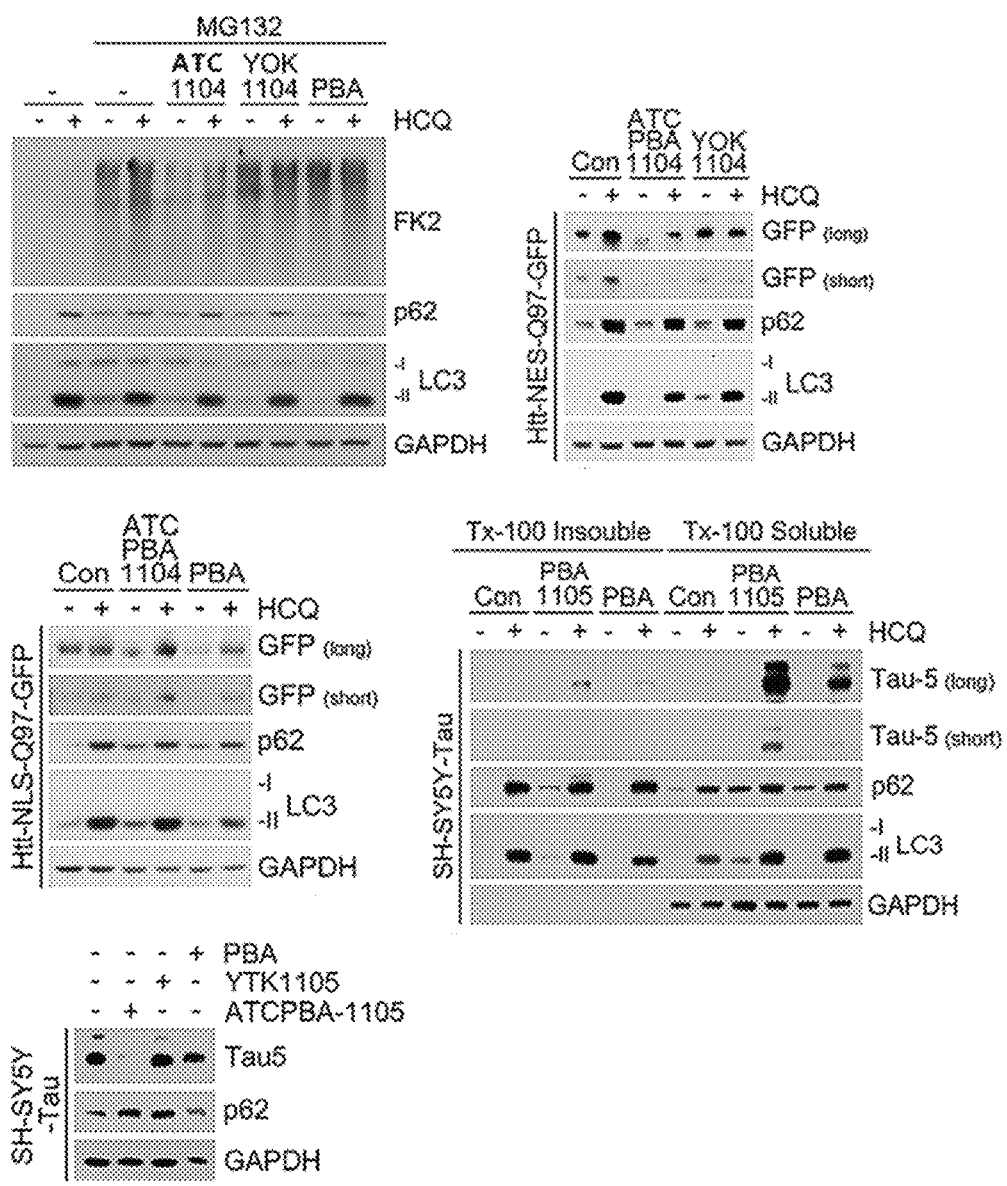

FIG. 5B is an immunoblot assay result showing that the target protein degradation efficacy of a cargo delivery system of an embodiment of the disclosure is superior to the target protein degradation efficacy of an autophagy targeting ligand alone or a target-binding ligand, respectively. This shows that an amount of the target protein after treatment with the cargo delivery system of an embodiment of the disclosure is significantly decreased as compared with that after treatment with the autophagy targeting ligand or the target-binding ligand. Immunoblotting shows representative results from three or more independent experiments.

Figure 5C:
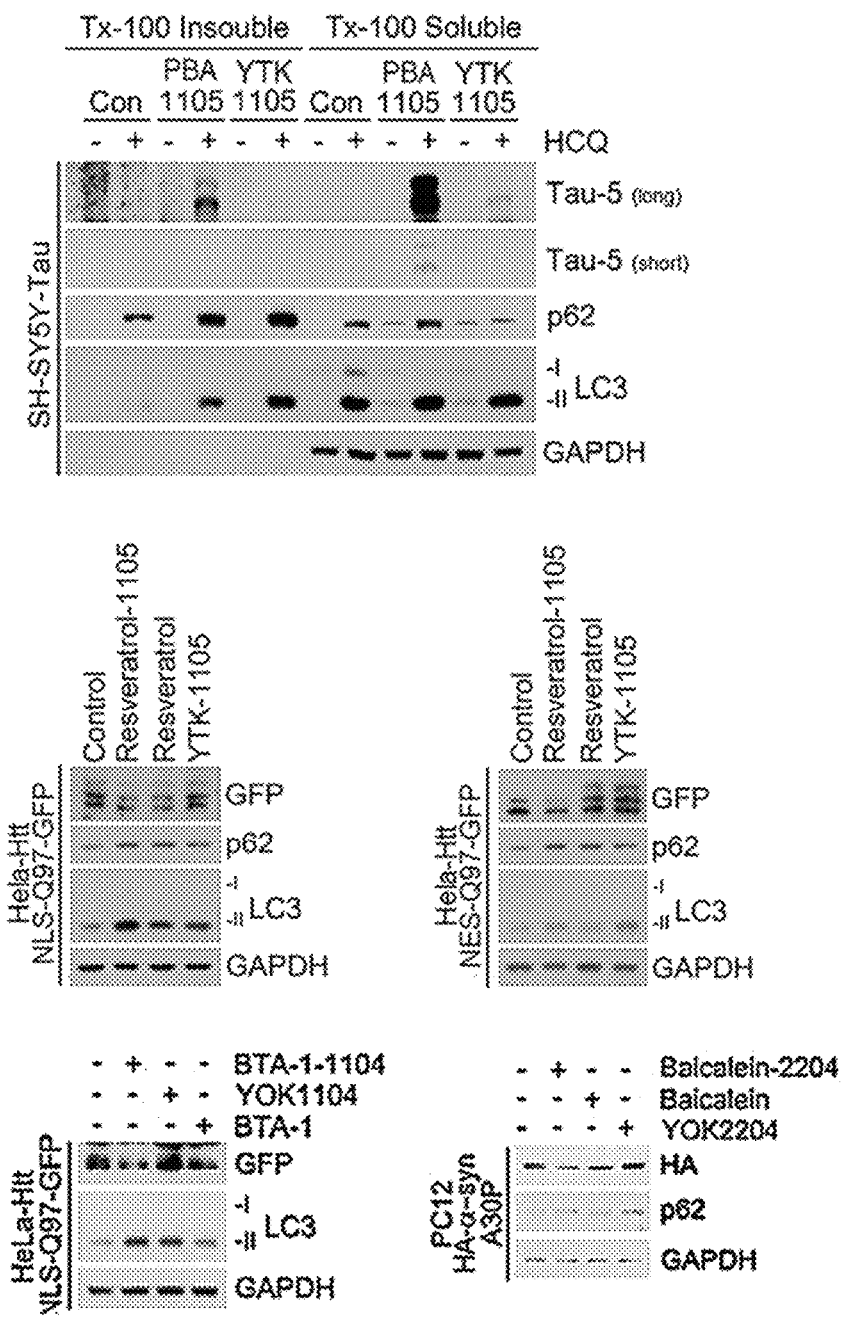

FIG. 5C is an immunoblot assay result showing that the target protein degradation efficacy of a cargo delivery system of an embodiment of the disclosure is superior to the target protein degradation efficacy of an autophagy targeting ligand alone or a target-binding ligand, respectively. This shows that an amount of the target protein after treatment with the cargo delivery system of an embodiment of the disclosure is significantly decreased as compared with that after treatment with the autophagy targeting ligand or the target-binding ligand. Immunoblotting shows representative results from three or more independent experiments.

Figure 6A:
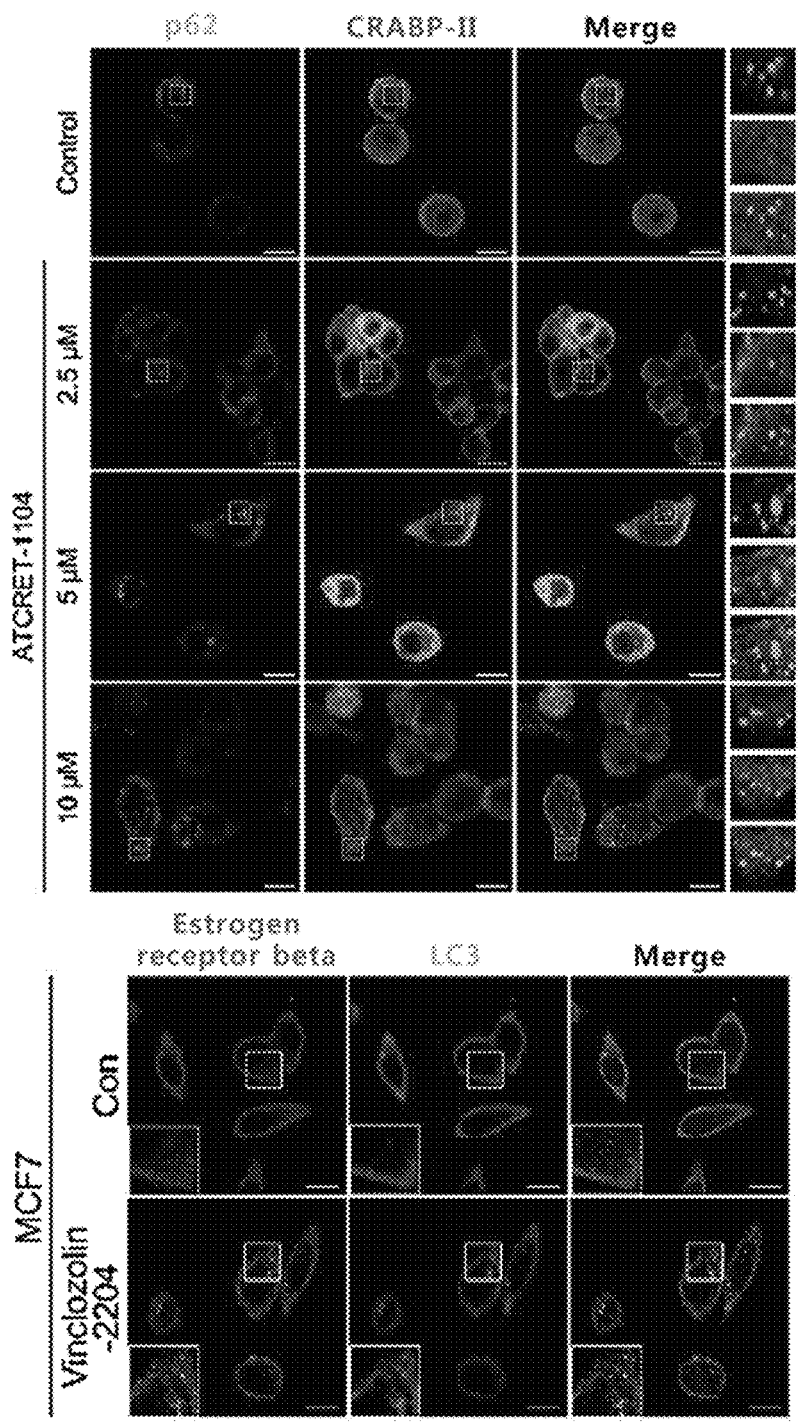

FIG. 6A is an immunofluorescence staining assay result showing the efficacy of delivering the target protein and p62 protein to the autophagy by a cargo delivery system of an embodiment of the disclosure. It can be confirmed that after treatment with the cargo delivery system of an embodiment of the disclosure, the intracellular puncta and co-existence of the target proteins and p62 protein of the cargo delivery system of an embodiment of the disclosure increase gradually.

Figure 6B:
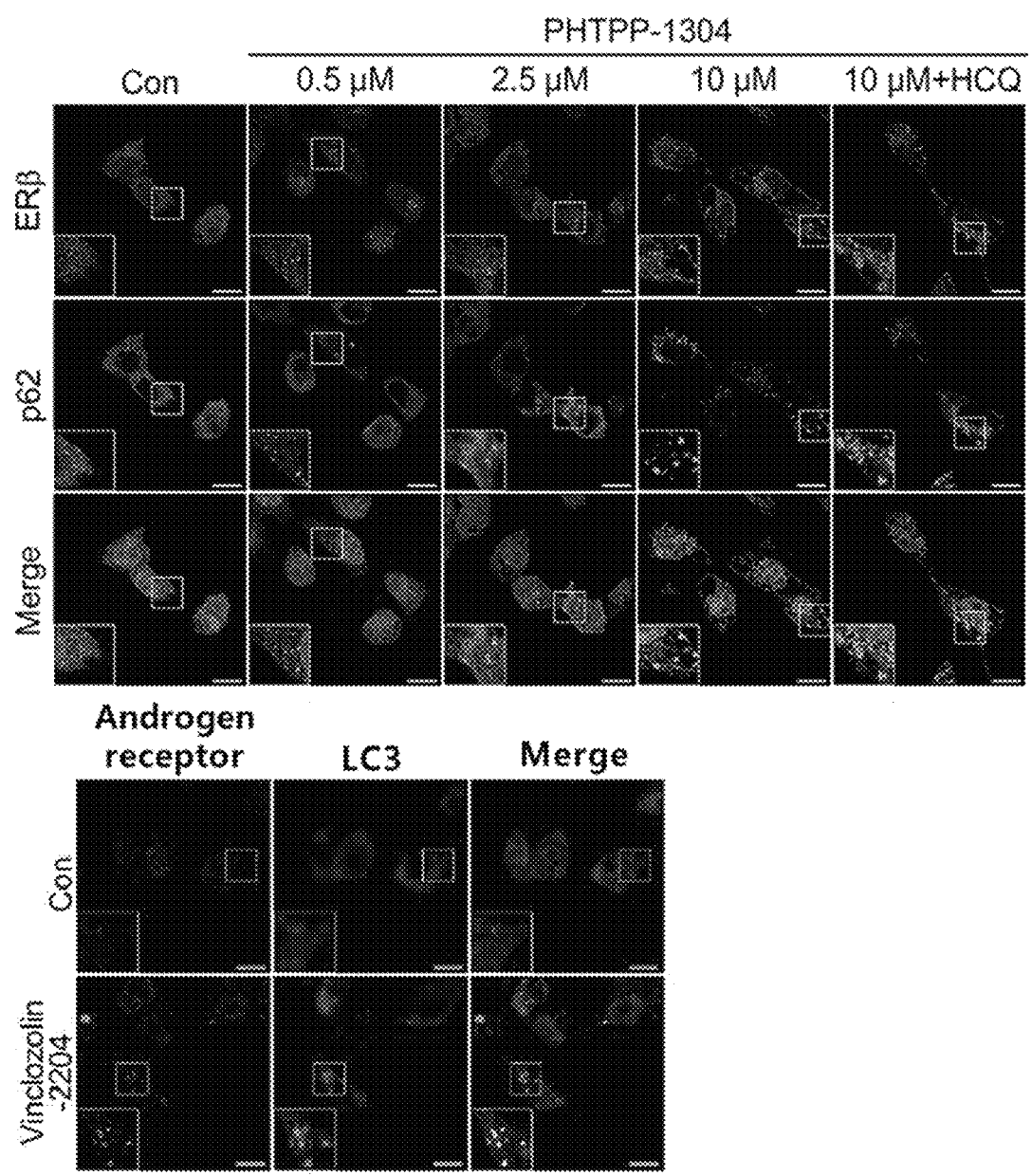

FIG. 6B is an immunofluorescence staining assay result showing the efficacy of delivering the target protein and p62 protein to the autophagy by a cargo delivery system of an embodiment of the disclosure. It can be confirmed that after treatment with the cargo delivery system of an embodiment of the disclosure, the intracellular puncta and co-existence of the target proteins and p62 protein of the cargo delivery system of an embodiment of the disclosure increase gradually.

Figure 6C:
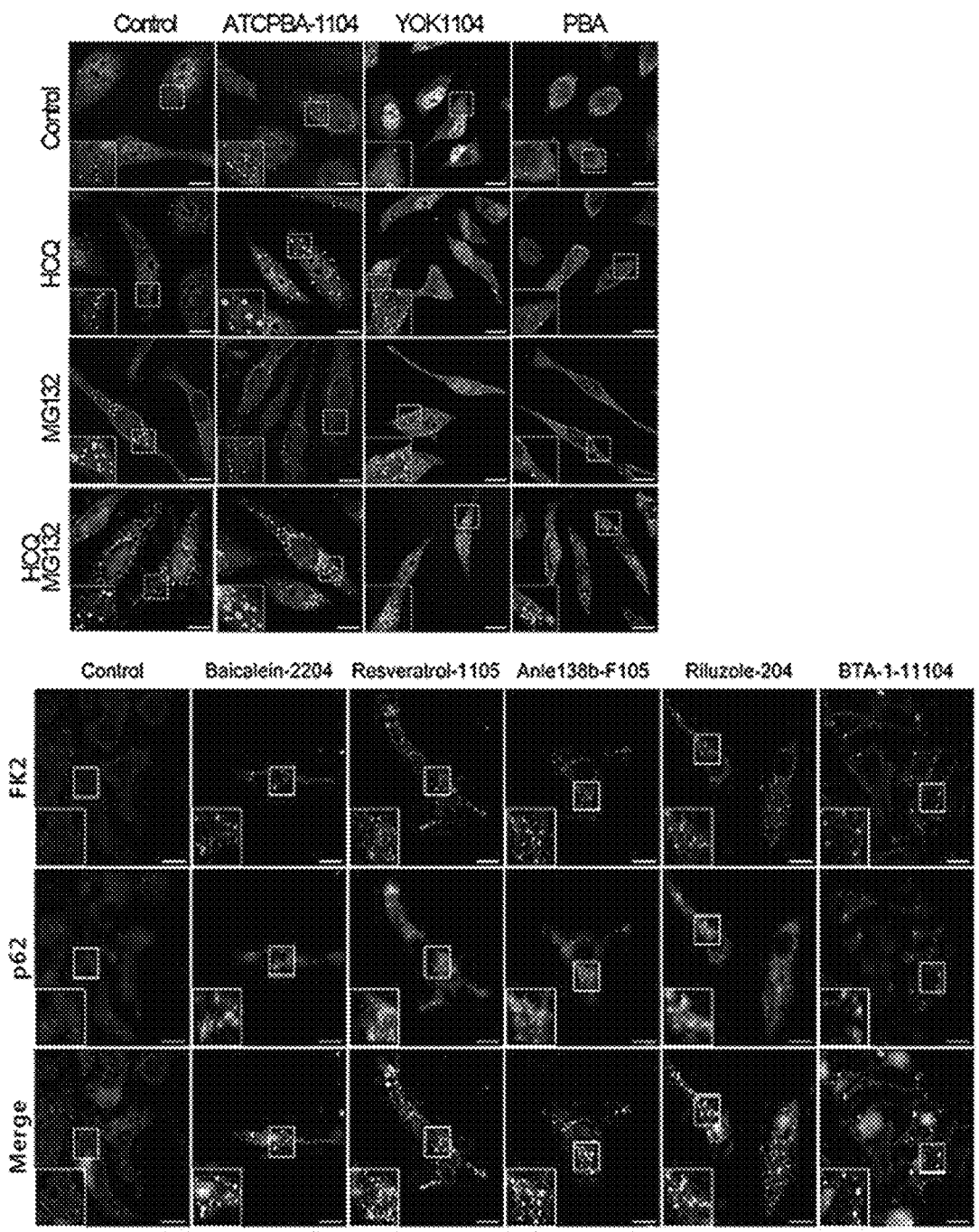

FIG. 6C is an immunofluorescence staining assay result showing the efficacy of delivering the target protein and p62 protein to the autophagy by a cargo delivery system of an embodiment of the disclosure. It can be confirmed that after treatment with the cargo delivery system of an embodiment of the disclosure, the intracellular puncta and co-existence of the target proteins and p62 protein of the cargo delivery system of an embodiment of the disclosure increase gradually.

Figure 7:
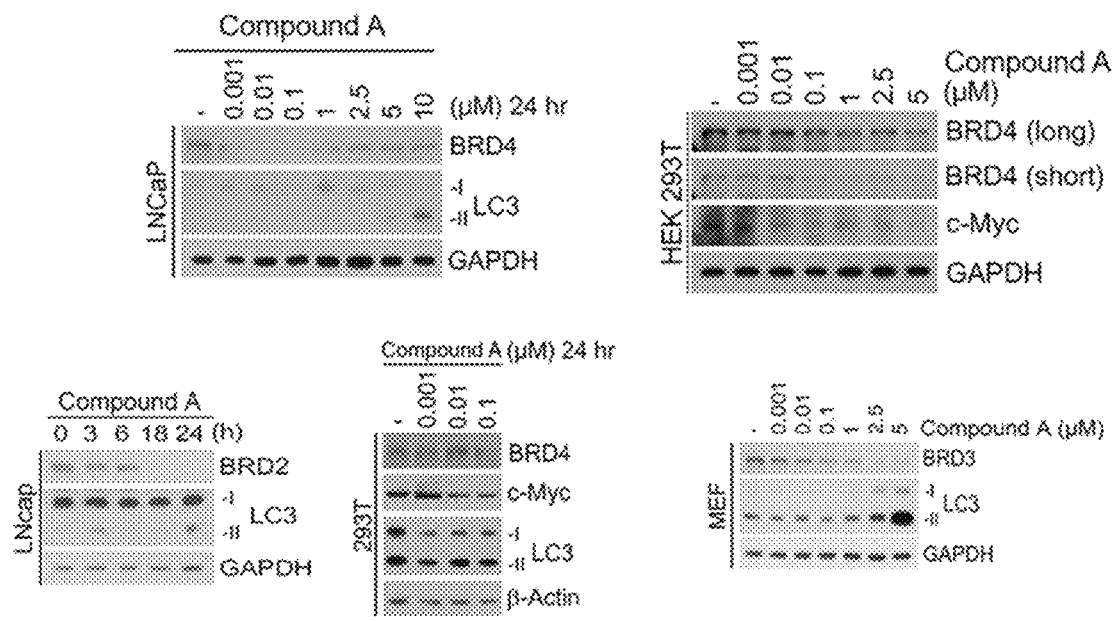

FIG. 7 is a immunoblot assay result confirming the degradation of a target protein BDR2, BDR3 or BDR4 by Compound A, as an embodiment of the disclosure.

Figure 8:
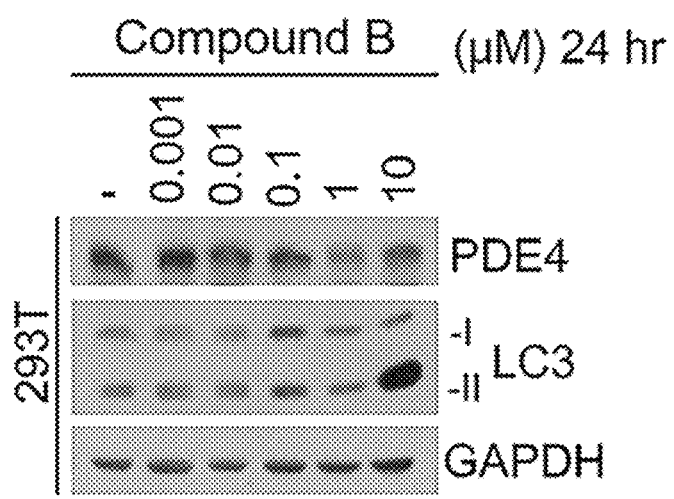

FIG. 8 is a immunoblot assay result confirming the degradation of a target protein PDE4 by Compound B, as an embodiment of the disclosure.

Figure 9:
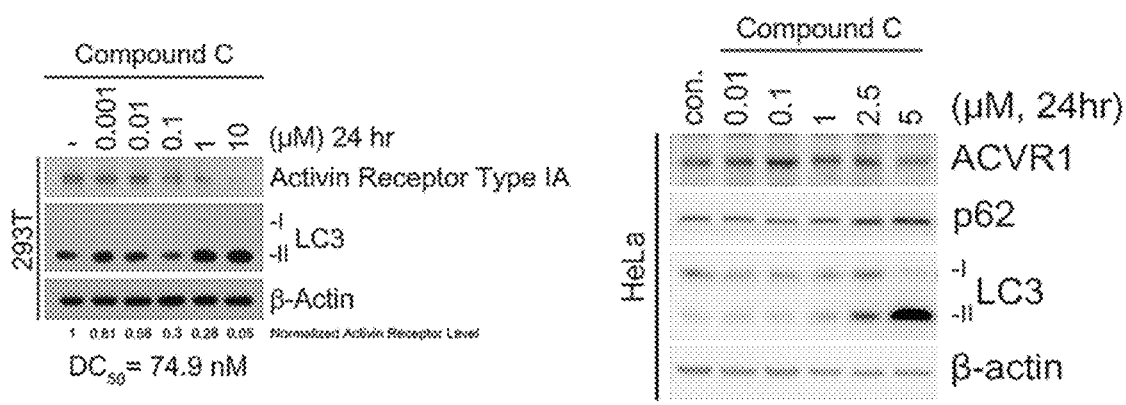

FIG. 9 is a immunoblot assay result confirming the degradation of a target protein ACVR1 by Compound C, as an embodiment of the disclosure.

Figure 10:
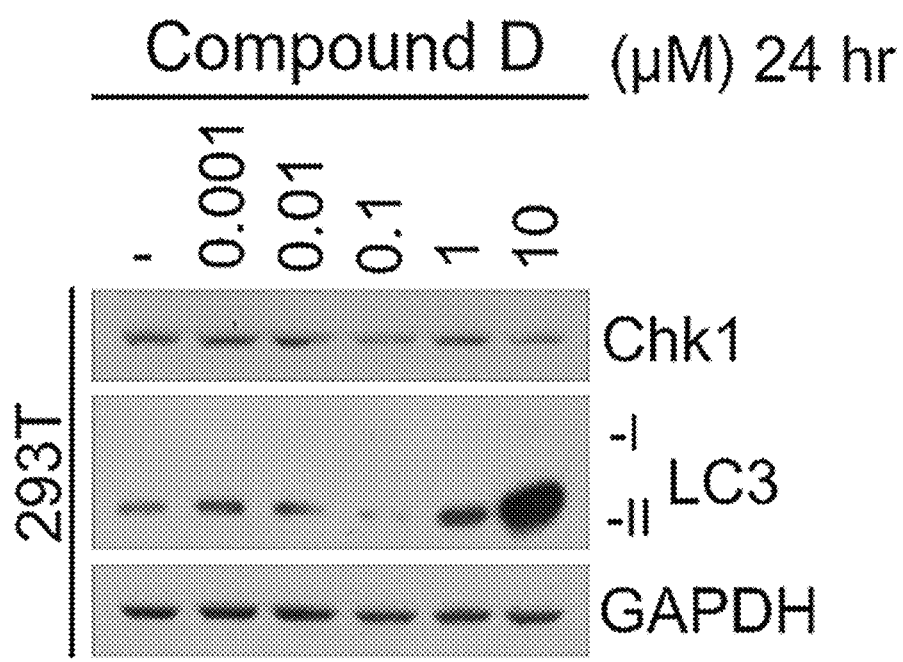

FIG. 10 is a immunoblot assay result confirming the degradation of a target protein Chk1 by Compound D, as an embodiment of the disclosure.

Figure 11:
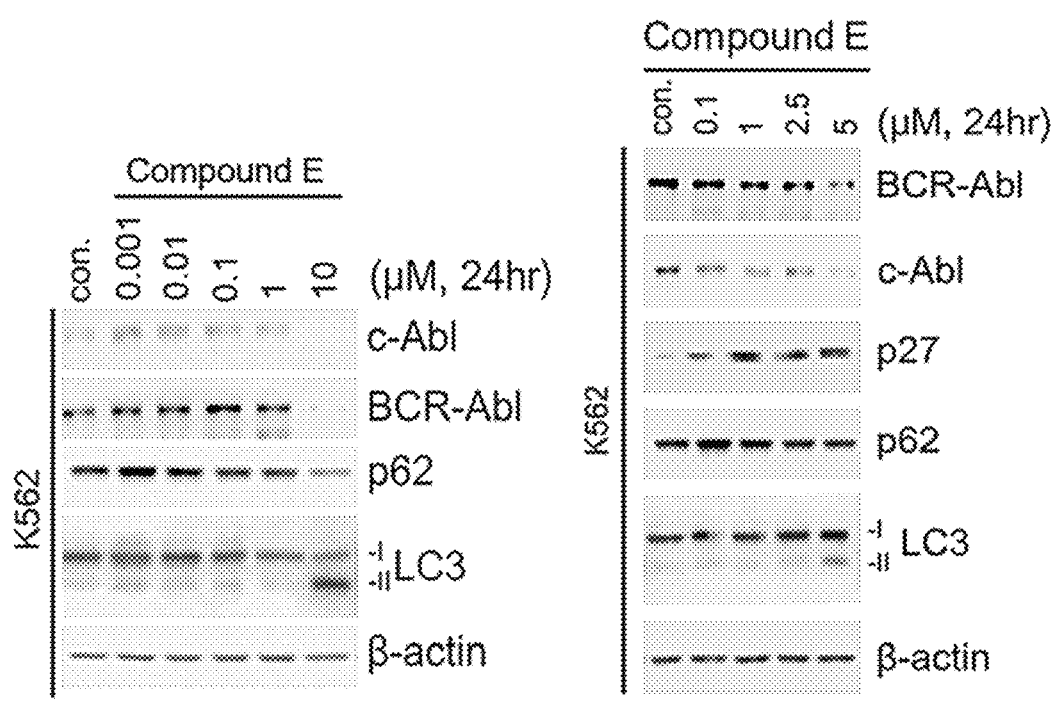

FIG. 11 is a immunoblot assay result confirming the degradation of a target protein c-Abl, BCR-Abl by Compound E, as an embodiment of the disclosure.

Figure 12:
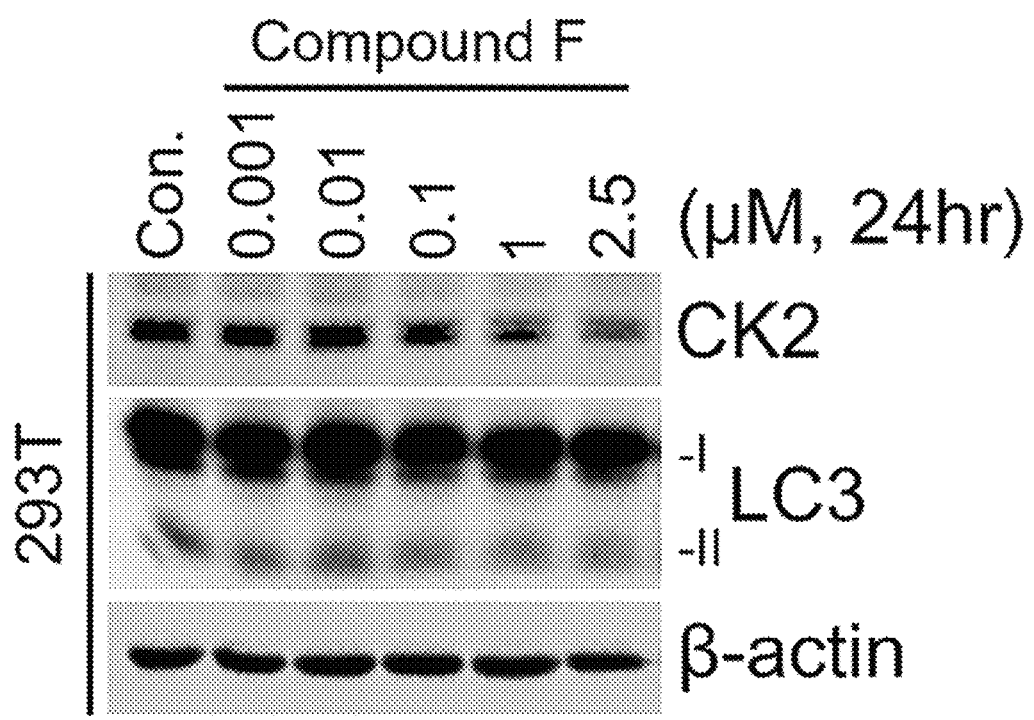

FIG. 12 is a immunoblot assay result confirming the degradation of a target protein CK2 by Compound F, as an embodiment of the disclosure.

Figure 13:
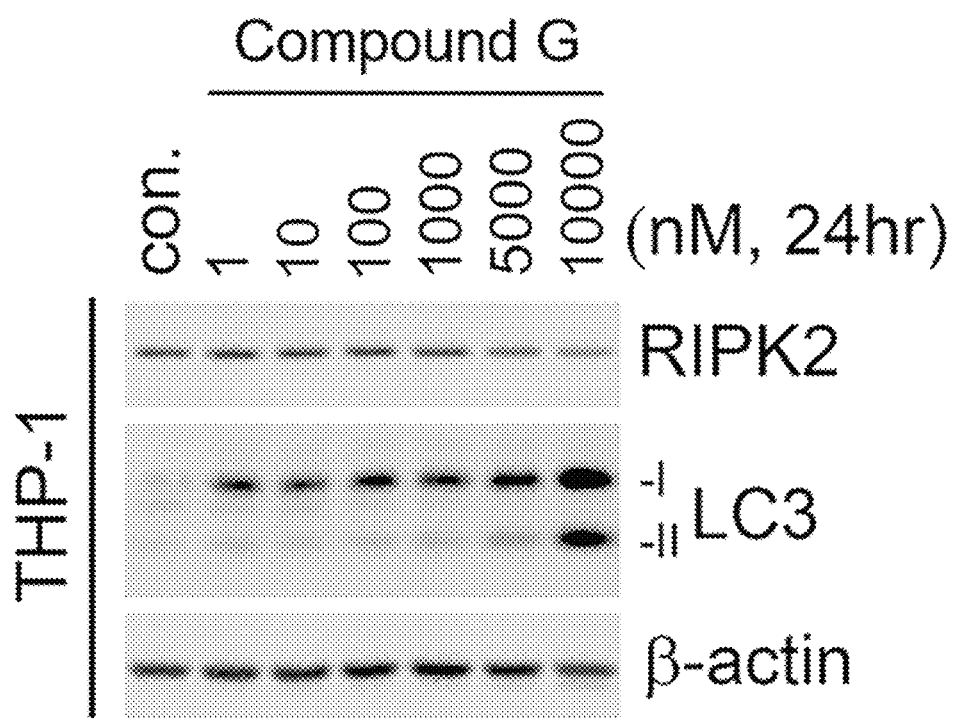

FIG. 13 is a immunoblot assay result confirming the degradation of a target protein RIPK2 by Compound G, as an embodiment of the disclosure.

Figure 14:
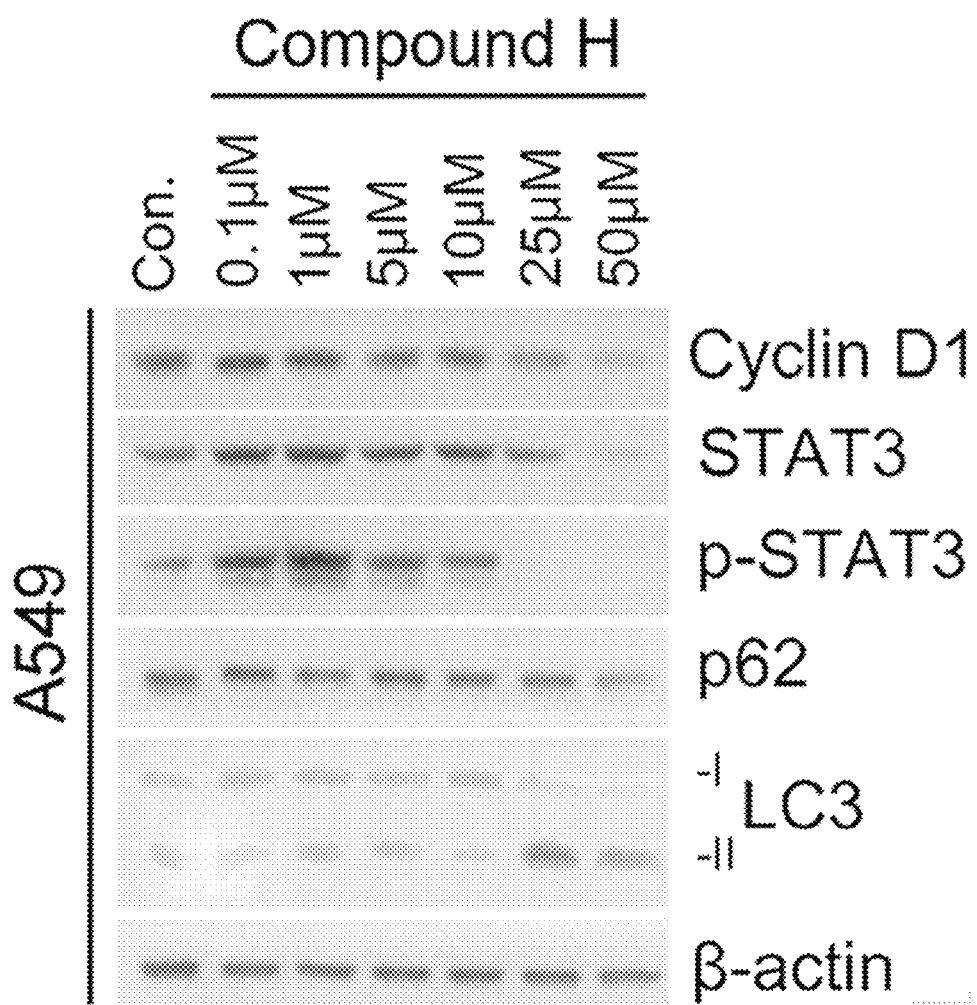

FIG. 14 is a immunoblot assay result confirming the degradation of a target protein Cyclin D1, STAT3, p-STAT3 by Compound H, as an embodiment of the disclosure.

Figure 15:
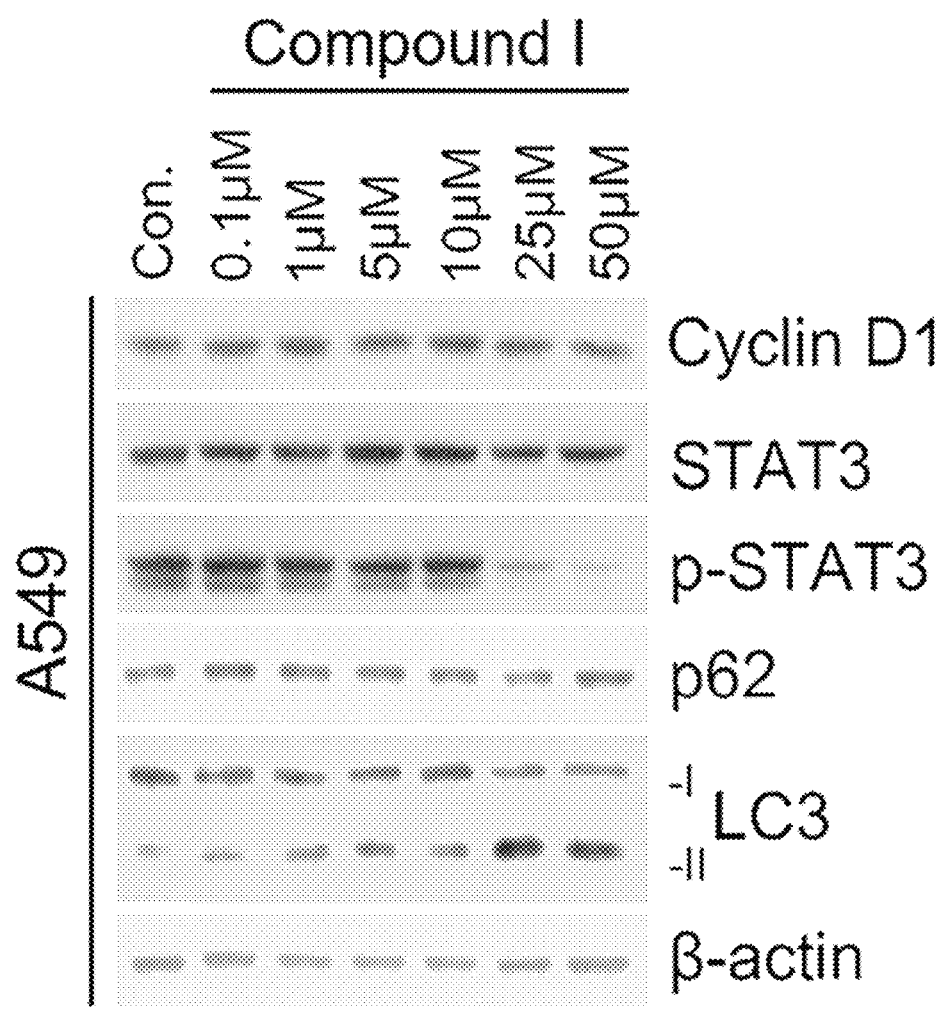

FIG. 15 is a immunoblot assay result confirming the degradation of a target protein Cyclin D1, STAT3, p-STAT3 by Compound I, as an embodiment of the disclosure.

Figure 16:
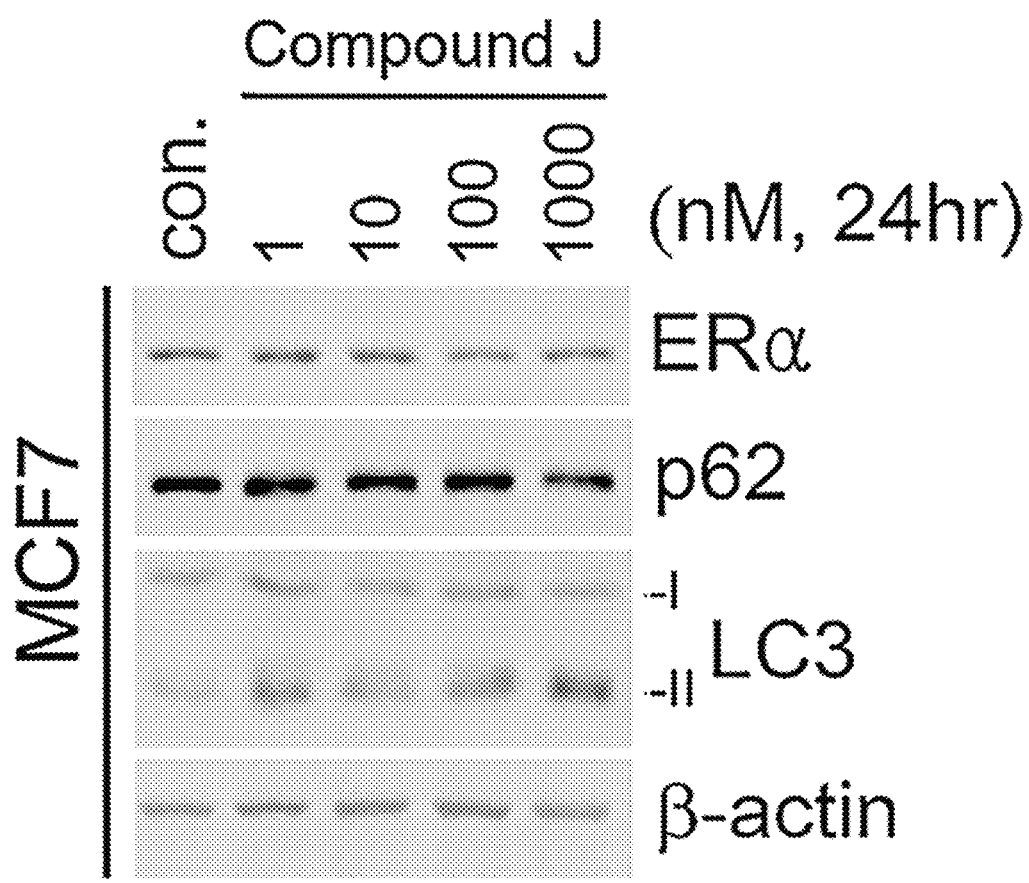

FIG. 16 is a immunoblot assay result confirming the degradation of a target protein ERα by Compound J, as an embodiment of the disclosure.

Figure 17:
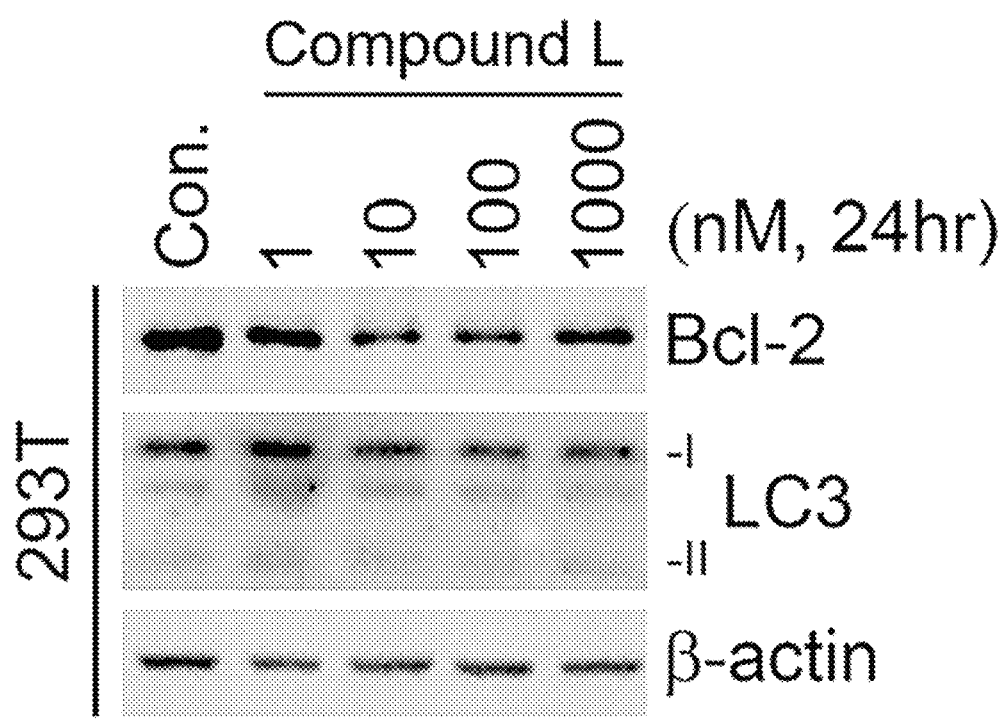

FIG. 17 is a immunoblot assay result confirming the degradation of a target protein Bcl-2 by Compound L, as an embodiment of the disclosure.

Figure 18:
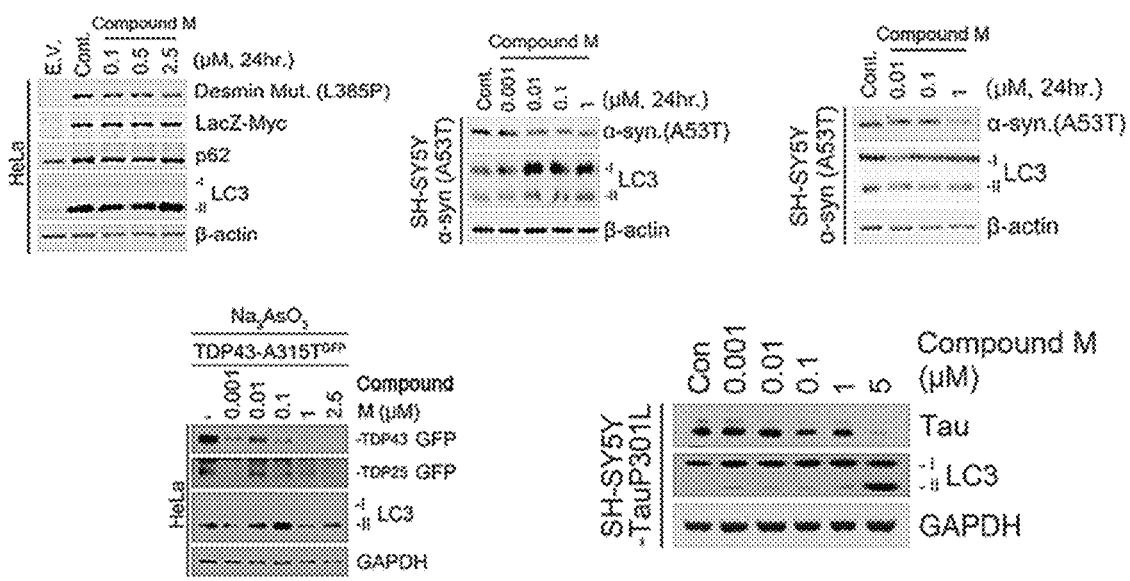

FIG. 18 is a immunoblot assay result confirming the degradation of a target protein Desmin Mut(L385P), α-synuclein(A53T), or Tau by Compound M, as an embodiment of the disclosure.

Figure 19:
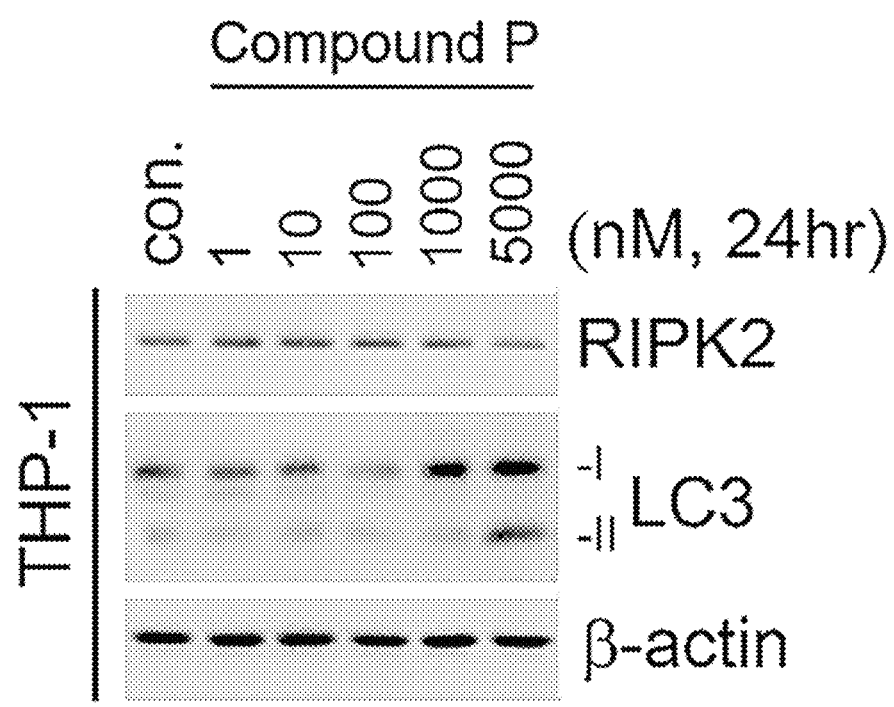

FIG. 19 is a immunoblot assay result confirming the degradation of a target protein RIPK2 by Compound P, as an embodiment of the disclosure.

Figure 20:
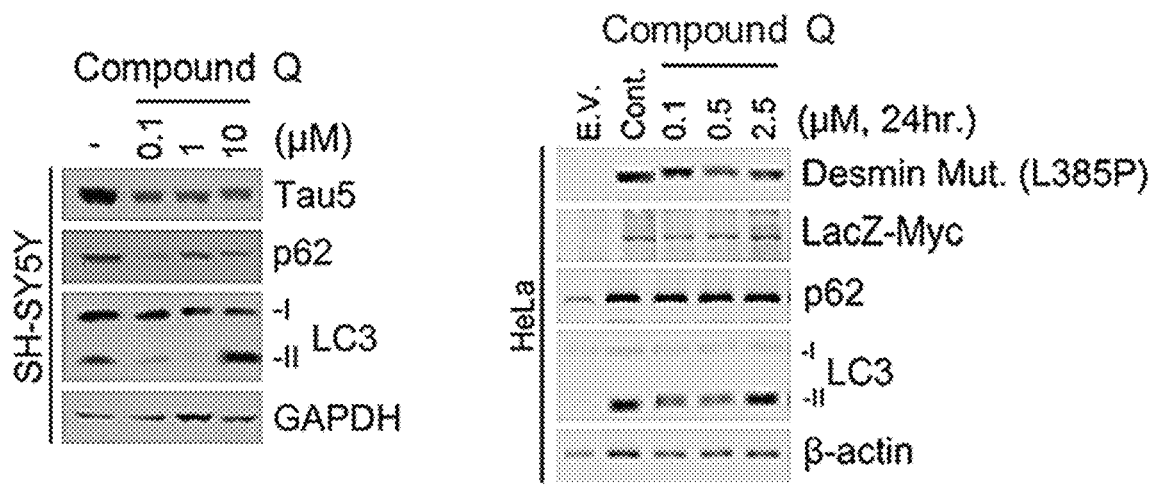

FIG. 20 is a immunoblot assay result confirming the degradation of a target protein Tau, Desmin Mut. (L385P) by Compound Q, as an embodiment of the disclosure.

Figure 21:
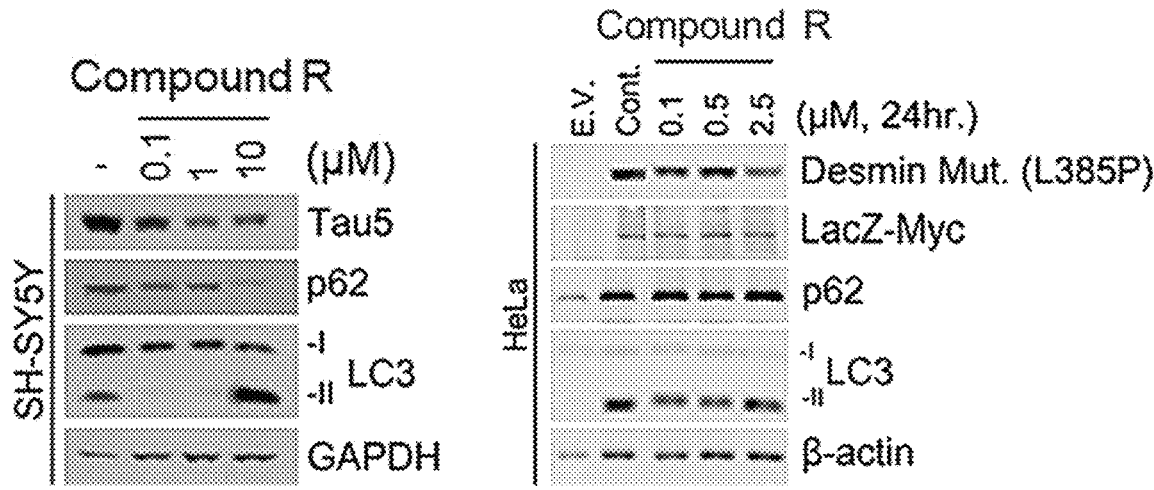

FIG. 21 is a immunoblot assay result confirming the degradation of a target protein Tau, Desmin Mut. (L385P) by Compound R, as an embodiment of the disclosure.

Figure 22:
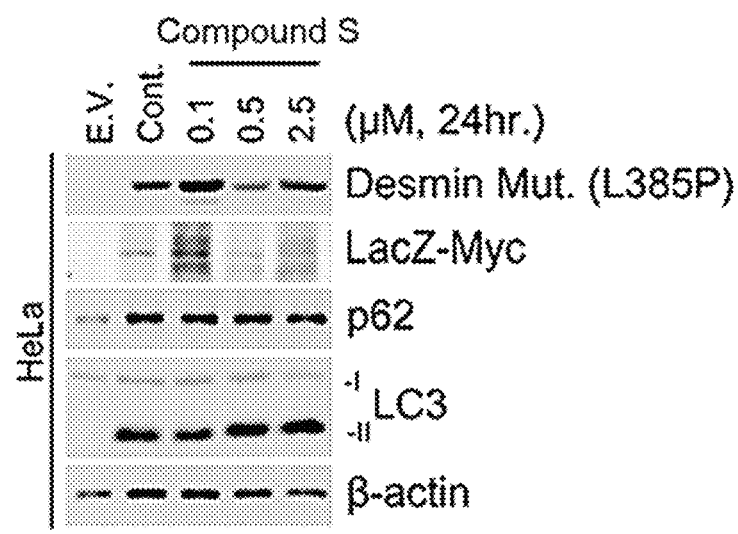

FIG. 22 is a immunoblot assay result confirming the degradation of a target protein Desmin Mut. (L385P) by Compound S, as an embodiment of the disclosure.

Figure 23A:
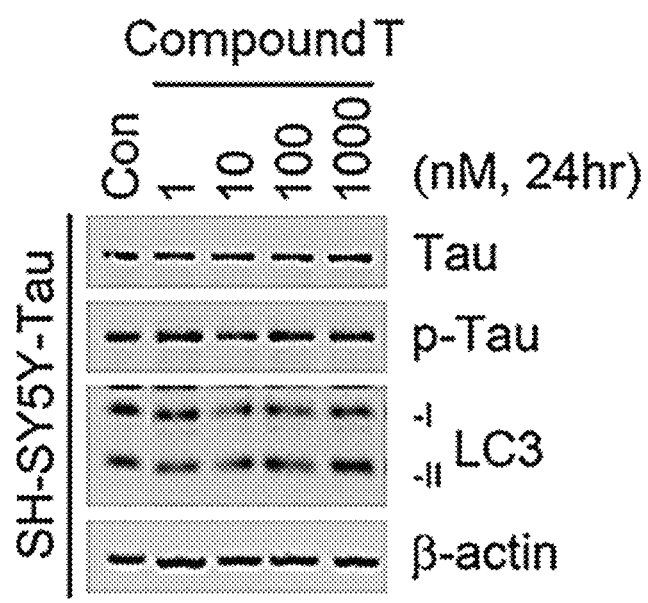

FIG. 23A is a immunoblot assay result confirming the degradation of a target protein Tau by Compound T, as an embodiment of the disclosure.

Figure 23B:
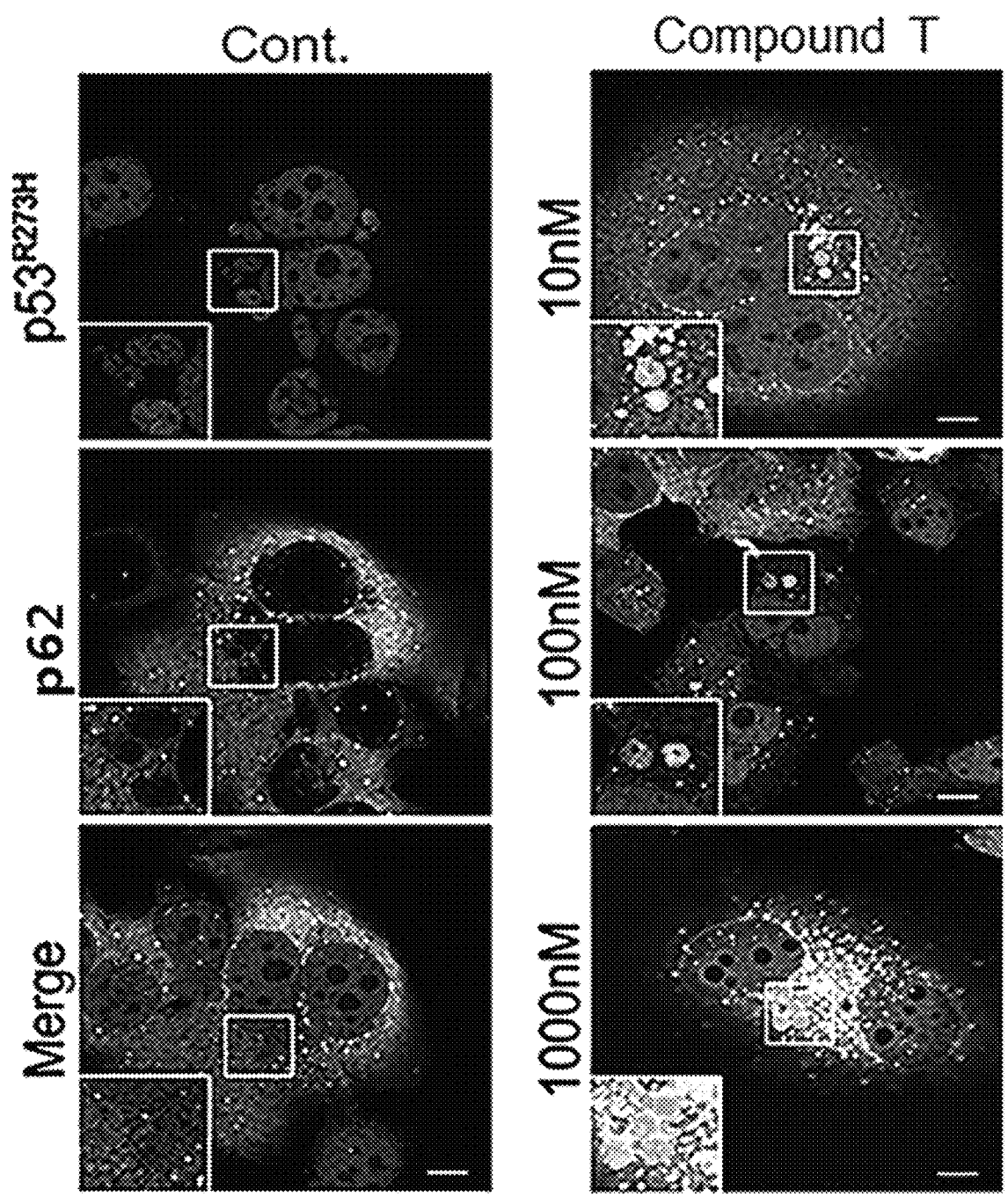

FIG. 23B is an immunofluorescence staining assay result showing the efficacy of delivering the target protein and p62 protein to the autophagy by Compound T, a cargo delivery system of an embodiment of the disclosure. It can be confirmed that after treatment with the cargo delivery system of an embodiment of the disclosure, the intracellular puncta and co-existence of the target proteins and p62 protein of the cargo delivery system of an embodiment of the disclosure increase gradually.

Figure 24:
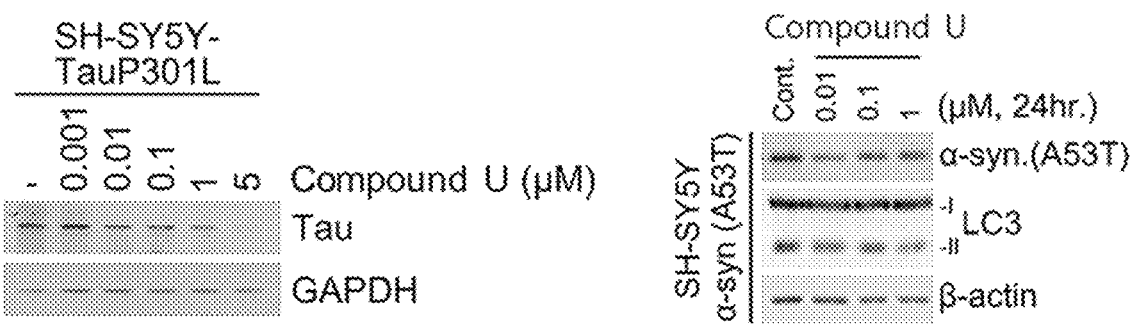

FIG. 24 is a immunoblot assay result confirming the degradation of a target protein Tau, α-syn by Compound U, as an embodiment of the disclosure.

Figure 25:
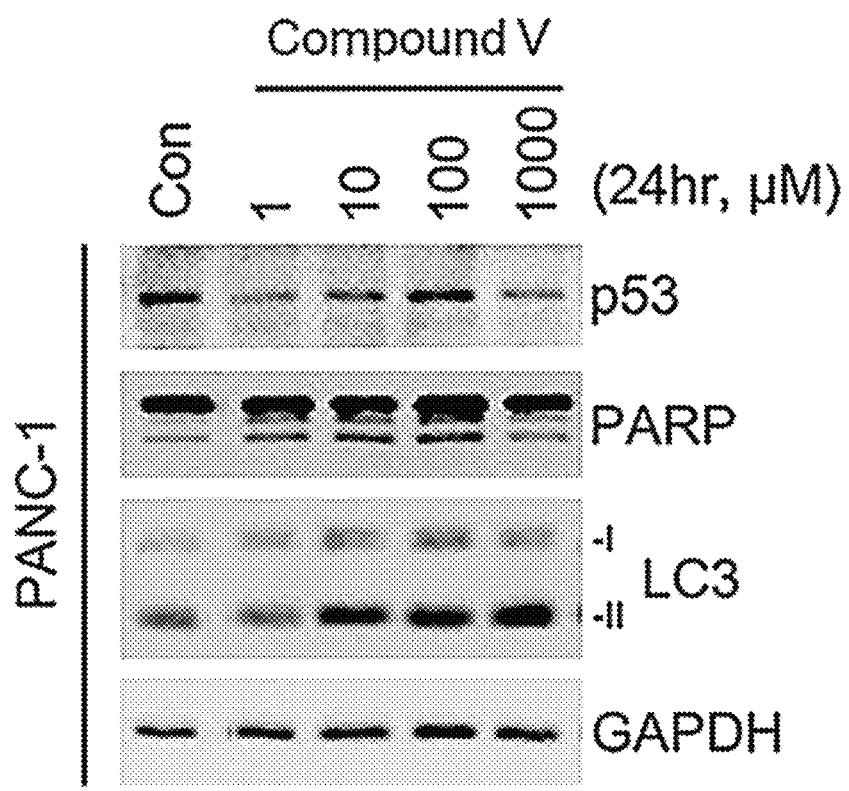

FIG. 25 is a immunoblot assay result confirming the degradation of a target protein p53 by Compound V, as an embodiment of the disclosure.

Figure 26:
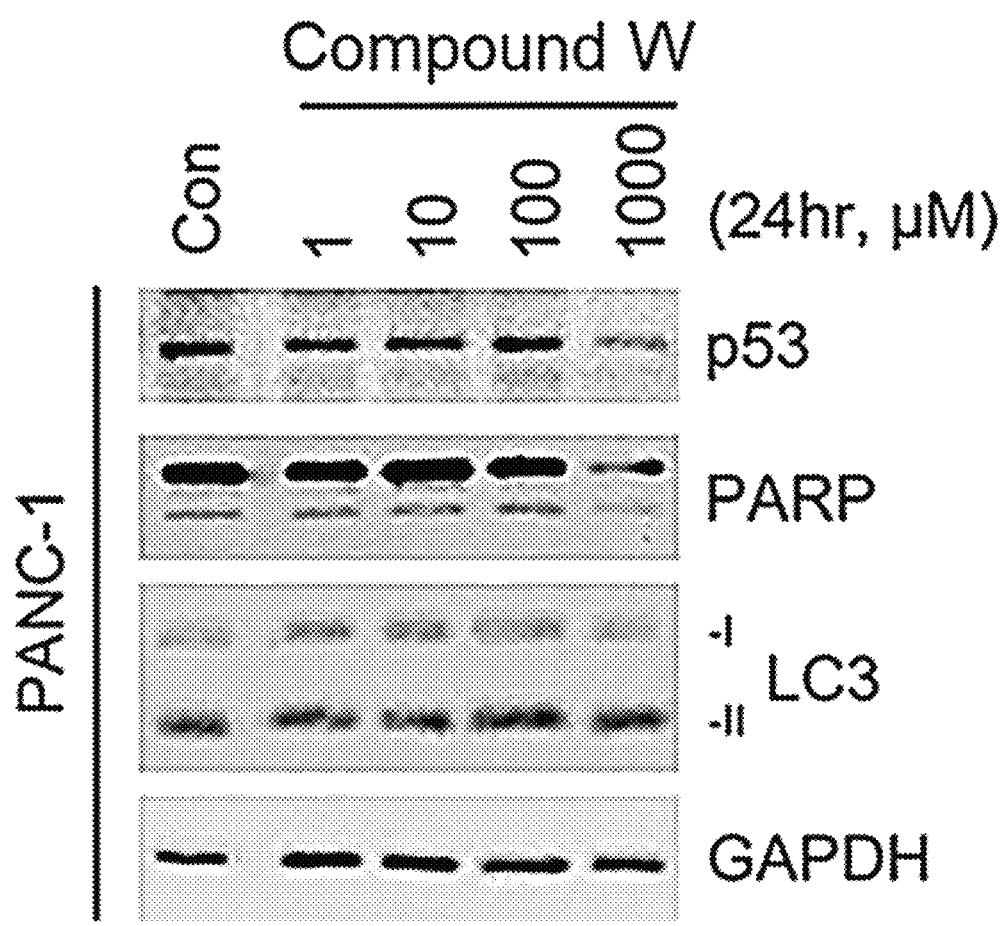

FIG. 26 is a immunoblot assay result confirming the degradation of a target protein p53 by Compound W, as an embodiment of the disclosure.

DETAILED DESCRIPTION

Exemplary embodiments now will be described more fully hereinafter with reference to the accompanying drawings. The technology disclosed in this application may, however, be embodied in many different forms and should not be construed as limited to the exemplary embodiments set forth therein. However, the embodiments disclosed herein are provided so that the disclosure may be thorough and complete and the technical gist of the disclosure may be conveyed sufficiently to those skilled in the art. In addition, the disclosure may be embodied in many different forms by those skilled in the art without departing from the scope of the disclosure.

An embodiment of the disclosure provides a cargo delivery system comprising an autophagy targeting ligand (ATL) and a target-binding ligand (TBL), which is cargo, carried by the autophagy targeting ligand.

In the specification, the term 'autophagy targeting ligand' refers to a novel small molecule ligand according to the disclosure that binds to the ZZ domain of p62 protein. As used herein, the term 'target-binding ligand' refers to a binding ligand that specifically binds to a target to be degraded or removed through the cargo delivery system of the disclosure, wherein the 'target' may comprise a pathological protein, organelle, aggregates thereof or the like.

In one embodiment, when the cargo delivery system of the disclosure is administered to the body, if the target is bound to the target-binding ligand, the autophagy targeting ligand delivers the target-binding ligand to which the target is bound to the p62 protein, which is involved in the autophagy mechanism. When the autophagy targeting ligand binds to the ZZ domain of the p62 protein, the PB1 domain and LIR domain of the p62 protein are activated, and thus, autophagy is activated. The p62 protein plays an important role in initiating formation of the autophagosome, which is a medium in the autophagy mechanism, and delivering the contents of the autophagosome to the lysosome. According to the disclosure, when the autophagy targeting ligand binds to the ZZ domain of the p62 protein, the p62 protein-autophagy targeting ligand-target-binding ligand-target complex is formed, and then the complex are degraded in lysosomes through the autophagy mechanism.

The autophagy targeting ligand according to an embodiment of the disclosure may be a compound having a structure of the following Chemical Formula 1, or a pharmaceutically acceptable salt, stereoisomer, solvate or hydrate thereof.

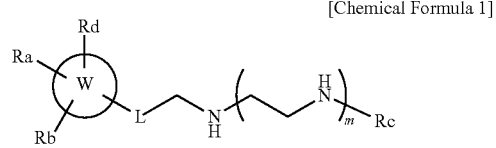

[Chemical Formula 1]

wherein,

W is C6-C10 aryl;

L is —$(CH_2)_{n1}$— or —O—$(CH_2)_{n2}$—CH(OH)—, provided that —O— in the —O—$(CH_2)_{n2}$—CH(OH)— is bonded to any one of carbones of W, where n1 is an integer of 1 to 4;

n2 is an integer of 1 to 4;

m is an integer of 0 to 2;

$R_a$ is $R_1$ or —$OR_1$, where $R_1$ is hydrogen or —$(CH_2)_{n3}$—$R'_1$, $R'_1$ is phenyl which is unsubstituted or substituted by hydroxy, halogen, $C_{1-4}$ alkyl, $C_{1-4}$ alkoxy, nitro, amino, ($C_{1-4}$ alkyl)amino, or di ($C_{1-4}$ alkyl)amino, n3 is an integer of 1 to 6;

$R_b$ is —$OR_2$, where $R_2$ is hydrogen or —$(CH_2)_{n4}$—$R'_2$, $R'_2$ is phenyl which is unsubstituted or substituted by hydroxy, halogen, $C_{1-4}$ alkyl, $C_{1-4}$ alkoxy, nitro, amino, ($C_{1-4}$ alkyl)amino, or di ($C_{1-4}$ alkyl)amino, n4 is an integer of 1 to 6;

$R_c$ is —$(CH_2)_{n5}$—OH, —$(CH_2)_{n5}$—NH—C(=NH)NH$_2$, —C(=NH)NH$_2$, —CH($R_3$)—COOH, —CH(COO—$R_4$)—CH$_2$CH$_2$CH$_2$—NH—C(=NH)NH$_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH(NH$_2$)—COOH, or —$(CH_2)_{n6}$—CONH$_2$, n5 is an integer of 2 to 4, n6 is an integer of 1 to 4, $R_3$ is hydrogen or $C_{1-4}$ alkyl, $R_4$ is $C_{1-4}$ alkyl, and $R_d$ is hydrogen, halogen, $C_{1-4}$ alkoxy or $C_{1-4}$ alkyl.

More specifically, the W may be phenyl.

More specifically, the L is —$(CH_2)_{n1}$— or —O—$(CH_2)_{n2}$—CH(OH)—, provided that —O— in the —O—$(CH_2)_{n2}$—CH(OH)— is bonded to a benzene ring.

More specifically, the n1 may be an integer of 0 to 1.

More specifically, the n2 may be an integer of 1 to 2.

More specifically, the $R_a$ may be hydrogen or —O—$(CH_2)_{n3}$—R'$_1$.

More specifically, the R'$_1$ may be phenyl that is unsubstituted or substituted by hydroxy, fluoro, chloro, bromo, methyl, ethyl, methoxy, ethoxy, nitro, amino or dimethylamino.

More specifically, the n3 may be an integer of 1 to 4.

More specifically, the $R_b$ may be hydroxy, or —O—$(CH_2)_{n4}$—R'$_2$.

More specifically, the R'$_2$ may be phenyl which is unsubstituted or substituted by hydroxy, fluoro, chloro, bromo, methyl, ethyl, methoxy, ethoxy, nitro, amino or dimethylamino.

More specifically, the n4 may be an integer of 1 to 4.

More specifically, the Rr may be —$(CH_2)_{n5}$—OH, —$(CH_2)_{n5}$—NH—C(=NH)NH$_2$, —C(=NH)NH$_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH(NH$_2$)—COOH, or —$(CH_2)_{n6}$—CONH$_2$.

More specifically, the n5 may be an integer of 2 to 3.

More specifically, the n6 may be an integer of 1 to 2.

More specifically, the $R_d$ may be hydrogen, halogen, $C_{1-2}$ alkoxy or $C_{1-2}$ alkyl.

Salts of the compounds of Chemical Formula 1 according to an embodiment of the disclosure can be used without particular limitation as long as they are salts which exhibit pharmacological activities equivalent to those of the compound of Chemical Formula 1. The term "pharmaceutically acceptable salt" used herein refers to any organic or inorganic addition salt of the compounds represented by Chemical Formula 1, in which the adverse effect caused by the salt does not impair the beneficial effect of the compound at a concentration exhibiting relatively non-toxic and non-harmful effective activity to a patient.

As the pharmaceutically acceptable sale according to an embodiment, an addition salt formed by pharmaceutically acceptable free acids may be used. The acid addition salt may be prepared by a common method, for example, by dissolving a compound in an excess amount of aqueous acid solution and precipitating the resulting salt using a water-miscible organic solvent, such as methanol, ethanol, acetone or acetonitrile. Alternatively, an equimolar amount of a compound and an acid in water or alcohol (e.g., glycol monomethyl ether) can be heated, and subsequently, the resulting mixture can be dried by evaporating, or precipitated salts can be filtered under suction.

In this case, the free acid may be an inorganic acid or an organic acid. Examples of the inorganic acids include, but are not limited to, hydrochloric acid, phosphoric acid, sulfuric acid, nitric acid and stannic acid. Examples of the organic acids include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, the pharmaceutically acceptable salt according to an embodiment may be a pharmaceutically acceptable metal salt prepared using a base. For example, the pharmaceutically acceptable metal salt may be an alkali metal salt or alkaline earth metal salt, which may be obtained, for example, by dissolving a compound in an excess amount of alkali metal hydroxide or alkaline earth metal hydroxide solution, filtering the undissolved compound salt, and then evaporating the filtrate until dry. At this time, as the metal salts, particularly sodium, potassium or calcium salts are pharmaceutically suitable, but the present disclosure is not limited thereto. Also, the corresponding silver salts may be obtained by reacting an alkali metal or alkaline earth metal salt with a proper silver salt (e.g., silver nitrate).

The pharmaceutically acceptable salts according to an example of the compound of the present disclosure, unless otherwise indicated herein, include salts of acidic or basic groups, which may be present in the compound of Chemical Formula 1. For example, the pharmaceutically acceptable salts include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

In one embodiment, the compounds represented by Chemical Formula 1 according to the disclosure comprise, but are not limited thereto, not only pharmaceutically acceptable salts thereof, but also all solvates or hydrates and all possible stereoisomers that can be prepared therefrom. In one embodiment, the stereoisomers comprise enantiomeric forms and diastereomeric forms, and all other stereoisomers (e.g., those which may exist due to asymmetric carbons on various substituents) are contemplated within the scope of the disclosure. Individual stereoisomers of the compounds of the present disclosure may, for example, be substantially free of other isomers (e.g., as a pure or substantially pure optical isomer having a specified activity), or may be admixed, for example, as racemates or with all other, or other selected, stereoisomers. The chiral centers of the compounds of the present disclosure may have the S or R configuration as defined by the IUPAC 1974 Recommendations. The racemic forms can be analyzed by physical methods, such as fractional crystallization, separation or crystallization of diastereomeric derivatives or separation by chiral column chromatography. The individual optical isomers can be obtained from the racemates by any suitable method, including without limitation, salt formation with an optically active acid followed by crystallization.

The solvate and stereoisomer of the compound represented by Chemical Formula 1 may be prepared from the compound represented by Chemical Formula 1 using methods known in the art.

Furthermore, the compound represented by Chemical Formula 1 according to the present disclosure may be prepared either in a crystalline form or in a non-crystalline form, When the compound is prepared in a crystalline form, it may be optionally hydrated or solvated. In the present disclosure, the compound of Chemical Formula 1 may not only include a stoichiometric hydrate, but also include a compound containing various amounts of water. The solvate of the compound of Chemical Formula 1 according to the present disclosure includes both stoichiometric solvates and non-stoichiometric solvates.

As an embodiment of the disclosure, the autophagy targeting ligand may be directly connected to the target-binding ligand or connected by a linker.

Figure 1:
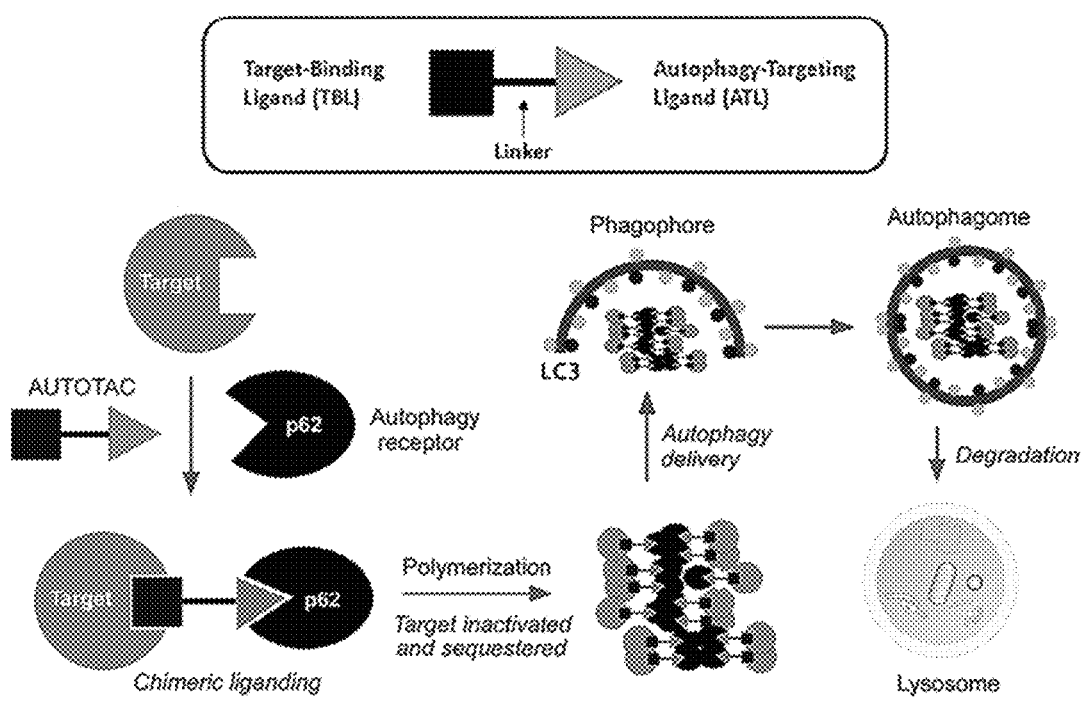
FIG. 1 is a schematic diagram showing a structure of a cargo delivery system comprising an autophagy targeting ligand and a target-binding ligand, and in which the cargo delivery system delivers a target to an autophagosome, and the target is finally degraded by lysosomes, as an embodiment of the disclosure.

FIG. 1 accompanied and Chemical Formula 2 below show an exemplary form of a cargo delivery system according to an embodiment of the disclosure.

[Chemical Formula 2]

In the above Formula, A represents a target-binding ligand, and B represents an autophagy targeting ligand. In Chemical Formula 2, A and B may be each connected to at least one linker. In the disclosure, a novel cargo delivery system in which the autophagy targeting ligand and the target-binding ligand are connected by a linker is named AUTOphagy TArgeting Chimera (AUTOTAC).

Unlike PROTAC compounds that use the Ubiquitin proteasome system (UPS) for target protein degradation, the disclosure provides a low-molecular compound capable of activating autophagy, so that the disclosure is possible not only to target and degrade proteins that PROTEC cannot degrade, such as misfolded protein aggregates, membrane-bound proteins, and subunits of complexes, but also to degrade intracellular structures (inflammasome, stress granule, etc.), organelles (endoplasmic reticulum, mitochondria, peroxisomes, etc.), aggregates, and pathogens (viruses, bacteria, etc.) that have invaded cells. In addition, unlike conventional PROTAC compounds, there is no need to optimize the length of linker for forming a ternary complex (target protein-linker-E3 ligase ligand) for the folding of pathological proteins, E3 ligase selectivity and effective degradation, so the disclosure can be easily used for the prevention, amelioration or treatment of diseases.

More specifically, referring to FIG. 1, a cargo delivery system (AUTOTAC) according to an embodiment of the disclosure acts as follows when administered to the body: (1) when a target is selectively bound to the target-binding ligand (cargo) of the cargo delivery system, an autophagy targeting ligand takes the target-binding ligand (cargo) to which the target is bound to the p62 protein, (2) the autophagy targeting ligand binds to the ZZ domain of the p62 protein to induce self-oligomerization. (3) In this case, the cargo delivery system to which the target is bound is formed as a complex with the p62 protein, and the target is biologically inactivated. (4) Then, the p62 protein-cargo delivery system complex is delivered to an autophagy membrane such as a phagophore to form an autophagosome, (5) The autophagosome is fused with the lysosome, and the p62-cargo delivery system complex is degraded by the lysosome. That is, since the cargo delivery system according to the disclosure comprises the autophagy targeting ligand and the target-binding ligand, the disclosure enables selective degradation of proteins that cannot be targeted by a conventional enzyme inhibition method, under autophagy mechanism.

In the disclosure, the linker connecting the target-binding ligand (A) and the autophagy targeting ligand (B) is not limited and can be used as long as it can be structurally linked to both A and B. In an exemplary embodiment, such a linker may be -Q-(CH$_2$CH$_2$O)$_x$—(CH$_2$)$_y$—P—, -Q-(CH$_2$CH$_2$CH$_2$O)$_x$—(CH$_2$)$_y$—P—, -Q-(CH$_2$CH$_2$NH)$_x$—(CH$_2$)$_y$—P—, or -Q-(CH$_2$CH$_2$CONH)$_x$—(CH$_2$)$_y$—P—, where Q comprises —NH—, —O—, =N—N(CH$_3$)—, which is a portion modified by binding to the target-binding ligand; P includes —NH—, —O—, —CH$_2$—, —C(=O)—, which is a portion modified by binding to p62 ligand; x is an integer of 0 to 4; and y is an integer of 0 to 3, but is not limited thereto. In an exemplary embodiment, the bond between P and the p62 ligand may be —CONH—, —O—, —NH—, —NHCO—, or —COO—.

As an example, for facilitating binding with the linker, the autophagy targeting ligand may be in the form of a derivative in which some substituents are changed to a form that facilitates binding with the linker. For example, a portion of the autophagy targeting ligand, e.g., the Rc portion, can be structurally modified. This can be changed by those skilled in the art appropriately using known techniques depending on the type of autophagy targeting ligand, the type of linker, and their binding form, and these modified derivative forms are also comprised in the autophagy targeting ligand of the disclosure. As an embodiment, the target-binding ligand may also have a partially modified structure for facilitating binding with the linker, and this can be changed by those skilled in the art appropriately using known techniques depending on the type of target-binding ligand, the type of linker and their binding form.

As an embodiment of the disclosure, the target-binding ligand is a ligand that binds to a target pathological protein, organelle, or aggregate thereof, and is not limited in type because it varies depending on a subject to be targeted. As an embodiment, the target-binding ligand may be a compound that specifically binds to a pathological protein, organelle, or aggregate thereof, more specifically, a drug. As an embodiment, the target-binding ligand may be a derivative in which a partial structure of the target-binding ligand is changed by binding to a linker. As an embodiment, the target-binding ligand may be a hydrocarbon compound having 5 to 35 carbon atoms, comprising an aliphatic or aromatic cyclic group. In one embodiment, the target-binding ligand may be an aliphatic or aromatic cyclic group. The target-binding ligand may be a 5-membered or 6-membered heterocyclic group comprising at least one heteroatom each independently selected from N, S, and O. As an embodiment, the target-binding ligand may comprise a substituent that is changed to a binding site of —NH—, —O—, =N—, or —N(CH$_3$)— by binding to a linker. As an embodiment, the target-binding ligand may comprise a carboxyl group, a hydroxyl group, an amino group, an alkyl group, an alkenyl group, a carbonyl group, a halogen group, or the like, as a substituent, and the substituent may be changed to a binding site of —NH—, —O—, =N— or —N(CH$_3$)— by binding to a linker. For example, in the case that the target-binding ligand has a carboxyl group as a substituent, the carboxyl group of the target-binding ligand may be changed into an amide group by binding to a linker having an amine group, and may be connected to the linker.

As used herein, the term "aggregation" refers to the formation of oligomeric or multimeric complexes of typically one or more types of proteins, which may be accompanied by the integration of additional biomolecules, like carbohydrates, nucleic acids and lipids, into the complexes. Such aggregated proteins may form deposits in specific tissue, more specifically in nerve tissue or tissue of the brain. The extent of aggregation depends on the particular disease.

As an example, the pathological protein may be a causative protein that induces cancer, proteinophagy, rare or intractable disease, or genetic disease, but is not limited thereto. In an exemplary embodiment, the proteinopathy refers to those diseases which are characterized by the presence of misfolded protein aggregates, and examples thereof comprise, but are not limited to, neurodegenerative diseases, alpha-1 antitrypsin deficiency, keratopathy, retinitis pigmentosa, type 2 diabetes, cystic fibrosis, and the like. For example, the neurodegenerative diseases may be at least one selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

As an example, the target protein may be a major protein of pathological protein-related diseases, and the type is not limited. For example, such target protein may be at least one selected from the group consisting of prion protein, amyloid precursor protein (APP), alpha-synuclein, superoxide dismutase 1, tau, immunoglobulin, amyloid-A, transthyretin, beta2-microglobulin, cystatin C, apolipoprotein A1, TDP-43, islet amyloid polypeptide, ANF, gelsolin, insulin, lysozyme, fibrinogen, huntingtin, alpha-1-antitrypsin Z, crystallin, c9 open reading frame 72 (c9orf72), glial fibrillary acidic protein, cystic fibrosis transmembrane conductance regulator protein, rhodopsin, and ataxin, and other proteins with a poly-Q stretch.

As an embodiment of the disclosure, the cargo delivery system may select the type of target-binding ligand according to the type of target disease to be prevented, ameliorated, or treated. For example, the following compounds or derivatives thereof may be comprised as the target-binding ligand according to the type of target disease.

TABLE 1

| Related diseases | Target-binding ligand structure | Target-binding ligand Name |
| --- | --- | --- |
| Aamyotrophic lateral sclerosis, Frontotemporal lobar degeneration) | | LCS-1 |
| Parkinson's disease, prion disease | | Anle138b |
| | | Methylene blue |
| Alzheimer's disease | | Azure A |
| Alzheimer's disease, Huntington's disease | | BTA-1 |

TABLE 1-continued

| Related diseases | Target-binding ligand structure | Target-binding ligand Name |
| --- | --- | --- |
| Protein aggregate-related degenerative brain disease | | 4-phenylbutyric acid (4-PBA) |
| Protein aggregate-related degenerative brain disease | | Baicalein |
| Protein aggregate-related degenerative brain disease | | Rresveratrol |
| Protein aggregate-related degenerative brain disease | | Curcumin |
| Breast cancer | | Beta-estradiol |
| Protein aggregate-related degenerative brain disease | | Riluzole |
| Breast cancer | | (Z)-4-OHT ((Z)-4-hydroxytamoxifen) |

TABLE 1-continued
| Related diseases | Target-binding ligand structure | Target-binding ligand Name |
|---|---|---|
| Kidney cancer | 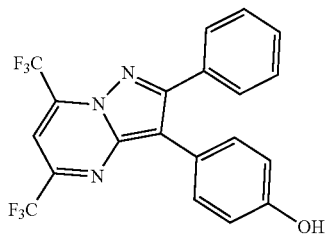 [SMILES: Oc1ccc(-c2c(-c3ccccc3)nn3c(C(F)(F)F)cc(C(F)(F)F)nc23)cc1] | PHTPP |
| Prostate cancer | 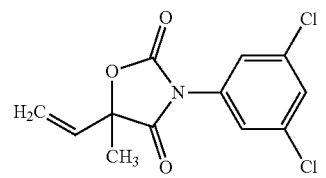 [SMILES: C=CC1(C)OC(=O)N(c2cc(Cl)cc(Cl)c2)C1=O] | Vinclozolin |
| Various cancers (angiogenesis and cancer metastasis) | 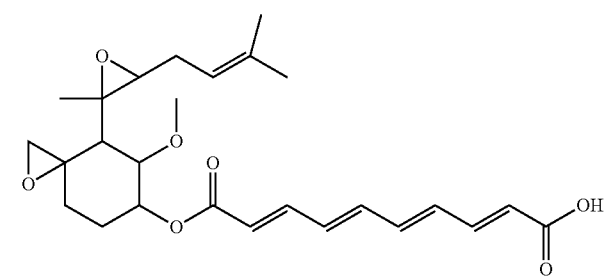 [SMILES: COC1C(OC(=O)/C=C/C=C/C=C/C=C/C(=O)O)CCC2(CO2)C1C1(C)OC1CC=C(C)C] | Fumagillin |
| Various cancers (PI3K-mediated cancer cell growth) | 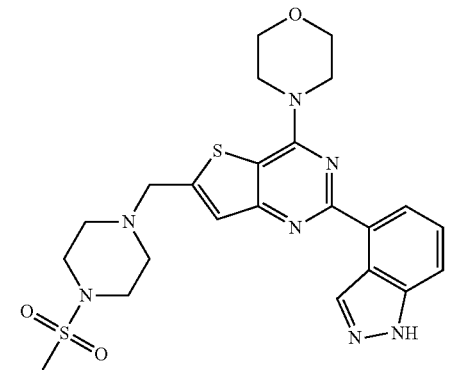 [SMILES: CS(=O)(=O)N1CCN(Cc2cc3nc(-c4cccc5[nH]ncc45)nc(N4CCOCC4)c3s2)CC1] | Pictisilib |
| Various cancers (CSK2-mediated cancer cell growth) | 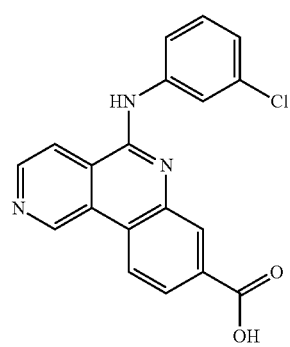 [SMILES: O=C(O)c1ccc2c(c1)nc(Nc1cccc(Cl)c1)c1ccncc12] | Silmitasertib |

TABLE 1-continued

| Related diseases | Target-binding ligand structure | Target-binding ligand Name |
|---|---|---|
| Various cancers (BMPR1-mediated cancer cell growth) | 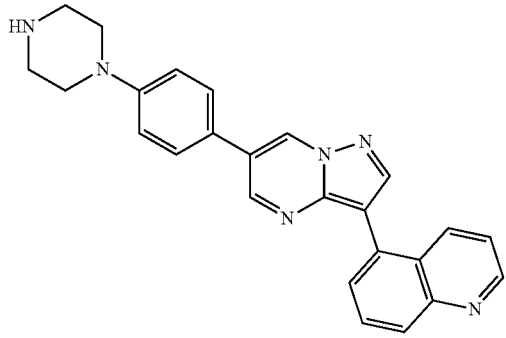 [SMILES: c1cc(-c2cnn3cc(-c4ccc(N5CCNCC5)cc4)cnc23)c2cccnc2c1] | LDN-212854 |
| Prostate cancer | 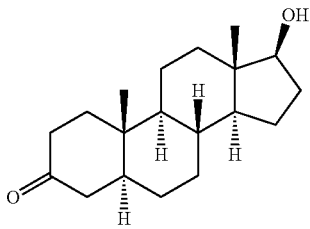 | Dihydrotestosterone (DHT) |
| Various cancers (MDM2-mediated cancer cell growth) | 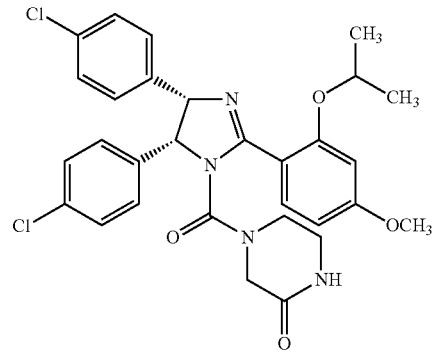 [SMILES: COc1ccc(C2=N[C@@H](c3ccc(Cl)cc3)[C@@H](c3ccc(Cl)cc3)N2C(=O)N2CCNC(=O)C2)c(OC(C)C)c1] | Nutilin-3a |
| Various cancers (BRD4-mediated cancer cell growth) | 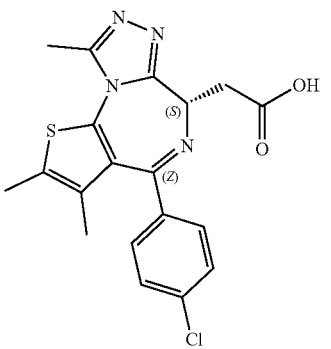 | JQ-1 |
| Chronic myelogenous leukemia, acute myelogenous leukemia, acute lymphoblastic leukemia | 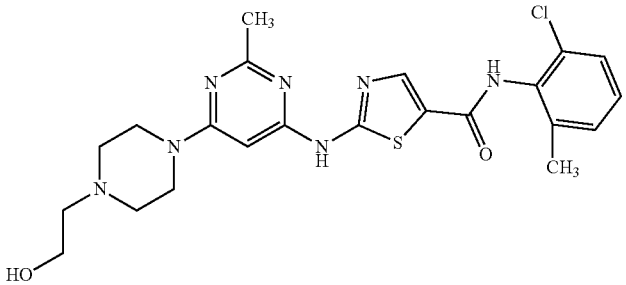 [SMILES: Cc1nc(Nc2ncc(C(=O)Nc3c(C)cccc3Cl)s2)cc(N2CCN(CCO)CC2)n1] | Dasatinib |

TABLE 1-continued

| Related diseases | Target-binding ligand structure | Target-binding ligand Name |
|---|---|---|
| Various cancers (PDE4-mediated cancer cell growth) | | Cilomilast |
| Various cancers (RIPK2-mediated cancer cell growth) | | GSK2983559 |
| Various cancers (MEK-mediated cancer cell growth) | | Selumetinib |
| Various cancers (Chk1, Chk2-mediated cancer cell growth) | | AZD7762 |
| Various cancers (MEK-mediated cancer cell growth) | | PD0325901 |
| Chronic myelogenous leukemia, acute myelogenous leukemia, acute lymphoblastic leukemia | | Rolipram |

TABLE 1-continued
| Related diseases | Target-binding ligand structure | Target-binding ligand Name |
|---|---|---|
| Various cancers (RIPK2-mediated cancer cell growth) | 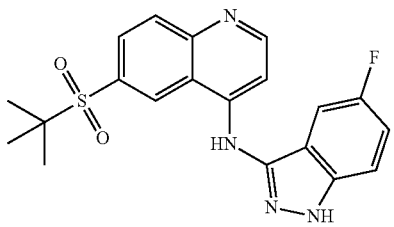 [SMILES: CC(C)(C)S(=O)(=O)c1ccc2nccc(Nc3n[nH]c4ccc(F)cc34)c2c1] | GSK583 |
| Cancer migration | 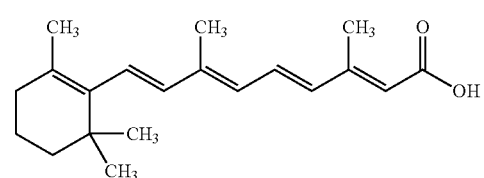 | Retinoic acid |
| STAT 3 | 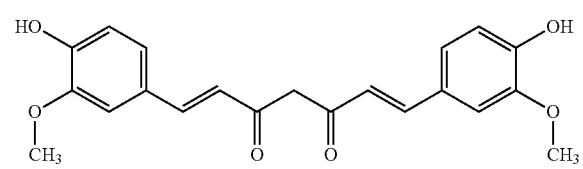 [SMILES: COc1cc(/C=C/C(=O)CC(=O)/C=C/c2ccc(O)c(OC)c2)ccc1O] | Curcumin |
|  | 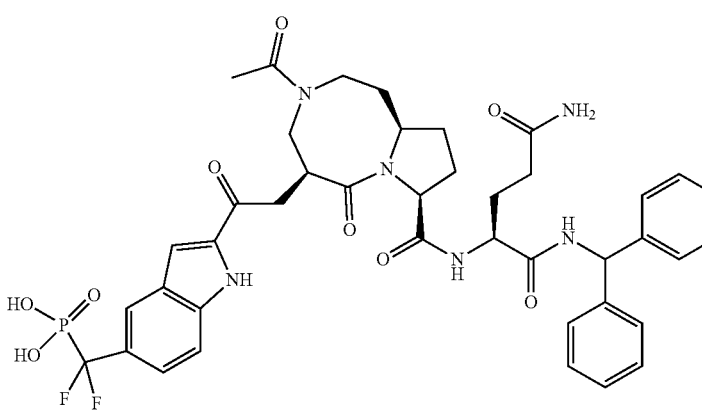 | SI-109 |
| ERa | 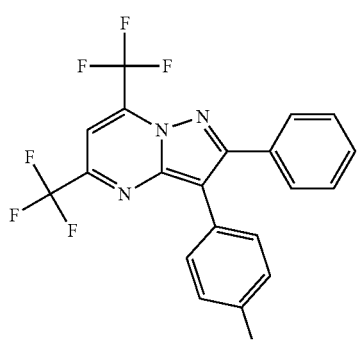 | PHTPP |

TABLE 1-continued

| Related diseases | Target-binding ligand structure | Target-binding ligand Name |
|---|---|---|
|  | 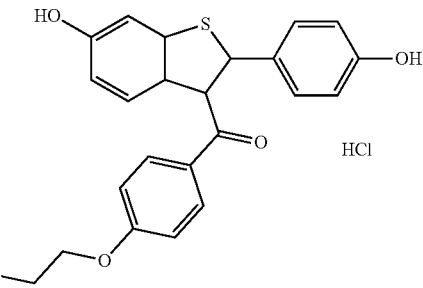 | Raloxifene HCl |
| Bcl2 | 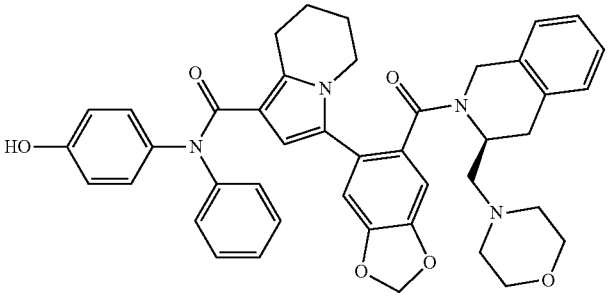 [SMILES: O=C(c1cc(-c2cc3c(cc2C(=O)N2Cc4ccccc4C[C@H]2CN2CCOCC2)OCO3)n2c1CCCC2)N(c1ccccc1)c1ccc(O)cc1] | S55746 |

In an exemplary embodiment, the target-binding ligand may be commercially available compounds, or may be synthesized by performing one or more reactions known in the art as they are or by appropriately modifying any one of known reactions. For example, in consideration of the presence, type and/or position of reactive functional groups and/or hetero elements contained in the skeletal structure, the reactants may be synthesized by performing one or more reactions in a series of order, but are not limited thereto.

One embodiment of the disclosure may provide a pharmaceutical composition comprising the above-described cargo delivery system as an active ingredient. The pharmaceutical composition according to one embodiment is to prevent or treat a disease targeted by a target-binding ligand, and can directly remove a causative protein inducing the disease. One embodiment of the disclosure exhibits the effects of (1) inducing oligomerization and structural activation of p62 protein, (2) increasing the binding of p62 protein to LC3, (3) promoting the formation of autophagosomes, (4) finally, activating autophagy, thereby removing the target. The pharmaceutical composition comprising this compound as an active ingredient can be used for the prevention, amelioration or treatment of various diseases or symptoms as described above. For example, it may comprise various diseases that can be expected to have a therapeutic effect when targeting and degrading specific proteins, such as cancer or proteinopathies, particularly, rare or intractable diseases or genetic diseases.

As used herein, the term "prevention" refers to all actions that suppress or delay target symptoms by administering the composition according to an embodiment of the disclosure. As used herein, the term "treatment" refers to all actions that alleviate or beneficially change target symptoms or diseases, by administering the composition according to an embodiment of the disclosure. As used herein, the term "amelioration" refers to all actions in which target symptoms are alleviated or beneficially changed by administering the composition according to an embodiment of the disclosure compared to before administration.

In an exemplary embodiment, the pharmaceutical composition may further comprise pharmaceutically acceptable carriers, diluents or excipients. In an exemplary embodiment, the composition can be used in the various forms such as oral dosage forms of powders, granules, tablets, capsules, suspensions, emulsions, syrups, aerosols and injections of a sterile injectable solution, which are formulated by the conventional method according to the purpose of each of the intended use. Examples of suitable carriers, excipients or diluents which can be comprised in this composition may comprise lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propylhydroxy benzoate, talc, magnesium stearate, mineral oil, and the like. In an exemplary embodiment, the composition may further comprise fillers, anti-coagulants, lubricants, humectants, fragrances, emulsifiers, preservatives, and the like.

As an embodiment, the composition can be administered through various routes comprising oral administration or intravenous, intraperitoneal, subcutaneous, rectal and topical administration. As used herein, the term "administration" means introduction of a prescribed amount of a substance into a patient in certain appropriate method, and the composition of the present disclosure can be administrated via any of the general routes as long as it can reach a target tissue. For example, intraperitoneal administration, intravenous administration, intramuscular administration, subcutaneous administration, intradermal administration, oral administration, topical administration, intranasal administration, intrapulmonary administration and intrarectal administration may be performed, but the present disclosure is not limited to these exemplified administration modes. Also, the pharmaceutical composition of the present disclosure can be administered using any device capable of delivering the active ingredients to target cells. Preferable administration mode and formulation are an intravenous injection, a subcutaneous injection, an intradermal injection, an intramuscular injection, intravenous drip injection, or the like. Injectable formulations may be prepared using saline, aqueous solutions such as Ringer's solution, and non-aqueous solutions, such as vegetable oils, high fatty acid esters (e.g., ethyl oleic acid, etc.), alcohols (e.g., ethanol, benzyl alcohol, propylene glycol, glycerin, etc.). The injectable preparations may comprise pharmaceutical carriers, comprising a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

In an exemplary embodiment, a formulation for parenteral administration comprises sterilized aqueous solutions, non-aqueous solvents, suspension agents, emulsion agents, lyophilizing agents and suppository agents. Non-aqueous solvent and suspending agent may comprise propylene glycol, polyethylene glycol, vegetable oil such as olive oil, and injectable esters such as ethyl oleate. As a substrate for the suppository agent, Witepsol, Macrogol, Tween 61, cacao butter, laurin butter, glycerogelatin or the like may be used. On the other hand, injections may comprise conventional additives such as solubilizing agents, isotonic agents, suspending agents, emulsifiers, stabilizers, or preservatives.

In an exemplary embodiment, a solid formulation for oral administration comprises tablets, pills, powders, granules, capsules and the like. Such solid dosage forms are formulated by mixing the composition of the present invention with one or more excipients, such as starch, calcium carbonate, sucrose, lactose, gelatin and the like. Also, lubricants such as magnesium stearate and talc can be comprised in addition to simple excipients.

In an exemplary embodiment, a liquid formulation for oral administration can be illustrated as suspensions, solutions, emulsions, syrups and the like, and can comprise various excipients such as humectants, sweeteners, fragrances, preservatives and the like, in addition to water and liquid paraffin which are commonly used diluents.

In an exemplary embodiment, the composition of the present disclosure may be administered in a pharmaceutically effective amount. The term "pharmaceutically effective amount" as used herein refers to an amount which is sufficient to treat the disease at a reasonable benefit/risk ratio applicable for any medical treatment, and also which is enough to not cause side effects. The level of effective amount can be determined depending on patient's health condition, disease type, severity of the disease, activity of the drug, sensitivity on the drug, administration method, administration time, administration route, excretion rate, treatment duration, combination, factors comprising other medicines used at the same time and other factors well-known in the medical field. The composition of the present disclosure may be administered as individual therapy or in combination with other therapies, and it can be administered simultaneously with or sequentially to conventional therapies, and once or multiple times. It is important to administer the minimum amount which can provide the maximum effect without the side effects in consideration of all the above factors, which can be easily determined by those skilled in the art. For example, the dosage may be increased or decreased depending on administration route, the severity of a disease, gender, weight, age and the like, and the scope of the present disclosure is not limited by the aforementioned dosage in any way.

As an embodiment, the dosage of the disclosure may be appropriately selected by those skilled in the art according to the patient's condition and weight, age, sex, health condition, diet, excretion rate, severity of disease, type of drug, administration route or administration period. As an embodiment, the dosage is generally about 1 ng to 10 mg/day or 1 mg to 1 g/day for an adult (60 kg). More specifically, for an adult (60 kg), the dosage may be 1 ng/day or more, 10 ng/day or more, 100 ng/day or more, 1 μg/day or more, 10 μg/day or more, 100 μg/day or more, 1 mg/day or more, 10 mg/day or more, or 100 mg/day or more, 1 g/day or less, 100 mg/day or less, 10 mg/day or less, 1 mg/day or less, 100 μg/day or less, 10 μg/day or less, 1 μg/day or less, 100 ng/day or less or 10 ng/day or less. As the dosage may vary depending on various conditions, it would be evident to those skilled in the art that the dosage may be increased or decreased. Accordingly, the scope of the disclosure is not limited by the aforementioned dosage in any way. As for the number of administration, the administration can be made either once or several divided times per day within a desired range, and the administration period is not particularly limited, either.

One embodiment of the disclosure may provide a food composition comprising the above-described cargo delivery system as an active ingredient. The food composition is a health functional food and it can be used through formulation itself or be comprised in other health functional foods as an additive of health functional food. The term "health functional food" used herein, means food having body modulating function such as prevention or amelioration of diseases, biodefense, immunity, recovery of convalescence, aging inhibition, etc., and it should be harmless to human body when taking in a long term. The mixing amount of active ingredients can be properly decided depending on purpose of use (prevention, health or therapeutic treatment). The kind of the food is not particularly limited. Examples of food where the above substances can be added are meat, sausage, bread, chocolates, candies, snack, cookies, pizza, ramen, other noodles, gum, dairy products comprising ice cream, sorts of soup, beverages, tea, drinks, alcohol beverages and vitamin complex, etc., and it comprises all the health functional foods in the common sense. In an exemplary embodiment, the food composition of the present disclosure can comprise common ingredients used in preparation of food or food additives, specifically, a flavoring agent; a natural sweetener such as monosaccharides like glucose, fructose, disaccharides like maltose, sucrose, and dextrin, cyclodextrin as a natural carbohydrate, or a synthetic sweetener such as saccharin, aspartame; a nutrient; vitamin; electrolyte; a coloring agent; an organic acid; a protective colloid viscosity agent; pH regulator; a stabilizer; a preservative; glycerin; alcohol; a carbonating agent which is used on carbonated drinks, etc.

As one embodiment, the disclosure may provide a method for activating autophagy, comprising administering to a subject a composition comprising the cargo delivery system in an effective amount. As another embodiment, the disclosure may provide a method for preventing, ameliorating, or treating a target disease, for example, cancer, pathological protein-related diseases, protein aggregate-related diseases, comprising administering a composition comprising the cargo delivery system in an effective amount to a subject in need thereof.

As used herein, the term "subject" refers to all animals comprising human, monkey, cow, horse, sheep, pig, chicken, turkey, quail, cat, dog, mouse, rat, rabbit, or guinea pig, which have target diseases for the prevention, amelioration or treatment. The target diseases, preferably cancer, diseases associated with pathological proteins, or diseases linked to misfolded protein aggregation can be effectively prevented, ameliorated or treated by administrating the composition of the present disclosure to the subject. In addition, since the composition of the present disclosure activates autophagy, eliminates aggregates of misfolded proteins due to the autophagy activation, and thus exhibits a prophylactic or therapeutic effect of diseases linked to these aggregated proteins, it can exhibit synergistic effects by administration in combination with existing therapeutic agents.

In another embodiment, the disclosure provides (i) a method for enhancing degradation of a target protein, organelle or structure; (ii) a method for inactivating a target protein, organelle, or structure, (iii) a method for delivering a drug or small molecule compound to a lysosome, (iv) a method for enhancing the degradation of viruses and bacteria that have invaded cells, (v) a method for enhancing the binding of p62 protein to LC3, (vi) a method for self-oligomerization and autophagy activation of p62 protein, and (vii) a method for enhancing degradation of a target protein, organelle, or structure by lysosomes, each comprising treating cells or p62 protein with a composition comprising the cargo delivery system in an effective amount.

In still another aspect, the disclosure provides a method of using a drug in which the cargo delivery system is connected to a therapeutic antibody that specifically binds to a protein exposed on a cell membrane, and delivering such a drug to lysosomes via endosomes. The therapeutic antibody may be used without limitation as long as it exhibits pharmacological activity against a disease requiring treatment.

EXAMPLE

Hereinafter, examples and experimental examples of the disclosure will be described in detail. These examples and experimental examples are intended to explain the disclosure in more detail, and the scope of the disclosure is not limited to the these examples and experimental examples.

In the case of the starting materials for synthesizing the compounds according to examples of the present disclosure, various synthesis methods have been known, and if available on the market, the starting materials may be purchased from the providers. Examples of the reagents suppliers include Sigma-Aldrich, TCI, Wako, Kanto, Fluorchem, Acros, Alfa, Fluka, and the like, but are not limited thereto.

The compounds according to examples of the present disclosure can be prepared from readily available starting materials using the following general methods and procedures.

As for typical or preferred process conditions (i.e., reaction temperature, time, molar ratio of reactants, solvents, pressure) and the like, other process conditions may also be used unless stated otherwise. The optimal reaction state may vary depending on the specific reactants or solvent used. Such conditions can be determined by one skilled in the art by conventional optimization procedures.

Specific embodiments of the disclosure below are examples of the autophagy targeting ligand represented by Chemical Formula 1 and the compounds obtained by binding a target-binding ligand thereto, and the names and structures of each compound are as follows.

TABLE 2

| Example No. | Compound ID. | Name of Compound | Chemical Structure |
|---|---|---|---|
| Example 1 | RTEG-1104 | (2E,4E,6E,8E)-N-(2-(2-(2-(((R)-3-(3,4-bis(benzyloxy)phenoxy)-2-hydroxypropy)amino)ethoxy)ethoxy)ethyl)-3,7-dimethyl-9-(2,6,6-trimethylcyclohex-1-en-1-yl)nona-2,4,6,8-tetraenamide | 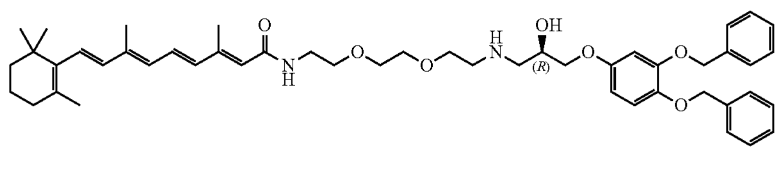 |
| Example 2 | RTEG-1105 | (2E,4E,6E,8E)-N-(2-(2-((3,4-bis(benzyloxy)benzyl)amino)ethoxy)ethoxy)ethyl)-3,7-dimethyl-9-(2,6,6-trimethylcyclohex-1-en-1-yl)nona-2,4,6,8-tetraenamide | 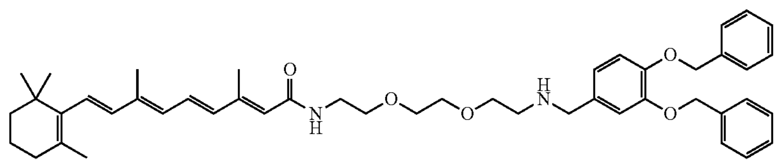 [SMILES: CC1=C(/C=C/C(C)=C/C=C/C(C)=C/C(=O)NCCOCCOCCNCc2ccc(OCc3ccccc3)c(OCc3ccccc3)c2)C(C)(C)CCC1] |
| Example 3 | PBA-1104 | (R)-N-(15-(3,4-bis(benzyloxy)phenoxy)-14-hydroxy-3,6,9-trioxa-12-azapentadecyl)-4-phenylbutanamide | 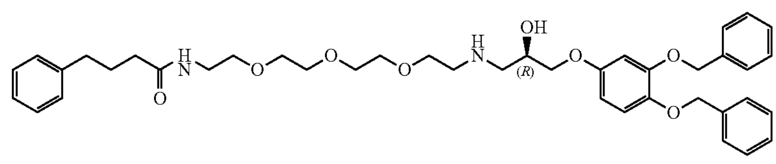 |
| Example 4 | PBA-1105 | N-(1-(3,4-bis(benzyloxy)phenyl)-5,8,11-trioxa-2-azatridecan-13-yl)-4-phenylbutanamide | 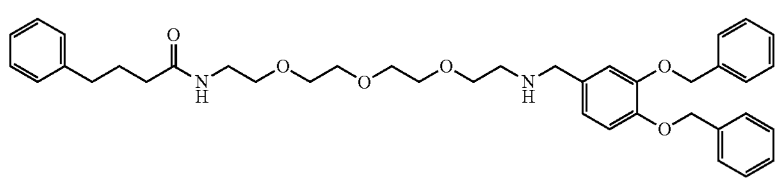 [SMILES: O=C(CCCc1ccccc1)NCCOCCOCCOCCNCc1ccc(OCc2ccccc2)c(OCc2ccccc2)c1] |

TABLE 2-continued

| Example No. | Compound ID. | Name of Compound | Chemical Structure |
|---|---|---|---|
| Example 5 | Anle-138b-F105 | 3-(3-(benzo[d][1,3]dioxol-5-yl)-1H-pyrazol-5-yl)-N-(2-(2-(2-((3-((4-fluorobenzyl)oxy))benzyl)amino)ethoxy)ethyl)aniline | 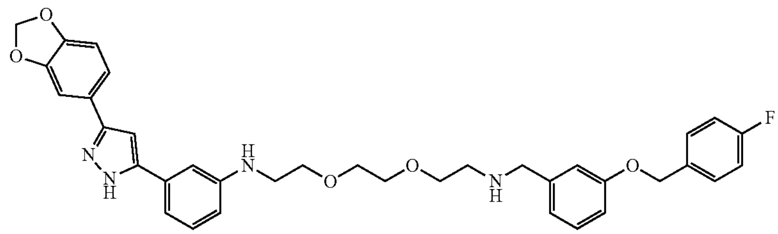 [SMILES: Fc1ccc(COc2cccc(CNCCOCCOCCNc3cccc(-c4cc(-c5ccc6c(c5)OCO6)n[nH]4)c3)c2)cc1] |
| Example 6 | Fumagillin-105 | (3R,4S,5S,6R)-5-methoxy-4-((2R,3R)-2-methyl-3-(3-methylbut-2-en-1-yl)oxirane-2-yl)-1-oxaspiro[2.5]octan-6-yl (13E,15E,17E,19E)-1-(3-(benzyloxy)phenyl)-12-oxo-5,8-dioxa-2,11-diazahenicosa-13,15,17,19-tetraene-21-oate | 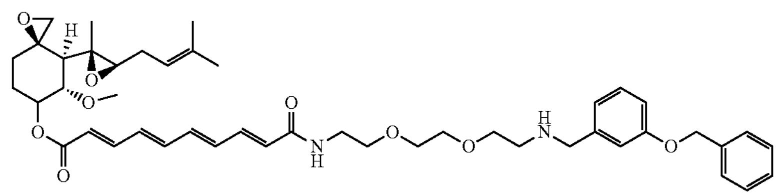 [SMILES: CO[C@@H]1C(OC(=O)/C=C/C=C/C=C/C=C/C(=O)NCCOCCOCCNCc2cccc(OCc3ccccc3)c2)CC[C@]2(CO2)[C@H]1[C@@]1(C)O[C@@H]1CC=C(C)C] |
| Example 7 | Vinclozolin-2204 | 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione | 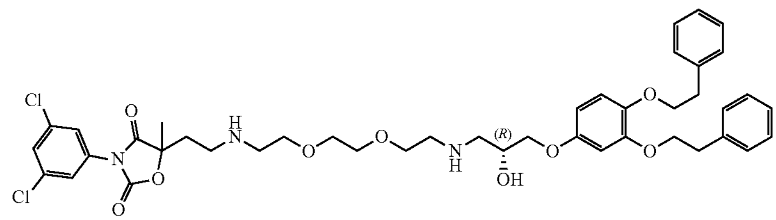 |
| Example 8 | PHTPP-1304 | (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol | 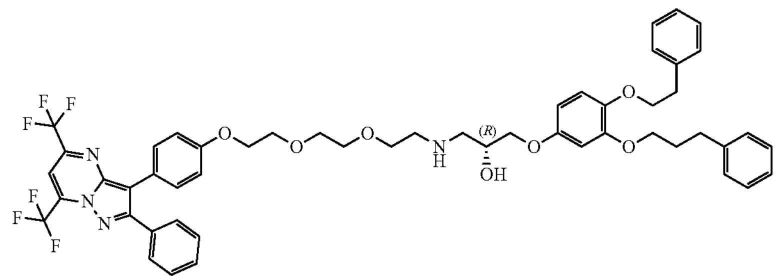 |
| Example 9 | Baicalein-2204 | (R,Z)-4-((2-(2-(2-((3-(3,4-diphenethoxyphenoxy)-2-hyroxypropyl)amino)ethoxy)ethoxy)ethyl)imino)-2-phenyl-4H-chromene-5,6,7-triol | 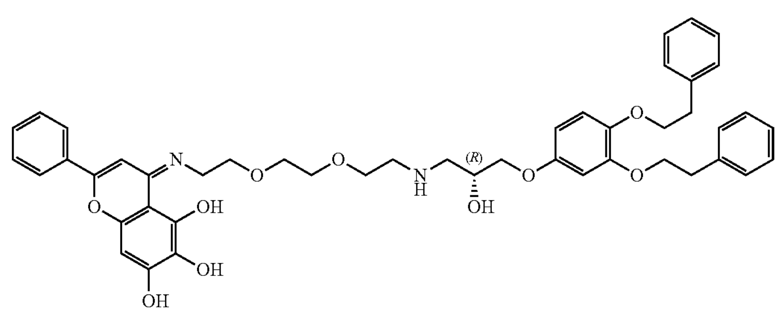 |
| Example 10 | Resveratrol-1105 | (E)-5-(4-(2-(2-(2-((3,4-bis(benzyloxy)benzyl)amino)ethoxy)ethoxy)ethoxy)styryl)benzene-1,3-diol | 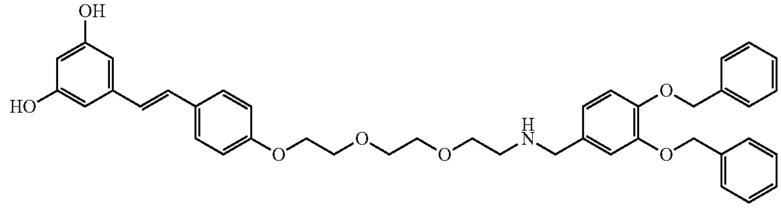 [SMILES: Oc1cc(O)cc(/C=C/c2ccc(OCCOCCOCCNCc3ccc(OCc4ccccc4)c(OCc4ccccc4)c3)cc2)c1] |

TABLE 2-continued

| Example No. | Compound ID. | Name of Compound | Chemical Structure |
|---|---|---|---|
| Example 11 | BTA-1-1104 | (R)-2-(4-(benzo[d]thiazol-2-yl)phenyl)-14-(3,4-bis(benzyloxy)phenoxy)-5,8-dioxa-2,11-diazatetradecane-13-ol | 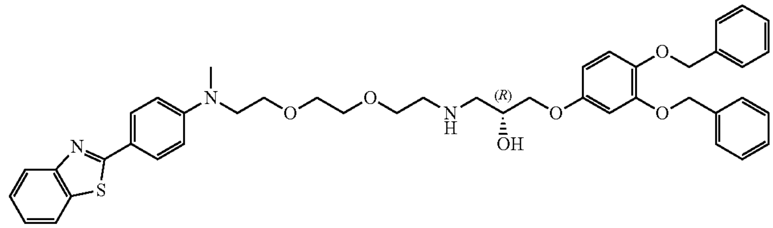 |
| Example 12 | Curcumin-1204 | (1E,6E)-1-(4-(2-(2-(2-(((R)-3-(3-(benzyloxy)-4-phenethoxyphenoxy)-2-hydroxypropyl)amino)ethoxy)ethoxy)-3-methoxyphenyl)-7-(4-hydroxy-3-methoxyphenyl)hepta-1,6-diene-3,5-dione | 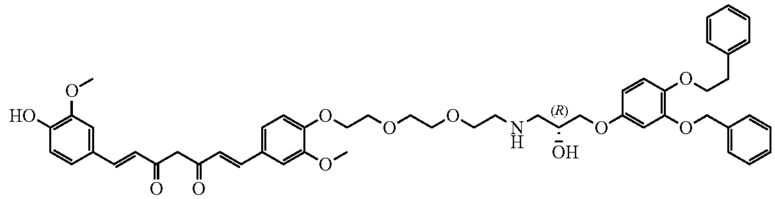 |
| Example 13 | Riluzole-204 | (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol | 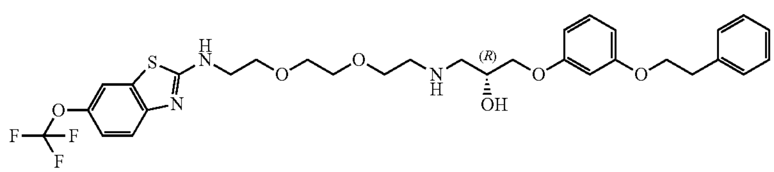 |

TABLE 3

| Example No. | Compound ID. | Chemical Name |
|---|---|---|
| Example 14 | Compound A | N-(2-(2-(2-(((R)-3-(3,4-bis(benzyloxy)phenoxy)-2-hydroxypropyl)-2-amino)ethoxy)ethoxy)ethyl)-2-((S)-4-(4-chlorophenyl)-2,3,9-trimethyl-6H-thieno[3,2-f][1,2,4]triazolo[4,3-a][1,4]diazaepin-6-yl)acetamide |
| Example 15 | Compound B | (1s,4s)-N-(2-(2-(2-((3,4-bis(benzyloxy)benzyl)amino)ethoxy)ethoxy)ethyl)-4-cyano-4-(3-(cyclopentyloxy)-4-methoxyphenyl)cyclohexane-1-carboxamide |
| Example 16 | Compound C | (R)-1-(3-phenethoxyphenoxy)-3-((2-(2-(2-(4-(4-(3-(quinolin-5-yl)pyrazolo[1,5-a]pyrimidin-6-yl)phenyl)piperazin-1-yl)ethoxy)ethoxy)ethyl)amino)propan-2-ol |
| Example 17 | Compound D | 5-(3-fluorophenyl)-N-((S)-1-(2-(2-(2-(((R)-2-hydroxy-3-(3-phenethoxyphenoxy)propyl)amino)ethoxy)ethoxy)ethyl)piperidin-3-yl)-3-ureidothiophene-2-carboxamide |
| Example 18 | Compound E | (R)-2-((6-(4-(15-(4-(benzyloxy)-3-(phenylpropoxy)phenoxy)-14-hydroxy-6,9-dioxa-3,12-diazapentadecyl)piperazin-1-yl)-2-methylpyrimidin-4-yl)amino)-N-(2-chloro-6-methylphenyl)thiazole-5-carboxamide |
| Example 19 | Compound F | (R)-5-((3-((2-(2-(2-((3-(4-(benzyloxy)-3-phenethoxyphenoxy)-2-hydroxypropyl)ethoxy)ethoxy)ethyl)amino)phenyl)amino)benzo[c][2,6]naphthyridine-8-carboxylic acid |
| Example 20 | Compound G | N-(7-((1-(3-(benzyloxy)phenyl)-5,8-dioxa-2,11-diazatridecan-13-yl)oxy)-6-(tert-butylsulfonyl)quinazolin-4-yl)benzo[d]thiazol-5-amine |
| Example 21 | Compound H | ((2-(((5S,8S,10aR)-8-(((S)-5-amino-1-(benzhydrylamino)-1,5-dioxopentan-2-yl)carbamoyl)-3-((R)-1-(3,4-bis((4-fluorobenzyl)oxy)phenoxy)-2-hydroxy-7,10,13,16-tetraoxa-4-azaicosan-20-oyl)-6-oxodecahydropyrrolo[1,2-a][1,5]diazocin-5-yl)carbamoyl)-1H-indol-5-yl)difluoromethyl)phosphonic acid |
| Example 22 | Compound I | ((2-(((5S,8S,10aR)-8-(((S)-5-amino-1-(benzhydrylamino)-1,5-dioxopentan-2-yl)carbamoyl)-3-(1-(3,4-bis(benzyloxy)phenyl)-5,8,11,14-tetraoxa-2-azaoctadecan-18-oyl)-6-oxodecahydropyrrolo[1,2-a][1,5]diazocin-5-yl)carbamoyl)-1H-indol-5-yl)difluoromethyl)phosphonic acid |
| Example 23 | Compound J | (4-((1-(3,4-bis(benzyloxy)phenyl)-16-ethyl-5,8-dioxa-2,11,16-triazaoctadecan-18-yl)oxy)phenyl)(6-hydroxy-2-(4-hydroxyphenyl)benzo[b]thiophen-3-yl)methanone |
| Example 24 | Compound L | (R)-5-((3-((21-(3,4-bis((4-fluorobenzyl)oxy)phenoxy)-20-hydroxy-3,6,9,12,15-pentaoxa-18-azaheniscosyl)amino)-5-chlorophenyl)amino)benzo[c][2,6]naphthyridine-8-carboxylic acid |
| Example 25 | Compound M | (S)-3-(6-(3-((4-(1-(4-(benzyloxy)-3-phenethoxyphenyl)-5,8,11,14-tetraoxa-2-azahexadecan-16-yl)piperazin-1-yl)methyl)-1,2,3,4-tetrahydroisoquinoline-2-carbonyl)benzo[d][1,3]dioxol-5-yl)-N-(4-hydroxyphenyl)-N-phenyl-5,6,7,8-tetrahydroindolizine-1-carboxamide |
| Example 26 | Compound P | (R)-1-((4-(benzo[d]thiazol-5-ylamino)-6-(tert-butylsulfonyl)quinazolin-7-yl)oxy)-24-(3,4-bis((4-fluorobenzyl)oxy)phenoxy)-6,9,12,15,18-pentaoxa-3,21-diazatetracosan-23-ol |
| Example 27 | Compound Q | N-(1-(3,4-bis(benzyloxy)phenyl)-5,8,11,14,17-pentaoxa-2-azanonadecan-19-yl)-4-phenylbutanamide |
| Example 28 | Compound R | N-(1-(3,4-bis(benzyloxy)phenyl)-5,8,11,14,17,20,23-heptaoxa-2-azapentacosan-25-yl)-4-phenylbutanamide |
| Example 29 | Compound S | (R)-N-(15-(3,4-bis((4-fluorobenzyl)oxy)phenoxy)-14-hydroxy-3,6,9-trioxa-12-azapentadecyl)-4-phenylbutanamide |
| Example 30 | Compound T | (R)-N-(15-(3-((4-fluorobenzyl)oxy)phenoxy)-14-hydroxy-3,6,9-trioxa-12-azapentadecyl)-4-phenylbutanamide |
| Example 31 | Compound U | N-(7-((1-(3,4-bis(benzyloxy)phenyl)-5,8,11-trioxa-2-azatridecan-13-yl)(methyl)amino)-3H-phenothiazin-3-ylidene)-N-methylmethanaminium 2,2,2-trifluoroacetate |

TABLE 3-continued

| Example 32 | Compound V | (R)-N-(7-((15-(3,4-bis((4-fluorobenzyl)oxy)phenoxy)-14-hydroxy-3,6,9-trioxa-12-azapentadecyl)(methyl)amino)-3H-phenothiazin-3-ylidene)-N-methylmethanium 2,2,2-trifluoroacetate |
| --- | --- | --- |
| Example 33 | Compound W | (R)-N-(7-((15-(3-((4-fluorobenzyl)oxy)phenoxy)-14-hydroxy-3,6,9-trioxa-12-azapentadecyl)(methyl)amino)-3H-phenothiazin-3-ylidene)-N-methylmethanium 2,2,2-trifluoroacetate |

| Example No. | Structure | Target |
| --- | --- | --- |
| Example 14 | 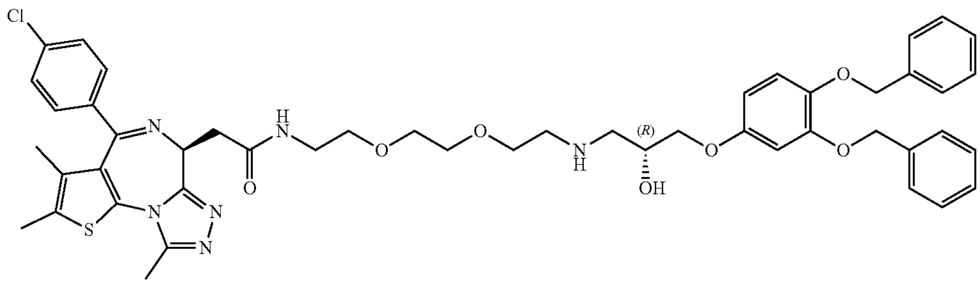 | BRD4 |
| Example 15 | 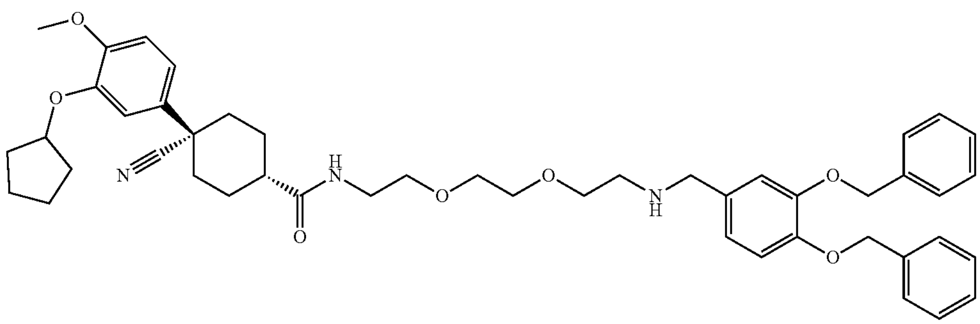 [SMILES: COc1ccc([C@]2(C#N)CC[C@@H](C(=O)NCCOCCOCCNCc3ccc(OCc4ccccc4)c(OCc4ccccc4)c3)CC2)cc1OC1CCCC1] | PDE4 |
| Example 16 | 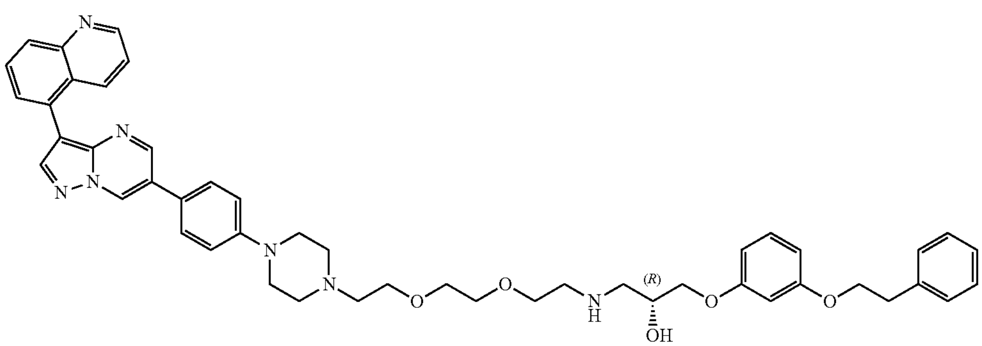 | BMP type 1 receptor (BMPR1) |
| Example 17 | 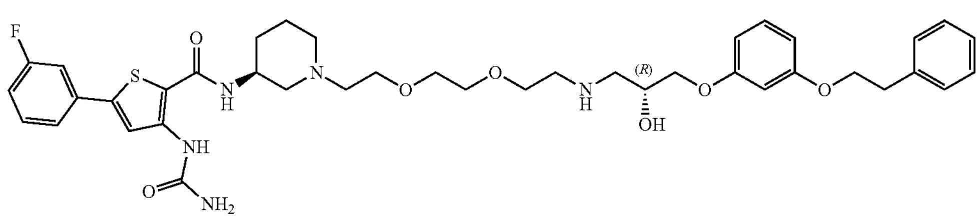 | Checkpoint kinase 1, 2 (Chk1, Chk2) |
| Example 18 | 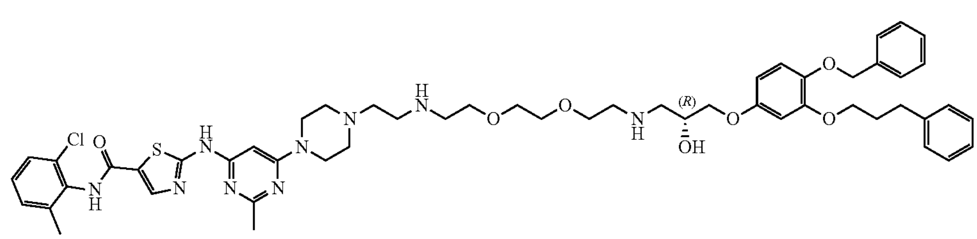 | BCR-ABL |

TABLE 3-continued
| Example 19 | 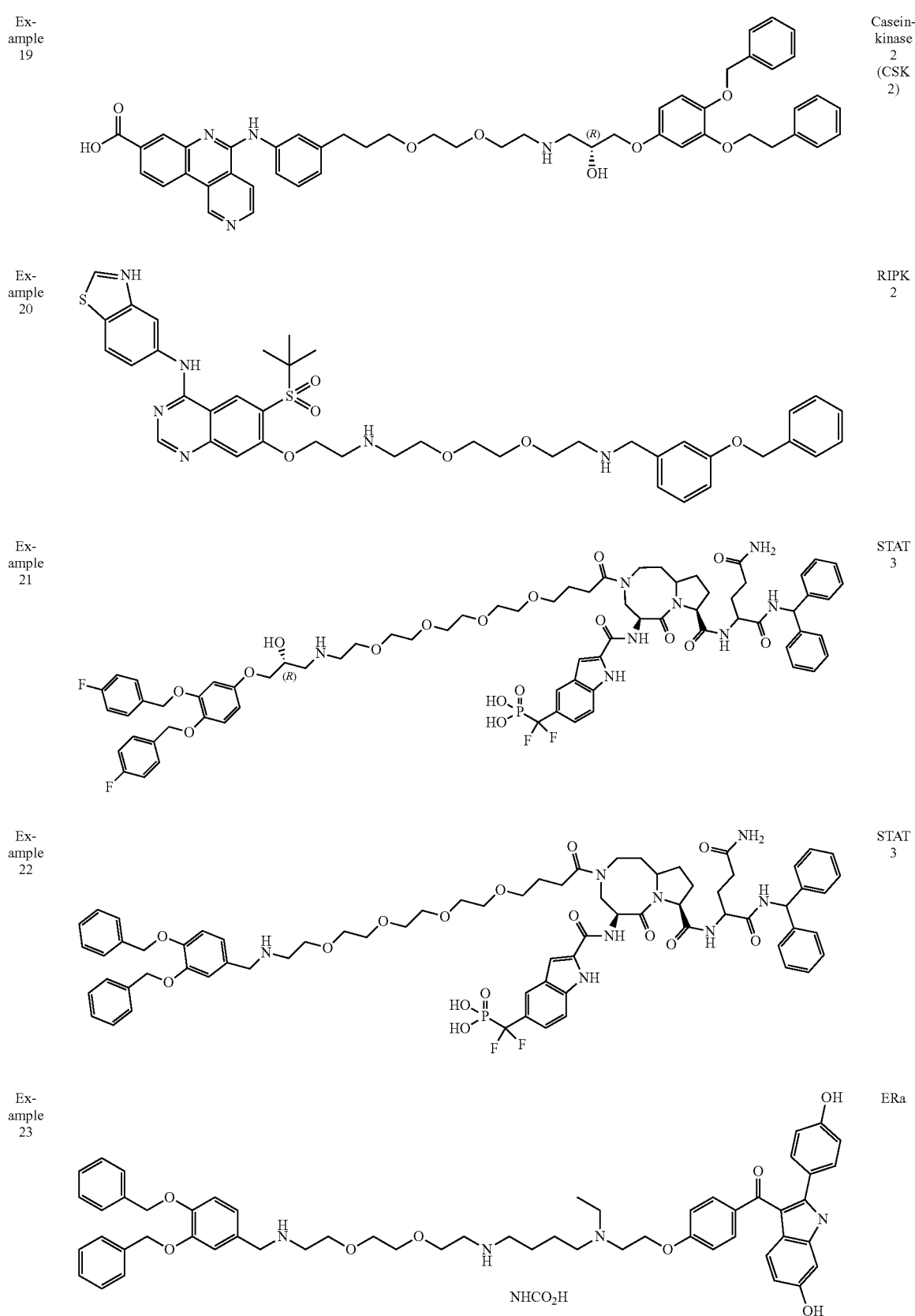 | Casein-kinase 2 (CSK 2) |
| Example 20 | | RIPK 2 |
| Example 21 | | STAT 3 |
| Example 22 | | STAT 3 |
| Example 23 | | ERα |

TABLE 3-continued
| Example | Structure | Target |
|---|---|---|
| Example 24 | 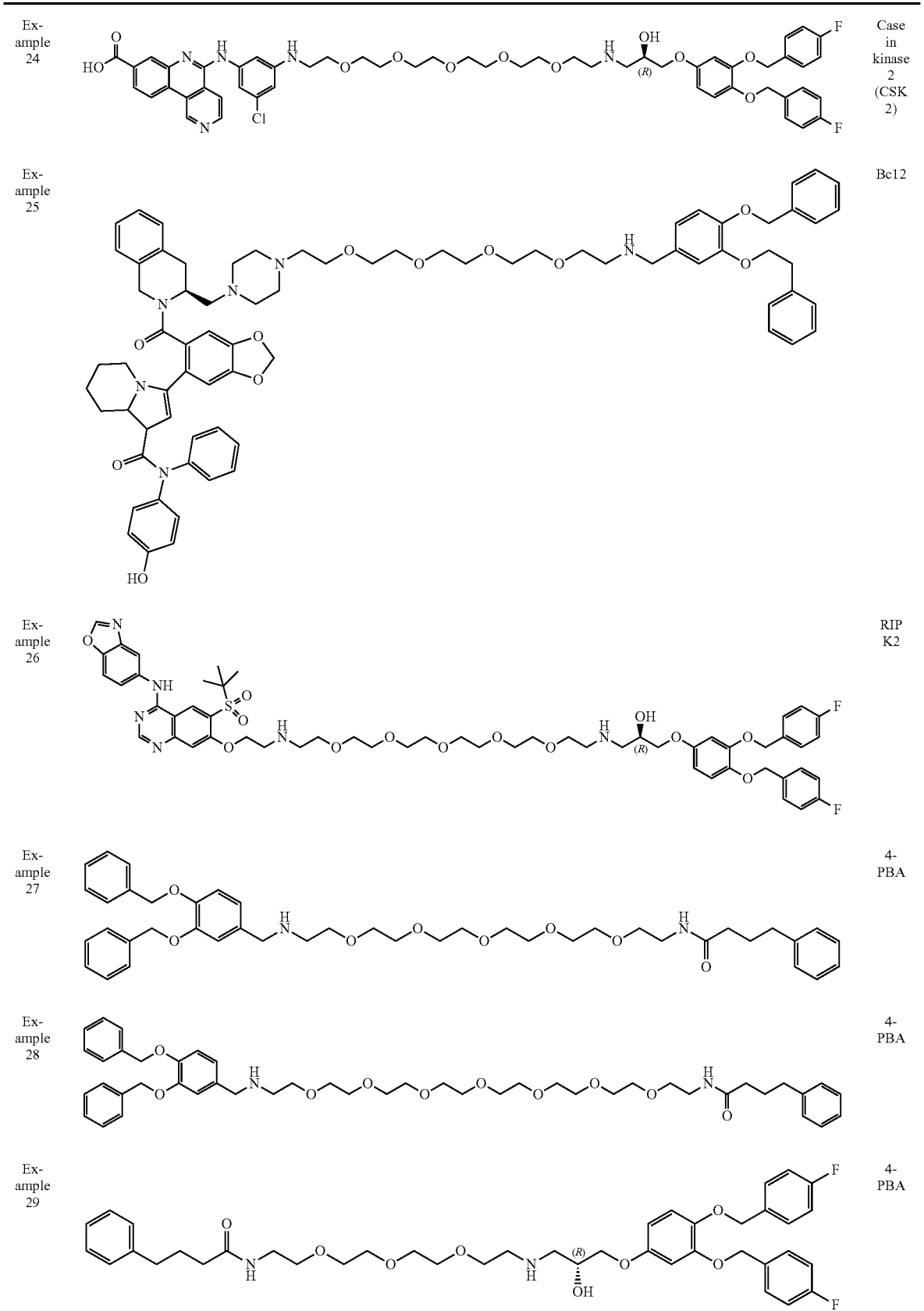 | Casein kinase 2 (CSK 2) |
| Example 25 | 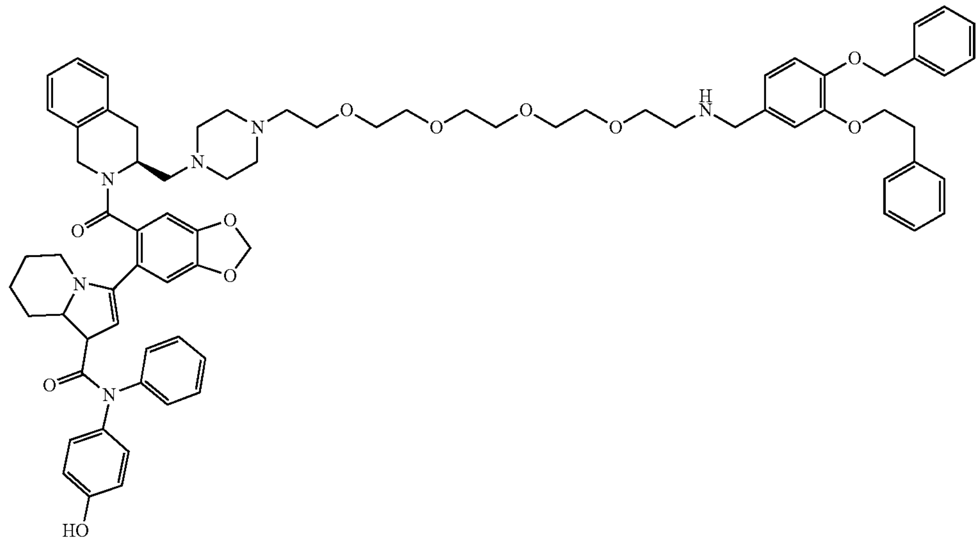 [SMILES: O=C(C1C=C(c2cc3c(cc2C(=O)N2Cc4ccccc4C[C@H]2CN2CCN(CCOCCOCCOCCOCCNCc4ccc(OCc5ccccc5)c(OCCc5ccccc5)c4)CC2)OCO3)N2CCCCC12)N(c1ccccc1)c1ccc(O)cc1] | Bcl2 |
| Example 26 | 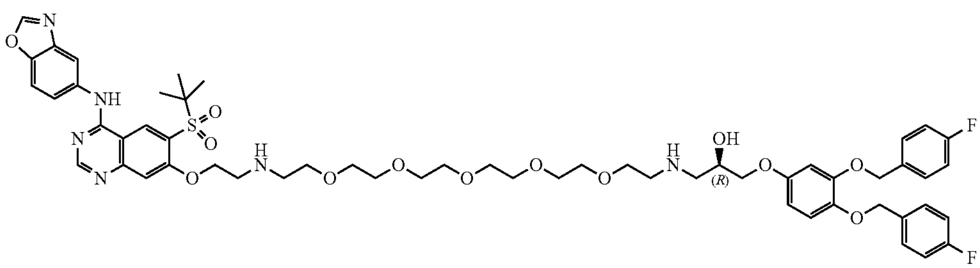 | RIPK2 |
| Example 27 | 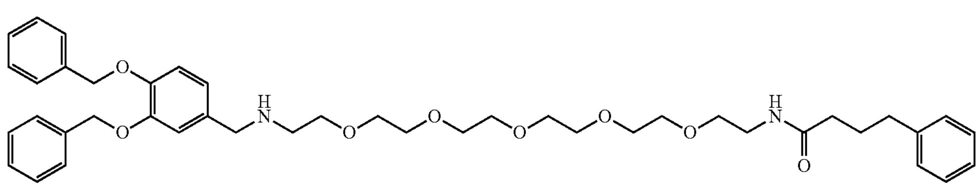 [SMILES: O=C(CCCc1ccccc1)NCCOCCOCCOCCOCCOCCNCc1ccc(OCc2ccccc2)c(OCc2ccccc2)c1] | 4-PBA |
| Example 28 | 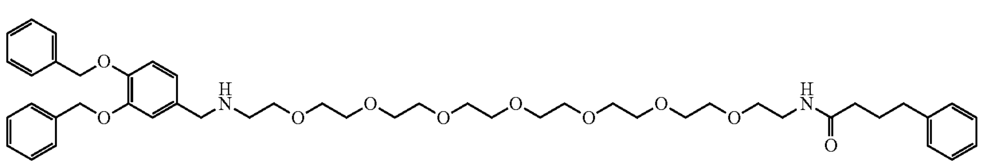 [SMILES: O=C(CCCc1ccccc1)NCCOCCOCCOCCOCCOCCOCCOCCNCc1ccc(OCc2ccccc2)c(OCc2ccccc2)c1] | 4-PBA |
| Example 29 | 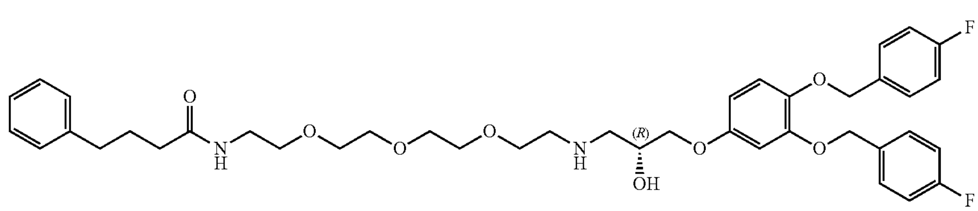 | 4-PBA |

TABLE 3-continued
| Example | Structure | |
|---|---|---|
| Example 30 | 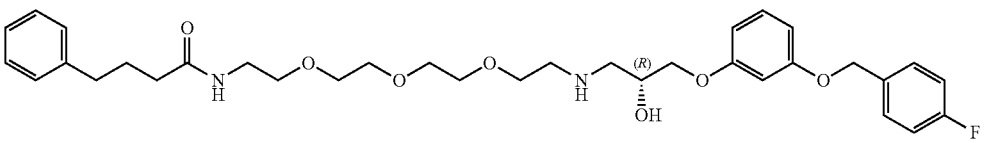 | 4-PBA |
| Example 31 | 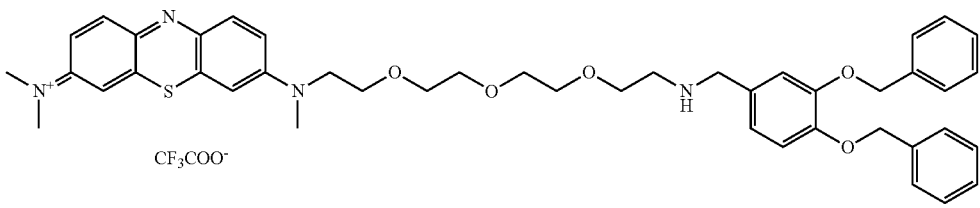 | Tau |
| Example 32 | 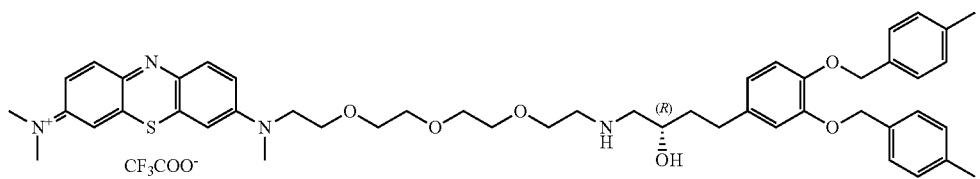 | Tau |
| Example 33 | | Tau |
Table 4 below shows the chemical structures of the autophagy targeting ligands used in the compounds of Table 3 above.
TABLE 4
| Example No. | Compound ID. | Structure |
|---|---|---|
| Example 14 | Compound A | 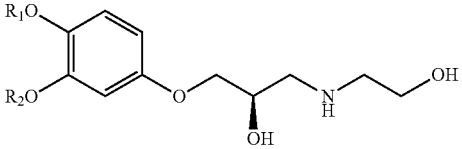 |
| Example 15 | Compound B | 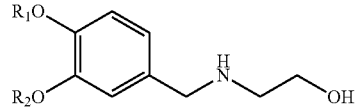 |
| Example 16 | Compound C | 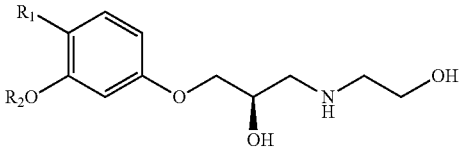 |
| Example 17 | Compound D | 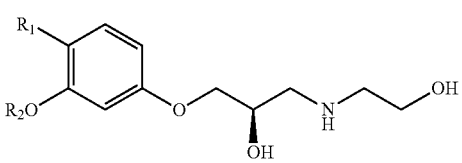 |

TABLE 4-continued

| Example No. | Compound ID. | Structure |
|---|---|---|
| Example 18 | Compound E | 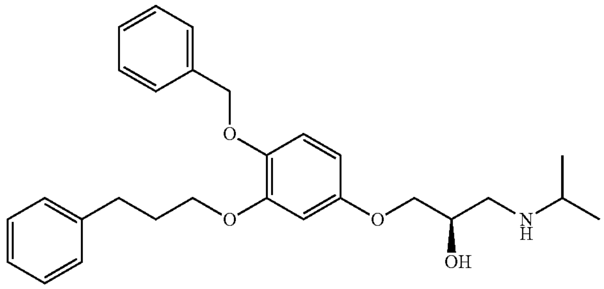 [SMILES: CC(C)NC[C@@H](O)COc1ccc(OCc2ccccc2)c(OCCCc2ccccc2)c1] |
| Example 19 | Compound F | 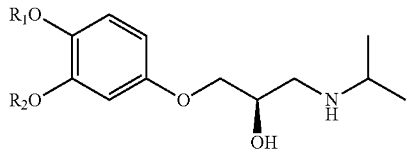 |
| Example 20 | Compound G | 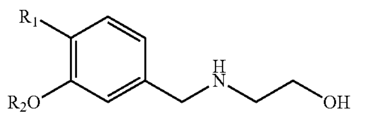 |
| Example 21 | Compound H | 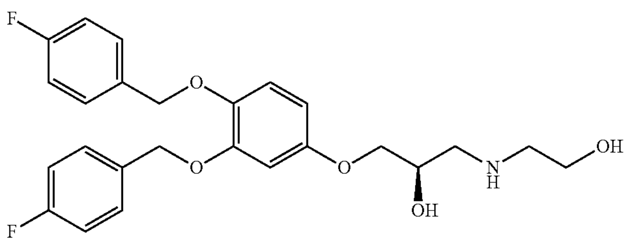 [SMILES: OCCNC[C@@H](O)COc1ccc(OCc2ccc(F)cc2)c(OCc2ccc(F)cc2)c1] |
| Example 22 | Compound I | 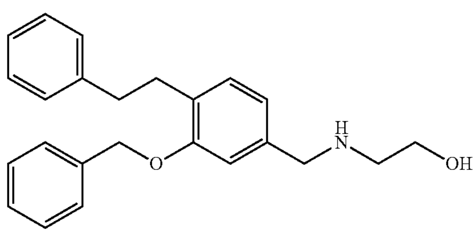 [SMILES: OCCNCc1ccc(CCc2ccccc2)c(OCc2ccccc2)c1] |
| Example 23 | Compound J | 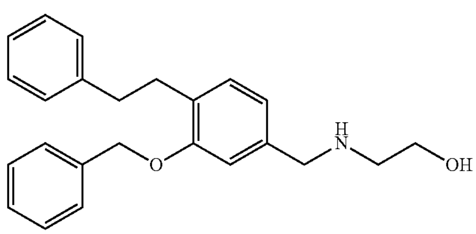 [SMILES: OCCNCc1ccc(CCc2ccccc2)c(OCc2ccccc2)c1] |
| Example 24 | Compound L | 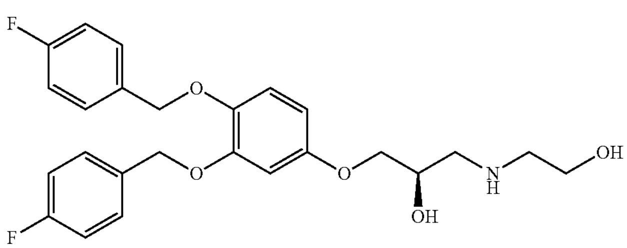 [SMILES: OCCNC[C@@H](O)COc1ccc(OCc2ccc(F)cc2)c(OCc2ccc(F)cc2)c1] |

TABLE 4-continued

| Example No. | Compound ID. | Structure |
|---|---|---|
| Example 25 | Compound M | (structure) |
| Example 26 | Compound P | (structure) |
| Example 27 | Compound Q | (structure) |
| Example 28 | Compound R | (structure) |
| Example 29 | Compound S | (structure) |
| Example 30 | Compound T | (structure) |
| Example 31 | Compound U | (structure) |
| Example 32 | Compound V | (structure) |

TABLE 4-continued

| Example No. | Compound ID. | Structure |
|---|---|---|
| Example 33 | Compound W | 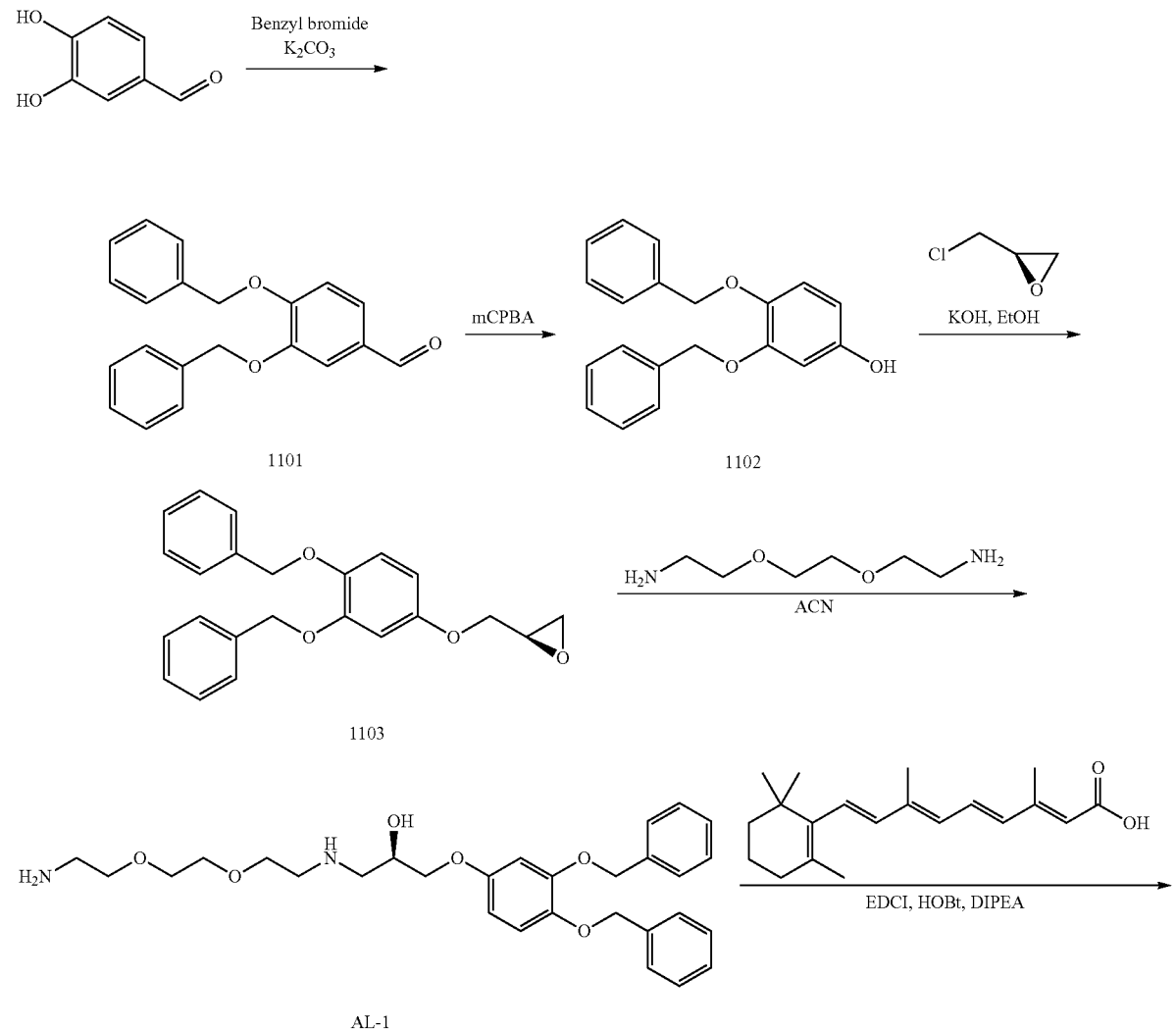 |

Hereinafter, the preparation methods of Examples 1 to 33 are described.

General Experimental Methods $^1$H NMR spectrum was recorded on Bruker Avance III 400 MHz and Bruker Fourier 300 MHz and TMS was used as an internal standard.

LCMS was taken on a quadrupole Mass Spectrometer on SHIMADZU LC/MS-2020 ((Column: C18 (4.6×5.0 mm, 5 μm) operating in ES (+) or (−) ionization mode; T=40° C.; flowrate=1.5 mL/min; detected wavelength: 190-800 nm) and Agilent 1260HPLC and 6120MSD ((Column: C18 (50× 4.6 mm, 5 μm) operating in ES (+) or (−) ionization mode; T=30° C.; flowrate=1.5 mL/min; detected wavelength: 220 nm).

Example 1: Preparation of (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide (RTEG-1104)

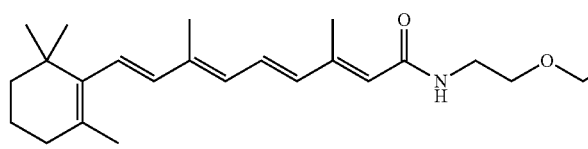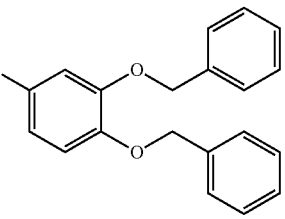

RTEG-1104

Step 1) Preparation of 3,4-bis(benzyloxy)benzaldehyde (1101)

After 3,4-dihydroxybenzaldehyde (0.50 g, 3.62 mmol) was dissolved in anhydrous DMF (5 ml), potassium carbonate ($K_2CO_3$, 1.50 g, 10.86 mmol) was added and benzyl bromide (0.92 mL, 7.96 mmol) was then slowly added to the reaction and stirred at 60° C. for 4 hours. When the reaction was completed, the reaction mixture was cooled to room temperature, diluted with purified water and extracted twice with diethyl ether (50 ml). The organic layer was washed twice with purified water (50 ml) and then once again with saturated aqueous sodium chloride solution (50 ml). Then, anhydrous sodium sulfate was added to the organic layer and stirred, followed by filtration under reduced pressure. The filtered solution was concentrated and then purified by column chromatography to give 3,4-bis(benzyloxy)benzaldehyde (1101, 1.04 g, yield: 90%). $^1$H NMR (CDCl$_3$, 300 MHz) δ 9.81 (s, 1H), 7.49-7.31 (m, 12H), 7.04 (d, J=8.3 Hz, 1H), 5.27 (s, 2H), 5.22 (s, 2H); ESIMS m/z: 319.33 [M+H]$^+$.

Step 2) Preparation of 3,4-bis(benzyloxy)phenol (1102)

Dichloromethane (15 ml) was added to and dissolved in 3,4-bis(benzyloxy)benzaldehyde (1101, 1.00 g, 3.0 mmol, 1 eq.), and then mCPBA (0.78 g, 4.5 mmol, 1.5 eq.) was added to the reaction and stirred at room temperature for 4 hours. The reaction mixture was diluted with ethyl acetate, washed with saturated aqueous sodium carbonate solution, and then the organic layer was separated. The organic layer was washed with an aqueous sodium chloride solution, then dehydrated with anhydrous sodium sulfate and filtered under reduced pressure. The filtered solution was concentrated and then dissolved in methanol (10 ml) again. 6N NaOH was added thereto and stirred at room temperature for 30 minutes. 4N HCl solution was added to the reaction, and further stirred for 30 minutes. The reaction mixture was diluted with ethyl acetate (50 ml), washed with brine, dehydrated with anhydrous sodium sulfate, and filtrated under reduced pressure. The filtered solution was concentrated and then purified by column chromatography (hexane/ethyl acetate ratio=7/3) to give 3,4-bis(benzyloxy)phenol (1102, 0.87 g, yield: 90%). $^1$H-NMR (CDCl$_3$, 300 MHz): δ 7.25-7.42 (m, 10H), 6.80 (d, 1H, J=9.0 Hz), 6.48 (d, 1H, J=3.0 Hz), 6.29 (dd, 1H, J=3.0 and 9.0 Hz), 5.08 (d, 4H, J=15 Hz), 4.55 (s, 1H); ESIMS m/z: 307.25 [M+H]$^+$.

Step 3) Preparation of R-2-((3,4-bis(benzyloxy)phenoxy)methyl)oxirane (1103)

3,4-Dibenzyloxyphenol (1102, 306 mg, 1.0 mmol) was diluted with ethanol (10 ml), and then aqueous KOH solution (KOH 66 mg, 1.2 mmol, 1 ml) and (R)-2-(chloromethyl)oxirane (410 ul, 5.0 mmol) were added sequentially. The reaction mixture was stirred at room temperature for 5 hours, and then the organic solvent was removed under reduced pressure. The concentrated reaction mixture was again diluted with ethyl acetate, washed with water and then with brine. The extracted organic layer was dehydrated with anhydrous sodium sulfate and then filtered under reduced pressure. The filtered organic layer was concentrated and purified by column chromatography to give pure R-2-((3,4-bis(benzyloxy)phenoxy)methyl)oxirane (1103, 297 mg, yield: 82%). ESIMS m/z: 363.5 [M+H]$^+$.

Step 4) Preparation of (R)-1-((2-(2-(2-aminoethoxy)ethoxy)ethyl)amino-3-(3,4-bis(benzyloxy)phenoxy)propan-2-ol (AL-1)

R-2-((3,4-bis(benzyloxy)phenoxy)methyl)oxirane (1103, 270 mg, 0.75 mmol) was dissolved in anhydrous ethanol (5 ml), and then 2,2'-(ethane-1,2-diylbis(oxy)) bis(ethane-1-amine) (880 mg, 5.9 mmol) was added and stirred at room temperature for 8 hours. After confirming the reaction by TLC, the reaction solvent was concentrated under reduced pressure. Water was added to the concentrated reaction and extracted with dichloromethane (3×5 mL). The extracted organic layer was dehydrated with anhydrous sodium sulfate and then filtered under reduced pressure. The filtered layer was concentrated and purified by column chromatography (dichloromethane:methanol=19:1) to give (R)-1-((2-(2-(2-aminoethoxy)ethoxy)ethyl) amino-3-(3,4-bis(benzyloxy)phenoxy)propan-2-ol (AL-1, 267 mg, yield: 70%). ESIMS m/z: 511.5 [M+H]$^+$.

Step 5) (R)-1-((2-(2-(2-aminoethoxy)ethoxy)ethyl)amino-3-(3,4-bis(benzyloxy)phenoxy)propan-2-ol (AL-1, 100 mg, 0.19 mmol) was dissolved in DMF (4 ml), and then 1-ethyl-3-(3-dimethylaminopropyl)carbodiimide (EDCI, 44 mg, 0.285 mmol), hydroxybenzotriazole (HOBt, 38.5 mg, 0.285 mmol) and retinoic acid (60 mg, 0.2 mol) were added sequentially. Then, N,N-diisopropylethylamine (DIPEA, 0.6 ml) was added thereto, and stirred at room temperature for 12 hours. Water was added to the reaction and extracted twice with ethyl acetate, and then the organic layer was once washed with brine. The organic layer was dehydrated with anhydrous sodium sulfate and filtered under reduced pressure. The filtrate was concentrated under reduced pressure and purified by high resolution liquid chromatography to give (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide (RTEG-1104, 60 mg, yield: 41%) as a white solid. $^1$H NMR (400 MHz, DMSO-d$_6$) δ (ppm) 1.01 (s, 6H), 1.53 (m, 2H), 1.74-1.79 (m, 5H), 1.96 (m, 2H), 2.12 (s, 3H), 2.42 (s, 3H), 2.56-2.81 (m, 4H), 3.04 (m, 2H), 3.52-3.54 (m, 6H), 3.67 (m, 2H), 3.95-4.05 (m, 3H), 5.16 (s, 4H), 5.37 (br s, 1H), 5.91 (br s, 1H), 6.22 (s, 2H), 6.51 (s, 4H), 6.57-6.61 (m, 2H), 6.98 (d, 1H), 7.32-7.48 (m, 10H), 8.51 (br s, 1H); ESI-MS Calcd m/z for $C_{49}H_{64}N_2O_7$ [M+H]$^+$ 794.35 Found 793.06

Example 2: Preparation of (2E,4E,6E,8E)-N-(2-(2-(2-((3,4-bis(benzyloxy)benzyl)amino)ethoxy)ethoxy)ethyl)-3,7-dimethyl-9-(2,6,6-trimethylcyclohex-1-en-1-yl)nona-2,4,6,8-tetraenamide (RTEG-1105)

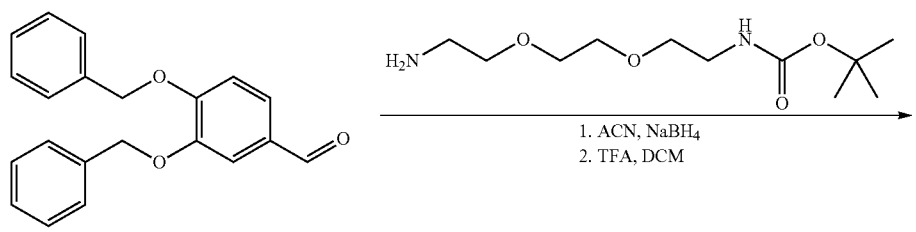

1101

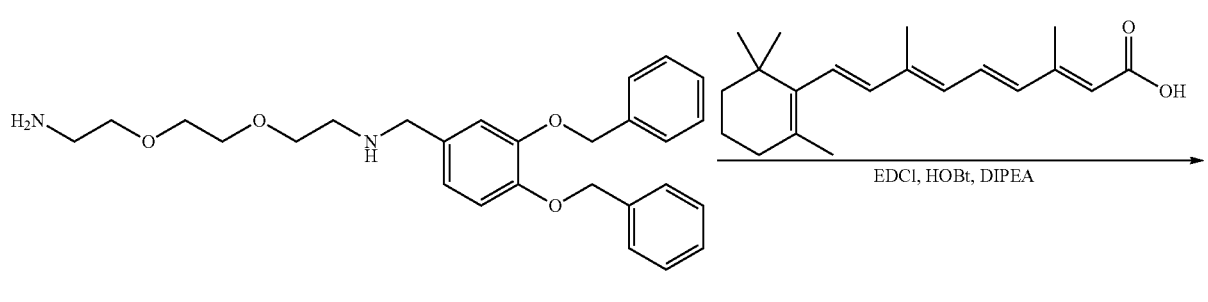

AL-2

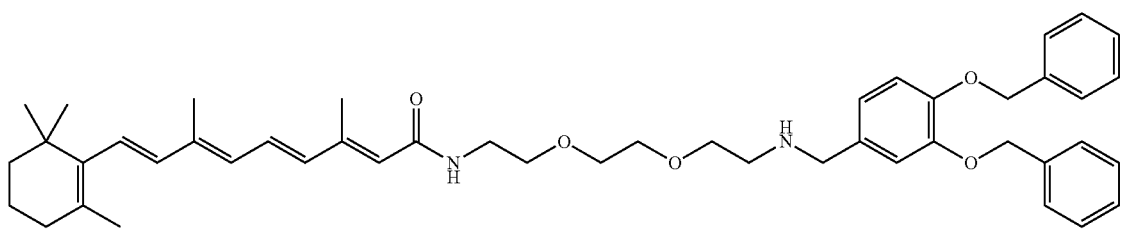

RTEG-1105

Step 1) Preparation of 2-(2-(2-aminoethoxy)ethoxy)-N-(3,4-bis(benzyloxy)benzyl)ethan-1-amine (AL-2)

3,4-Bis(benzyloxy)benzaldehyde (1101, 0.5 g, 1.57 mmol) was dissolved in acetonitrile (CAN, 10 ml), and then tert-butyl(2-(2-(2-aminoethoxy)ethoxy)ethyl)carbamate (468 mg, 1.88 mmol) was added thereto, and stirred at 60 to 70° C. for 5 hours. After cooling to room temperature, sodium borohydride (NaBH$_4$, 106 mg, 2.82 mmol) was slowly added to the reaction, and then stirred at room temperature for about 5 hours. Water was added to the reaction solution to complete the reaction, and the compound was extracted with ethyl acetate (50 mL×3). The extracted organic solvent layer was washed with brine and dehydrated using sodium sulfate. The filtered solvent was concentrated, and then again dissolved in dichloromethane (6 ml). Trifluoroacetic acid (TFA, 2 ml) was then added thereto and stirred at room temperature for 2 hours, and the solvent was concentrated under reduced pressure. The concentrate was purified by column chromatography (methylene chloride/methanol=15:1) to give 2-(2-(2-aminoethoxy)ethoxy)-N-(3,4-bis(benzyloxy)benzyl)ethan-1-amine (AL-2, 590 mg, yield: 84%) as a pale yellow liquid. $^1$H NMR (400 MHz, DMSO-d$_6$) δ (ppm) 2.59 (t, 2H), 3.32-3.61 (m, 12H), 4.62 (br s, 1H), 5.10 (s, 4H), 6.82 (d, 1H), 6.97 (d, 1H, 7.06 (s, 1H), 7.30-7.46 (m, 10H).

Step 2) (2E,4E,6E,8E)-N-(2-(2-(2-((3,4-bis(benzyloxy)benzyl)amino)ethoxy)ethoxy)ethyl)-3,7-dimethyl-9-(2,6,6-trimethylcyclohex-1-en-1-yl)nona-2,4,6,8-tetraenamide (RTEG-1105) was synthesized in a similar manner to step 5 of Example 1. $^1$H NMR (400 MHz, DMSO-d$_6$) δ (ppm) 1.01 (s, 6H), 1.54 (m, 2H), 1.75-1.80 (m, 5H), 1.98 (m, 2H), 2.12 (s, 3H), 2.42 (s, 3H), 2.72 (t, 2H), 3.04 (t, 2H), 3.51-3.54 (m, 6H), 3.67 (t, 2H), 3.76 (s, 2H), 5.14 (s, 4H), 6.22 (m, 2H), 6.37 (br s, 1H), 6.51 (s, 4H), 6.80 (d, 1H), 6.87 (d, 1H), 6.99 (s, 1H), 7.31-7.46 (m, 10H), 8.41 (br s, 1H); ESI-MS Calcd m/z for $C_{47}H_{60}N_2O_5$ [M+H]$^+$ 734.3 Found 733.01

Example 3: Preparation of (R)—N-(15-(3,4-bis(benzyloxy)phenoxy)-14-hydroxy-3,6,9-trioxa-12-azapentadecyl)-4-phenylbutaneamide (PBA-1104)

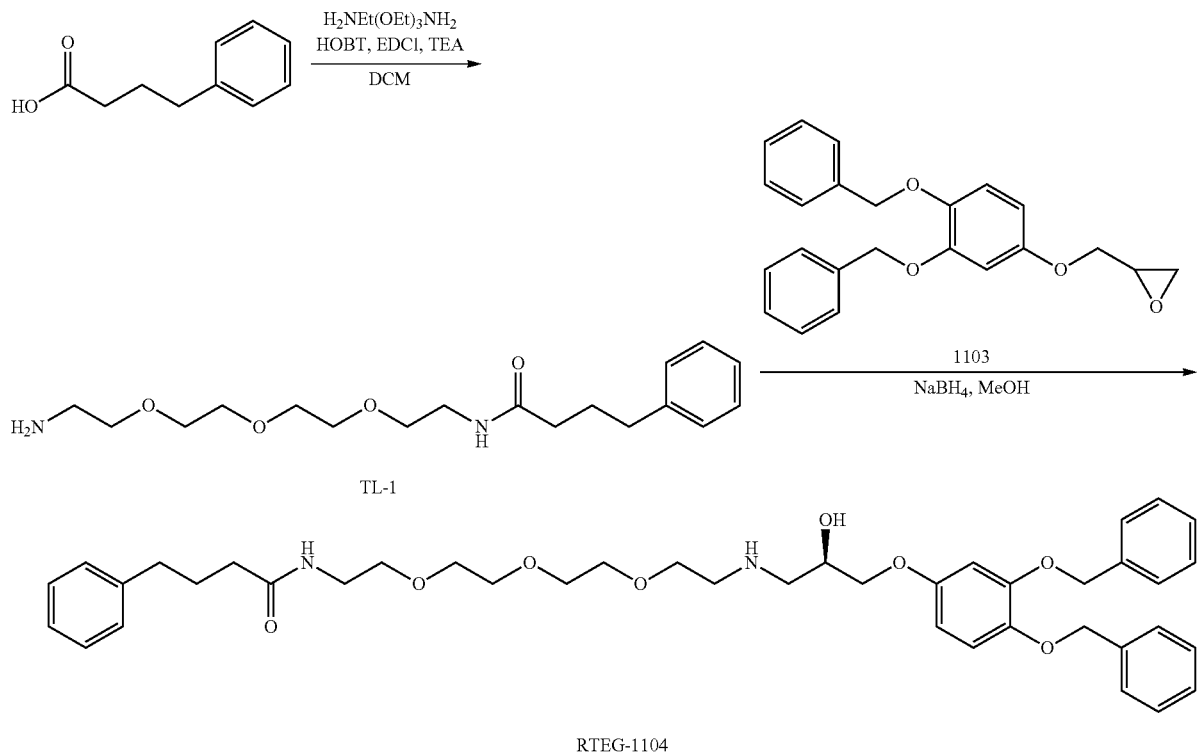

Step 1) 2,2'-(2,2'-oxybis(ethane-2,1-diyl)bis (oxy))diethanamine (21 g, 73.1 mmol) was dissolved in dichloromethane (400 ml), and then hydroxybenzotriazole (HOBt, 12.3 g, 91.5 mmol) and 1-ethyl-3-(3-dimethylaminopropyl) carbodiimide (EDCI, 17.6 g, 91.5 mmol) was added sequentially. Triethylamine (Et₃N, 18.5 g, 180 mmol) was added thereto and cooled to 0° C. 4-Phenylbutyric acid (15 g, 91.5 mmol) was dissolved in dichloromethane (200 ml) and then added to the reaction, followed by stirring at room temperature for 12 hours. The reaction mixture was diluted with water, and then extracted with dichloromethane (50 ml*3 times), the organic layer is dehydrated with anhydrous sodium sulfate and filtered. The filtrate was concentrated under reduced pressure, and then purified by silica gel column chromatography to give N-(2-(2-(2-(2-aminoethoxy)ethoxy)ethoxy)ethyl)-4-phenylbutanamide (TL-1, 12 g) as a yellow liquid. ESIMS m/z: 339.1 [M+H]⁺.

Step 2) N-(2-(2-(2-(2-aminoethoxy)ethoxy)ethoxy)ethyl)-4-phenylbutanamide (TL-1, 100 mg, 0.295 mmol) was dissolved in methanol (6 ml), and then R-2-((3,4-bis(benzyloxy)phenoxy)methyl)oxirane (1103, 128 mg, 0.354 mmol) was added thereto, and stirred at 50° C. for 10 hours. The reaction mixture was concentrated under reduced pressure and purified by silica gel column chromatography to give (R)—N-(15-(3,4-bis(benzyloxy)phenoxy)-14-hydroxy-3,6,9-trioxa-12-azapentadecyl)-4-phenylbutanamide (PBA-1104, 2013 mg, yield: 50%) as a white solid. ¹H NMR (400 MHz, DMSO-d₆) δ (ppm) 1.25 (s, 1H), 1.92 (m, 2H), 2.31 (t, 2H), 2.56-2.81 (m, 4H), 3.28 (m, 2H), 3.51-3.53 (m, 10H), 3.67 (t, 2H), 3.95-4.20 (m, 3H), 5.14 (s, 4H), 5.37 (br s, 1H), 5.90 (br s, 1H), 6.57 (s, 1H), 6.67 (d, 1H), 6.96 (d, 1H), 7.16 (m, 3H), 7.30 (mk 8H), 7.45 (m, 4H); ESI-MS Calcd m/z for C₄₁H₅₂N₂O₈ [M+H]⁺ 701.5 Found 700.87

Example 4: Preparation of N-(1-(3,4-bis(benzyloxy)phenyl)-5,8,11-trioxa-2-azatridecan-13-yl)-4-phenylbutanamide (PBA-1105)

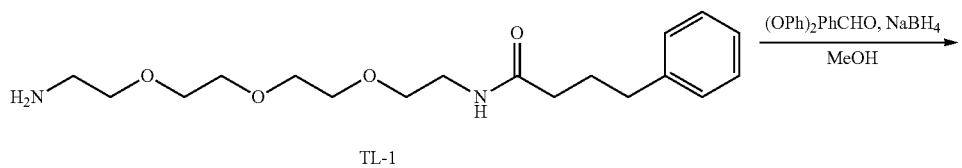

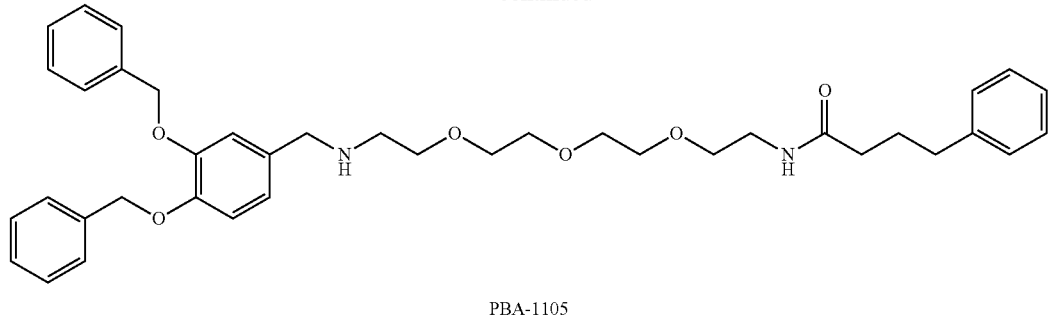

PBA-1105

Step 1) Preparation of N-(1-(3,4-bis(benzyloxy)phenyl)-5,8,11-trioxa-2-azatridecan-13-yl)-4-phenylbutanamide (PBA-1105)

N-(2-(2-(2-(2-aminoethoxy)ethoxy)ethoxy)ethyl)-4-phenylbutanamide (TL-1) (10 g, 29.6 mmol) was dissolved in methanol (MeOH, 150 mL), and then 3,4-dihydroxybenzaldehyde (10.3 g, 32.3 mmol) was added thereto. Thereafter, the mixture was stirred at 65° C. for about 5 hours. After cooling to room temperature, sodium borohydride (NaBH$_4$, 2.2 g, 57.9 mmol) was added and stirred at room temperature for about 5 hours. Water was added to the reaction solution to complete the reaction, and the compound was extracted with ethyl acetate (50 mL×3). The extracted organic solvent layer was washed with brine and water was removed using sodium sulfate. The filtered solvent was concentrated and then purified by column chromatography using silica gel (methylene chloride/methanol=15:1). Thereby, N-(1-(3,4-bis(benzyloxy)phenyl)-5,8,11-trioxa-2-azatridecan-13-yl)-4-phenylbutanamide (PBA-1105) (10.3 g) as a yellow liquid) was obtained. $^1$H NMR (CDCl$_3$, 400 MHz) δ (ppm) 7.45-7.42 (m, 4H), 7.36-7.29 (m, 7H), 7.27-7.26 (m, 1H), 7.18-7.15 (m, 3H), 6.99 (d, 1H), 6.83 (d, 1H), 6.41 (brs, 1H), 5.15 (d, 4H), 3.71 (s, 2H), 3.60-3.55 (m, 10H), 3.55-3.49 (m, 2H), 3.42-3.39 (m, 2H), 2.75-2.73 (m, 2H), 2.65-2.61 (m, 2H), 2.18-2.15 (m, 2H), 1.97-1.93 (m, 2H), 1.25 (brs, 1H); ESI-MS Calcd m/z for C$_{39}$H$_{48}$N$_2$O$_6$ [M+H]$^+$ 641.00 Found 640.82

Example 5: Preparation of 3-(3-(benzo[d][1,3]dioxol-5-yl)-1H-pyrazol-5-yl)-N-(2-(2-(2-((3-((4-fluorobenzyl)oxy))benzyl)amino)ethoxy)ethoxy)ethyl)aniline (Anle138b-F105)

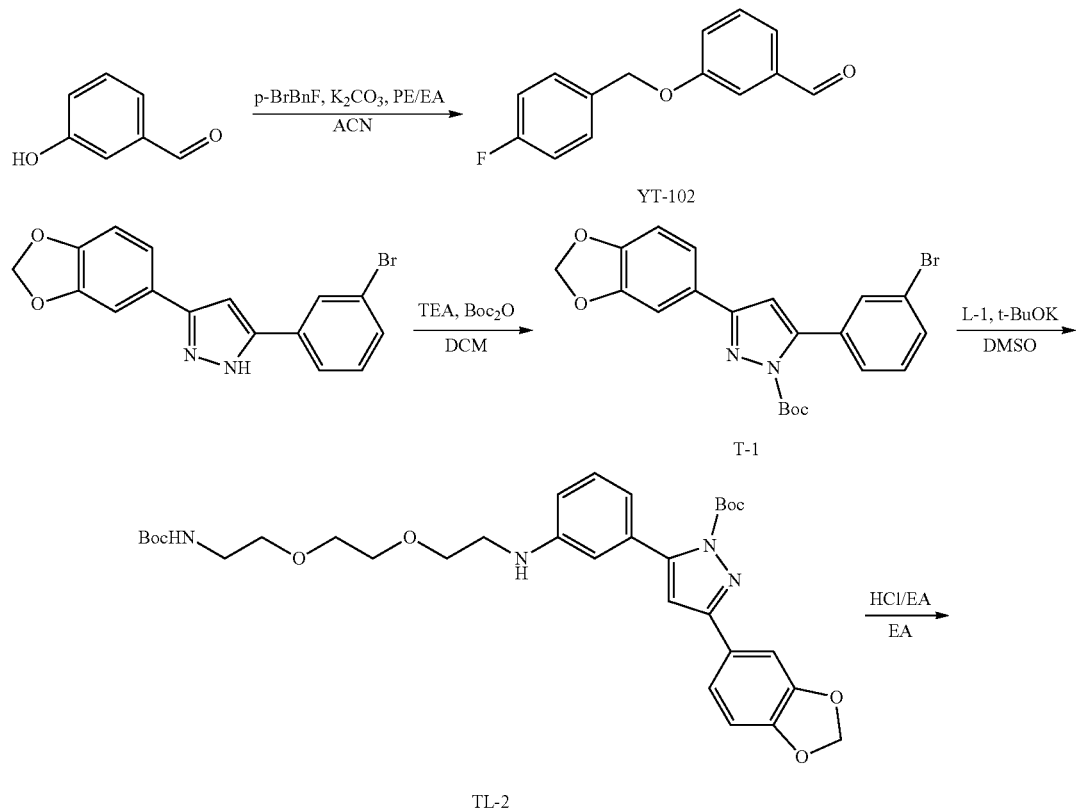

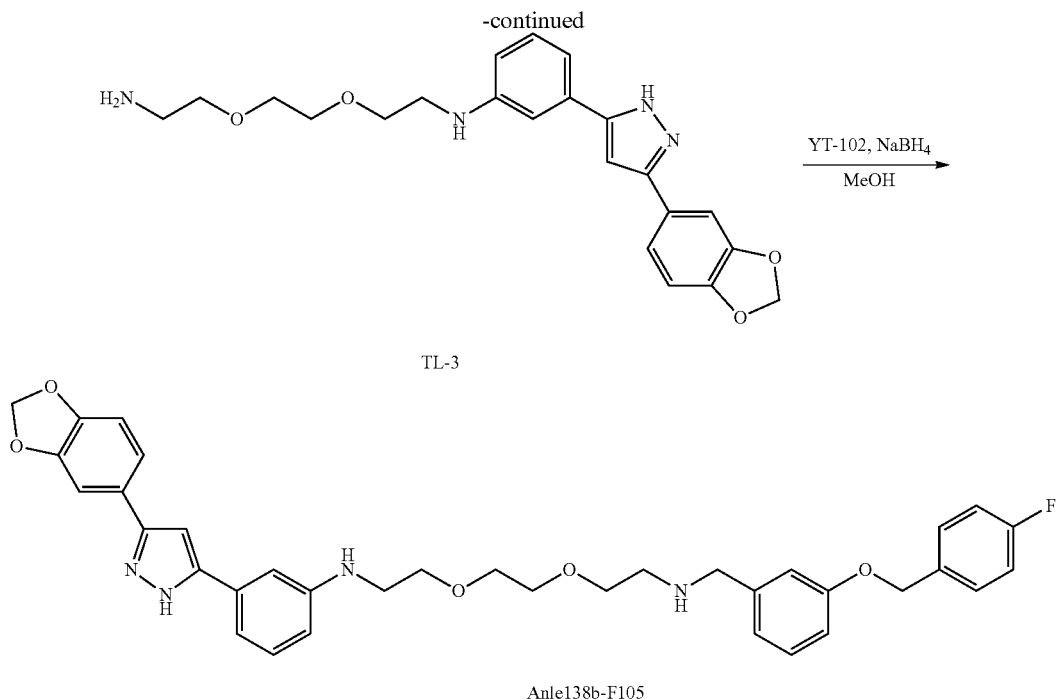

TL-3

Anle138b-F105

Step 1) Preparation of 3-((4-fluorobenzyl)oxy)benzaldehyde (YT-102)

Potassium carbonate ($K_2CO_3$, 112.5 g, 0.81 mol) and 1-(bromomethyl)-4-fluorobenzene (95 g, 0.50 mol) were added to a solution of 3-hydroxybenzaldehyde (50 g, 0.41 mol) in acetonitrile (ACN, 500 mL). The mixture was stirred at 60° C. for about 10 hours. After the reaction was completed, the reaction solution was filtered and concentrated. Petroleum ether/ethyl acetate (PE/EA, 20:1, 20 mL) was added thereto, and further stirred for about 1 hour, and then concentrated through a filter. Thereby, 3-((4-fluorobenzyl)oxy)benzaldehyde (YT-102, 25 g) was obtained as a greyish white solid. $^1H$ NMR (DMSO-$d_6$, 400 MHz) δ (ppm) 9.98 (s, 1H), 7.54-7.50 (m, 5H), 7.36 (m, 1H), 7.23 (m, 2H), 5.18 (s, 2H)

Step 2) Preparation of tert-butyl 3-(benzo[d][1,3]dioxol-5-yl)-5-(3-bromophenyl)-1H-pyrazole-1-carboxylate (T-1)

3-(Benzo[d][1,3]dioxol-5-yl)-5-(3-bromophenyl)-1H-pyrazole (200 mg, 0.58 mmol) was dissolved in methylene chloride (DCM, 4 mL), and then triethylamine (TEA, 88 mg, 0.87 mmol) and di-tert-butyl dicarbonate ($Boc_2O$, 153 mg, 0.70 mmol) were added. The mixture was stirred at room temperature for about 4 hours. After the reaction was completed, the filtered solution was concentrated and purified by column chromatography using silica gel (ethyl acetate/petroleum ether=1:15 to 1:5). Thereby, tert-butyl 3-(benzo[d][1,3]dioxol-5-yl)-5-(3-bromophenyl)-1H-pyrazole-1-carboxylate (T-1, 200 mg) was obtained as a white solid. $^1H$ NMR (DMSO-$d_6$, 400 MHz) δ (ppm) 8.09-7.43 (m, 5H), 7.11-6.94 (m, 3H), 6.08 (s, 2H), 1.34 (d, J=20 Hz, 9H)

Step 3) Preparation of tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2)

Tert-butyl 3-(benzo[d][1,3]dioxol-5-yl)-5-(3-bromophenyl)-1H-pyrazole-1-carboxylate (T-1, 200 mg, 0.45 mmol) was dissolved in dimethylsulfoxide (DMSO, 4 mL), and then tert-butyl (2-(2-(2-aminoethoxy)ethoxy)ethyl)carbamate (L-1, 168 mg, 0.68 mmol) and potassium tert-butoxide (t-BuOK, 101 mg, 0.90 mmol) were added thereto. The mixture was stirred at 120° C. for about 16 hours. The reacted compound was filtered and concentrated, and then purified by preparative high performance liquid chromatography (Prep-HPLC). Thereby, tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2, 180 mg) was obtained as a pale yellow solid.

Step 4) Preparation of N-(2-(2-(2-aminoethoxy)ethoxy)ethyl)-3-(3-(benzo[d][1,3]dioxol-5-yl)-1H-pyrazol-5-yl)aniline (TL-3)

Tert-butyl 3-(benzo[d][1,3]dioxol-5-yl)-5-(3-((2,2-dimethyl-4-oxo-3,8,11-trioxa-5-azatridecane-13-yl)amino)phenyl)-1H-pyrazole-1-carboxylate (TL-2, 180 mg, 0.29 mmol) was dissolved in ethyl acetate (EA, 4 mL), and then hydrochloric acid/ethyl acetate (1 mL, 3N) solution was added thereto. The mixture was stirred at room temperature for about 2 hours. The reacted compound was filtered and concentrated. Thereby, N-(2-(2-(2-aminoethoxy)ethoxy)ethyl)-3-(3-(benzo[d][1,3]dioxol-5-yl)-1H-pyrazol-5-yl)aniline (TL-3, 100 mg) was obtained as a white solid.

Step 5) Preparation of 3-(3-(benzo[d][1,3]dioxol-5-yl)-1H-pyrazol-5-yl)-N-(2-(2-(2-((3-((4-fluorobenzyl)oxy)) benzyl)amino)ethoxy)ethoxy)ethyl)aniline (Anle138b-F105)

N-(2-(2-(2-aminoethoxy)ethoxy)ethyl)-3-(3-(benzo[d][1,3]dioxol-5-yl)-1H-pyrazol-5-yl)aniline (TL-3, 90 mg, 0.22 mmol) was dissolved in methanol (MeOH, 2 mL), and then 3-((4-fluorobenzyl)oxy) benzaldehyde (YT-102, 50 mg, 0.22 mmol) was added and stirred at 65° C. Then, sodium borohydride (NaBH$_4$, 16 mg, 0.44 mmol) was added thereto at 5° C. and further stirred for about 1 hour. The reacted compound was concentrated and purified by preparative high performance liquid chromatography (Prep-HPLC). Thereby, 3-(3-(benzo[d][1,3]dioxol-5-yl)-1H-pyrazol-5-yl)-N-(2-(2-(2-((3-((4-fluorobenzyl)oxy))benzyl)amino) ethoxy)ethoxy)ethyl)aniline (Anle138b-F105, 15 mg) was obtained as a colorless liquid. $^1$H NMR (DMSO-d$_6$, 400 MHz) δ (ppm) 13.08 (brs, 1H), 7.47 (q, J=6 Hz, 2H), 7.37-7.31 (m, 2H), 7.21-7.17 (m, 3H), 7.11 (t, J=8 Hz, 1H), 7.00-6.96 (m, 5H), 6.88-6.82 (m, 2H), 6.56 (d, J=8 Hz, 1H), 6.04 (s, 2H), 5.59 (brs, 1H), 5.04 (s, 2H), 3.66 (s, 2H), 3.60-3.52 (m, 6H), 3.47 (t, J=6 Hz, 2H), 3.26-3.22 (m, 2H), 2.61 (t, J=5.6 Hz, 2H); ESI-MS Calcd m/z for C$_{36}$H$_{37}$FN$_4$O$_5$ [M+H]$^+$ 625.10 Found 624.71

Example 6: Preparation of (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E, 15E,17E,19E)-1-(3-(benzyloxy)phenyl)-12-oxo-5,8-dioxa-2,11-diazahenicosa-13,15,17,19-tetraene-21-oate (Fumagillin-105)

solid. $^1$H NMR (DMSO-d$_6$, 400 MHz) δ (ppm) 9.97 (s, 1H), 7.54-7.51 (m, 3H), 7.47 (d, J=7.2 Hz, 2H), 7.42-7.34 (m, 4H), 5.19 (s, 2H)

Step 2) Preparation of 2-(2-(2-aminoethoxy) ethoxy)-N-(3-(benzyloxy)benzyl)ethan-1-amine (AL-3)

3-(Benzyloxy)benzaldehyde (201, 50 g, 235.8 mmol) was dissolved in methanol (MeOH, 500 mL), and then 2,2'-(ethane-1,2-diylbis(oxy))diethanamine (L-2, 34.9 g, 235.8 mmol) was added thereto. The mixture was stirred at 65° C. for about 6 hours. After cooling to room temperature, sodium borohydride (NaBH$_4$, 8.95 g, 235.8 mmol) was added and stirred at 50° C. overnight. Water was added to compete the reaction, and the compound was extracted with ethyl acetate (EtOAc, 50 mL×3). The extracted organic solvent layer was washed with brine, and water was removed by adding sodium sulfate (Na$_2$SO$_4$). The solution was concentrated and then purified by column chromatography using silica gel (methylene chloride/methanol=12:1). Thereby, 2-(2-(2-aminoethoxy)ethoxy)-N-(3-(benzyloxy) benzyl)ethan-1-amine (AL-3, 20 g) was obtained as a yellow liquid. $^1$H NMR (DMSO+D$_2$O, 400 MHz) δ (ppm) 7.41-7.29 (m, 5H), 7.18 (t, J=8 Hz, 1H), 6.94 (s, 1H), 6.86-6.81 (m, 2H), 5.03 (s, 2H), 3.60 (s, 2H), 3.45-3.42 (m, 6H), 3.33

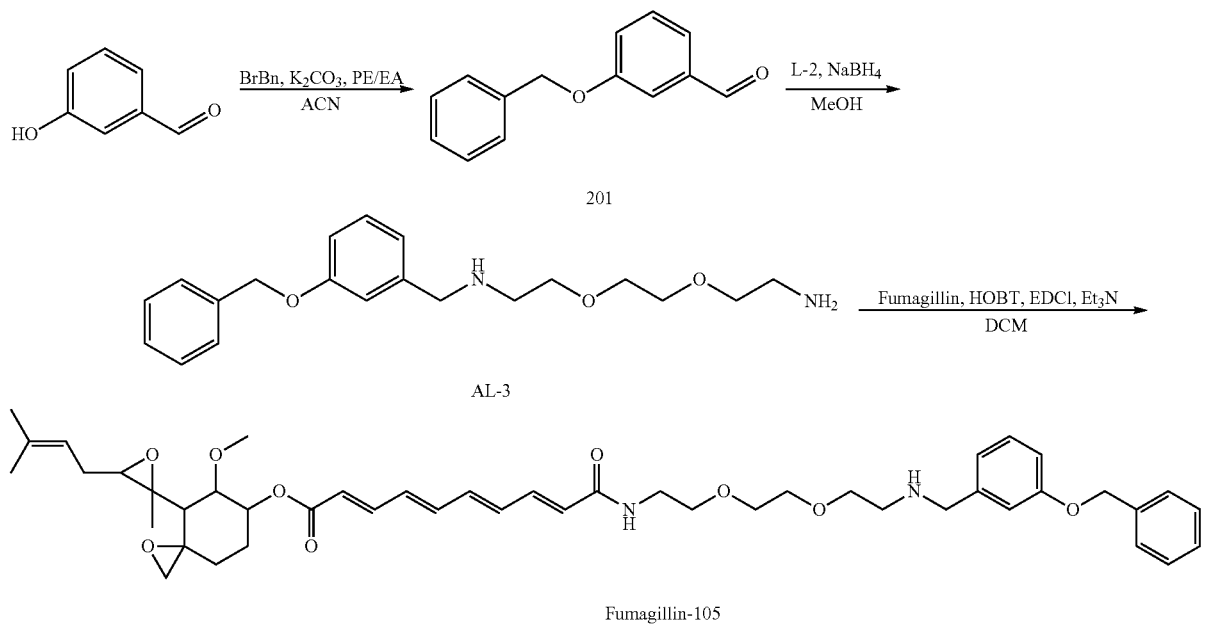

Fumagillin-105

Step 1) Preparation of 3-(benzyloxy)benzaldehyde (201)

Potassium carbonate (K$_2$CO$_3$, 112.5 g, 0.81 mol) and bromomethylbenzene (85 g, 0.50 mol) were added to a solution of 3-hydroxybenzaldehyde (50 g, 0.41 mol) in acetonitrile (ACN, 500 mL). The mixture was stirred at 60° C. for about 10 hours. After the reaction was completed, the reaction solution was filtered and then concentrated. Then, petroleum ether/ethyl acetate (PE/EA, 20:1, 20 mL) was added thereto, and further stirred for about 1 hour, followed by concentration through a filter. Thereby, 3-(benzyloxy) benzaldehyde (201, 25 g) was obtained as a grayish white (t, J=5.6 Hz, 2H), 2.57-2.52 (m, 4H); ESI-MS Calcd m/z for C$_{20}$H$_{28}$N$_2$O$_3$ [M+H]$^+$ 345.10 Found 344.46

Step 3) Preparation of (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E, 19E)-1-(3-(benzyloxy)phenyl)-12-oxo-5,8-dioxa-2, 11-diazahenicosa-13,15,17,19-tetraene-21-oate (Fumagillin-105)

2-(2-(2-Aminoethoxy)ethoxy)-N-(3-(benzyloxy)benzyl) ethan-1-amine (AL-3, 70 mg, 0.22 mmol) was dissolved in methylene chloride (DCM, 2 mL), and then fumagillin (100 mg, 0.22 mmol), hydroxy benzotriazole (HOBT, 34 mg, 0.25) mmol), 1-ethyl-3-(3-dimethylaminopropyl)carbodiimide (EDCI, 48 mg, 0.25 mmol) and triethylamine (Et₃N, 44 mg, 0.44 mmol) were added thereto. The mixture was stirred at 30° C. for about 10 hours. After the reaction was completed, the compound was extracted with methylene chloride (DCM, 50 mL×3). The extracted organic solvent layer was washed with brine. and water was removed using sodium sulfate. The filtered solvent was concentrated and then purified by preparative high performance liquid chromatography (Prep-HPLC). Thereby (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate (Fumagillin-105, 3 mg) was obtained as a yellow solid. ESI-MS Calcd m/z for $C_{46}H_{60}N_2O_9$ [M]⁺784.90 Found 784.99

Example 7: Preparation of 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204)

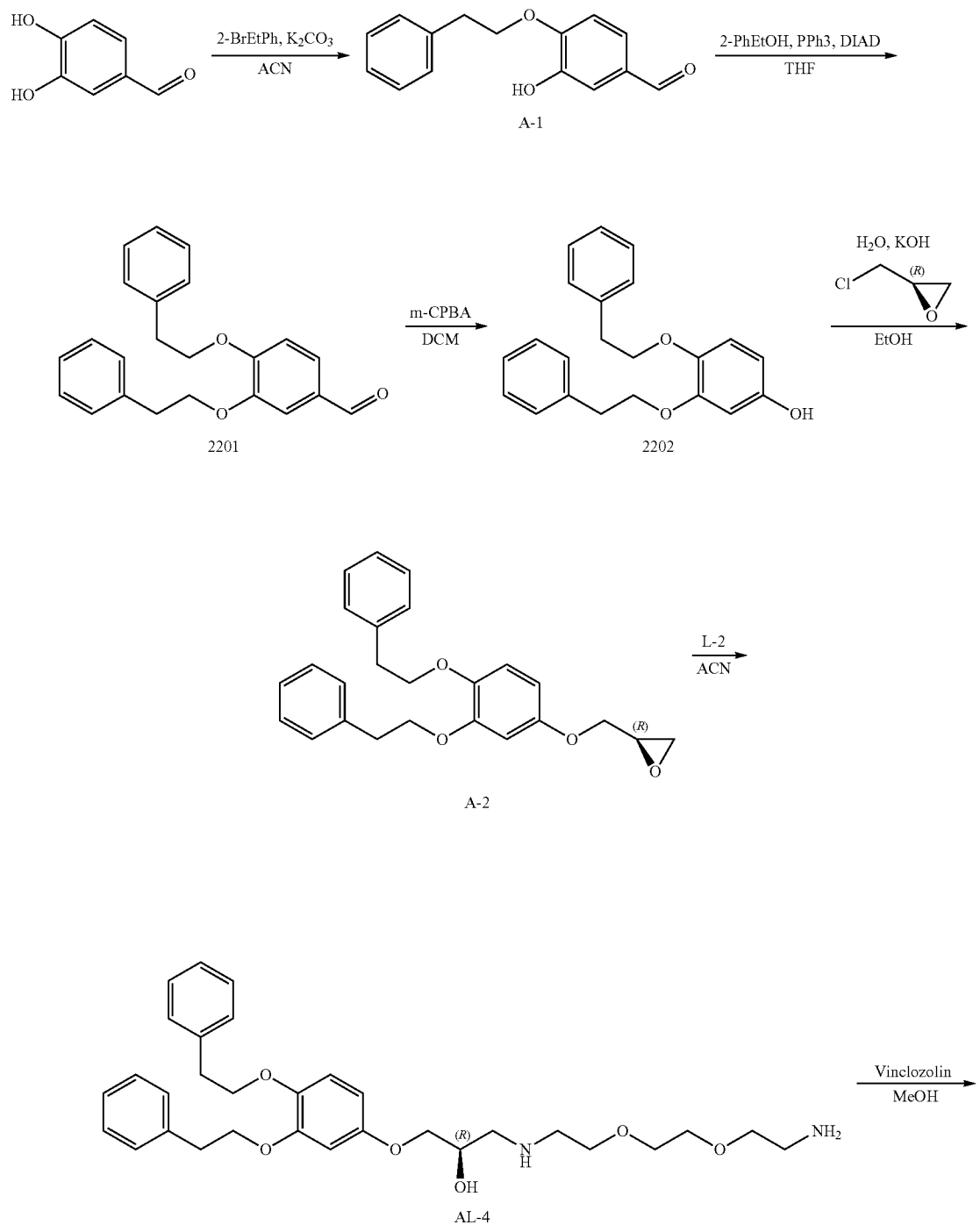

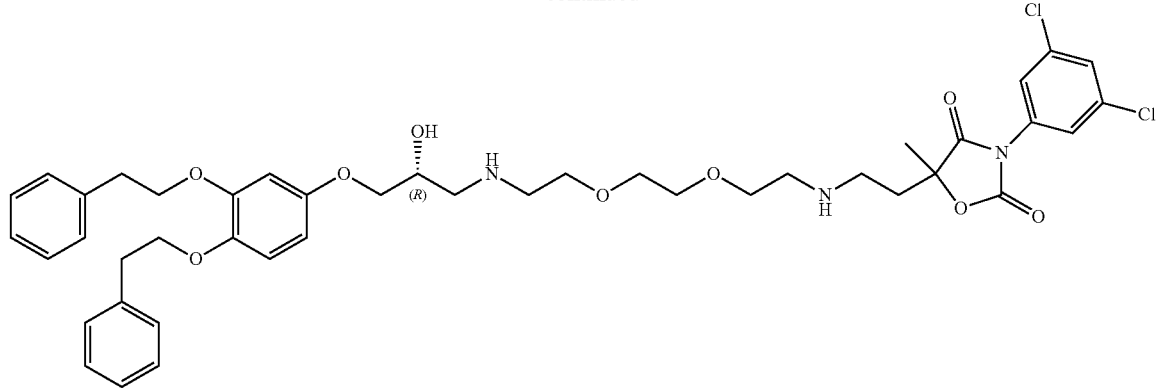

Vinclozolin-2204

Step 1) Preparation of 3-hydroxy-4-phenethoxybenzaldehyde (A-1)

3,4-Dihydroxybenzaldehyde (200 g, 1.4 mol) was dissolved in acetonitrile (ACN, 2 L), and then potassium carbonate ($K_2CO_3$, 260 g, 1.9 mol) and 1-(2-bromoethyl)benzene (267 g, 1.4 mol) were added thereto. The mixture was stirred at 80° C. for about 16 hours. After the reaction was completed using hydrochloric acid (1.5L, 1N), the compound was extracted with ethyl acetate (EA, 1 L×3). The extracted organic solvent layer was washed with brine, water was removed with sodium sulfate and then filtered. The concentrated solution was purified by column chromatography using silica gel (ethyl acetate/petroleum ether=20:1 to 10:1). Thereby, 3-hydroxy-4-phenethoxybenzaldehyde (A-1, 320 g) was obtained as a while solid. ESI-MS Calcd m/z for $C_{15}H_{14}O_3[M+H]^+$ 243.0 Found 242.27

Step 2) Preparation of 3,4-diphenethoxybenzaldehyde (2201)

3-Hydroxy-4-phenethoxybenzaldehyde (A-1, 320 g, 1.32 mol) was dissolved in tetrahydrofuran (THF, 5 L), and then, 2-phenylethanol (193.5 g, 1.59 mol), triphenylphosphine ($PPh_3$, 520 g, 1.98 mol) and diisopropyl azodicarboxylate (DIAD, 400 g, 1.98 mol) were added thereto. The mixture was stirred at 65° C. for about 16 hours. Water (100 mL) was added to the reaction solution to complete the reaction, and extracted with ethyl acetate (100 mL×2). Sodium sulfate was added to the extracted organic solvent layer to remove water, filtered and then concentrated. The concentrated compound was purified by column chromatography using silica gel (ethyl acetate/petroleum ether=1:15 to 1:10). Thereby, 3,4-diphenenthoxybenzaldehyde (2201, 160 g) was obtained as a white solid. $^1$H NMR (DMSO-$d_6$, 400 MHz) δ (ppm) 9.81 (s, 1H), 7.51 (dd, J=8 Hz and 1.6 Hz, 1H), 7.40-7.17 (m, 12H), 4.27 (t, J=6.8 Hz, 211), 4.22 (t, J=6.8 Hz, 2H), 3.06 (q, J=6.4 Hz, 4H); ESI-MS Calcd m/z for $C_{23}H_{22}O_3[M+H]^+$ 346.90 Found 346.43

Step 3) Preparation of 3,4-diphenethoxyphenol (2202)

3,4-Diphenethoxybenzaldehyde (2201, 160 g, 0.46 mmol) was dissolved in methylene chloride (DCM, 2 L), and then meta-chloroperoxybenzoic acid (m-CPBA, 119 g, 069 mmol) was added thereto. The mixture was stirred at room temperature for about 16 hours. When the reaction was completed, the solution was filtered and then concentrated. The concentrated solution was purified by column chromatography using silica gel (ethyl acetate/petroleum ether=1: 15 to 1:5). Thereby, 3,4-diphenoxyphenol (2202, 100 g) was obtained as a grayish white solid. ESI-MS Calcd m/z for $C_{22}H_{22}O_3[M+H]^+$ 335.00 Found 334.42

Step 4) Preparation of (R)-2-((3,4-diphenethoxyphenoxy)methyl)oxirane (A-2)

3,4-Diphenethoxyphenol (2202) (5 g, 15 mmol) was dissolved in ethanol (EtOH, 50 mL), and then water (2.5 mL) and potassium hydroxide (KOH, 1.93 g, 34.5 mmol) were added thereto. Then, (R)-2-(chloromethyl)oxirane (8 g, 87 mmol) was added and stirred at room temperature for about 16 hours. Water (50 mL) was added to the reaction solution to complete the reaction, and the compound was extracted with ethyl acetate (EA, 20 mL×3). The extracted organic solvent was washed with brine, water was removed with sodium sulfate, filtered and concentrated. The concentrated compound was purified by column chromatography using silica gel (ethyl acetate/petroleum ether=1:15 to 1:10). Thereby, (R)-2-((3,4-diphenethoxyphenoxy)methyl)oxirane (A-2, 2.5 g) was obtained as a white solid. ESI-MS Calcd m/z for $C_{25}H_{26}O_4[M+H]^+$ 391.00 Found 390.48

Step 5) Preparation of (R)-1-((2-(2-(2-aminoethoxy)ethoxy)ethyl)amino)-3-(3,4-diphenethoxyphenoxy)propan-2-ol (AL-4)

(R)-2-((3,4-diphenethoxyphenoxy)methyl)oxirane (A-2, 20 g, 51.2 mmol) was dissolved in acetonitrile (ACN, 200 mL), and then 2-(2-(2-aminoethoxy)ethoxy)ethanamine (L-2, 15.2 g, 102.5 mmol) was added thereto. The mixture was stirred at 70° C. for about 40 hours. When the reaction was completed, the reaction solution was filtered and concentrated. The concentrated solution was purified by column chromatography using silica gel (methylene chloride/methanol=100:1 to 30:1). Thereby, (R)-1-((2-(2-(2-aminoethoxy)ethoxy)ethyl)amino)-3-(3,4-diphenethoxyphenoxy)propan-2-ol (AL-4, 12 g) was obtained as a yellow liquid. $^1$H NMR (CD$_3$OD, 400 MHz) δ (ppm) 8.52 (s, 3H), 7.30-7.20 (m, 10H), 6.85 (d, J=8 Hz, 1H), 6.60 (d, J=2.8 Hz, 1H), 6.47 (dd, J=8 Hz and 2 Hz, 1H), 4.16 (t, J=6.8 Hz, 3H), 4.08 (t, J=6.8 Hz, 2H), 3.96 (q, J=4 Hz, 2H), 3.79 (t, J=5.2 Hz, 2H), 3.70

(m, 7H), 3.32-3.25 (m, 3H), 3.17-2.98 (m, 8H); ESI-MS Calcd m/z for $C_{31}H_{42}N_2O_6$ [M+H]$^+$ 539.20 Found 538.69

Step 6) Preparation of liquid 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204)

(R)-1-((2-(2-(2-aminoethoxy)ethoxy)ethyl) amino)-3-(3,4-diphenethoxyphenoxy)propan-2-ol (AL-4, 120 mg, 0.22 mmol) was dissolved in methanol (MeOH, 2 mL), and then vinclozolin (117 mg, 0.33 mmol) was added thereto. The mixture was stirred at 65° C. for about 16 hours. When the reaction was completed, the solution was filtered and concentrated. The concentrated solution was purified by preparative high performance liquid chromatography (Prep-HPLC). Thereby, 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione (Vinclozolin-2204, 15 mg) was obtained as a colorless liquid. $^1$H NMR (DMSO-d$_6$, 400 MHz) δ (ppm) 1.65 (m, 3H), 2.65 (m, 4H), 2.97 (m, 4H), 3.17 (m, 2H), 3.42 (m, 8H), 3.57 (d, J=8 Hz, 1H), 3.80 (m, 3H), 4.02 (t, J=8 Hz, 2H), 4.13 (t, J=8 Hz, 2H), 4.90 (b, 1H), 5.33 (m, 2H), 6.20 (m, 1H), 6.38 (d, J=8 Hz, 1H), 6.54 (m, 1H), 6.82 (d, J=8 Hz, 1H), 7.25 (m, 11H), 7.49 (d, J=1 Hz, 1H), 7.76 (s, 1H), 9.70 (s, 1H); ESI-MS Calcd m/z for $C_{43}H_{51}Cl_2N_3O_9$ [M+H]$^+$ 825.00 Found 824.79

Example 8: Preparation of (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304)

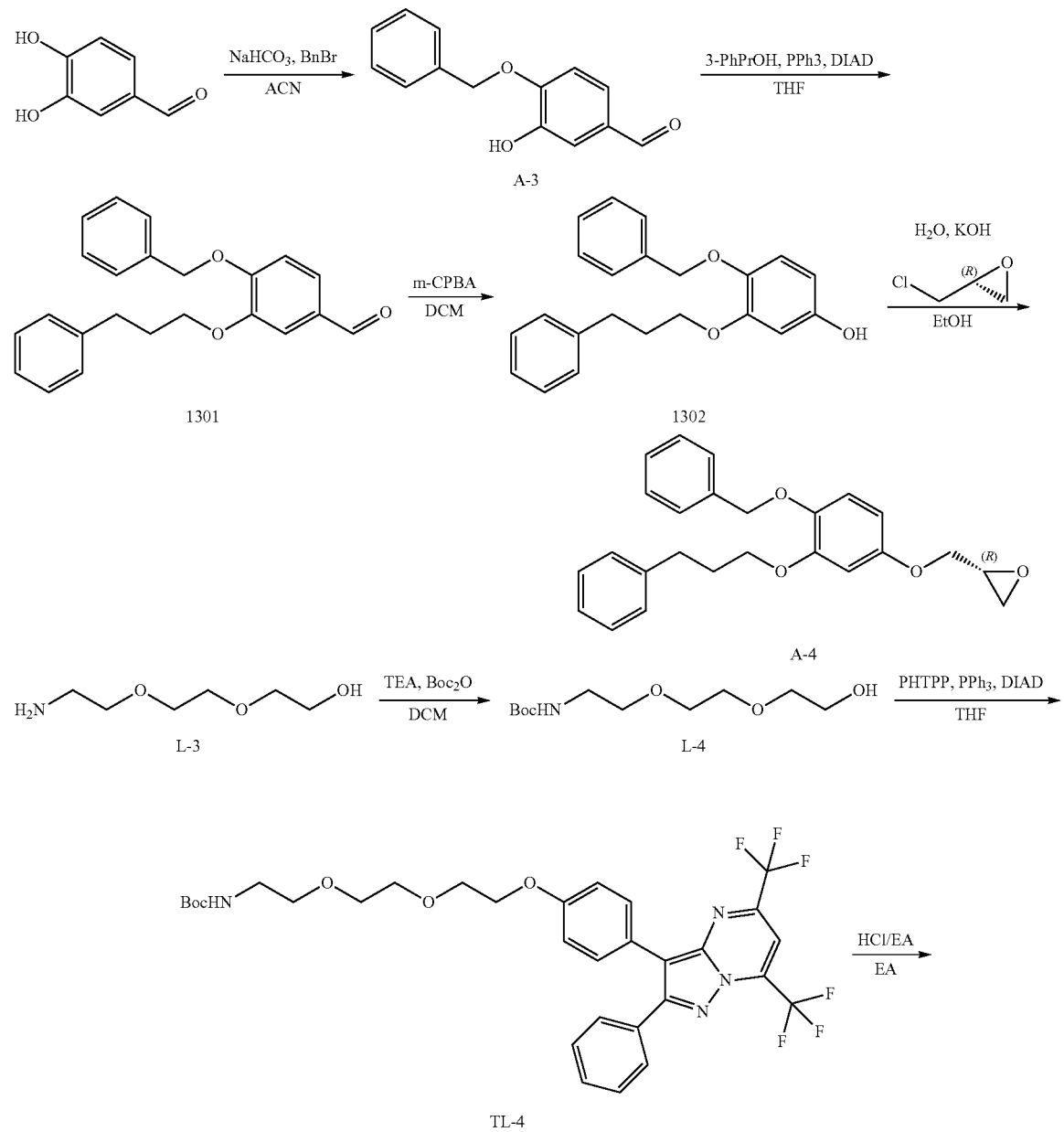

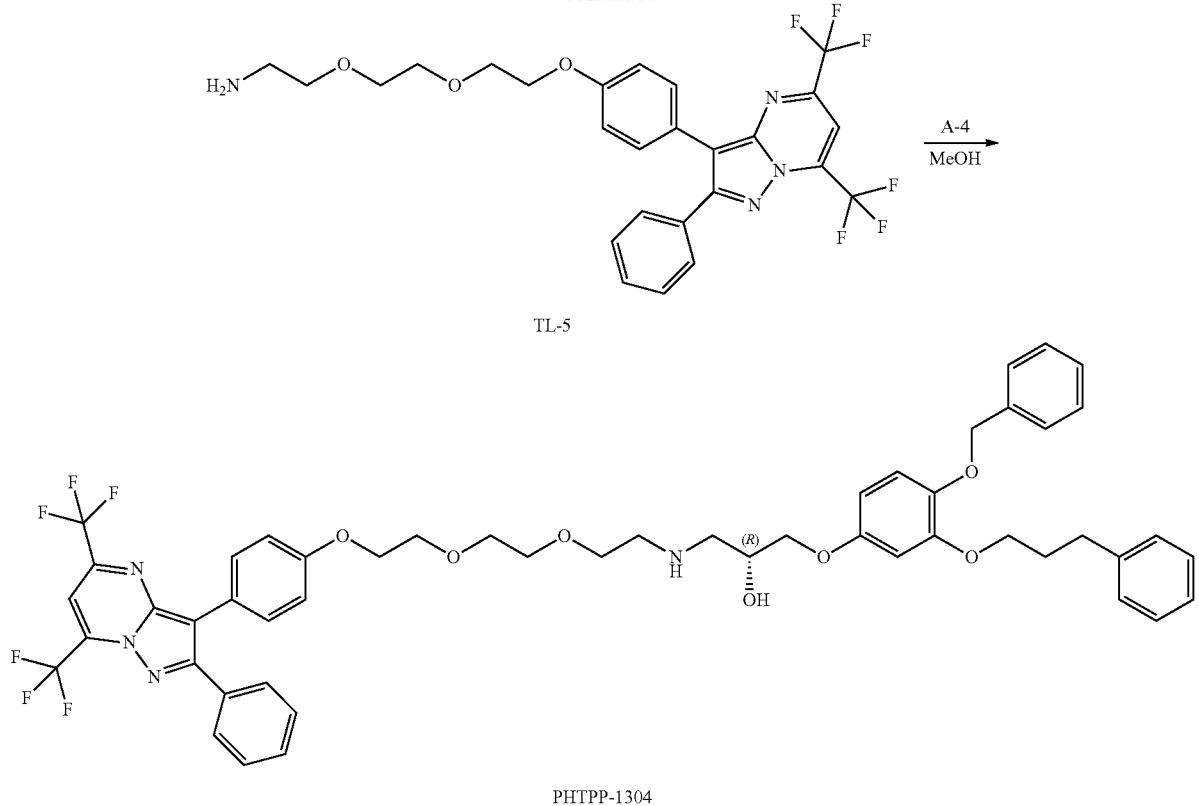

PHTPP-1304

Step 1) Preparation of 4-(benzyloxy)-3-hydroxybenzaldehyde (A-3)

3,4-Dihydroxybenzaldehyde (500 g, 3.62 mol) was dissolved in acetonitrile (ACN, 7 L), and then sodium bicarbonate (NaHCO₃, 395 g, 4.71 mol) and benzylbromide (BnBr, 619 g, 3.62 mol) were added thereto. The mixture was stirred at 80° C. for about 16 hours. The reaction was completed using hydrochloric acid (3 L, 1N), and the compound was extracted with ethyl acetate (3 L×3). The extracted organic solvent layer was washed with brine, and the remaining water was removed with sodium sulfate, filtered to remove impurities and concentrated. The concentrated solution was purified by column chromatography using silica gel (EA/PE=20:1 to 10:1). Thereby, 4-(benzyloxy)-3-hydroxybenzaldehyde (A-3, 250 g) was obtained as a white solid. $^1$H NMR (DMSO-d$_6$, 400 MHz) δ (ppm) 9.76 (s, 1H), 9.65 (s, 1H), 7.49 (d, J=6.8 Hz, 2H), 7.42-7.34 (m, 4H), 7.29 (d, J=2 Hz, 1H), 7.19 (d, J=8 Hz, 1H), 5.23 (s, 2H)

Step 2) Preparation of 4-(benzyloxy)-3-(3-phenyl-propoxy)benzaldehyde (1301)

4-(Benzyloxy)-3-hydroxybenzaldehyde (A-3, 120 g, 526 mmol) was dissolved in tetrahydrofuran (THF, 2 L), and then 3-phenylpropan-1-ol (85.9 g, 631 mmol), triphenylphosphine (PPh₃, 206.9 g, 789 mmol) and diisopropyl azodicarboxylate (DIAD, 159.5 g, 789 mmol) were added thereto. The mixture was stirred at 65° C. for about 16 hours. When the reaction was completed, the reaction mixture was filtered and concentrated. The concentrated solution was purified by column chromatography using silica gel (ethyl acetate/petroleum ether=1:15 to 1:10). Thereby, 4-(benzy-loxy)-3-(3-phenylpropoxy)benzaldehyde (1301, 100 g) was obtained as a white solid. $^1$H NMR (DMSO-d$_6$, 400 MHz) δ (ppm) 9.82 (s, 1H), 7.55-7.50 (m, 3H), 7.38 (t, J=7.2 Hz, 3H), 7.36-7.34 (m, 1H), 7.29-7.25 (m, 3H), 7.21-7.16 (m, 3H), 5.26 (s, 2H), 4.04 (t, J=6.4 Hz, 2H), 2.76 (t, J=8 Hz, 2H), 2.04 (t, J=7.2 Hz, 2H)

Step 3) Preparation of 4-(benzyloxy)-3-(3-phenyl-propoxy)phenol (1302)

4-(Benzyloxy)-3-(3-phenylpropoxy)benzaldehyde (1301, 100 g, 289 mmol) was dissolved in methylene chloride (DCM, 900 mL), and then meta-chloroperoxybenzoic acid (m-CPBA, 74.7 g, 433 mmol) was added thereto. The mixture was stirred at room temperature for about 16 hours. When the reaction was completed, the reaction mixture was filtered and then concentrated. The concentrated solution was purified by column chromatography using silica gel (ethyl acetate/petroleum ether=1:15 to 1:5). Thereby, 4-(benzyloxy)-3-(3-phenylpropoxy)phenol (1302, 66 g) was obtained as a grayish white solid. $^1$H NMR (DMSO-d$_6$, 400 MHz) δ (ppm) 9.00 (s, 1H), 7.44-7.18 (m, 10H), 6.81 (d, J=8 Hz, 1H), 6.39 (d, J=2.8 Hz, 1H), 6.22 (dd, J=8.8 Hz and 2.8 Hz, 1H), 4.96 (s, 2H), 3.90 (t, J=6 Hz, 2H), 2.74 (t, J=8 Hz, 2H), 2.01 (q, J=5.6 Hz, 2H)

Step 4) Preparation of (R)-2-((4-(benzyloxy)-3-(3-phenylproxy)phenoxy)methyl)oxirane (A-4)

4-(Benzyloxy)-3-(3-phenylpropoxy)phenol (1302, 40 g, 60 mmol) was dissolved in ethanol (EtOH, 800 mL), and then water (40 mL) and potassium hydroxide (KOH, 8.0 g, 143 mmol) were added thereto. Then, (R)-2-(chloromethyl)

oxirane (33.2 g, 359 mmol) was added and then stirred at room temperature for about 16 hours. When the reaction was completed, water (1600 mL) was added to the reaction solution to complete the reaction, and the compound was extracted with ethyl acetate (1600 mL×3). The extracted organic solvent layer was washed with brine, and then the remaining water was removed with sodium sulfate. The impurities were removed by a filter and then concentrated. The concentrated solution was purified by column chromatography using silica gel (ethyl acetate/petroleum ether=1: 15 to 1:10). Thereby, (R)-2-((4-(benzyloxy)-3-(3-phenylproxy)phenoxy)methyl)oxirane (A-4, 30 g) was obtained as a white solid. $^1$H NMR (DMSO-$d_6$, 400 MHz) δ (ppm) 7.46-7.17 (m, 10H), 6.93 (d, J=8.8 Hz, 1H), 6.61 (d, J=3.2 Hz, 1H), 6.43 (dd, J=8.8 Hz and 2.8 Hz, 1H), 5.02 (s, 2H), 4.23 (dd, J=7.6 Hz and 2.8 Hz, 1H), 3.97 (t, J=6.4 Hz, 2H), 3.75 (dd, J=7.2 Hz and 1.6 Hz, 1H), 3.28 (m, 1H), 2.82 (dd, J=5.2 Hz and 4 Hz, 1H), 2.75 (t, J=7.6 Hz, 2H), 2.73-2.67 (m, 1H), 2.01 (m, 2H)

Step 5) Preparation of tert-butyl (2-(2-(2-hydroxyethoxy)ethoxy)ethyl)carbamate (L-4)

2-(2-(2-Aminoethoxy)ethoxy)ethan-1-ol (L-3, 5 g, 33 mmol) was dissolved in methylene chloride (DCM, 100 mL), and then triethylamine (TEA, 4.1 g, 40 mmol) and di-tert-butyl dicarbonate (Boc$_2$O, 8.1 g, 37 mmol) were added thereto. The mixture was stirred at room temperature for about 16 hours. When the reaction was completed, the reaction mixture was filtered and then concentrated. The concentrated solution was purified by column chromatography using silica gel (EA/PE=1:3 to 1:1). Thereby, tert-butyl (2-(2-(2-hydroxyethoxy)ethoxy)ethyl)carbamate (L-4, 4.2 g) was obtained as a colorless liquid. $^1$H NMR (DMSO-$d_6$, 400 MHz) δ (ppm) 6.74 (m, 1H), 4.56 (t, J=5.6 Hz, 1H), 3.51-3.46 (m, 6H), 3.42-3.37 (m, 4H), 3.07-3.03 (m, 2H), 1.37 (s, 9H)

Step 6) Preparation of tert-butyl(2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4)

Tert-butyl (2-(2-(2-hydroxyethoxy)ethoxy)ethyl)carbamate (L-4, 300 mg, 1.2 mmol) was dissolved in tetrahydrofuran (THF, mL), and then 4-[2-phenyl-5,7-bis(trifluoromethyl)pyrazolo[1,5-a]pyrimidin-3-yl]phenol (PHTPP, 509 mg, 1.2 mmol), triphenylphosphine (PPh$_3$, 377 mg, 1.44 mmol) and diisopropyl azodicarboxylate (DIAD, 291 mg, 1.44 mmol) were added thereto. The mixture was stirred at 65° C. for about 16 hours. After the reaction was completed, the reaction was terminated, and the solution was filtered and concentrated. The concentrated solution was purified by column chromatography using silica gel (DCM/MeOH=100:1 to 50:1). Thereby, tert-butyl (2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4, 200 mg) was obtained as a yellow solid.

Step 7) Preparation of 2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5)

Tert-butyl(2-(2-(2-(4-(2-phenyl-5,7-bis(trifluoromethyl)pyrazolo[1,5-a]pyrimidin-3-yl)phenoxy)ethoxy)ethoxy)ethyl)carbamate (TL-4, 200 mg, 0.31 mmol) was dissolved in ethyl acetate (EA, 4 mL), and then hydrochloric acid (g)/ethyl acetate (1 mL) was added thereto. The mixture was stirred at room temperature for about 2 hours. After the reaction was completed, the reaction was terminated and the solution was filtered and concentrated. The concentrated solution was subjected to a purification process, and thereby 2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5, 120 mg) was obtained as a yellow solid.

Step 8) Preparation of (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304)

2-(2-(2-(4-(2-phenyl-5,7-bis(trifluoromethyl)pyrazolo[1,5-a]pyrimidin-3-yl)phenoxy)ethoxy)ethoxy)ethan-1-amine (TL-5, 120 mg, 0.22 mmol) was dissolved in methanol (MeOH, 2 mL), and then (R)-2-((4-(benzyloxy)-3-(3-phenylproxy)phenoxy)methyl)oxirane (A-4, 117 mg, 0.33 mmol) was added thereto. The mixture was stirred at 65° C. for about 16 hours. After the reaction was completed, the reaction was terminated, and the solution was filtered and concentrated. The concentrated solution was purified by preparative high performance liquid chromatography (Prep-HPLC). Thereby, (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol (PHTPP-1304, 15 mg) was obtained as a yellow solid. $^1$H NMR (DMSO-$d_6$, 400 MHz) δ (ppm) 1.99 (m, 2H), 2.73 (m, 6H), 3.55 (m, 8H), 3.80 (m, 5H), 3.94 (t, J=8 Hz, 2H), 4.13 (t, J=4 Hz, 2H), 4.99 (s, 2H), 6.40 (d, J=8 Hz, 1H), 6.55 (d, J=4 Hz, 1H), 6.89 (d, J=8 Hz, 1H), 7.04 (d, J=8 Hz, 2H), 7.18 (t, J=4 Hz, 3H), 7.27 (dd, J=4 Hz and 4 Hz, 3H), 7.35 (m, 4H), 7.44 (m, 5H), 7.61 (m, 2H), 8.07 (s, 1H), 8.42 (s, 1H); ESI-MS Calcd m/z for $C_{51}H_{50}F_6N_4O_7$ [M+H]$^+$ 945.10 Found 944.97

Example 9: Preparation of (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204)

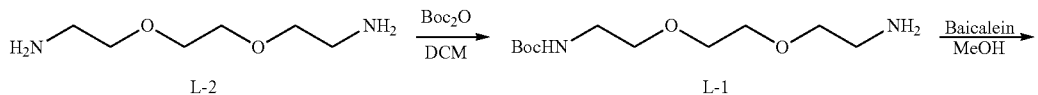

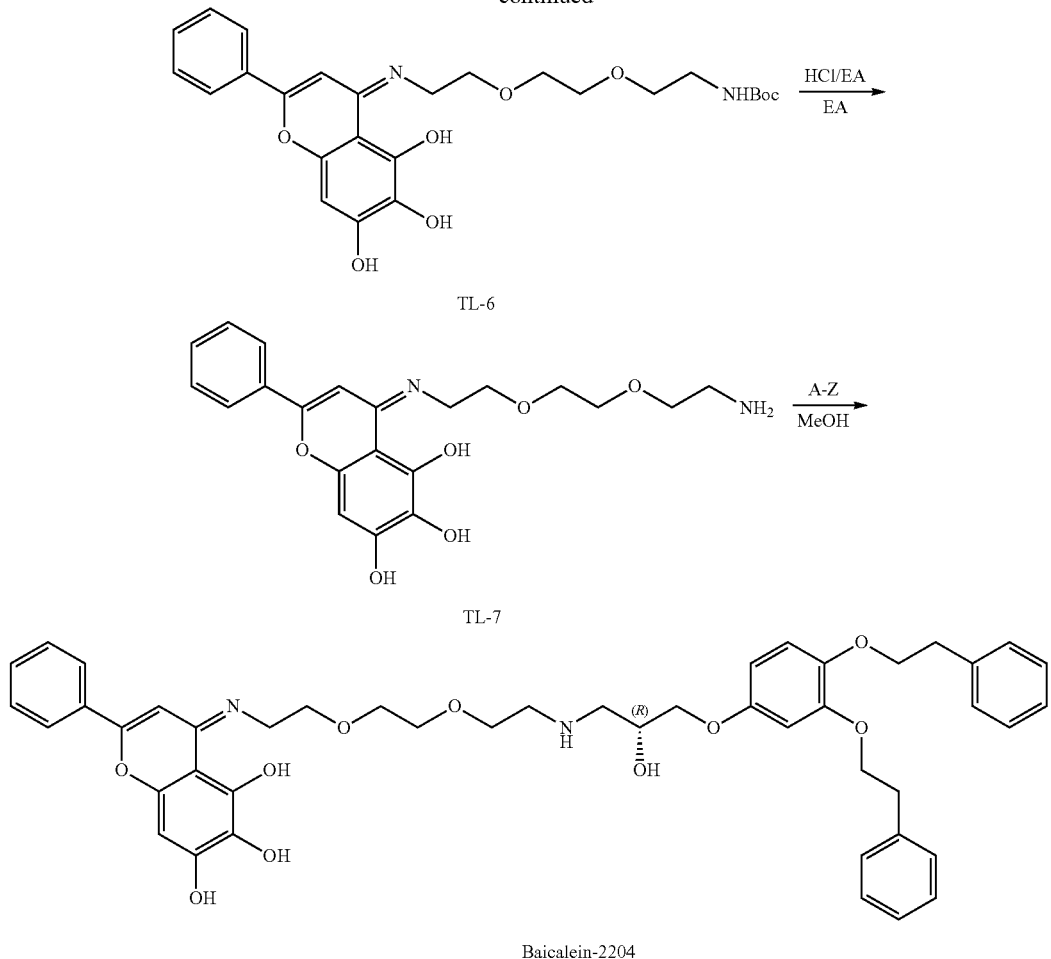

Baicalein-2204

Step 1) Preparation of tert-butyl (2-(2-(2-aminoethoxy)ethoxy)ethyl)carbamate (L-1)

2,2'-(Ethane-1,2-diylbis(oxy))dietanamine (L-2, 5 g, 33.7 mmol) was dissolved in methylene chloride (DCM, 100 mL), and then di-tert-butyl dicarbonate (Boc$_2$O, 7.36 g, 33.7 mmol) was added thereto. The mixture was stirred at room temperature for about 16 hours. After the reaction was completed, the reaction solution was filtered and concentrated. The concentrated solution was purified by column chromatography using silica gel (ethyl acetate/petroleum ether=1:3 to 1:1). Thereby, tert-butyl (2-(2-(2-aminoethoxy)ethoxy)ethyl)carbamate (L-2, 2.2 g) was obtained as a colorless liquid.

Step 2) Preparation of tert-butyl (Z)-(2-(2-(2-((5,6,7-trihydroxy-2-phenyl-4H-chromen-4-ylidene)amino)ethoxy)ethoxy)ethyl)carbamate (TL-6)

Tert-butyl (2-(2-(2-aminoethoxy)ethoxy)ethyl)carbamate (TL-6, 300 mg, 1.21 mmol) was dissolved in methanol (MeOH, 5 mL), and then 5,6,7-trihydroxyflavone (Baicalein, 326 mg, 1.21 mmol) was added thereto. The mixture was stirred at 65° C. for about 16 hours. When the reaction was completed, the reaction solution was filtered and then concentrated. The concentrated solution was purified by preparative high performance liquid chromatography (Prep-HPLC). Thereby, tert-butyl (Z)-(2-(2-(2-((5,6,7-trihydroxy-2-phenyl-4H-chromen-4-ylidene)amino)ethoxy)ethoxy)ethyl)carbamate (TL-6, 120 mg) was obtained as a yellow solid.

Step 3) Preparation of (Z)-4-((2-(2-(2-aminoethoxy)ethoxy)ethyl)imino)-2-phenyl-4H-chromen-5,6,7-triol (TL-7)

Tert-butyl (Z)-(2-(2-(2-((5,6,7-trihydroxy-2-phenyl-4H-chromen-4-ylidene)amino)ethoxy)ethoxy)ethyl)carbamate (TL-6, 120 mg, 0.24 mmol) was dissolved in ethyl acetate (EA, 2 mL), and then hydrochloric acid (g)/ethyl acetate (1 mL) was added thereto. The mixture was stirred at room temperature for about 2 hours. When the reaction was completed, the reaction mixture was extracted with ethyl acetate, filtered and concentrated. Thereby, (Z)-4-((2-(2-(2-aminoethoxy)ethoxy)ethyl)imino)-2-phenyl-4H-chromen-5,6,7-triol (TL-7, 90 mg) was obtained as a yellow solid.

Step 4) Preparation of (R, Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204)

(Z)-4-((2-(2-(2-aminoethoxy)ethoxy)ethyl)imino)-2-phenyl-4H-chromen-5,6,7-triol (TL-7, 90 mg, 0.22 mmol) was dissolved in methanol (MeOH, 2 mL), and then (R)-2-((3,4-diphenethoxyphenoxy)methyl)oxirane (A-2, 87 mg, 0.22 mmol) was added thereto. The mixture was stirred at 65° C. for about 16 hours. When the reaction was completed, the reaction solution was filtered and then concentrated. The concentrated solution was purified by preparative high performance liquid chromatography (Prep-HPLC). Thereby, (R, Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol (Baicalein-2204, 12 mg) was obtained as a yellow solid. $^1$H NMR (DMSO-d$_6$, 400 MHz) δ (ppm) 2.91 (m, 7H), 3.35 (m, 11H), 3.80 (m, 3H), 3.96 (t, J=8 Hz, 2H), 4.08 (t, J=8 Hz, 2H), 6.32 (dd, J=4 Hz and 4 Hz, 1H), 6.37 (s, 1H), 6.47 (s, 1H), 6.76 (d, J=12 Hz, 2H), 7.25 (m, 10H), 7.58 (t, J=4 Hz, 3H), 7.99 (d, J=8 Hz, 2H), 8.42 (s, 1H); ESI-MS Calcd m/z for $C_{46}H_{50}N_2O_{10}$ [M+H]$^+$ 791.20 Found 790.91

Example 10: Preparation of E)-5-(4-(2-(2-(2-((3,4-bis(benzyloxy)benzyl)amino)ethoxy)ethoxy)ethoxy)styryl)benzene-1,3-diol (Resveratrol-1105)

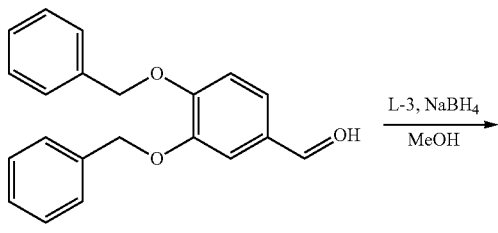

1101

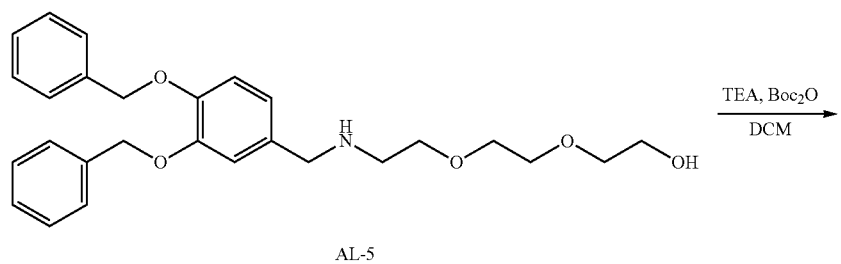

AL-5

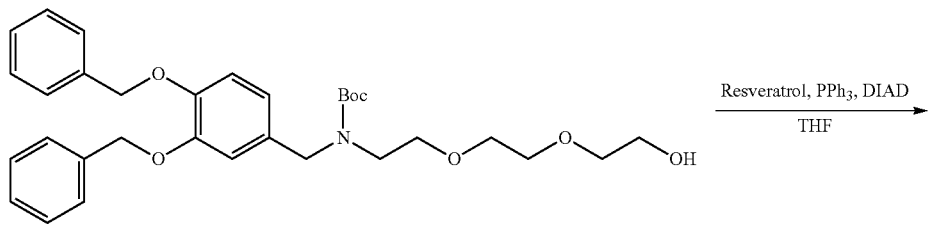

AL-6

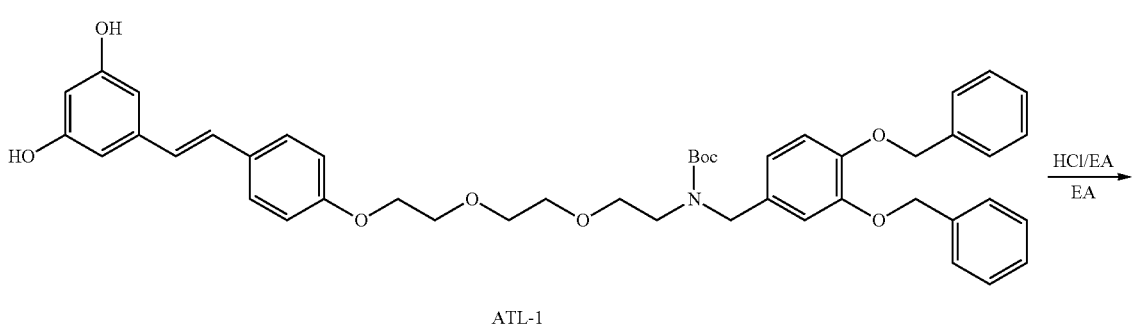

ATL-1

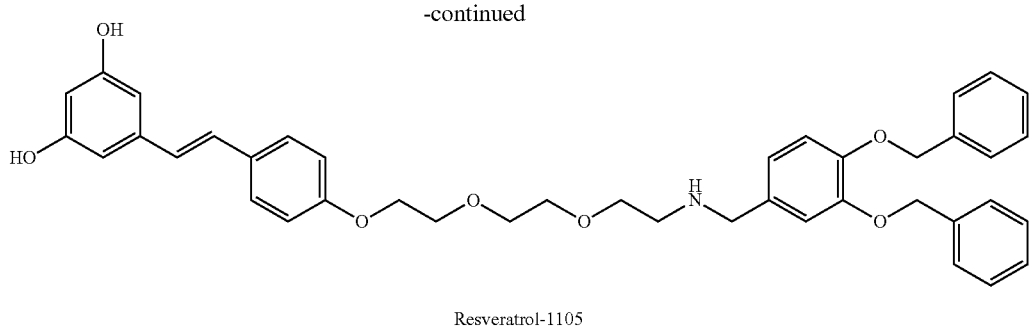

Resveratrol-1105

Step 1) Preparation of 2-(2-(2-((3,4-bis(benzyloxy)benzyl)amino)ethoxy)ethoxy)ethan-1-ol (AL-5)

3,4-Bis(benzyloxy)benzaldehyde (1101, 25 g, 78.6 mmol) was dissolved in methanol (MeOH, 250 mL), and then 2-(2-(2-aminoethoxy)ethoxy)ethanol (L-3, 11.7 g, 78.6 mmol) was added thereto. The mixture was stirred at 65° C. for about 6 hours. After cooling to room temperature, sodium borohydride (NaBH$_4$, 3 g, 78.6 mmol) was further added and then stirred at 50° C. overnight. Water was added to the reaction solution to complete the reaction, and the compound was extracted with ethyl acetate (EtOAc, 50 mL×3). The extracted compound was washed with brine, and the remaining water was removed with sodium sulfate. After filtering, the solution was concentrated and the concentrated solution was purified by column chromatography using silica gel (methylene chloride/methanol=20:1). Thereby, 2-(2-(2-((3,4-bis(benzyloxy)benzyl)amino)ethoxy)ethoxy)ethan-1-ol (AL-5, 13 g) was obtained as a yellow liquid. $^1$H NMR (DMSO-d$_6$, 400 MHz) δ (ppm) 7.46-7.30 (m, 10H), 7.06 (d, J=1.6 Hz, 1H), 6.97 (d, J=8 Hz, 1H), 6.82 (d, J=1.2 Hz, 1H), 5.10 (d, J=4 Hz, 4H), 3.61 (s, 2H), 3.50-3.39 (m, 11H), 2.58 (t, J=6 Hz, 2H) ESI-MS Calcd m/z for C$_{27}$H$_{33}$N$_5$O$_5$ [M+H]$^+$ 452.10 Found 451.56

Step 2) Preparation of tert-butyl (3,4-bis(benzyloxy)benzyl) (2-(2-(2-hydroxyethoxy)ethoxy)ethyl)carbamate (AL-6)

2-(2-(2-((3,4-Bis(benzyloxy)benzyl)amino)ethoxy)ethoxy)ethan-1-ol (AL-5, 500 mg, 1.11 mmol) was dissolved in methylene chloride (DCM, 6 mL), and then triethylamine (TEA, 168 mg, 1.66 mmol) and di-tert-butyl dicarbonate (Boc$_2$O, 290 mg, 1.33 mmol) were added thereto. The mixture was stirred at room temperature for about 4 hours. When the reaction was completed, the reaction solution was filtered and then concentrated. The concentrated solution was purified by column chromatography using silica gel (ethyl acetate/petroleum ether=1:5 to 1:1). Thereby, colorless tert-butyl (3,4-bis(benzyloxy)benzyl) (2-(2-(2-hydroxyethoxy)ethoxy)ethyl)carbamate (AL-6, 520 mg) was obtained.

Step 3) Preparation of tert-butyl (E)-(3,4-bis(benzyloxy)benzyl) (2-(2-(2-(4-(3,5-dihydroxystyryl)phenoxy)ethoxy)ethoxy)ethyl)carbamate (ATL-1)

Tert-butyl (3,4-bis(benzyloxy)benzyl) (2-(2-(2-hydroxyethoxy)ethoxy)ethyl)carbamate (AL-6, 300 mg, 0.54 g) was dissolved in tetrahydrofuran (THF, 5 mL), and then resveratrol (149 mg, 0.65 mmol), triphenylphosphine (PPh$_3$, 214 mg, 0.82 mmol) and diisopropyl azodicarboxylate DIAD (165 mg, 0.82 mmol) were added thereto. The mixture was stirred at 65° C. for about 16 hours. After the reaction was completed, the reaction solution was filtered and then concentrated. The concentrated solution was purified by column chromatography using silica gel (methylene chloride/methanol=100:1 to 50:1). Thereby, tert-butyl (E)-(3,4-bis(benzyloxy)benzyl) (2-(2-(2-(4-(3,5-dihydroxystyryl)phenoxy)ethoxy)ethoxy)ethyl)carbamate (ATL-1, 200 mg) was obtained as a yellow solid.

Step 4) Preparation of E)-5-(4-(2-(2-(2-((3,4-bis(benzyloxy)benzyl)amino)ethoxy)ethoxy)ethoxy)styryl)benzene-1,3-diol (Resveratrol-1105)

Tert-butyl (E)-(3,4-bis(benzyloxy)benzyl) (2-(2-(2-(4-(3,5-dihydroxystyryl)phenoxy)ethoxy)ethoxy)ethyl)carbamate (ATL-1, 200 mg) was dissolved in ethyl acetate (EA, 4 mL), and then hydrochloric acid (g)/ethyl acetate (1 mL) was added thereto. The mixture was stirred at room temperature for about 2 hours. After the reaction was completed, the reaction solution was filtered and then concentrated. The concentrated solution was purified by high resolution liquid chromatography (Prep-HPLC). Thereby, E)-5-(4-(2-(2-(2-((3,4-bis(benzyloxy)benzyl)amino)ethoxy)ethoxy)ethoxy)styryl)benzene-1,3-diol (Resveratrol-1105, 15 mg) was obtained as a white solid. $^1$H NMR (DMSO-d$_6$, 400 MHz) δ (ppm) 2.58 (t, J=4 Hz, 2H), 3.45 (t, J=4 Hz, 2H), 3.51 (m, 2H), 3.57 (m, 4H), 3.73 (m, 2H), 4.06 (m, 2H), 5.07 (m, 4H), 6.12 (m, 1H), 6.40 (m, 2H), 6.90 (m, 7H), 7.39 (m, 12H), 9.20 (s, 2H); ESI-MS Calcd m/z for C$_{41}$H$_{43}$NO$_7$ [M+H]$^+$ 662.10 Found 661.80

Example 11: Preparation of (R)-2-(4-(benzo[d]thiazol-2-yl)phenyl)-14-(3,4-bis(benzyloxy)phenoxy)-5,8-dioxa-2,11-diazatetradecane-13-ol (BTA-1-1104)

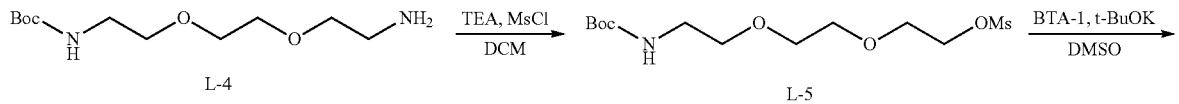

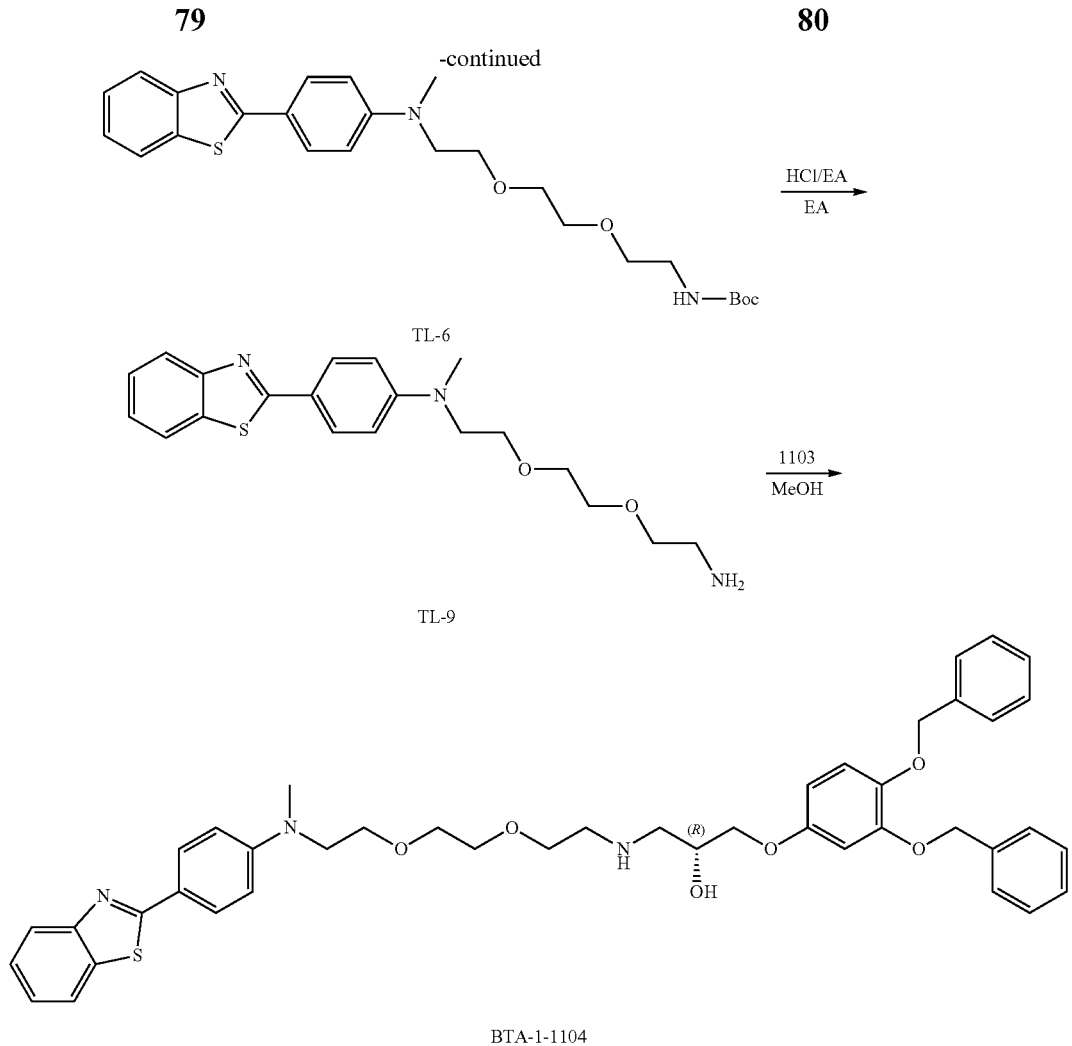

Step 1) Preparation of 2,2-dimethyl-4-oxo-3,8,11-trioxa-5-azatridecane-13-yl-methanesulfonate (L-5)

Tert-butyl (2-(2-(2-hydroxyethoxy)ethoxy)ethyl)carbamate (L-4, 1 g, 4.0 mmol) was dissolved in methylene chloride (DCM, 15 mL), and then triethylamine (TEA, 0.486 g, 4.8 mmol) and methanesulfonyl chloride (MsCl, 0.504 g, 4.4 mmol) were added thereto. The mixture was stirred at room temperature for about 4 hours. When the reaction was completed, the compound was extracted, filtered and then concentrated. The concentrated solution was purified by column chromatography using silica gel (ethyl acetate/petroleum ether=1:5 to 1:1). Thereby, 2,2-dimethyl-4-oxo-3,8,11-trioxa-5-azatridecane-13-yl-methanesulfonate (L-5, 1 g) was obtained as a colorless liquid.

Step 2) Preparation of tert-butyl (2-(2-(2-((4-(benzo[d]thiazol-2-yl)phenyl) (methyl)amino)ethoxy)ethoxy)ethyl)carbamate (TL-8)

2,2-Dimethyl-4-oxo-3,8,11-trioxa-5-azatridecane-13-yl-methanesulfonate (L-5, 300 mg, 0.92 mmol) was dissolved in dimethyl sulfoxide (DMSO, 5 mL), and then 2-(4'-methylaminophenyl)benzothiazole (BTA-1, 220 mg, 0.92 mmol) and potassium tert-butoxide (t-BuOK, 154 mg, 1.37 mmol) were added thereto. The mixture was stirred at 120° C. for about 16 hours. When the reaction was completed, the reaction solution was filtered and then concentrated. The concentrated solution was purified by preparative high performance liquid chromatography (Prep-HPLC). Thereby, tert-butyl (2-(2-(2-((4-(benzo[d]thiazol-2-yl)phenyl) (methyl)amino)ethoxy)ethoxy)ethyl)carbamate (TL-8, 180 mg) was obtained as a yellow liquid.

Step 3) Preparation of N-(2-(2-(2-aminoethoxy)ethoxy)ethyl)-4-(benzo[d]thiazol-2-yl)-N-methylaniline (TL-9)

Tert-butyl (2-(2-(2-((4-(benzo[d]thiazol-2-yl)phenyl)(methyl)amino)ethoxy)ethoxy)ethyl)carbamate (TL-8, 180 mg, 0.38 mmol) was dissolved in ethyl acetate (EA, 4 mL), and then hydrochloric acid (g)/ethyl acetate (1 mL) was added thereto. The mixture was stirred at room temperature for 2 hours. When the reaction was completed, the compound was extracted, filtered and then concentrated. Thereby, N-(2-(2-(2-aminoethoxy)ethoxy)ethyl)-4-(benzo[d]thiazol-2-yl)-N-methylaniline (TL-9, 120 mg) was obtained as a yellow solid.

Step 4) Preparation of (R)-2-(4-(benzo[d]thiazol-2-yl)phenyl)-14-(3,4-bis(benzyloxy)phenoxy)-5,8-dioxa-2,11-diazatetradecane-13-ol (BTA-1-1104)

N-(2-(2-(2-aminoethoxy)ethoxy)ethyl)-4-(benzo[d]thiazol-2-yl)-N-methylaniline (TL-9, 120 mg, 0.33 mmol) was dissolved in methanol (MeOH, 2 mL), and then (R)-2-((3,4-bis(benzyloxy)phenoxy)methyl)oxirane (1103, 117 mg, 0.33 mmol) was added thereto. The mixture was stirred at 65° C. for about 16 hours. When the reaction was completed, the compound was extracted, filtered and then concentrated. The concentrated solution was purified by preparative high performance liquid chromatography (Prep-HPLC). Thereby, (R)-2-(4-(benzo[d]thiazol-2-yl)phenyl)-14-(3,4-bis(benzyloxy)phenoxy)-5,8-dioxa-2,11-diazatetradecane-13-ol (BTA-1-1104, 8 mg) was obtained as a yellow solid. $^1$H NMR (DMSO-$d_6$, 400 MHz) δ (ppm) 1.15 (d, J=8 Hz, 3H), 1.23 (s, 1H), 2.67 (m, 4H), 3.50 (m, 11H), 3.81 (m, 4H), 5.01 (s, 2H), 5.10 (s, 2H), 6.27 (d, J=8 Hz, 1H), 6.41 (d, J=8 Hz, 1H), 6.69 (m, 3H), 6.91 (d, J=12 Hz, 1H), 7.38 (m, 12H), 7.79 (d, J=8 Hz, 2H), 7.89 (d, J=8 Hz, 1H), 7.90 (d, J=8 Hz, 1H), 8.40 (s, 1H); ESI-MS Calcd m/z for $C_{43}H_{47}N_3O_6S$ [M+H]$^+$ 734.10 Found 733.92

Example 12: Preparation of (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione (Curcumin-1204)

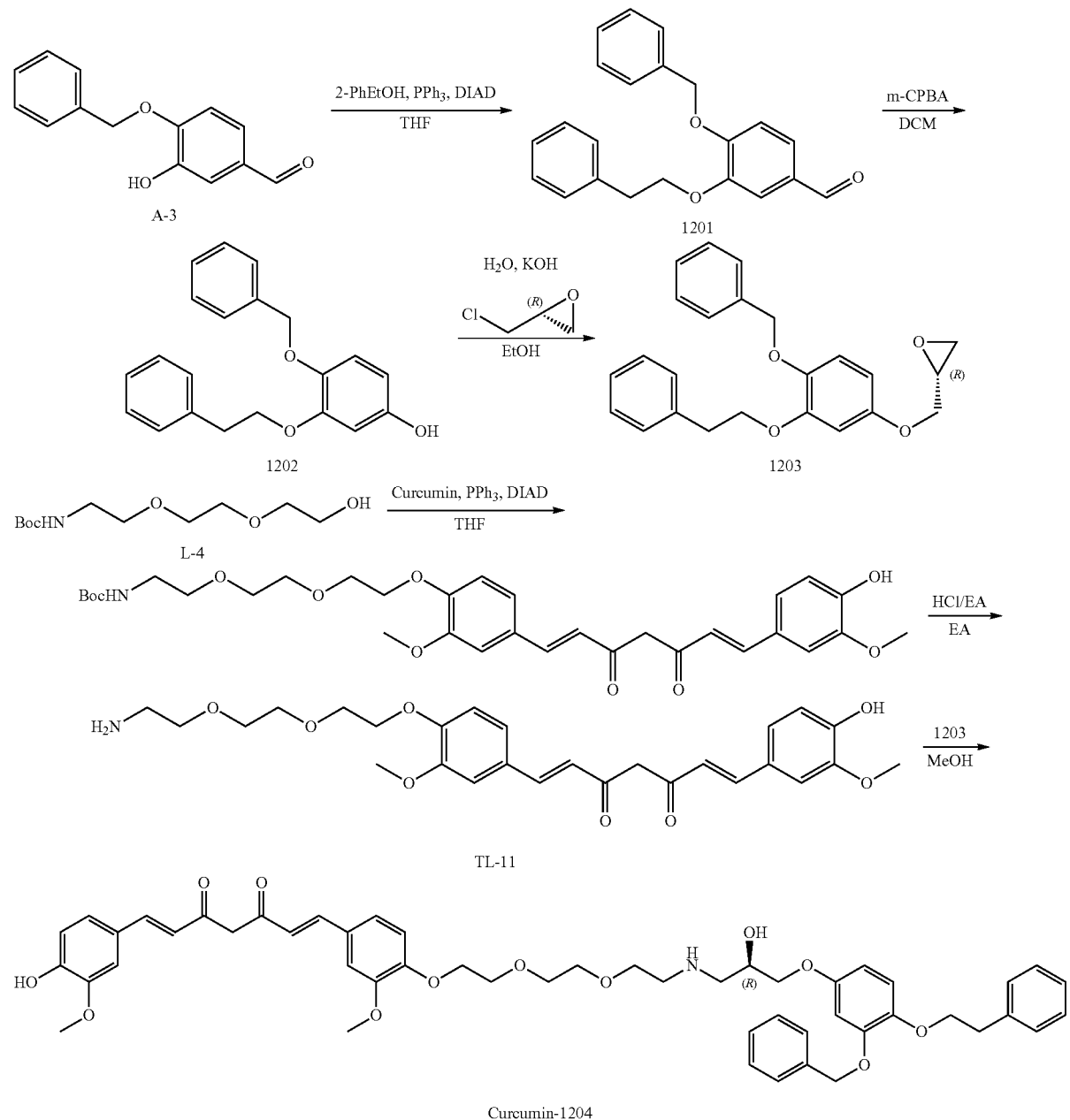

Curcumin-1204

Step 1) Preparation of 4-(benzyloxy)-3-phenethoxybenzaldehyde (1201)

4-(Benzyloxy)-3-hydroxybenzaldehyde (A-3, 50 g, 219 mmol) was dissolved in tetrahydrofuran (THF, 1 L), and then 2-phenylethanol (32.1 g, 263 mmol), triphenylphosphine (PPh$_3$, 86.2 g, 329 mmol) and diisopropyl azodicarboxylate (DIAD, 66.4 g, 329 mmol) were added thereto. The mixture was stirred at 65° C. for about 16 hours. When the reaction was completed, the compound was extracted, filtered and concentrated. The concentrated solution was purified by column chromatography using silica gel (ethyl acetate/petroleum ether=1:15 to 1:10). Thereby, 4-(benzyloxy)-3-phenethoxybenzaldehyde (1201, 25 g) was obtained as a white solid.

$^1$H NMR (DMSO-d$_6$, 400 MHz) δ (ppm) 9.82 (s, 1H), 7.52 (dd, J=8 Hz and 2 Hz, 1H), 7.43-7.40 (m, 5H), 7.37-7.32 (m, 3H), 7.28-7.21 (m, 4H), 5.21 (s, 2H), 4.26 (t, J=6.4 Hz, 2H), 3.05 (t, J=6.4 Hz, 2H)

Step 2) Preparation of 4-(benzyloxy)-3-phenethoxyphenol (1202)

4-(benzyloxy)-3-phenethoxybenzaldehyde (1201, 50 g, 150 mmol) was dissolved in methylene chloride (DCM, 500 mL), and then meta-chloroperoxybenzoic acid (m-CPBA, 39 g, 225 mmol) was added thereto. The mixture was stirred at room temperature for about 16 hours. When the reaction was completed, the compound was extracted, filtered and concentrated. The concentrated solution was purified by column chromatography using silica gel (ethyl acetate/petroleum ether=1:15 to 1:5). Thereby, 4-(benzyloxy)-3-phenethoxyphenol (1202, 32 mg) was obtained as a white solid. $^1$H NMR (DMSO-d$_6$, 400 MHz) δ (ppm) 9.00 (s, 1H), 7.36-7.20 (m, 10H), 6.78 (d, J=8 Hz, 1H), 6.43 (d, J=2.8 Hz, 1H), 6.22 (dd, J=8 Hz and 2.8 Hz, 1H), 4.86 (s, 2H), 4.13 (t, J=6.8 Hz, 2H), 3.02 (t, J=6.4 Hz, 2H)

Step 3) Preparation of (R)-2-((4-(benzyloxy)-3-phenethoxyphenoxy)methyl)oxirane (1203)

4-(Benzyloxy)-3-phenethoxyphenol (1203, 40 g, 64 mmol) was dissolved in ethanol (EtOH, 800 mL), and then water (40 mL) and potassium hydroxide (KOH, 8.2 g, 146 mmol) were added thereto. Then, (R)-2-(chloromethyl)oxirane (34.6 g, 374 mmol) was added and further stirred at room temperature for 16 hours. Water (1600 mL) was added to the reaction solution to complete the reaction, and extracted with ethyl acetate (1600 mL×3). The extracted organic solvent layer was washed with brine, and the remaining water was removed with sodium sulfate. The resulting material was filtered to remove impurities, and concentrated. The concentrated solution was purified by column chromatography using silica gel (ethyl acetate/petroleum ether=1:15 to 1:10). Thereby, (R)-2-((4-(benzyloxy)-3-phenethoxyphenoxy)methyl)oxirane (1203, 34 g) was obtained as a white solid. $^1$H NMR (DMSO-d$_6$, 400 MHz) δ (ppm) 7.38-7.20 (m, 10H), 6.90 (d, J=8.8 Hz, 1H), 6.64 (d, J=2 Hz, 1H), 6.41 (dd, J=8.8 Hz and 2.8 Hz, 1H), 4.93 (s, 2H), 4.25-4.17 (m, 3H), 3.75 (dd, J=11.2 Hz and 6.4 Hz, 1H), 3.28 (m, 1H), 3.03 (t, J=6.8 Hz, 2H), 2.81 (t, J=4.4 Hz, 1H), 2.67 (dd, J=5.2 Hz and 2.8 Hz, 1H)

Step 4) Preparation of tert-butyl (2-(2-(2-(4-((1E, 6E)-7-(4-hydroxy-3-methoxyphenyl)-3,5-dioxohepta-1,6-dien-1-yl)-2-methoxyphenoxy)ethoxy)ethoxy)ethyl)carbamate (TL-10)

Tert-butyl (2-(2-(2-hydroxyethoxy)ethoxy)ethyl)carbamate (L-4, 300 mg, 1.2 mmol) was dissolved in tetrahydrofuran (THF, 5 mL), and then curcumin (442 mg, 1.2 mmol), triphenylphosphine (PPh$_3$, 377 mg, 1.44 mmol) and diisopropyl azodicarboxylate (DIAD, 291 mg, 1.44 mmol) were added thereto. The mixture was stirred at 65° C. for about 16 hours. When the reaction was completed, the compound was extracted, filtered and concentrated. The concentrated solution was purified by column chromatography using silica gel (methylene chloride/methanol=100:1 to 50:1). Thereby, tert-butyl (2-(2-(2-(4-((1E,6E)-7-(4-hydroxy-3-methoxyphenyl)-3,5-dioxohepta-1,6-dien-1-yl)-2-methoxyphenoxy)ethoxy)ethoxy)ethyl)carbamate (TL-10, 200 mg) was obtained as a yellow solid. $^1$H NMR (DMSO-d$_6$, 400 MHz) δ (ppm) 9.87 (brs, 1H), 7.57 (dd, J=16 Hz and 4 Hz, 2H), 3.34 (dd, J=12 Hz and 1.6 Hz, 2H), 7.24 (dd, J=8 Hz and 1.2 Hz, 1H), 7.16 (dd, J=8 Hz and 1.2 Hz, 1H), 7.02 (d, J=8 Hz, 1H), 6.85-6.74 (m, 4H), 6.08 (s, 1H), 4.13 (t, J=4 Hz, 2H), 3.83 (m, 6H), 3.75 (t, J=4 Hz, 2H), 3.59 (q, J=4 Hz, 2H), 3.52 (q, J=4 Hz, 2H), 3.40-3.38 (m, 4H), 3.06 (q, J=6 Hz, 2H), 1.36 (s, 9H)

Step 5) Preparation of (1E,6E)-1-(4-(2-(2-(2-aminoethoxy)ethoxy)ethoxy)-3-methoxyphenyl)-7-(4-hydroxy-3-methoxyphenyl)hepta-1,6-diene-3,5-dione (TL-11)

Tert-butyl (2-(2-(2-(4-((1E,6E)-7-(4-hydroxy-3-methoxyphenyl)-3,5-dioxohepta-1,6-dien-1-yl)-2-methoxyphenoxy)ethoxy)ethoxy)ethyl)carbamate (TL-10, 200 mg, 0.33 mmol) was dissolved in ethyl acetate (EA, 4 mL), and then hydrochloric acid (g)/ethyl acetate (1 mL) was added thereto. The mixture was stirred at room temperature for about 2 hours. After the reaction was completed, the compound was extracted, filtered and then concentrated. Thereby, (1E,6E)-1-(4-(2-(2-(2-aminoethoxy)ethoxy)ethoxy)-3-methoxyphenyl)-7-(4-hydroxy-3-methoxyphenyl)hepta-1,6-diene-3,5-dione (TL-11, 120 mg) was obtained as a yellow solid.

Step 6) Preparation of (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione (Curcumin-1204)

(1E,6E)-1-(4-(2-(2-(2-aminoethoxy)ethoxy)ethoxy)-3-methoxyphenyl)-7-(4-hydroxy-3-methoxyphenyl)hepta-1,6-diene-3,5-dione (TL-11, 120 mg, 0.24 mmol) was dissolved in methanol (MeOH, 2 mL), and then (R)-2-((4-(benzyloxy)-3-phenethoxyphenoxy)methyl)oxirane (1203, 90 mg, 0.24 mmol) was added thereto. The mixture was stirred at 65° C. for about 16 hours. When the reaction was completed, the compound was extracted, filtered and then concentrated. The concentrated solution was purified by preparative high performance liquid chromatography (Prep-HPLC). Thereby, (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione (Curcumin-1204, 12 mg) was obtained as a yellow solid. $^1$H NMR (DMSO-d$_6$+D$_2$O, 400 MHz) δ (ppm) 2.81 (m, 1H), 2.92 (m, 3H), 3.00 (t, J=6.4 Hz, 2H), 3.56 (m, 9H), 3.80 (m, 9H), 3.97 (b, 2H), 4.09 (m, 2H), 4.14 (t, J=6.4 Hz, 2H), 4.88 (s, 2H), 6.36 (dd, J=8.8 Hz and 2.8 Hz, 1H), 6.56 (d, J=2.8 Hz, 1H), 6.79 (m, 4H), 6.97 (d, J=8 Hz, 1H), 7.23 (m, 14H), 7.53 (d, J=16 Hz, 2H), 8.33 (s, 1H); ESI-MS Calcd m/z for C$_{51}$H$_{57}$NO$_{12}$ [M]$^+$876.10 Found 876.01

Example 13: Preparation of (R)-1-(3-phenethoxyphenoxy)-3-((2-(2-(2-((6-(trifluoromethoxy))benzo[d]thiazol-2-yl)amino)ethoxy)ethoxy)ethyl) amino) propan-2-ol (Riluzole-204)

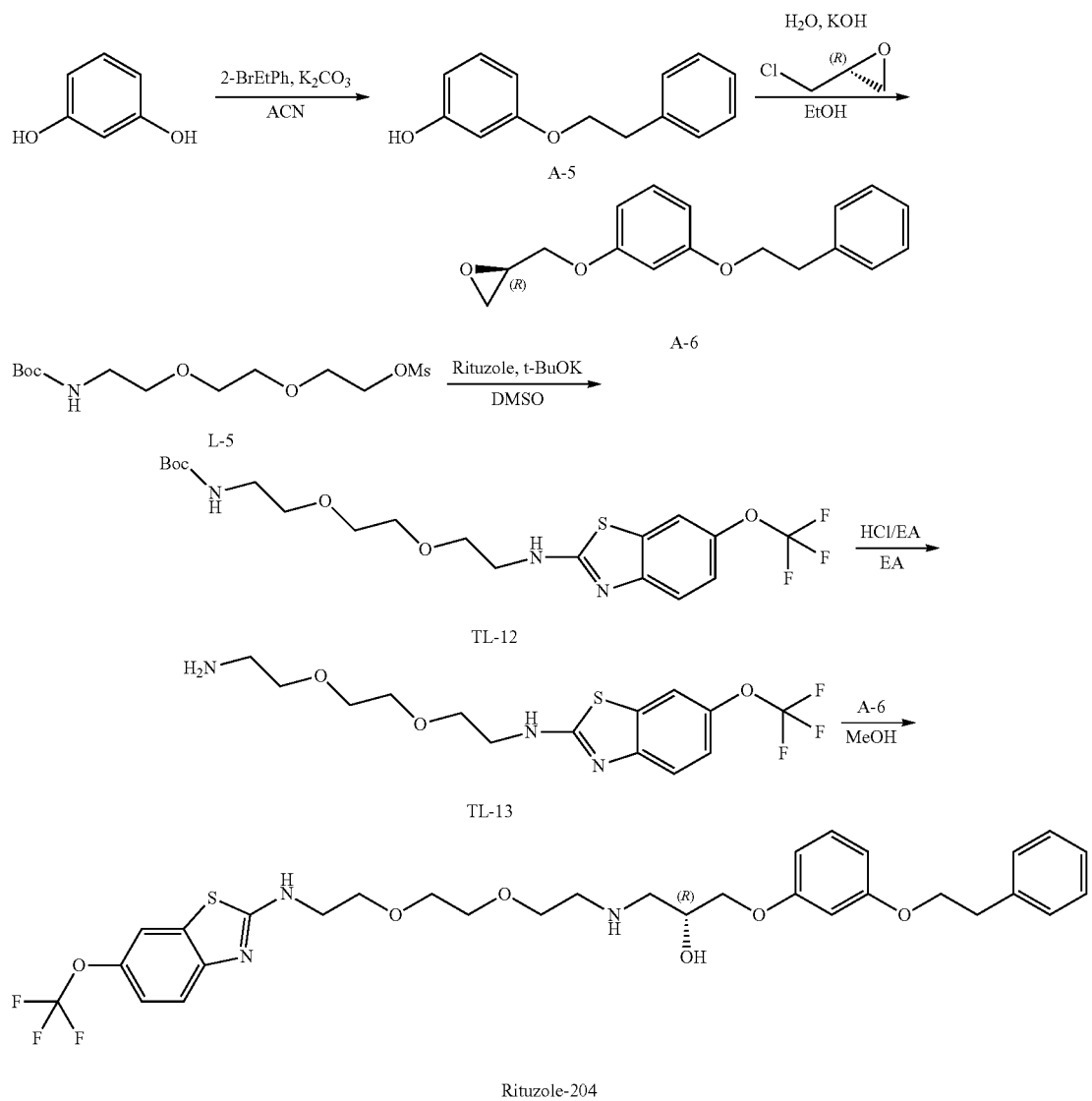

Rituzole-204

Step 1) Preparation of 3-phenethoxyphenol (A-5)

Resorcinol (50 g, 0.45 mol) was dissolved in acetonitrile (ACN, 500 mL), and then potassium carbonate (K₂CO₃, 112.5 g, 0.81 mol) and (2-bromoethyl)benzene (83.2 g, 0.45 mol) were added thereto. The mixture was stirred at 60° C. for about 10 hours. After the reaction was completed, the compound was extracted, filtered and concentrated. The concentrated solution was purified by column chromatography using silica gel (petroleum ether/ethyl acetate=5:1). Thereby, 3-phenethoxyphenol (A-5, 25 g) was obtained as a yellow liquid. $^1$H NMR (CDCl₃, 400 MHz) δ (ppm) 7.31-7.23 (m, 5H), 7.11 (t, J=8 Hz, 1H), 6.50-6.39 (m, 3H), 4.74 (s, 1H), 4.14 (m, 2H), 3.08 (t, J=7.2 Hz, 2H)

Step 2) Preparation of (R)-2-((3-phenethoxyphenoxy)methyl)oxirane (A-6)

3-Phenethoxyphenol (A-5, 25 g, 116.8 mmol) was dissolved in ethanol (EtOH, 500 mL), and then water (25 mL) and potassium hydroxide (KOH, 11.1 g, 278.3 mmol) were added thereto. Then, (R)-2-(chloromethyl)oxirane (64.6 g, 698.8 mmol) was added and then stirred at room temperature for about 16 hours. Water (1000 mL) was added to the reaction solution to complete the reaction, and the compound was extracted with ethyl acetate (500 mL×3). The extracted organic solvent layer was washed with brine, and the remaining water was removed with sodium sulfate. The resulting material was filtered to remove impurities, and concentrated. The concentrated solution was purified by column chromatography using silica gel (ethyl acetate/petroleum ether=1:15 to 1:10). Thereby, (R)-2-((3-phenethoxyphenoxy)methyl)oxirane (A-6, 18 g) was obtained as a yellow liquid. $^1$H NMR (DMSO-d₆, 400 MHz) δ (ppm) 7.32-7.28 (m, 4H), 7.24-7.14 (m, 2H), 6.52 (m, 3H), 4.29 (dd, J=11.2 Hz and 2 Hz, 1H), 4.16 (t, J=6.8 Hz, 2H), 3.79 (m, 1H), 3.34 (s, 1H), 3.01 (t, J=6 Hz, 2H), 2.82 (t, J=4 Hz, 1H), 2.69-2.67 (m, 1H)

Step 3) Preparation of tert-butyl (2-(2-(2-((6-(trifluoromethoxy)benzo) [d]thiazol-2-yl)amino)ethoxy)ethoxy)ethyl)carbamate (TL-12)

2,2-Dimethyl-4-oxo-3,8,11-trioxa-5-azatridecane-13-yl-methanesulfonate (L-5, 300 mg, 0.92 mmol) was dissolved in dimethylsulfoxide (DMSO, 5 mL), and then riluzole (214 mg, 0.92 mmol) and potassium tert-butoxide (t-BuOK, 154 mg, 1.37 mmol) were added thereto. The mixture was stirred at 120° C. for about 16 hours. After the reaction was completed, the compound was extracted, filtered and then concentrated. The concentrated solution was purified by preparative high performance liquid chromatography (Prep-HPLC). Thereby, tert-butyl(2-(2-(2-((6-(trifluoromethoxy)benzo[d]thiazol-2-yl)amino)ethoxy)ethoxy)ethyl)carbamate (TL-12, 180 mg) was obtained as a pale yellow liquid. $^1$H NMR (DMSO-$d_6$, 400 MHz) δ (ppm) 8.27-8.25 (m, 1H), 7.78 (d, J=1.6 Hz, 1H), 7.41 (d, J=8 Hz, 1H), 7.18 (dd, J=8 Hz and 1.6 Hz, 1H), 6.74 (m, 1H), 3.63-3.51 (m, 12H), 3.05 (q, J=6 Hz, 2H), 1.36 (s, 11H)

Step 4) Preparation of N-(2-(2-(2-aminoethoxy)ethoxy)ethyl)-6-(trifluoromethoxy)benzo[d]thiazol-2-amine (TL-13)

Tert-butyl(2-(2-(2-((6-(trifluoromethoxy)benzo[d]thiazol-2-yl)amino)ethoxy)ethoxy)ethyl)carbamate (TL-12, 180 mg, 0.39 mmol) was dissolved in ethyl acetate (EA, 4 mL), and then hydrochloric acid (g)/ethyl acetate (1 mL) was added thereto. The mixture was stirred at room temperature for about 2 hours. When the reaction was completed, the compound was extracted, filtered and concentrated. Thereby, N-(2-(2-(2-aminoethoxy)ethoxy)ethyl)-6-(trifluoromethoxy)benzo[d]thiazol-2-amine (TL-13, 120 mg) was obtained as a yellow solid.

Step 5) Preparation of (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol (Riluzole-204)

N-(2-(2-(2-aminoethoxy)ethoxy)ethyl)-6-(trifluoromethoxy)benzo[d]thiazol-2-amine (TL-13, 120 mg, 0.33 mmol) was dissolved in methanol (MeOH, 2 mL), and then (R)-2-((3-phenethoxyphenoxy)methyl)oxirane (A-6, 89 mg, 0.33 mmol) was added thereto. The mixture was stirred at 65° C. for about 16 hours. After the reaction was completed, the compound was extracted, filtered and concentrated. The concentrated solution was purified by preparative high performance liquid chromatography (Prep-HPLC). Thereby, (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol (Riluzole-204, 15 mg) was obtained as a colorless liquid. $^1$H NMR (400 MHz, DMSO-$d_6$) δ (ppm) 2.60 (m, 4H), 3.00 (t, J=8 Hz, 2H), 3.52 (m, 10H), 3.85 (m, 3H), 4.15 (t, J=8 Hz, 2H), 6.48 (dd, J=12 Hz and 8 Hz, 3H), 7.18 (m, 3H), 7.31 (d, J=4 Hz, 4H), 7.43 (d, J=12 Hz, 1H), 7.75 (s, 1H); ESI-MS Calcd m/z for $C_{31}H_{36}F_3N_3O_6S$ [M+H]$^+$ 636.10 Found 635.70

Example 14. Preparation of Compound A (N-(2-(2-(2-(((R)-3-(3,4-bis(benzyloxy)phenoxy)-2-hydroxypropyl)amino)ethoxy)ethoxy)ethyl)-2-((S)-4-(4-chlorophenyl)-2,3,9-trimethyl-6H-thieno[3,2-f][1,2,4]triazolo[4,3-a][1,4]diazepin-6-yl)acetamide)

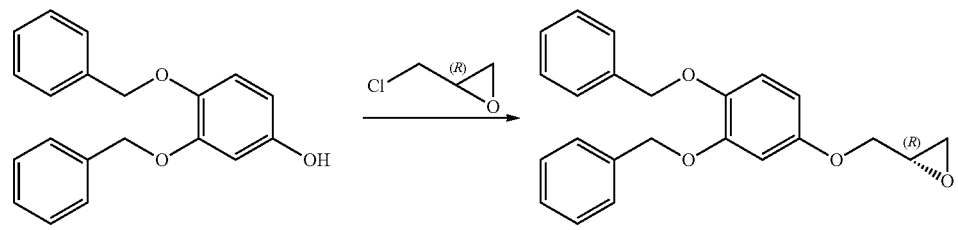

A-4

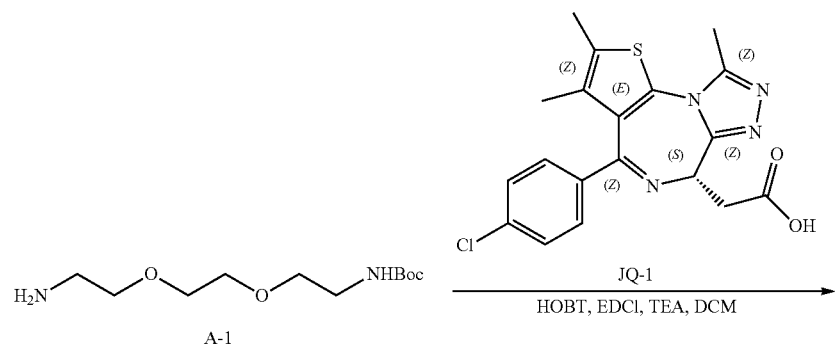

-continued

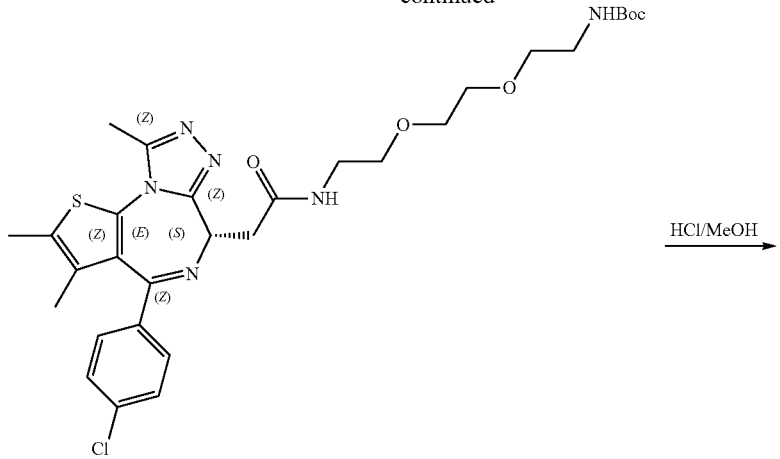

A-2

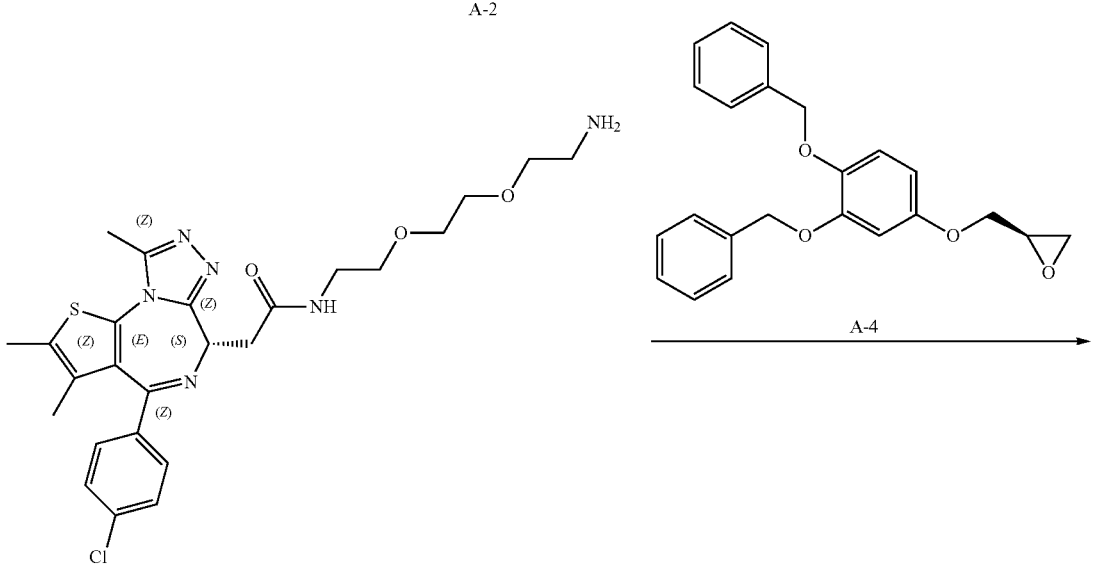

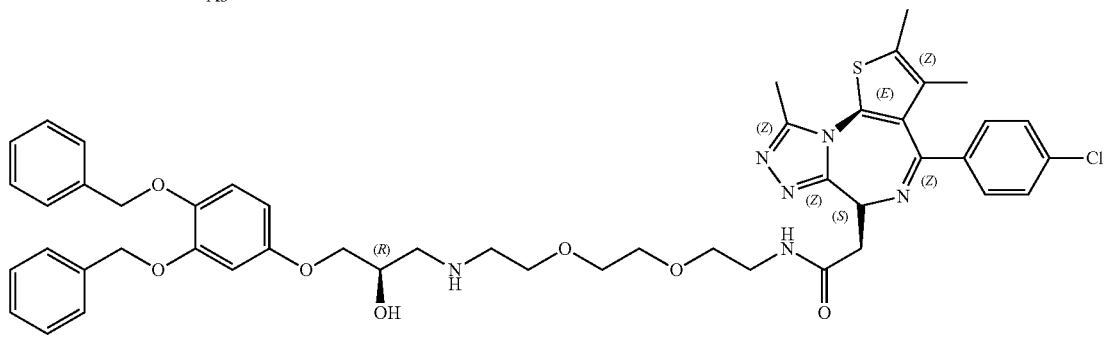

Compound A

Step 1) Synthesis of A-4

To a solution of 3,4-bis(benzyloxy)phenol (62 g, 202 mmol) in EtOH (1000 mL) were added water (40 mL) and KOH (18.8 g, 472 mmol). Then (R)-2-(chloromethyl)oxirane (55.8 g, 606 mmol) was added to the reaction. The resulting mixture was stirred at room temperature for 16 hrs. Then the reaction was quenched by addition water (1800 mL), extracted with EA (600 mL×3). The organic layer was washed with brine, dried over $Na_2SO_4$, filtered and concentrated. The residue was purified by silica gel, eluted with EA/PE (1:15~1:10) to afford A-4 ((R)-2-((3,4-bis(benzyloxy)phenoxy)methyl)oxirane, 32 g) as a white solid.

$^1$H-NMR (DMSO_$d_6$, 400 MHz) δ (ppm) 7.46-7.30 (m, 10H), 6.94 (d, 1H), 6.72 (s, 1H), 6.44 (d, 1H), 5.13 (s, 2H), 5.04 (s, 2H), 4.25-4.22 (m, 1H), 3.76-3.72 (m, 1H), 3.29-3.27 (m, 1H), 2.82 (m, 1H), 2.67 (m, 1H)

Step 2) Synthesis of A-2

To a solution of A-1 (tert-butyl (2-(2-(2-aminoethoxy)ethoxy)ethyl)carbamate, 70 mg, 0.28 mmol), HOBT (40.5 mg, 0.30 mmol), EDCI (57.6 mg, 0.30 mmol) and Et$_3$N (50.5 mg, 0.50 mmol) in DCM (5 mL) was added JQ-1 (CAS No.: 1268524-70-4, 100 mg, 0.25 mmol). The mixture was stirred at room temperature overnight. The above solution was poured into water and extracted with DCM (10 mL×3). The combined organic layers were washed with brine, dried over Na$_2$SO$_4$ and concentrated to give A-2 (tert-butyl (S)-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate, 60 mg, 33.9%) as yellow oil without further purification.

Step 3) Synthesis of A-3

To a solution of A-2 (60 mg, 0.06 mmol) in MeOH (3 mL) was added HCl/MeOH (2N, 2 mL). The mixture was stirred for 4 hrs at r.t. The solution was concentrated and purification by pre-HPLC to give A-3 ((S)—N-(2-(2-(2-aminoethoxy)ethoxy)ethyl)-2-(4-(4-chlorophenyl)-2,3,9-trimethyl-6H-thieno[3,2-f][1,2,4]triazolo[4,3-a][1,4]diazepin-6-yl)acetamide, 17 mg, 53.2%) as yellow oil.

ESI-MS Calcd m/z for $C_{25}H_{31}ClN_6O_3S$ [M+H]$^+$ 532.07 Found 532.90

Step 4) Synthesis of Compound A

To a solution of A-3 (17 mg, 0.03 mmol) in MeOH (5 mL) was added A-4 (14 mg, 0.03 mmol). The mixture was stirred at 50° C. overnight. The solution was concentrated and purification by pre-HPLC to give Compound A (N-(2-(2-(2-(((R)-3-(3,4-bis(benzyloxy)phenoxy)-2-hydroxypropyl)amino)ethoxy)ethoxy)ethyl)-2-((S)-4-(4-chlorophenyl)-2,3,9-trimethyl-6H-thieno[3,2-f][1,2,4]triazolo[4,3-a][1,4]diazepin-6-yl)acetamide, 8 mg, 29.8%) as white solid.

$^1$H-NMR (DMSO+D$_2$O, 400 MHz) δ (ppm) 8.35 (s, 1H), 7.49-7.30 (m, 14H), 6.93 (d, J=8.8 Hz, 1H), 6.66 (d, J=2.4 Hz, 1H), 6.41 (dd, J=8.8, 28 Hz, 1H), 5.10 (s, 2H), 5.02 (s, 2H), 4.51 (t, J=7.6 Hz, 1H), 3.84-3.81 (m, 1H), 3.60 (m, 2H), 3.56 (s, 6H), 3.47 (t, J=6 Hz, 2H), 3.29-3.23 (m, 4H), 2.88-2.85 (m, 3H), 2.75-2.71 (m, 1H), 2.59 (s, 3H), 2.40 (s, 3H), 1.61 (s, 3H); ESI-MS Calcd m/z for $C_{48}H_{53}ClN_6O_7S$ [M+H]$^+$ 894.50 Found 894.80

Example 15. Preparation of Compound B ((1s,4s)-N-(2-(2-(2-((3,4-bis(benzyloxy)benzyl)amino)ethoxy)ethoxy)ethyl)-4-cyano-4-(3-(cyclopentyloxy)-4-methoxyphenyl)cyclohexane-1-carboxamide)

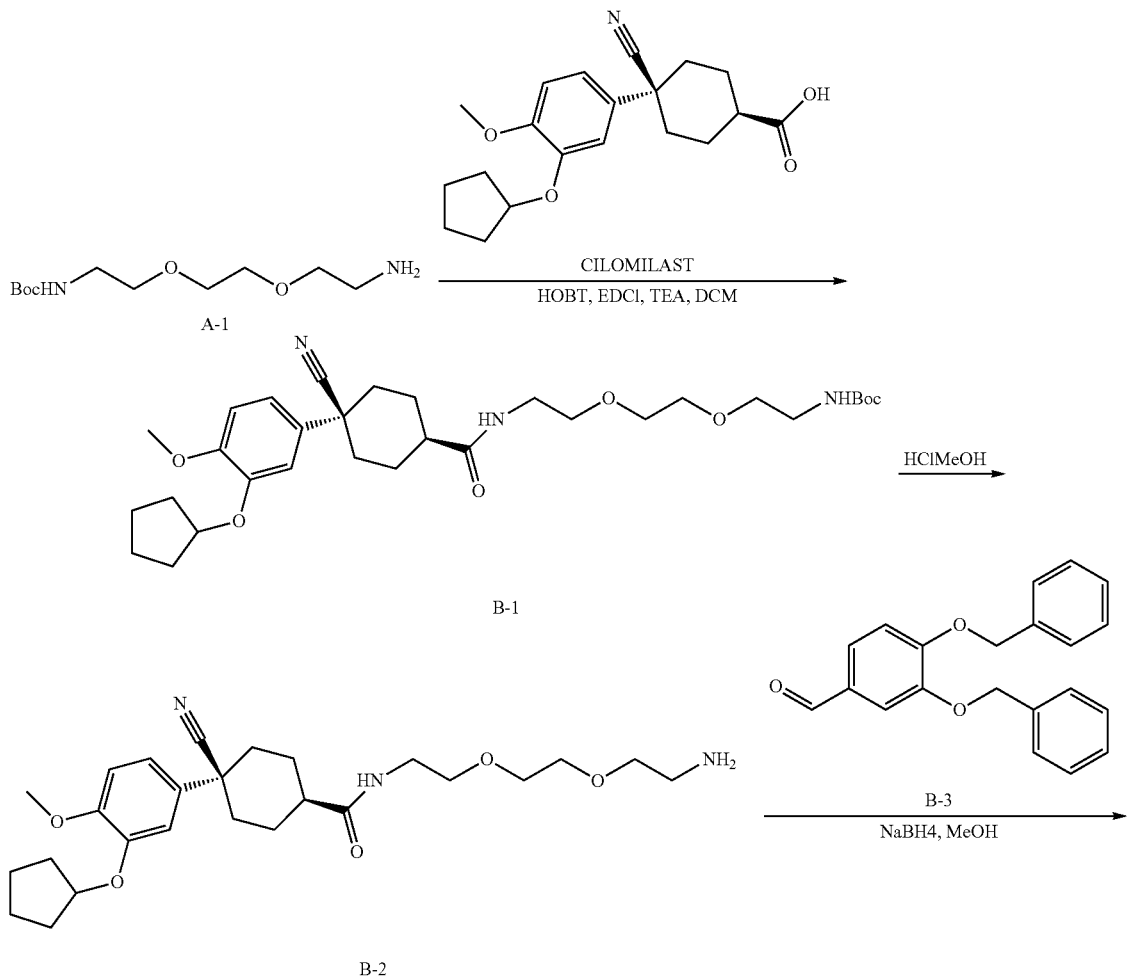

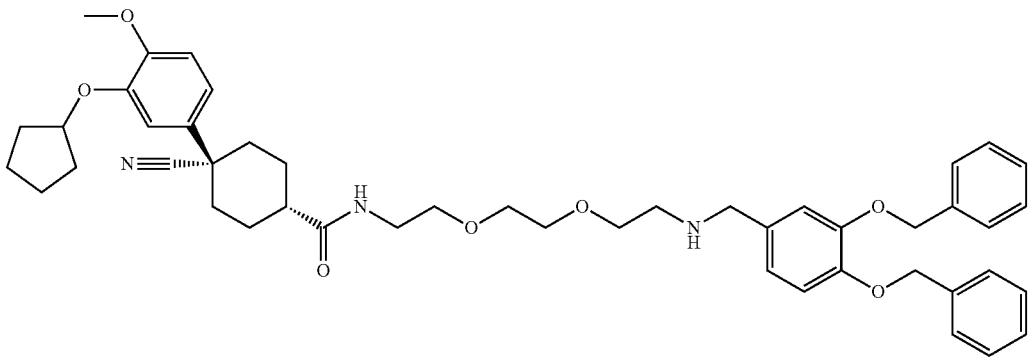

Compound B

Step 1) Synthesis of B-1

To a solution of A-1 (tert-butyl (2-(2-(2-aminoethoxy)ethoxy)ethyl)carbamate, 87 mg, 0.35 mmol), HOBT (47.2 mg, 0.35 mmol), EDCI (67.2 mg, 0.35 mmol) and Et$_3$N (70.7 mg, 0.70 mmol) in DCM (5 mL) was added CILOMLAST (CAS No.: 153259-65-5, 100 mg, 0.29 mmol). The mixture was stirred at room temperature overnight. The above solution was poured into water and extracted with DCM. The combined organic layers were washed with brine, dried over Na$_2$SO$_4$ and concentrated to give B-1 (tert-butyl (2-(2-(2-((1s,4s)-4-cyano-4-(3-(cyclopentyloxy)-4-methoxyphenyl)cyclohexane-1-carboxamido)ethoxy)ethoxy)ethyl)carbamate, 70 mg, 34.9%) as yellow oil without further purification.

Step 2) Synthesis of B-2

To a solution of B-1 (70 mg, 0.12 mmol) in MeOH (3 mL) was added HCl/MeOH (2N, 2 mL). The mixture was stirred for 5 hours at r.t. The solution was concentrated and purification by pre-HPLC to give B-2 ((1s,4s)-N-(2-(2-(2-aminoethoxy)ethoxy)ethyl)-4-cyano-4-(3-(cyclopentyloxy)-4-methoxyphenyl)cyclohexane-1-carboxamide, 19 mg, 33.4%) as yellow oil.

Step 3) Synthesis of Compound B

To a solution of B-2 (19 mg, 0.04 mmol) in MeOH (5 mL) was added B-3 (3,4-bis(benzyloxy)benzaldehyde, 15.3 mg, 0.05 mmol). The mixture was stirred for 5 hours at 65° C. NaBH$_4$ (2 mg, 0.05 mmol) was added at r.t. The reaction mixture was stirred 6 hours at r.t. The solution was concentrated and purification by pre-HPLC to give Compound B ((1s,4s)-N-(2-(2-(2-((3,4-bis(benzyloxy)benzyl)amino)ethoxy)ethoxy)ethyl)-4-cyano-4-(3-(cyclopentyloxy)-4-methoxyphenyl)cyclohexane-1-carboxamide, 10 mg, 32.2%) as yellow oil.

$^1$H-NMR (CD$_3$OD, 400 MHz) δ (ppm) 7.45 (t, J=7.6 Hz, 5H), 7.36-7.31 (m, 5H), 7.14 (s, 1H), 7.03 (t, J=5.2 Hz, 3H), 6.97-6.95 (m, 2H), 5.15 (s, 2H), 5.12 (s, 2H), 3.91 (s, 2H), 3.81 (s, 3H), 3.68-3.65 (m, 6H), 3.56 (t, J=5.2 Hz, 2H), 3.37 (t, J=5.2 Hz, 2H), 2.92-2.90 (m, 2H), 2.20-2.15 (m, 3H), 1.96-1.82 (m, 15H); ESI-MS Calcd m/z for C$_{47}$H$_{57}$N$_3$O$_7$ [M+H]$^+$ 776.40 Found 776.00

Example 16. Preparation of Compound C ((R)-1-(3-phenethoxyphenoxy)-3-((2-(2-(2-(4-(4-(3-(quinolin-5-yl)pyrazolo[1,5-a]pyrimidin-6-yl)phenyl)piperazin-1-yl)ethoxy)ethoxy)ethyl)amino)propan-2-ol)

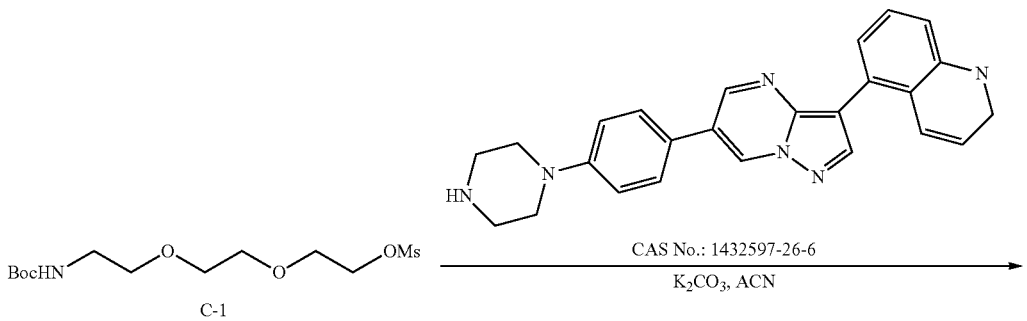

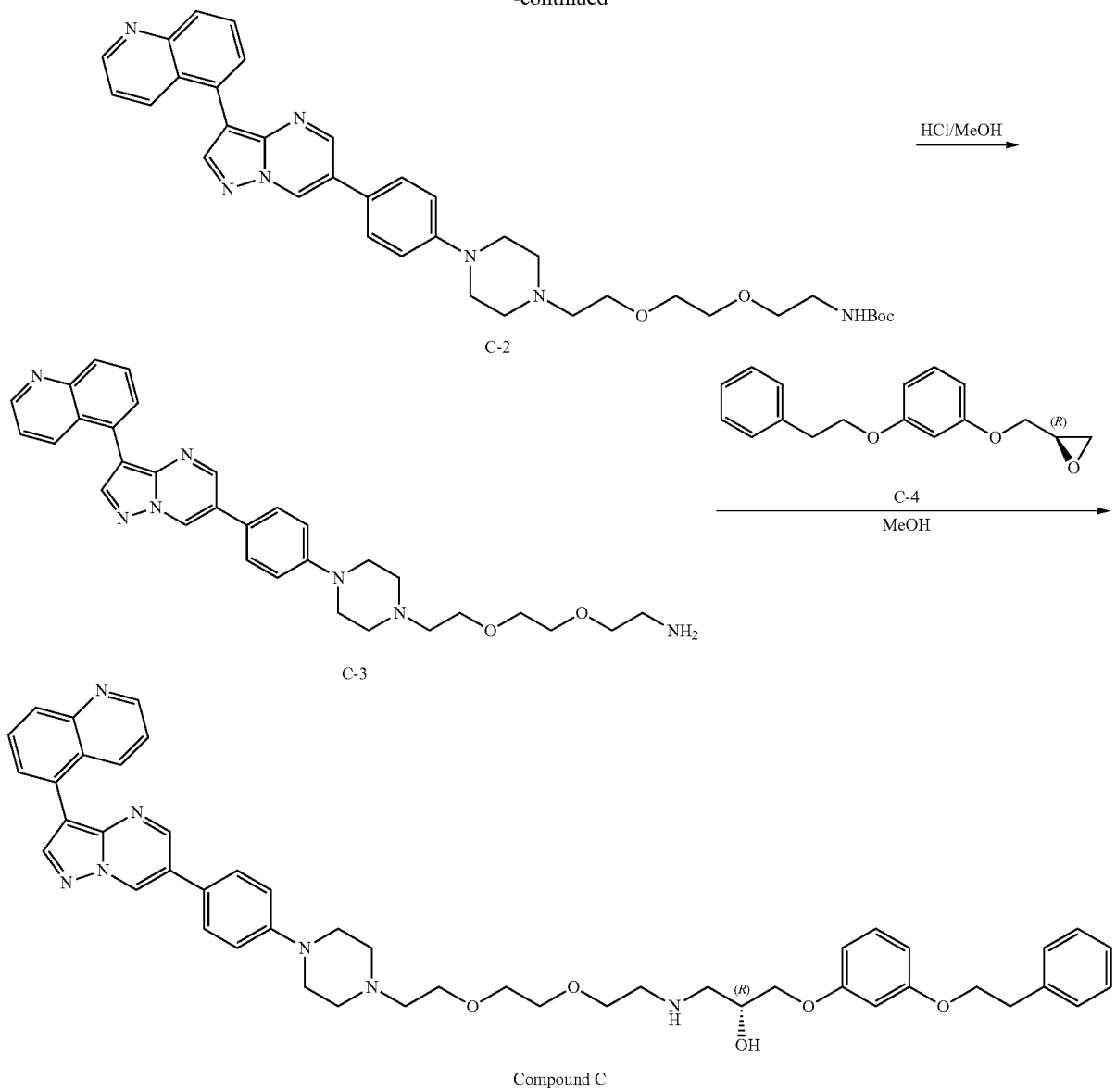

Compound C

Step 1) Synthesis of C-2

To a solution of 5-(6-(4-(piperazin-1-yl)phenyl)pyrazolo[1,5-a]pyrimidin-3-yl)quinoline (LDN-212854 (Cas No.: 1432597-26-6), 100 mg, 0.25 mmol) in ACN (3 mL) were added C-1 (2,2-dimethyl-4-oxo-3,8,11-trioxa-5-azatridecan-13-yl methanesulfonate, 120 mg, 0.37 mmol) and K$_2$CO$_3$ (86 mg, 0.62 mmol) The mixture was stirred at 80° C. for 24 hrs. The reaction was filtered. The filtration was concentrated. The residue was purified by Prep-TLC (DCM: MeOH=20:1) to afford C-2 (tert-butyl (2-(2-(2-(4-(4-(3-(quinolin-5-yl)pyrazolo[1,5-a]pyrimidin-6-yl)phenyl)piperazin-1-yl)ethoxy)ethoxy)ethyl)carbamate, 100 mg, 62.7%) as a yellow solid.

$^1$H-NMR (DMSO_d$_6$, 400 MHz) δ (ppm) 9.48 (d, J=2.4 Hz, 1H), 8.97-8.94 (m, 2H), 8.55 (s, 1H), 8.41 (d, J=8 Hz, 1H), 8.06 (d, J=8.4 Hz, 1H), 7.89-7.80 (m, 2H), 7.74 (d, J=8.8 Hz, 2H), 7.52 (dd, J=8.4, 4.4 Hz, 1H), 7.08 (d, J=8.8 Hz, 2H), 6.77-6.76 (m, 1H), 3.57-3.51 (m, 7H), 3.43-3.38 (m, 3H), 3.22 (t, J=4 Hz, 4H), 3.07 (q, J=6 Hz, 2H), 2.60-2.54 (m, 6H), 1.38 (s, 9H)

Step 2) Synthesis of C-3

To a solution of C-2 (100 mg, 0.15 mmol) in MeOH (3 mL) was added HCl/MeOH (2 N, 2 mL). The mixture was stirred at room temperature for 4 hrs. The solution was concentrated to give crude C-3 (2-(2-(2-(4-(4-(3-(quinolin-5-yl)pyrazolo[1,5-a]pyrimidin-6-yl)phenyl)piperazin-1-yl)ethoxy)ethoxy)ethan-1-amine, 70 mg, 86.7%) as a yellow solid.

Step 3) Synthesis of Compound C

To a solution of C-3 (70 mg, 0.13 mmol) in MeOH (3 mL) was added C-4 ((R)-2-((3-phenethoxyphenoxy)methyl)oxirane, 30 mg, 0.11 mmol). The mixture was stirred at 65° C. for 16 hrs. The solution was concentrated and purification by pre-HPLC to give Compound C ((R)-1-(3-phenethoxyphenoxy)-3-((2-(2-(2-(4-(4-(3-(quinolin-5-yl)pyrazolo[1,5-a]pyrimidin-6-yl)phenyl)piperazin-1-yl)ethoxy)ethoxy)ethyl)amino)propan-2-ol, 8 mg, 7.6%) as a yellow solid.

$^1$H-NMR (CD$_3$OD, 400 MHz) δ (ppm) 9.08 (s, 1H), 8.87 (s, 1H), 8.78 (s, 1H), 8.48-8.41 (m, 3H), 8.07 (s, 1H), 7.87-7.84 (m, 2H), 7.58-7.52 (m, 3H), 7.23-7.07 (m, 8H), 6.50-6.47 (m, 3H), 4.18-4.15 (m, 3H), 3.94 (s, 2H), 3.73-3.67 (m, 8H), 3.31-3.14 (m, 7H), 3.04-2.99 (m, 3H), 2.70 (s, 6H); ESI-MS Calcd m/z for C$_{48}$H$_{53}$N$_7$O$_5$ [M+H]$^+$ 808.41 Found 808.00

Example 17. Preparation of Compound D (5-(3-fluorophenyl)-N—((S)-1-(2-(2-(2-(((R)-2-hydroxy-3-(3-phenethoxyphenoxy) propyl)amino)ethoxy)ethoxy)ethyl) piperidin-3-yl)-3-ureidothiophene-2-carboxamide)

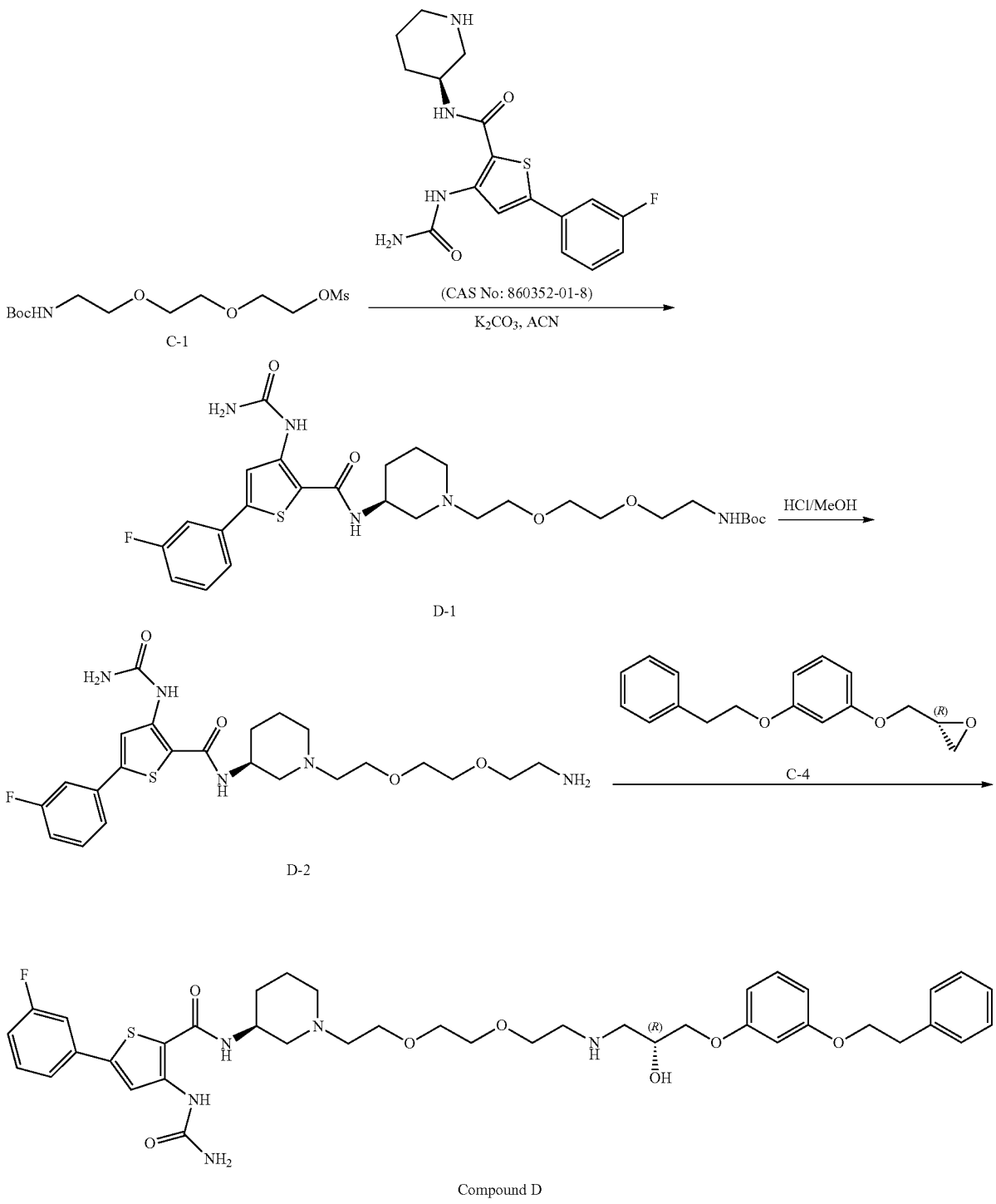

Compound D

Step 1) Synthesis of D-1

To a solution of (S)-5-(3-fluorophenyl)-N-(piperidin-3-yl)-3-ureidothiophene-2-carboxamide (CAS No.: 860352-01-8, 100 mg, 0.27 mmol) in ACN (3 mL) were added C-1 (2,2-dimethyl-4-oxo-3,8,11-trioxa-5-azatridecan-13-yl methanesulfonate, 120 mg, 0.37 mmol) and $K_2CO_3$ (95 mg, 0.69 mmol). The mixture was stirred at 80° C. for 24 hrs. The reaction was filtered. The filtration was concentrated. The residue was purified by Prep-TLC (DCM:MeOH=20:1) to afford D-1 (tert-butyl (S)-(2-(2-(2-(3-(5-(3-fluorophenyl)-3-ureidothiophene-2-carboxamido)piperidin-1-yl)ethoxy)ethoxy)ethyl)carbamate, 100 mg, 62.4%) as a yellow solid.

$^1$H-NMR (DMSO_$d_6$, 400 MHz) δ (ppm) 10.05 (s, 1H), 8.28 (s, 1H), 7.80 (d, J=8 Hz, 1H), 7.55-7.43 (m, 3H), 7.27-7.22 (m, 1H), 6.74-6.64 (m, 2H), 3.91-3.89 (m, 2H), 3.52-3.38 (m, 6H), 3.33-3.30 (m, 3H), 3.07-3.03 (m, 2H), 2.85 (dd, J=4, 1.6 Hz, 1H), 2.75-2.67 (m, 1H), 2.05-1.99 (m, 2H), 1.75-1.35 (m, 4H), 1.27 (s, 9H)

Step 2) Synthesis of D-2

To a solution of D-1 (100 mg, 0.17 mmol) in MeOH (3 mL) was added HCl/MeOH (2 N, 2 mL). The mixture was stirred at room temperature for 4 hrs. The solution was concentrated to give crude D-2 ((S)—N-(1-(2-(2-(2-aminoethoxy)ethoxy)ethyl)piperidin-3-yl)-5-(3-fluorophenyl)-3-ureidothiophene-2-carboxamide, 70 mg, 83.4%) as a yellow solid.

Step 3) Synthesis of Compound D

To a solution of D-2 (70 mg, 0.13 mmol) in MeOH (3 mL) was added C-4 ((R)-2-((3-phenethoxyphenoxy)methyl)oxirane, 30 mg, 0.11 mmol). The mixture was stirred at 65° C. for 16 hrs. The solution was concentrated and purification by pre-HPLC to give Compound D (5-(3-fluorophenyl)-N—((S)-1-(2-(2-(2-(((R)-2-hydroxy-3-(3-phenethoxyphenoxy)propyl)amino)ethoxy)ethoxy)ethyl)piperidin-3-yl)-3-ureidothiophene-2-carboxamide, 8 mg, 8.05%) as a white solid.

$^1$H-NMR (CD$_3$OD, 400 MHz) δ (ppm) 8.05 (brs, 1H), 8.18 (s, 1H), 7.48-7.38 (m, 3H), 7.27-7.10 (m, 7H), 6.52-6.47 (m, 3H), 4.23-3.98 (m, 4H), 3.98-3.94 (m, 2H), 3.77-3.67 (m, 8H), 3.26-3.12 (m, 4H), 3.02 (t, J=6.8 Hz, 2H), 2.81-2.79 (m, 3H), 2.53 (s, 1H), 2.45-2.39 (m, 2H), 1.86-1.83 (m, 3H), 1.65-1.63 (m, 1H) ESI-MS Calcd m/z for $C_{40}H_{50}FN_5O_7S$ [M+H]$^+$ 764.34 Found 763.90

Example 18. Preparation of Compound E ((R)-2-((6-(4-(15-(4-(benzyloxy)-3-(3-phenylpropoxy)phenoxy)-14-hydroxy-6,9-dioxa-3,12-diazapentadecyl)piperazin-1-yl)-2-methylpyrimidin-4-yl)amino)-N-(2-chloro-6-methylphenyl) thiazole-5-carboxamide)

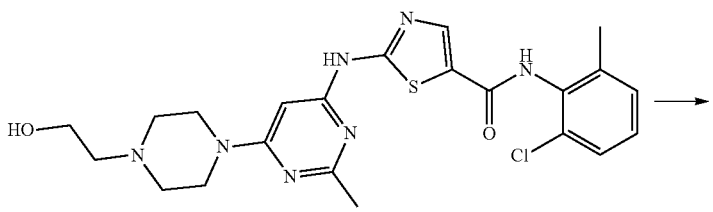

CAS No: 302962-49-8

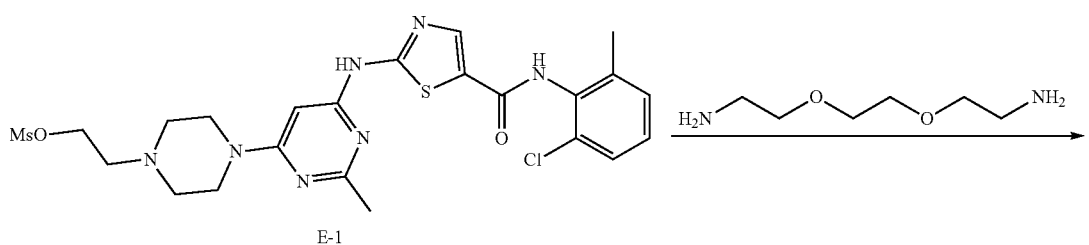

E-1

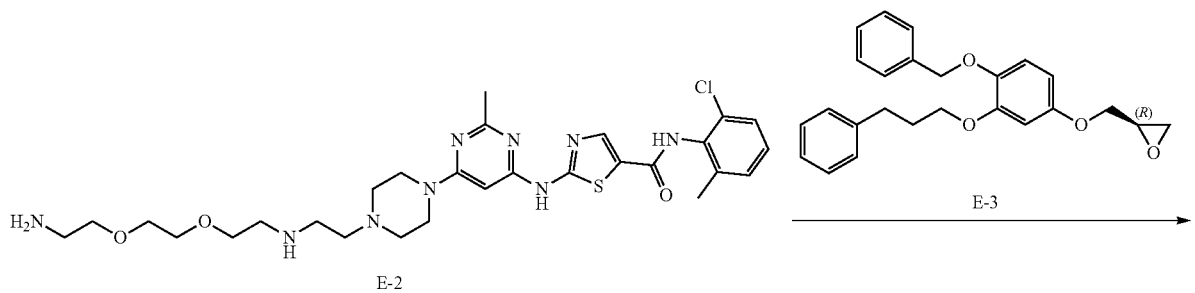

E-2

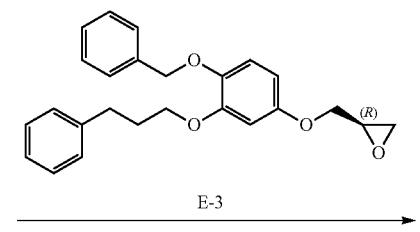

E-3

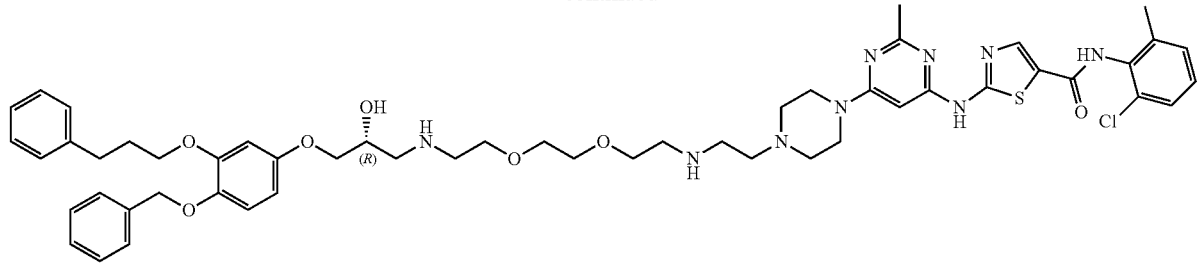

Compound E

Step 1) Synthesis of E-1

To a solution of Dasatinib (CAS No.: 302962-49-8, 200 mg, 0.41 mmol) in DCM (3 mL) were added Et$_3$N (82 mg, 0.82 mmol). MsCl (95 mg, 0.82 mmol) was added at 0° C. under N$_2$. The mixture was stirred at 35° C. for 36 hrs. The mixture was monitored by TLC. The solution was concentrated to afford E-1 (2-(4-(6-((5-((2-chloro-6-methylphenyl)carbamoyl)thiazol-2-yl)amino)-2-methylpyrimidin-4-yl)piperazin-1-yl)ethyl methanesulfonate, 390 mg) as a yellow oil without further purification.

Step 2) Synthesis of E-2

To a solution of E-1 (390 mg, 0.69 mmol) in ACN (5 mL), 2,2'-(ethane-1,2-diylbis(oxy))bis(ethan-1-amine) (4 equiv.) and Cs$_2$CO$_3$ (337 mg, 1.03 mmol) was added. The mixture was stirred at 60° C. for 25 hrs. The mixture was monitored by TLC. The solution was concentrated and purification by prep-HPLC to give E-2 (2-((6-(4-(2-((2-(2-(2-aminoethoxy)ethoxy)ethyl)amino)ethyl)piperazin-1-yl)-2-methylpyrimidin-4-yl)amino)-N-(2-chloro-6-methylphenyl)thiazole-5-carboxamide, 50 mg) as a yellow solid.

LC-MS Calcd m/z for C$_{28}$H$_{40}$ClN$_9$O$_3$S [M+H]$^+$ 619.2 Found 619.3.

Step 3) Synthesis of Compound E

To a solution of E-2 (50 mg, 0.08 mmol) in MeOH (4 mL) was added (R)-2-((4-(benzyloxy)-3-(3-phenylpropoxy)phenoxy)methyl)oxirane (32 mg, 0.08 mmol). The mixture was stirred at 65° C. for 18 hrs. The solution was concentrated and purification by pre-HPLC to give Compound E ((R)-2-((6-(4-(15-(4-(benzyloxy)-3-(3-phenylpropoxy)phenoxy)-14-hydroxy-6,9-dioxa-3,12-diazapentadecyl)piperazin-1-yl)-2-methylpyrimidin-4-yl)amino)-N-(2-chloro-6-methylphenyl)thiazole-5-carboxamide, 13 mg) as a yellow solid.

$^1$H-NMR (CD$_3$OD, 400 MHz) δ (ppm) 8.56 (br s, 1H), 8.14 (s, 1H), 7.44-7.43 (m, 2H), 7.35-7.22 (m, 8H), 7.17-7.14 (m, 3H), 6.91 (d, 1H), 6.59 (d, 1H), 6.46 (m, 1H), 5.99 (s, 1H), 5.02 (s, 2H), 4.03 (m, 1H), 3.98-3.93 (m, 4H), 3.69-3.62 (m, 10H), 3.09 (m, 2H), 2.87-2.60 (m, 15H), 2.46 (s, 3H), 2.33 (s, 3H), 2.08-2.08 (m, 2H); LC-MS Calcd m/z for C$_{53}$H$_{66}$ClN$_9$O$_7$S [M]1008.6 Found 1008.2 and 1010.2.

Example 19. Preparation of Compound F ((R)-5-((3-((2-(2-(2-((3-(4-(benzyloxy)-3-phenethoxyphenoxy)-2-hydroxypropyl)amino)ethoxy)ethoxy)ethyl)amino)phenyl)amino)benzo[c][2,6]naphthyridine-8-carboxylic acid)

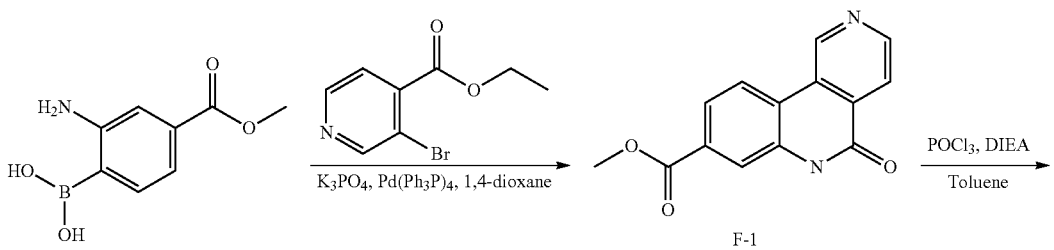

F-1

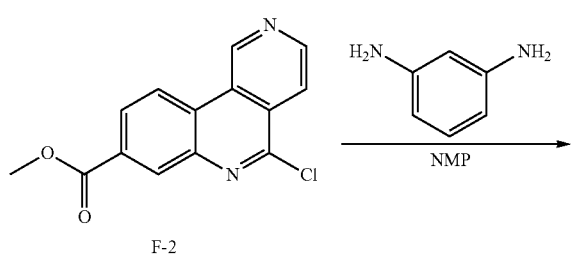

F-2

-continued
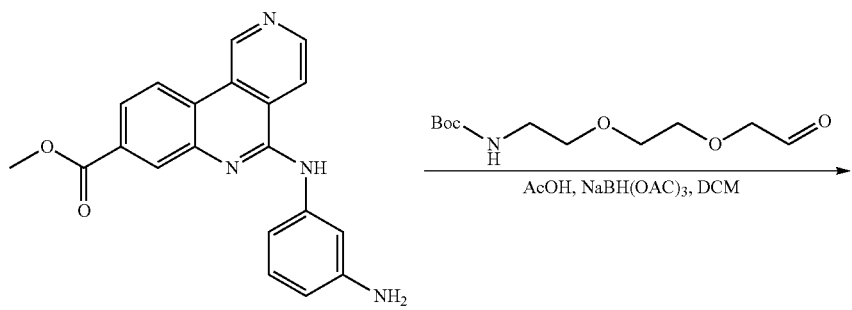
F-3
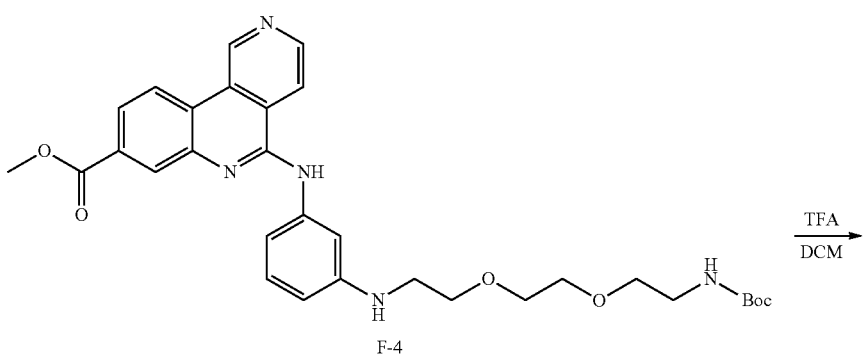
F-4
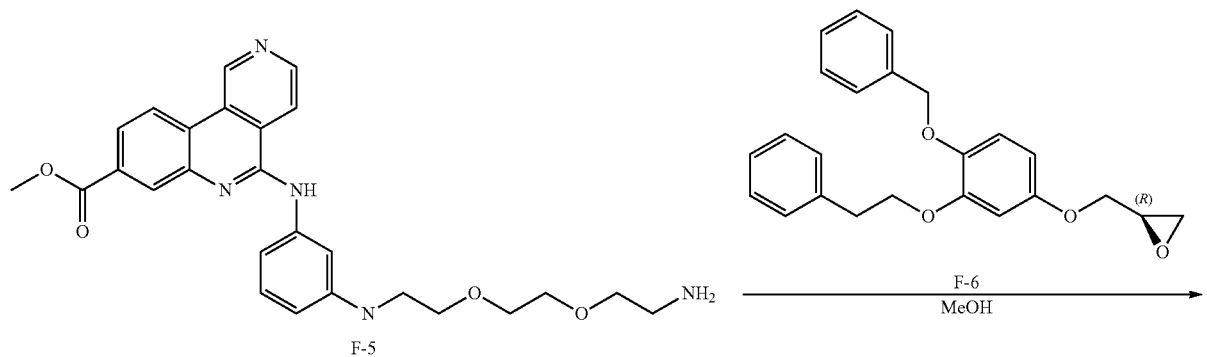
F-5
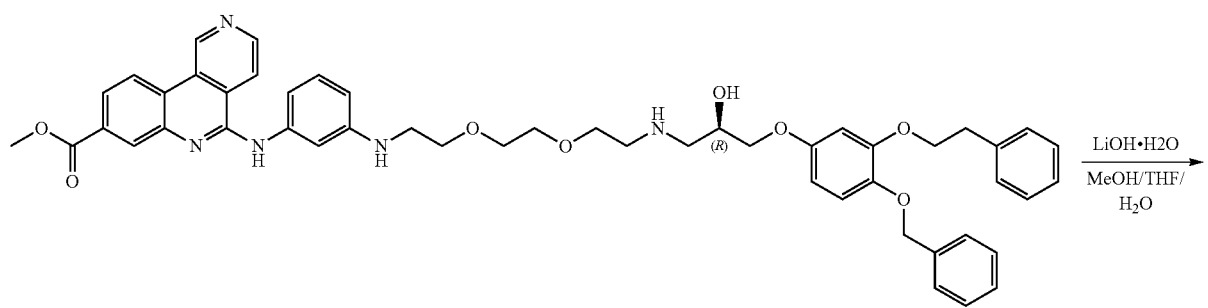
F-7

-continued

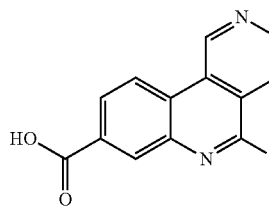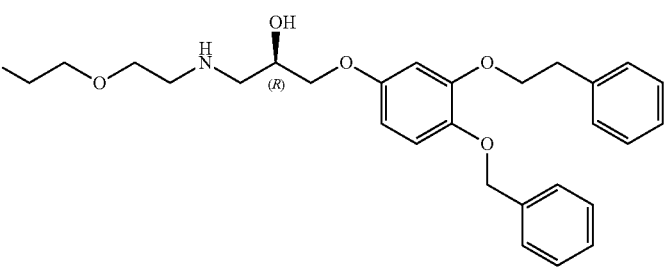

Compound F

Step 1) Synthesis of F-1

To a solution of (2-amino-4-(methoxycarbonyl)phenyl) boronic acid hydrochloride (10.0 g, 43.2 mmol) and methyl 3-bromoisonicotinate (9.9 g, 43.2 mmol) in 1,4-dioxane (300 mL) was added $K_3PO_4$ (27.5 g, 129.6 mmol) and $Pd(Ph_3P)_4$ (3.0 g, 30%) under $N_2$. The mixture was stirred at 100° C. overnight. The mixture was cooled to rt and filtered. The filtrate was concentrated and purified by chromatography (DCM/MeOH=10/1) to give F-1 (methyl 5-oxo-5,6-dihydrobenzo[c][2,6]naphthyridine-8-carboxylate, 5.0 g, 45.5%) as yellow solid.

$^1$H-NMR (DMSO_$d_6$, 400 MHz) δ (ppm) 12.18 (s, 1H), 9.94 (s, 1H), 8.89 (d, J=4.8 Hz, 1H), 8.72 (d, J=8.4 Hz, 1H), 8.14 (d, J=4.8 Hz, 1H), 8.01 (s, 1H), 7.82 (dd, J=1.2, 8.0 Hz, 1H), 3.91 (s, 3H); ESI-MS Calcd m/z for $C_{14}H_{10}N_2O_3$[M+H]$^+$ 255.07 Found 255.10

Step 2) Synthesis of F-2

To a suspension of F-1 (methyl 5-oxo-5,6-dihydrobenzo[c][2,6]naphthyridine-8-carboxylate, 5.0 g, 19.7 mmol) in toluene (100 mL) was added $POCl_3$ (4.5 g, 29.5 mmol) and DIEA (2.5 g, 19.7 mmol). The mixture was stirred at 100° C. for 6 hrs under $N_2$. The mixture was concentrated and added cold $Na_2CO_3$ solution to pH>7. The mixture was filtered to give F-2 (methyl 5-chlorobenzo[c][2,6]naphthyridine-8-carboxylate, 2.0 g, 37.0%) as yellow solid.

$^1$H-NMR (DMSO_$d_6$, 400 MHz) δ (ppm) 10.38 (s, 1H), 9.19 (d, J=8.8 Hz, 1H), 9.10 (d, J=5.6 Hz, 1H), 8.57 (s, 1H), 8.33-8.28 (m, 2H), 3.97 (s, 3H); ESI-MS Calcd m/z for $C_{14}H_9ClN_2O_2$ [M+H]$^+$ 273.03 Found 273.00

Step 3) Synthesis of F-3

The mixture of F-2 (2.0 g, 7.3 mmol) and benzene-1,3-diamine (0.8 g, 7.3 mmol) in NMP (60 mL) was stirred at 80° C. overnight. The mixture was added water (200 mL), extracted with EA (100 mL×6), concentrated F-3 (methyl 5-((3-aminophenyl)amino)benzo[c][2,6]naphthyridine-8-carboxylate, 2.0 g, crude).

Step 4) Synthesis of F-4

To a solution of F-3 (2.0 g, 5.8 mmol) in DCM (20 mL) was added tert-butyl 2-(2-(2-oxoethoxy)ethoxy)ethylcarbamate (2.2 g, 8.7 mmol) and AcOH (104.7 mg, 1.7 mmol). The mixture was stirred at r.t for 4 hrs. Then the mixture was added NaBH(OAc)$_3$ (6.2 g, 29.1 mmol) in portions at 0° C. The mixture was stirred at r.t overnight. It was poured into water and extracted with DCM (20 mL×5), the organic layer was washed with brine solution (100 mL), dried over $Na_2SO_4$ and concentrated under reduced pressure. The mixture was purified by prep-TLC (DCM/MeOH=10/1) to give F-4 (methyl 5-((3-((2,2-dimethyl-4-oxo-3,8,11-trioxa-5-azatridecan-13-yl)amino)phenyl)amino)benzo[c][2,6]naphthyridine-8-carboxylate, 0.8 g, 24.2%) as yellow solid.

$^1$H-NMR (DMSO_$d_6$, 400 MHz) δ (ppm) 10.06 (s, 1H), 8.92 (d, J=5.6 Hz, 1H), 8.77 (d, J=8.4 Hz, 1H), 8.52 (d, J=5.6 Hz, 1H), 8.21 (s, 1H), 7.93-7.90 (m, 1H), 7.41 (s, 1H), 7.18 (d, J=7.6 Hz, 1H), 7.11-7.07 (t, J=8 Hz, 1H), 6.37 (d, J=8 Hz, 1H), 3.90 (s, 3H), 3.63-3.60 (m, 2H), 3.56-3.50 (m, 4H), 3.37-3.31 (m, 2H), 3.28-3.22 (m, 2H), 3.05-3.02 (m, 2H), 1.30 (s, 9H); LC-MS Calcd m/z for $C_{31}H_{37}N_5O_6$ [M+H]$^+$ 576.27 Found 576.30

Step 5) Synthesis of F-5

To a solution of F-4 (0.8 g, 1.4 mmol) in DCM (4 mL) was add TFA (4 mL) slowly at 0° C. The mixture was stirred at r.t for 1 hr. The mixture was poured into saturated aqueous NaHCO$_3$ solution, and extracted with EA, washed with brine, then concentrated to give F-5 (methyl 5-((3-((2-(2-(2-aminoethoxy)ethoxy)ethyl)amino)phenyl)amino)benzo[c][2,6]naphthyridine-8-carboxylate, 650.0 mg, 98.5%).

Step 6) Synthesis of F-7

The mixture of F-5 (650.0 mg, 1.4 mmol) and F-6 ((R)-2-((4-(benzyloxy)-3-phenethoxyphenoxy)methyl)oxirane, 515.0 mg, 1.4 mmol) in MeOH (10 mL) was stirred overnight at 50° C. The reaction mixture was concentrated and purified by prep-TLC (DCM/MeOH=10/1) to give the F-7 (methyl (R)-5-((3-((2-(2-(2-((3-(4-(benzyloxy)-3-phenethoxyphenoxy)-2-hydroxypropyl)amino)ethoxy)ethoxy)ethyl)amino)phenyl)amino)benzo[c][2,6]naphthyridine-8-carboxylate, 270.0 mg, 23.3%)

Step 7) Synthesis of Compound F

To a solution of F-7 (270.0 mg, 0.3 mmol) in MeOH/THF/H$_2$O (3/3/2 mL) was added LiOH·H$_2$O (27.0 mg, 0.6 mmol). The mixture was stirred for 1 hr at r.t. The mixture was added 1N HCl to pH=7. The mixture was concentrated and purified by prep-HPLC to give Compound F ((R)-5-((3-((2-(2-(2-((3-(4-(benzyloxy)-3-phenethoxyphenoxy)-2-hydroxypropyl)amino)ethoxy)ethoxy)ethyl)amino)phenyl)amino)benzo[c][2,6]naphthyridine-8-carboxylic acid, 20 mg, 7.5%) as yellow solid.

¹H-NMR (DMSO_d₆, 400 MHz) δ (ppm) 10.12 (s, 1H), 9.73 (s, 1H), 8.72 (d, J=4.8 Hz, 1H), 8.59 (s, 1H), 8.33 (s, 1H), 8.30 (s, 1H), 8.10 (m, 1H), 7.98 (d, J=8 Hz, 1H), 7.36-7.18 (m, 10H), 7.05 (t, J=8 Hz, 1H), 6.88 (m, 1H), 6-74 (m, 1H), 6.63 (s, 1H), 6.41 (d, J=7.6 Hz, 1H), 6.34 (d, J=7.6 Hz, 1H), 5.63 (brs, 1H), 4.90 (s, 2H), 4.23-4.08 (m, 3H), 3.93-3.70 (m, 10H), 3.40 (s, 2H), 3.35-3.20 (m, 3H), 3.10-2.90 (m, 3H); ESI-MS Calcd m/z for $C_{49}H_{51}N_5O_8$ [M+H]⁺ 838.37 Found 838.80
Example 20. Preparation of Compound G (N-(7-((1-(3-(benzyloxy)phenyl)-5,8-dioxa-2,11-diazatridecan-13-yl)oxy)-6-(tert-butylsulfonyl) quinazolin-4-yl)benzo[d]thiazol-5-amine)
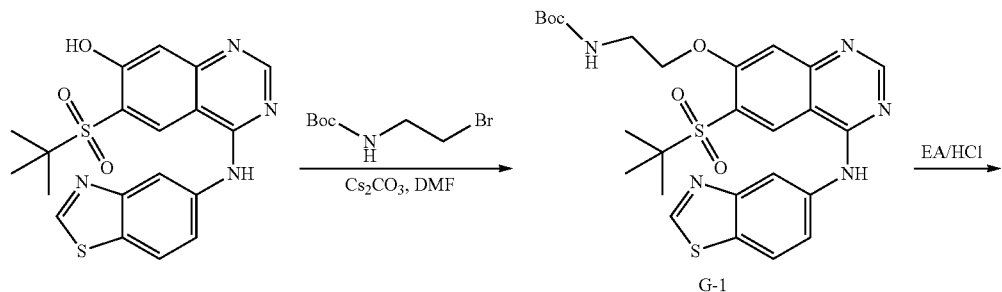
G-1
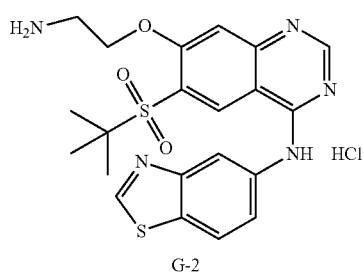
G-2
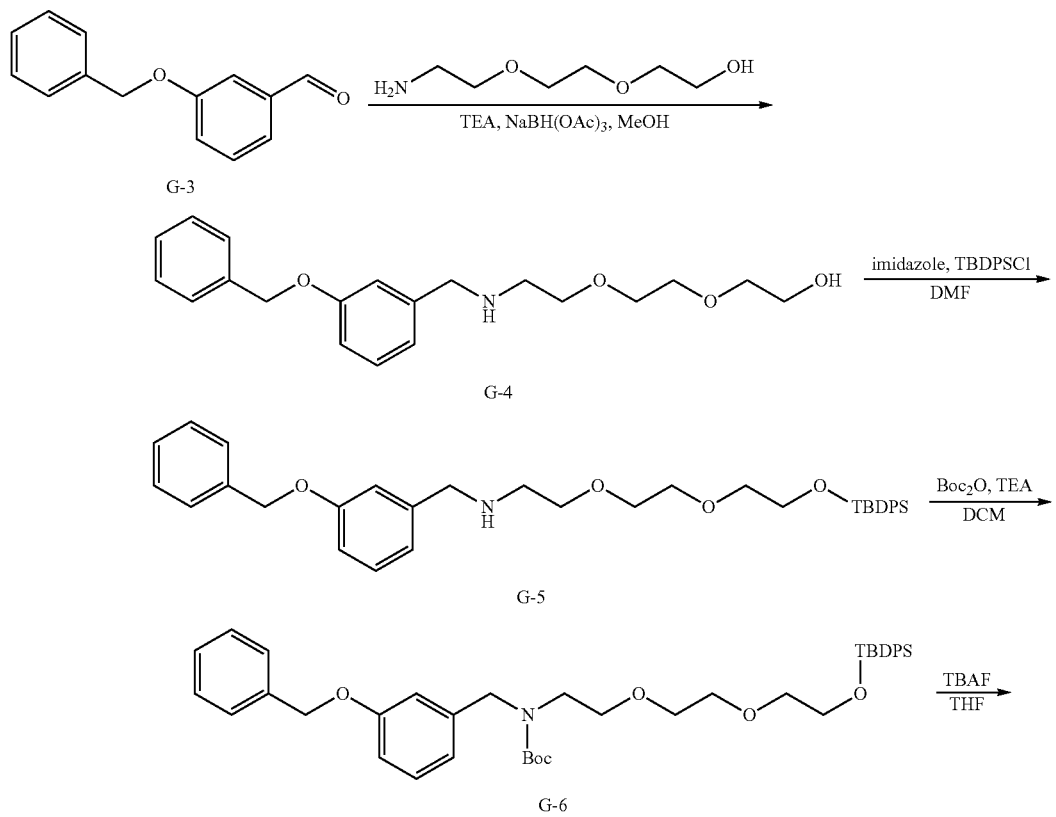
G-3
G-4
G-5
G-6

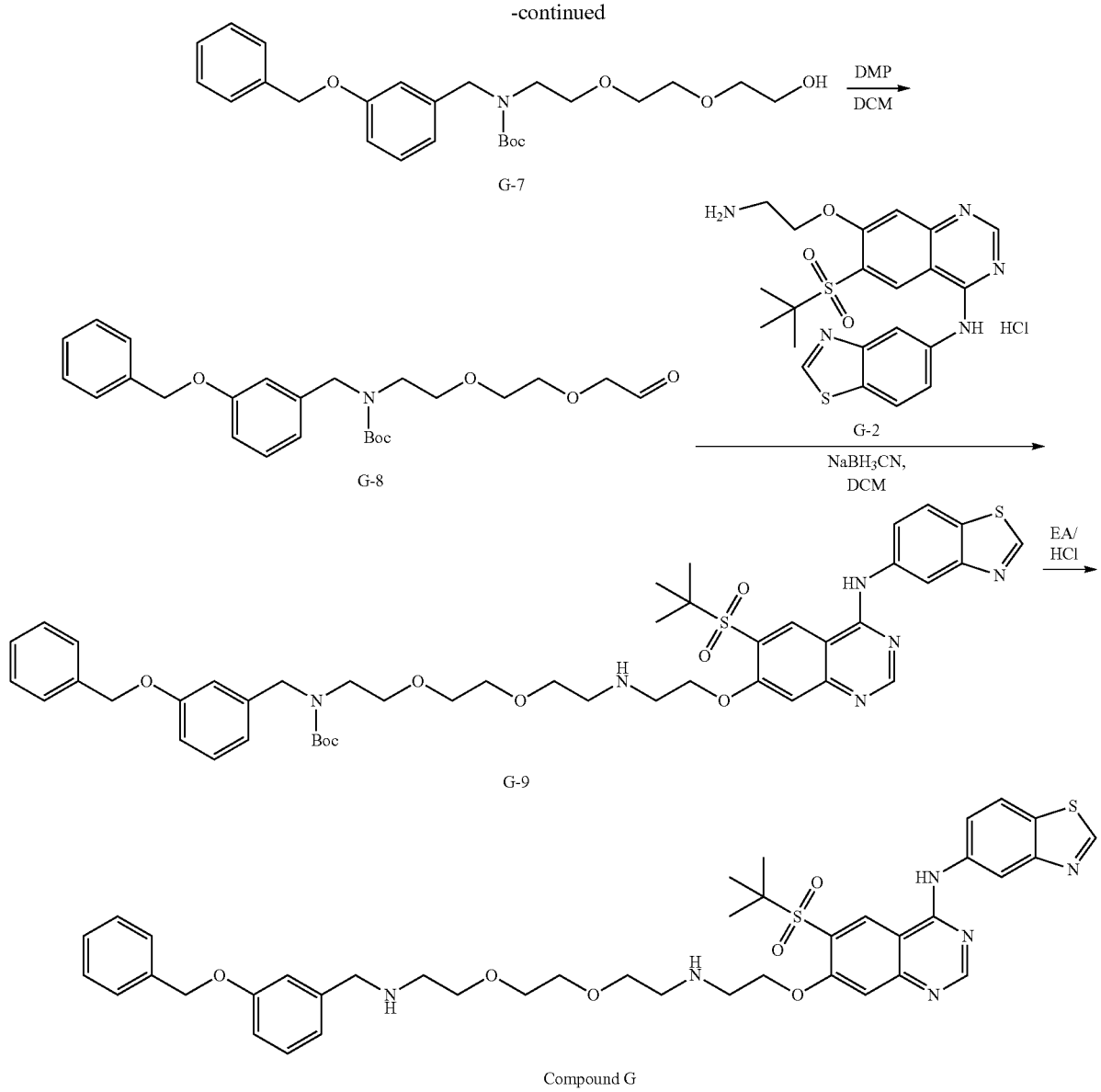

Step 1) Synthesis of G-1

To a solution of 4-(benzo[d]thiazol-5-ylamino)-6-(tert-butylsulfonyl)quinazolin-7-ol (300 mg, 0.72 mmol) in DMF (5 ml) was added cesium carbonate (703.77 mg, 2.16 mmol). The reaction mixture was stirred for 30 minutes at ambient temperature, followed by the tert-Butyl N-(2-bromoethyl)carbamate (193.54 mg, 0.86 mmol) was added to the solution. The reaction mixture was heated at 45-50° C. for 48 hrs. The solvent was removed in vacuo, and the residue was purified by column chromatography to afford G-1 (tert-butyl (2-((4-(benzo[d]thiazol-5-ylamino)-6-(tert-butylsulfonyl)quinazolin-7-yl)oxy)ethyl)carbamate, 162 mg, 40.3%) ESI-MS Calcd m/z for $C_{26}H_{31}N_5O_5S_2$[M+H]$^+$ 558.18 Found 558.10

Step 2) Synthesis of G-2

G-1 (92 mg, 0.17 mmol) was added into the solution EA/HCl at R. T. and stirred for 2 hours. The solvent was removed in vacuo to give crude G-2 (N-(7-(2-aminoethoxy)-6-(tert-butylsulfonyl)quinazolin-4-yl)benzo[d]thiazol-5-amine hydrochloride, 80.2 mg) as white solid.

ESI-MS Calcd m/z for $C_{21}H_{23}N_5O_3S_2$ [M+H]$^+$ 458.12 Found 458.10

Step 3) Synthesis of G-4

A solution of G-3 (3-(benzyloxy)benzaldehyde, 2.00 g, 9.43 mmol), 2-(2-(2-aminoethoxy)ethoxy)ethanol (3.52 g, 23.58 mmol), triethylamine (3.81 g, 37.72 mmol) and Sodium triacetoxyborohydride (5.99 g, 28.29 mmol) in MeOH (20.0 mL) was stirred at r.t for 16 hrs. The mixture was poured into water and extracted with EA. The combined organic layers was washed by brine, dried over $Na_2SO_4$ and concentrated to give crude G-4 (2-(2-(2-((3-(benzyloxy)benzyl)amino)ethoxy)ethoxy) ethan-1-ol, 2.00 g) as yellow oil.

ESI-MS Calcd m/z for $C_{20}H_{27}NO_4$ [M+H]$^+$ 346.19 Found 346.00

Step 4) Synthesis of G-5

A solution of G-4 (2.00 g, 5.79 mmol), imidazole (0.79 g, 11.59 mmol) and TBDPSCl (CAS No.: 58479-61-1, 2.07 g, 7.53 mmol) in DMF (20.0 mL) was stirred at 90° C. for 1 hr. The mixture was poured into water and extracted with EA. The combined organic layers was washed by brine, dried over $Na_2SO_4$ and concentrated to give crude G-5 (N-(3-(benzyloxy)benzyl)-2,2-dimethyl-3,3-diphenyl-4,7,10-trioxa-3-siladodecan-12-amine, 3.55 g) as yellow oil.

Step 5) Synthesis of G-6

A solution of G-5 (3.55 g, 6.08 mmol), $(Boc)_2O$ (1.33 g, 9.13 mmol) and TEA (1.23 g, 12.16 mmol) in DCM (10.0 mL) was stirred at r.t for 4 hrs. The mixture was poured into water and extracted with DCM. The combined organic layers was washed by brine, dried over $Na_2SO_4$ and concentrated to give crude G-6 (tert-butyl (3-(benzyloxy)benzyl) (2,2-dimethyl-3,3-diphenyl-4,7,10-trioxa-3-siladodecan-12-yl)carbamate, 4.86 g) as brown oil.

ESI-MS Calcd m/z for $C_{41}H_{53}NO_6Si[M-C_5H_9O_2]^+$ 584.36 Found 584.00

Step 6) Synthesis of G-7

A solution of G-6 (4.86 g, 7.11 mmol) and TBAF (CAS No. 22206-57-1, 6.74 g, 21.35 mmol) in THF (10.0 mL) was stirred at r.t for 5 hrs. The mixture was poured into water and extracted with EA. The combined organic layers was washed by brine, dried over $Na_2SO_4$ and concentrated to give crude G-7 (tert-butyl (3-(benzyloxy)benzyl) (2-(2-(2-hydroxyethoxy)ethoxy)ethyl)carbamate, 1.00 g) as brown oil.

ESI-MS Calcd m/z for $C_{25}H_{35}NO_6$ $[M-C_5H_9O_2]^+$ 346.25 Found 346.00

Step 7) Synthesis of G-8

A solution of G-7 (1.00 g, 2.25 mmol) and dess-Martin periodinane (DMP, 1.91 g, 4.50 mmol) in DCM (10.0 mL) was stirred at 0° C. for 16 hrs. The solvent was removed in vacuo, and the residue was purified by column chromatography to afford G-8 (tert-butyl (3-(benzyloxy)benzyl) (2-(2-(2-oxoethoxy)ethoxy)ethyl)carbamate, 375 mg, 37.6%).

Step 8) Synthesis of G-9

A solution of G-8 (72.1 mg, 0.16 mmol) and G-2 (80.2 mg, 0.16 mmol) in DCM (10.0 mL) was added sodium cyanoborohydride (10.7 mg, 0.17 mmol) and stirred at r.t for 16 hrs. The solvent was removed in vacuo, and the residue was purified by column chromatography to afford G-9 (tert-butyl (2-(2-(2-((2-((4-(benzo[d]thiazol-5-ylamino)-6-(tert-butylsulfonyl)quinazolin-7-yl)oxy)ethyl)amino) ethoxy)ethoxy)ethyl) (3-(benzyloxy)benzyl)carbamate, 97 mg, 68.5%).

$^1$H-NMR (CDCl$_3$, 400 MHz) δ (ppm) 9.04 (s, 1H), 8.78 (s, 1H), 8.68 (s, 1H), 8.54 (s, 1H), 7.99 (s, 2H), 7.40-7.36 (m, 6H), 7.20 (brs, 2H), 6.83-6.79 (m, 3H), 5.02 (m, 3H), 4.35 (m, 4H), 3.89 (s, 2H), 3.63-3.52 (m, 8H), 3.35 (m, 4H), 1.48-1.39 (m, 9H), 1.28 (s, 10H)

Step 9) Synthesis of Compound G

G-9 (97 mg, 0.11 mmol) was added into the solution EA/HCl at r.t and stirred for 2 hrs. The solvent was prepared by high pressure to afford Compound G (N-(7-((1-(3-(benzyloxy)phenyl)-5,8-dioxa-2,11-diazatridecan-13-yl)oxy)-6-(tert-butylsulfonyl)quinazolin-4-yl)benzo[d]thiazol-5-amine, 10.0 mg, 11.6%).

$^1$H-NMR (CDCl$_3$, 400 MHz) δ (ppm) 9.06 (s, 1H), 8.78-8.69 (m, 3H), 7.99-7.84 (m, 2H), 7.44-7.30 (m, 5H), 7.23-7.05 (m, 4H), 6.86-6.84 (m, 1H), 5.02 (s, 2H), 4.49 (brs, 2H), 4.12 (s, 2H), 3.77 (m, 4H), 3.65 (brs, 4H), 3.29 (m, 2H), 3.19 (m, 2H), 3.07 (m, 2H), 1.28-1.24 (m, 9H); LC-MS Calcd m/z for $C41H_{48}N_6O_6S_2$ $[M+H]^+$ 785.31 Found 785.80.

Example 21. Preparation of Compound H (((2-(((5S,8S,10aR)-8-(((S)-5-amino-1-(benzhydrylamino)-1,5-dioxopentan-2-yl) carbamoyl)-3-((R)-1-(3,4-bis((4-fluorobenzyl)oxy)phenoxy)-2-hydroxy-7,10,13,16-tetraoxa-4-azaicosan-20-oyl)-6-oxodecahydropyrrolo[1,2-a][1,5]diazocin-5-yl) carbamoyl)-1H-indol-5-yl)difluoromethyl)phosphonic acid)

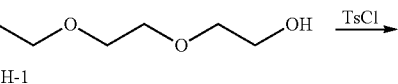

H-1

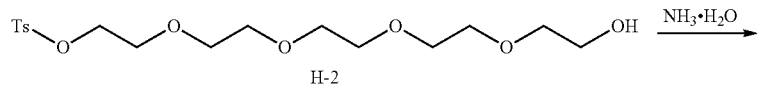

H-2

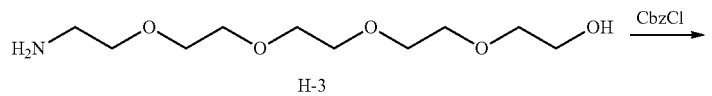

H-3

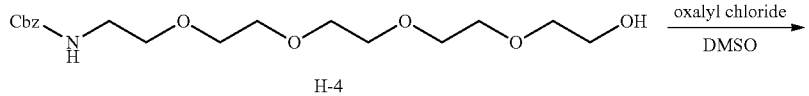

H-4

-continued
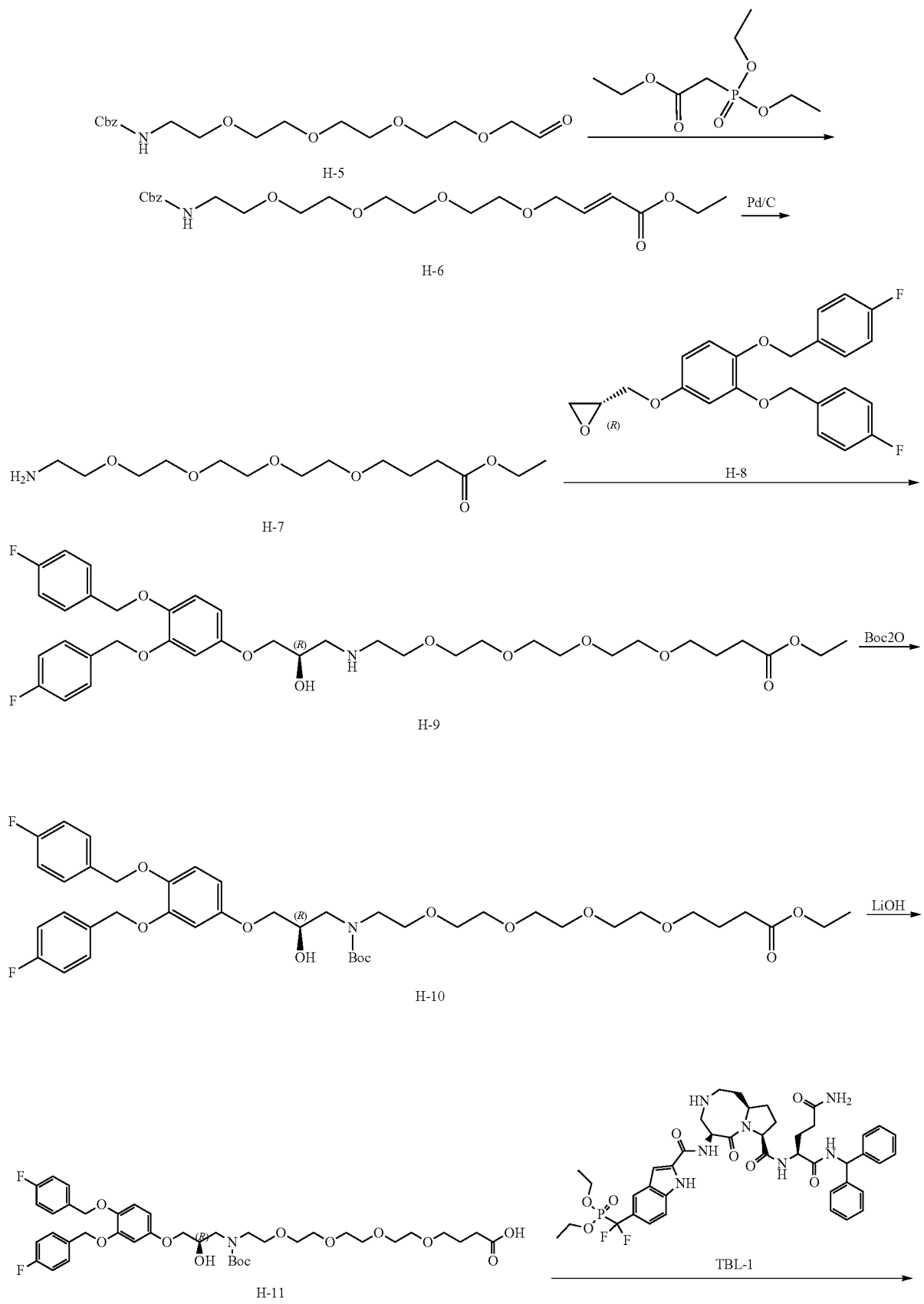

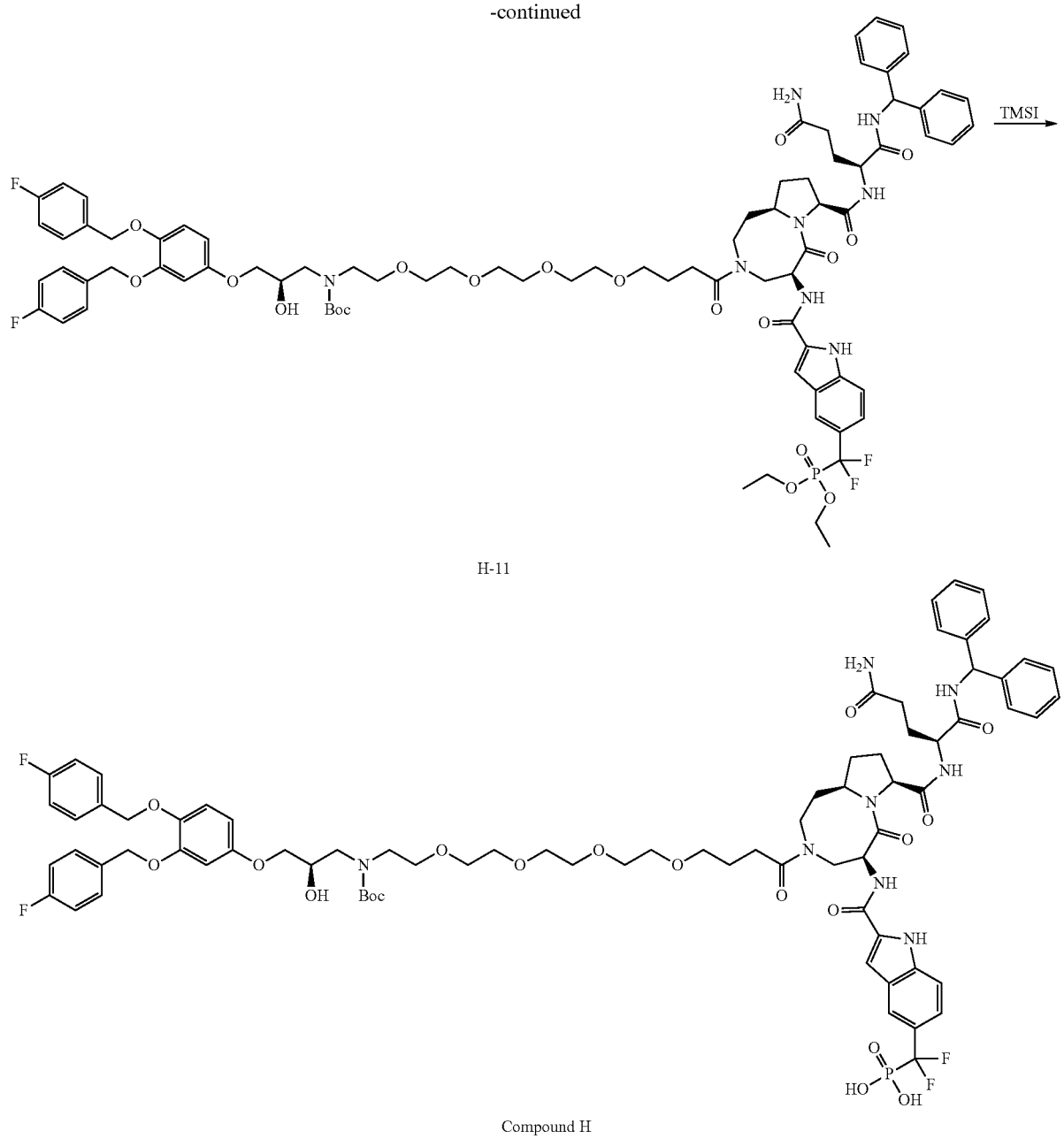

H-11

Compound H

Step 1) Synthesis of H-2

To a solution of H-1 (3,6,9,12-tetraoxatetradecane-1,14-diol, 20 g, 84 mmol) in TH (150 mL) was added NaOH (3.36 g, 84 mmol) in water (150 mL) and TsCl (8 g, 42 mmol) in THF (30 mL) dropwise at 0° C. The reaction mixture was stirred at room temperature for 4 h. The above solution was extracted with EA. The combined organic layers were washed with brine, dried over Na2SO4 and concentrated. The crude was purified by column chromatography on silica gel (DCM/MeOH=100:1) to give H-2 (14-hydroxy-3,6,9,12-tetraoxatetradecyl 4-methylbenzenesulfonate, 7.2 g) as colorless oil.

$^1$H-NMR (CDCl$_3$, 400 MHz) δ (ppm) 7.80 (d, 2H), 7.35 (d, 2H), 4.18-4.16 (m, 2H), 3.73-3.60 (m, 19H), 2.46 (s, 3H); LC-MS Calcd m/z for C$_{17}$H$_{28}$O$_8$S [M+H]$^+$ 393.4 Found 393.1.

Step 2) Synthesis of H-3

To a solution of H-2 (7.2 g, 18.4 mmol) in ammonium hydroxide (35 mL) was added NH$_4$Cl (2.95 g, 55.1 mmol). The reaction mixture was stirred at 40° C. overnight. The above solution was concentrated to give H-3 (14-amino-3,6,9,12-tetraoxatetradecan-1-ol, 7 g, crude) as yellow oil.

LC-MS Calcd m/z for C$_{10}$H$_{23}$NO$_5$ [M+H]$^+$ 238.3 Found 238.0.

Step 3) Synthesis of H-4

To a solution of H-3 (7 g, 18.4 mmol) in DCM (70 mL) was added TEA (5.6 g, 55.2 mmol) and CbzCl (3.77 g, 22.1 mmol) dropwise at 0° C. The reaction mixture was stirred at room temperature overnight. The above solution was poured into water and extracted with DCM. The combined organic layers were washed with brine, dried over $Na_2SO_4$ and concentrated. The crude was purified by column chromatography on silica gel to give H-4 (benzyl (14-hydroxy-3,6,9,12-tetraoxatetradecyl)carbamate, 4 g) as yellow oil.

$^1$H-NMR (CDCl$_3$, 400 MHz) δ (ppm) 7.39-7.32 (m, 5H), 5.91 (br s, 1H), 5.12 (s, 2H), 3.71-3.57 (m, 17H), 3.41 (m, 2H), 2.5 (m, 2H); LC-MS Calcd m/z for $C_{18}H_{29}NO_7$ [M+H]$^+$ 372.4 Found 372.1.

Step 4) Synthesis of H-5

To a solution of DMSO (524.2 mg, 6.72 mmol) in DCM (20 mL) was added oxalyl chloride (683.3 mg, 5.38 mmol) at −78° C. under $N_2$. After 30 min, a solution of H-4 (1 g, 2.69 mmol) in DCM was added. After an hour, TEA (2.17 g, 21.52 mmol) was added and the mixture was stirred for 2 h. The reaction solution was quenched with water and extracted with DCM. The combined organic layers were washed with 1N HCl, saturated sodium bicarbonate aqueous solution, dried over $Na_2SO_4$ and concentrated to give H-5 (benzyl (14-oxo-3,6,9,12-tetraoxatetradecyl)carbamate, 900 mg) as yellow oil.

$^1$H-NMR (CDCl$_3$, 400 MHz) δ (ppm) 9.72 (s, 1H), 7.38-7.33 (m, 5H), 5.41 (br s, 1H), 5.12 (s, 2H), 4.13 (s, 1H) 3.70-3.42 (m, 15H), 3.42-3.39 (m, 2H); LC-MS Calcd m/z for $C_{18}H_{27}NO_7$ [M+H]$^+$ 370.4 Found 370.1.

Step 5) Synthesis of H-6

To a solution of diethoxyphosphoryl-acetic acid ethyl ester (CAS No.: 867-13-0, 1.09 g, 4.86 mmol) in THF (30 mL) was added NaH (195 mg, 4.86 mmol) at 0° C. After an hour, a solution of H-5 (1.5 g, 4.05 mmol) in THF was added. The mixture was stirred at rt for 2 h. The above solution was poured into ice-water and extracted with EA. The combined organic layers were washed with brine, dried over $Na_2SO_4$ and concentrated. The crude was purified by column chromatography on silica gel (DCM/MeOH=100:1) to give H-6 (ethyl (E)-3-oxo-1-phenyl-2,7,10,13,16-pentaoxa-4-azaicos-18-en-20-oate, 1.2 g) as yellow oil.

$^1$H-NMR (CDCl$_3$, 400 MHz) δ (ppm) 7.38-7.32 (m, 5H), 6.97-6.92 (d, 1H), 6.11-6.07 (d, 1H), 5.21 (s, 2H), 4.25-4.14 (m, 4H), 3.69-3.57 (m, 12H), 3.43-3.39 (m, 2H), 1.39-1.25 (m, 6H); LC-MS Calcd m/z for $C_{22}H_{33}NO_8$ [M+H]$^+$ 440.5 Found 440.2.

Step 6) Synthesis of H-7

To a solution of H-6 (1.2 g, 2.73 mmol) in MeOH (30 mL) was added AcOH (1 mL) and Pd/C (500 mg). The reaction mixture was stirred at 0° C. under $H_2$ overnight. The above solution was filtered and the filtrate was concentrated. The residue was diluted with water, adjusted pH=8 with saturated sodium bicarbonate aqueous solution and extracted with DCM. The combined organic layers were washed with brine, dried over $Na_2SO_4$ and concentrated to give H-7 (ethyl 1-amino-3,6,9,12-tetraoxahexadecan-16-oate, 800 mg) as yellow oil.

$^1$H-NMR (CDCl$_3$, 400 MHz) δ (ppm) 4.13 (q, 2H), 3.68-3.58 (m, 13H), 3.54-3.49 (m, 4H), 2.88 (t, 2H), 2.40 (t, 2H), 1.91 (quin, 2H), 1.27 (t, 3H); LC-MS Calcd m/z for $C_{14}H_{29}NO_6$ [M+H]$^+$ 308.3 Found 308.2.

Step 7) Synthesis of H-9

To a solution of H-7 (600 mg, 1.95 mmol) in MeOH (10 mL) was added H-8 ((R)-2-((3,4-bis((4-fluorobenzyl)oxy)phenoxy)methyl)oxirane, 775 mg, 1.95 mmol). The reaction mixture was stirred at 65° C. overnight. The above solution was concentrated, diluted with water and extracted with DCM. The combined organic layers were washed with brine, dried over $Na_2SO_4$ and concentrated. The crude was purified by column chromatography on silica gel to give H-9 (ethyl (R)-1-(3,4-bis((4-fluorobenzyl)oxy)phenoxy)-2-hydroxy-7,10,13,16-tetraoxa-4-azaicosan-20-oate, 400 mg) as yellow oil.

$^1$H-NMR (CDCl$_3$, 400 MHz) δ (ppm) 7.43-7.36 (m, 4H), 7.12-7.02 (m, 4H), 6.85 (d, 1H), 6.61 (s, 1H), 6.44-6.41 (m, 1H), 5.08 (s, 2H), 5.02 (s, 2H), 4.13 (q, 2H), 4.07 (m, 1H), 3.92 (m, 2H), 3.67-3.58 (m, 14H), 3.51 (t, 2H), 2.95-2.79 (m, 4H), 2.41-2.35 (m, 3H), 1.91 (quin, 2H), 1.27 (t, 3H); LC-MS Calcd m/z for $C_{37}H_{49}F_2NO_{10}$ [M+H]$^+$ 706.7 Found 706.3.

Step 8) Synthesis of H-10

To a solution of H-9 (550 mg, 0.779 mmol) in DCM (10 mL) was added TEA (157.4 mg, 1.558 mmol) and Boc$_{2O}$ (204 mg, 0.935 mmol). The reaction mixture was stirred at room temperature overnight. The above solution was poured into water and extracted with DCM. The combined organic layers were washed with brine, dried over $Na_2SO_4$ and concentrated. The crude was purified by column chromatography on silica gel to give H-10 (ethyl (R)-5-(3-(3,4-bis((4-fluorobenzyl)oxy)phenoxy)-2-hydroxypropyl)-2,2-dimethyl-4-oxo-3,8,11,14,17-pentaoxa-5-azahenicosan-21-oate, 400 mg) as yellow oil.

$^1$H-NMR (CDCl$_3$, 400 MHz) δ (ppm) 7.43-7.37 (m, 4H), 7.10-7.02 (m, 4H), 6.86 (d, 1H), 6.62-6.60 (m, 1H), 6.43-6.41 (m, 1H), 5.08 (s, 2H), 5.02 (s, 2H), 4.35 (m, 1H), 4.17-4.11 (m, 3H), 3.88 (m, 2H), 3.68-3.46 (m, 19H), 2.40 (t, 2H), 1.91 (quin, 2H), 1.49 (m, 8H), 1.27 (t, 3H)

Step 9) Synthesis of H-11

To a solution of H-10 (400 mg, 0.497 mmol) in MeOH (8 mL) and water (2 mL) was added LiOH (25 mg, 0.596 mmol). The reaction mixture was stirred at room temperature overnight. The above solution was concentrated, adjusted pH=2 with 1N HCl and extracted with EA. The combined organic layers were washed with brine, dried over $Na_2SO_4$ and concentrated to give H-11 (350 mg) as colorless oil.

$^1$H-NMR (CDCl$_3$, 400 MHz) δ (ppm) 7.44-7.37 (m, 4H), 7.10-7.02 (m, 4H), 6.86 (d, 1H), 6.63-6.60 (m, 1H), 6.43-6.41 (m, 1H), 5.08 (s, 2H), 5.02 (s, 2H), 4.21 (m, 1H), 3.91-3.90 (m, 2H), 3.67-3.48 (m, 20H), 2.45 (t, 2H), 1.92 (quin, 2H), 1.49 (m, 9H)

Step 10) Synthesis of H-12

To a solution of H-11 (457.6 mg, 0.589 mmol) in DMF (10 mL) was added TBL-1 (500 mg, 0.589 mmol), DIEA (228 mg, 1.77 mmol) and HATU (224 mg, 0.589 mmol). The reaction mixture was stirred at room temperature overnight. The above solution was poured into water and extracted with EA. The combined organic layers were washed with brine, dried over Na$_2$SO$_4$ and concentrated. The crude was purified by column chromatography on silica gel (DCM/MeOH=20:1) to give H-12 (700 mg) as yellow solid.

$^1$H-NMR (CDCl$_3$, 400 MHz) δ (ppm) 7.94 (s, 1H), 7.54-7.51 (m, 2H), 7.40-7.26 (m, 16H), 7.07-7.00 (m, 4H), 6.94 (m, 1H), 6.83-6.76 (m, 1H), 6.73-6.65 (m, 1H), 6.46-6.39 (m, 1H), 5.04 (s, 2H), 5.01 (s, 2H), 4.56 (m, 1H), 4.22-4.12 (m, 6H), 3.87 (m, 3H), 3.88-3.45 (m, 17H), 2.56-2.15 (m, 6H), 2.07-1.97 (m, 5H), 1.67 (m, 17H), 1.45 (m, 8H), 1.33-1.26 (m, 6H)

Step 11) Synthesis of Compound H

H-12 (250 mg, 0.155 mmol) and DCM (6 mL) were placed in a round bottomed flask. The solution was cooled to 0° C. before adding CF$_3$CON(TMS)$_2$ (236.8 mg, 0.932 mmol) and TMS-I (124.3 mg, 0.621 mmol). The reaction mixture was stirred at 0° C. for 30 min, and then the solvent was removed under vacuum at 0° C. The residue was purified by prep-HPLC to give Compound H (((2-(((5S,8S,10aR)-8-(((S)-5-amino-1-(benzhydrylamino)-1,5-dioxopentan-2-yl)carbamoyl)-3-((R)-1-(3,4-bis((4-fluorobenzyl)oxy)phenoxy)-2-hydroxy-7,10,13,16-tetraoxa-4-azaicosan-20-oyl)-6-oxodecahydropyrrolo[1,2-a][1,5]diazocin-5-yl)carbamoyl)-1H-indol-5-yl)difluoromethyl)phosphonic acid, 30 mg) as white solid.

$^1$H-NMR (DMSO_d$_6$, 400 MHz): δ 11.86 (s, 1H), 9.65-9.43 (m, 2H), 9.11-8.91 (m, 2H), 8.79 (d, 1H), 8.40-8.32 (m, 1H), 8.27-8.19 (m, 1H), 7.86 (s, 1H), 7.64-7.11 (m, 18H), 6.94 (d, 1H), 6.83-6.76 (m, 1H), 6.73-6.65 (m, 1H), 6.46-6.39 (m, 1H), 6.13-6.07 (m, 1H), 5.17-4.92 (m, 5H), 4.53-4.15 (m, 5H), 4.08-3.71 (m, 6H), 3.32-2.68 (m, 21H), 2.26-1.55 (m, 16H); LC-MS Calcd m/z for C$_{73}$H$_{85}$F$_4$N$_8$O$_{17}$P [M+1]$^+$1454.4 Found 1455.4.

Example 22. Preparation of Compound I ((R)-5-((3-((21-(3,4-bis((4-fluorobenzyl)oxy)phenoxy)-20-hydroxy-3,6,9,12,15-pentaoxa-18-azahenicosyl)amino)-5-chlorophenyl)amino)benzo[c][2,6]naphthyridine-8-carboxylic acid)

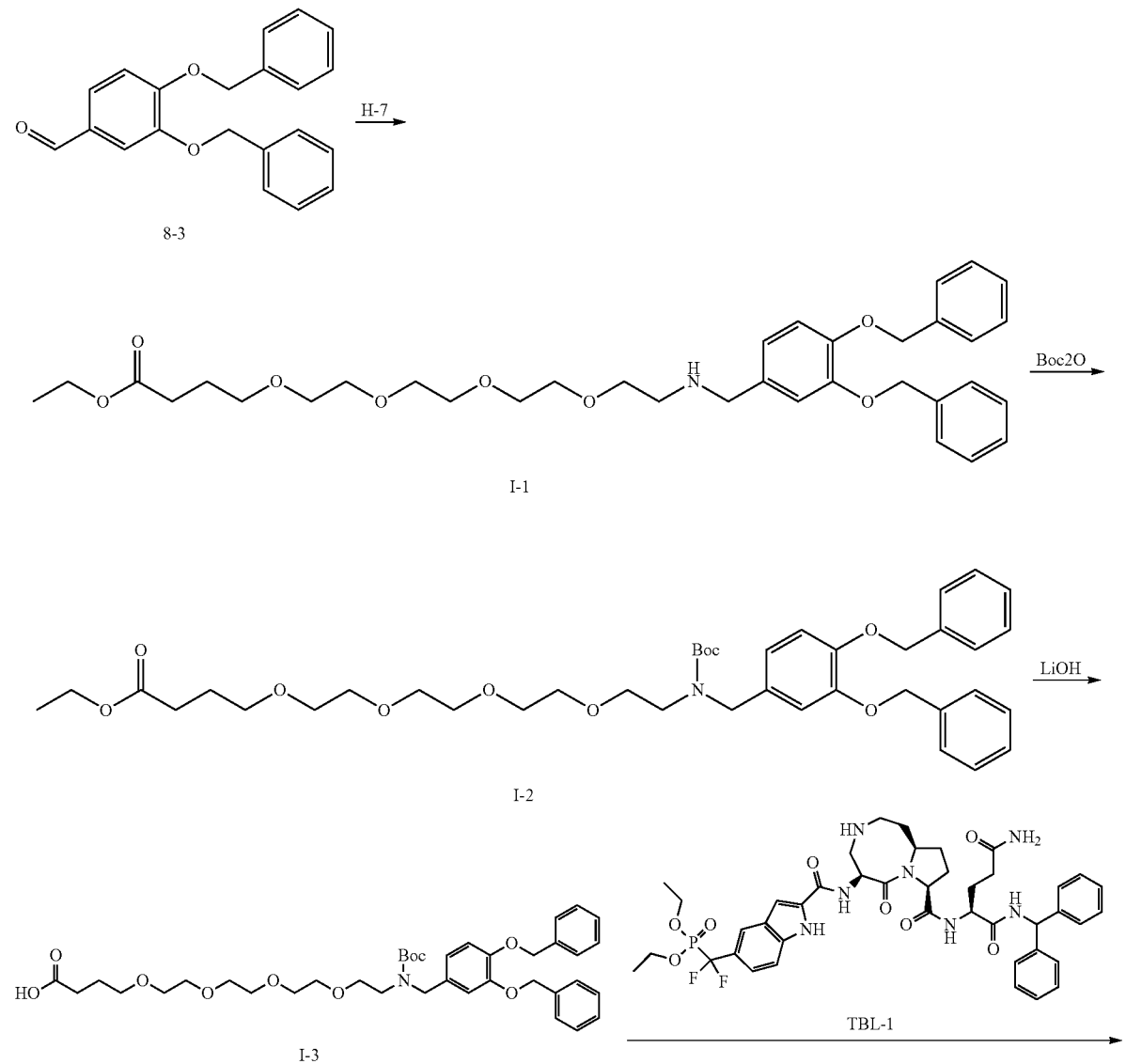

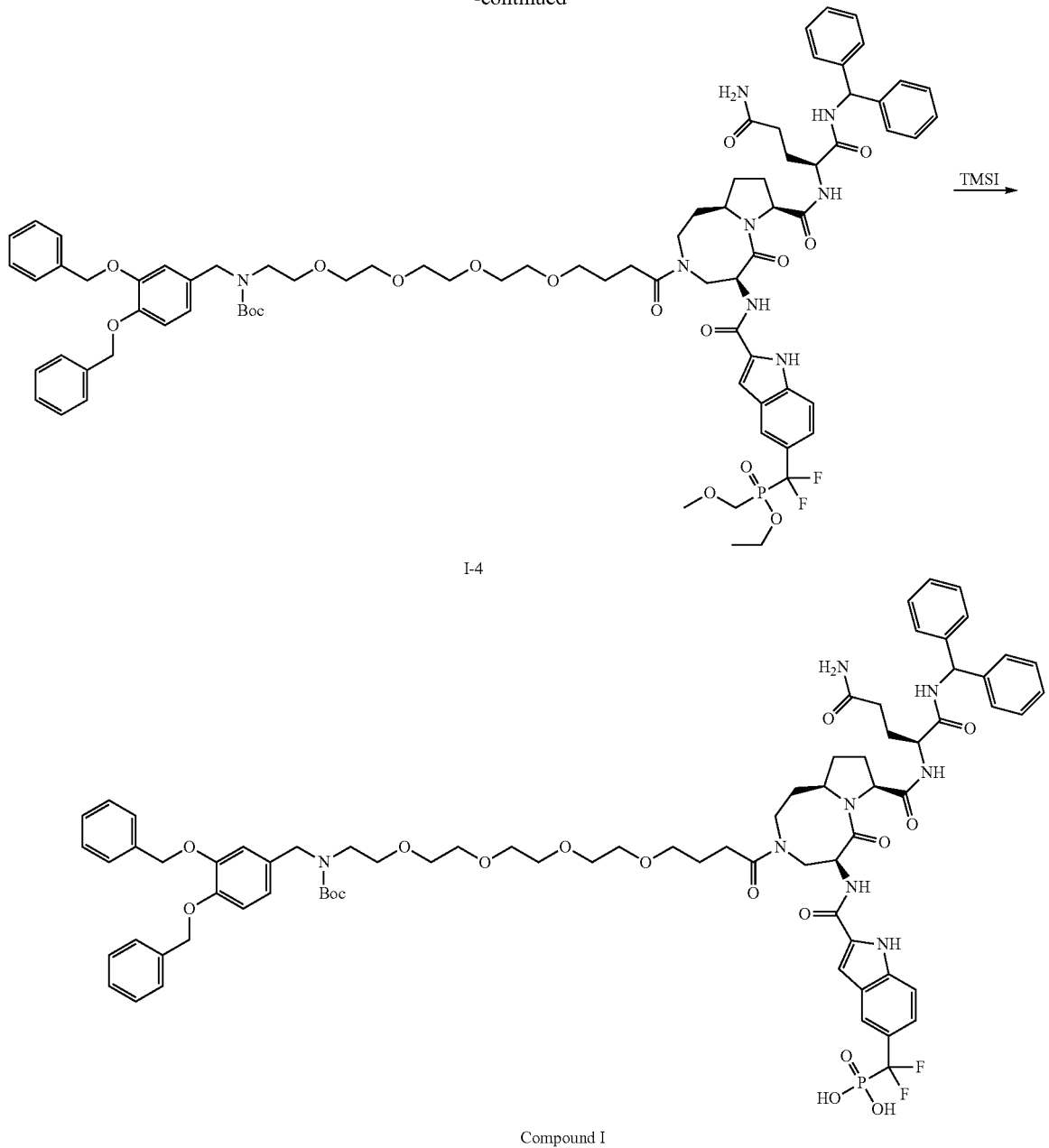

Step 1) Synthesis of I-1

A solution of H-7 (250 mg, 0.81 mmol) and B-3 (258 mg, 0.81 mmol) in MeOH (6 mL) was stirred at 65° C. for 3 h. NaBH₄ (46 mg, 1.21 mmol) was added at 0° C. The reaction mixture was stirred at room temperature overnight. The above solution was poured into water and extracted with DCM. The combined organic layers were washed with brine, dried over Na₂SO₄ and concentrated to give I-1 (ethyl 1-(3,4-bis(benzyloxy)phenyl)-5,8,11,14-tetraoxa-2-azaoctadecan-18-oate, 520 mg) as yellow oil.

LC-MS Calcd m/z for $C_{35}H_{47}NO_8$ [M]⁺609.7 Found 610.4.

Step 2) Synthesis of I-2

To a solution of I-1 (520 mg, 0.85 mmol) in DCM (10 mL) was added TEA (172 mg, 1.7 mmol) and Boc₂O (223 mg, 1.02 mmol). The reaction mixture was stirred at room temperature overnight. The above solution was poured into water and extracted with DCM. The combined organic layers were washed with brine, dried over Na₂SO₄ and concentrated. The crude was purified by column chromatography on silica gel to give I-2 (ethyl 5-(3,4-bis(benzyloxy)benzyl)-2,2-dimethyl-4-oxo-3,8,11,14,17-pentaoxa-5-azahenicosan-21-oate, 400 mg) as colorless oil.

¹H-NMR (CDCl₃, 400 MHz): δ 7.45 (d, 4H), 7.39-7.29 (m, 6H), 6.90-6.87 (m, 2H), 6.76 (m, 1H), 5.15 (m, 4H), 4.41

(m, 2H), 4.20-4.11 (m, 2H), 3.68-3.48 (m, 16H), 3.34 (s, 1H), 3.24 (s, 1H), 2.40 (t, 2H), 1.91 (quin., 2H), 1.47 (m, 9H), 1.27 (t, 3H).

Step 3) Synthesis of I-3

To a solution of I-2 (360 mg, 0.51 mmol) in MeOH (6 mL) and water (2 mL) was added LiOH (25.6 mg, 0.61 mmol). The reaction mixture was stirred at room temperature overnight. The above solution was concentrated, adjusted pH=2 with 1N HCl and extracted with EA. The combined organic layers were washed with brine, dried over $Na_2SO_4$ and concentrated to give I-3 (5-(3,4-bis(benzyloxy)benzyl)-2,2-dimethyl-4-oxo-3,8,11,14,17-pentaoxa-5-azahenicosan-21-oic acid, 300 mg) as yellow oil.

$^1$H-NMR (CDCl$_3$, 400 MHz): δ 7.46 (d, 4H), 7.39-7.29 (m, 6H), 6.90-6.88 (m, 2H), 6.76 (m, 1H), 5.16 (m, 4H), 4.43-4.39 (m, 2H), 3.67-3.50 (m, 16H), 3.34 (s, 1H), 3.24 (s, 1H), 2.45 (t, 2H), 1.93 (quin, 2H), 1.50-1.45 (m, 9H).

Step 4) Synthesis of I-4

To a solution of I-3 (401 mg, 0.589 mmol) in DMF (10 mL) was added TBL-1 (diethyl ((2-(((5S,8S,10aR)-8-(((S)-5-amino-1-(benzhydrylamino)-1,5-dioxopentan-2-yl)carbamoyl)-6-oxodecahydropyrrolo[1,2-a][1,5]diazocin-5-yl)carbamoyl)-1H-indol-5-yl)difluoromethyl)phosphonate, 500 mg, 0.589 mmol), DIEA (228 mg, 1.77 mmol) and HATU (224 mg, 0.589 mmol). The reaction mixture was stirred at room temperature overnight. The above solution was poured into water and extracted with EA. The combined organic layers were washed with brine, dried over $Na_2SO_4$ and concentrated. The crude was purified by column chromatography on silica gel (DCM/MeOH=20:1) to give I-4 (600 mg) as white solid.

LC-MS Calcd m/z for $C_{80}H_{99}F_2N_8O_{17}P$ [M+1]$^+$1514.6 Found 1513.7 and 1414.7.

Step 5) Synthesis of Compound I

I-4 (210 mg, 0.139 mmol) and DCM (6 mL) were placed in a round bottomed flask. The solution was cooled to 0° C. before adding CF$_3$CON(TMS)$_2$ (211.5 mg, 0.833 mmol) and TMS-I (111.2 mg, 0.556 mmol). The reaction mixture was stirred at 0° C. for 30 min, and then the solvent was removed under vacuum at 0° C. The residue was purified by prep-HPLC to give Compound I (((2-(((5S,8S,10aR)-8-(((S)-5-amino-1-(benzhydrylamino)-1,5-dioxopentan-2-yl)carbamoyl)-3-(1-(3,4-bis(benzyloxy)phenyl)-5,8,11,14-tetraoxa-2-azaoctadecan-18-oyl)-6-oxodecahydropyrrolo[1,2-a][1,5]diazocin-5-yl)carbamoyl)-1H-indol-5-yl)difluoromethyl) phosphonic acid, 30 mg) as white solid.

$^1$H-NMR (DMSO_d$_6$, 400 MHz): δ 711.85 (s, 1H), 9.75-9.57 (m, 2H), 8.79 (d, 1H), 8.38-8.29 (m, 1H), 8.27-8.19 (m, 1H), 7.86 (s, 1H), 7.56-7.18 (m, 23H), 7.05-6.92 (m, 2H), 6.78 (s, 1H), 6.11 (d, 1H), 5.23-5.08 (m, 4H), 5.02-4.92 (m, 1H), 4.49-4.32 (m, 2H), 4.27-4.16 (m, 1H), 3.98-3.72 (m, 4H), 3.47-3.34 (m, 19H), 3.08-2.93 (m, 4H), 2.23-1.53 (m, 14H); LC-MS Calcd m/z for $C_{71}H_{83}F_2N_8O_{15}P$ [M+1]$^+$ 1358.4 Found 1359.4

Example 23. Preparation of Compound J ((4-((1-(3,4-bis(benzyloxy)phenyl)-16-ethyl-5,8-dioxa-2,11,16-triazaoctadecan-18-yl)oxy)phenyl) (6-hydroxy-2-(4-hydroxyphenyl)benzo[b]thiophen-3-yl) methanone)

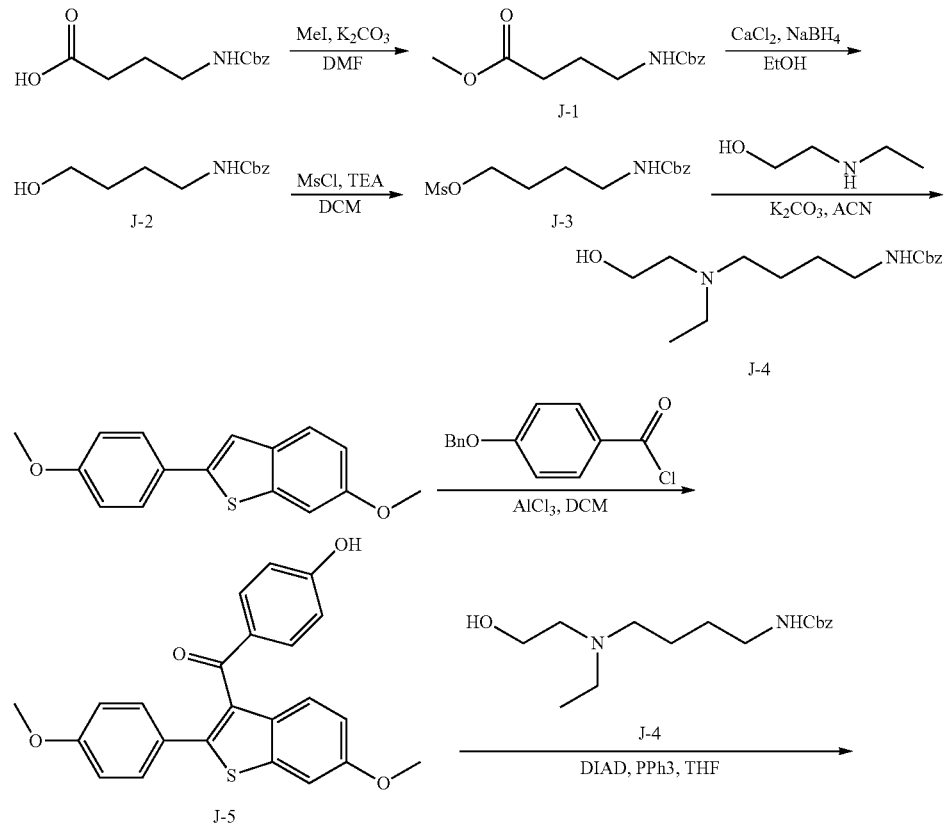

-continued
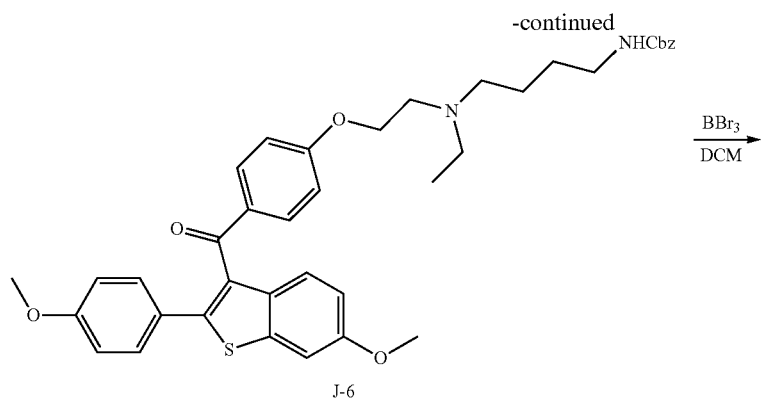
J-6
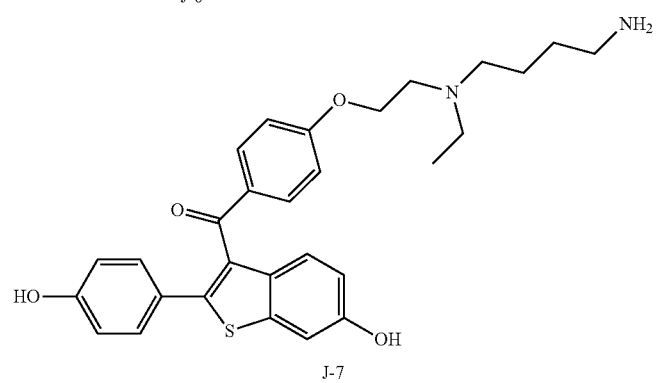
J-7
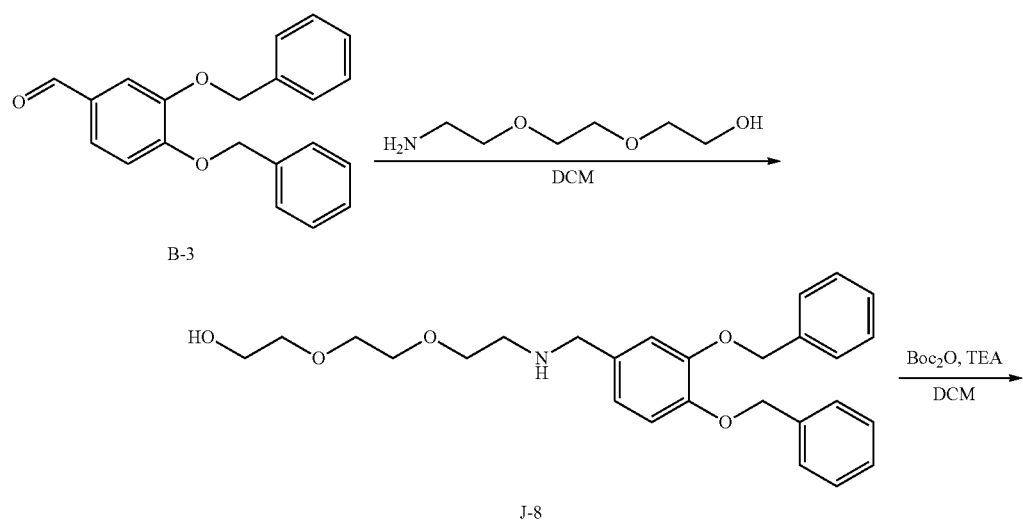
B-3
J-8
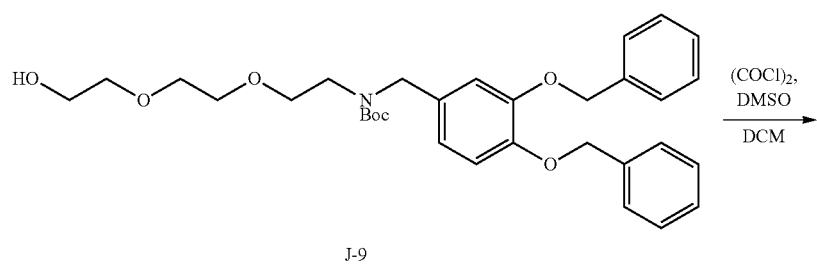
J-9

-continued

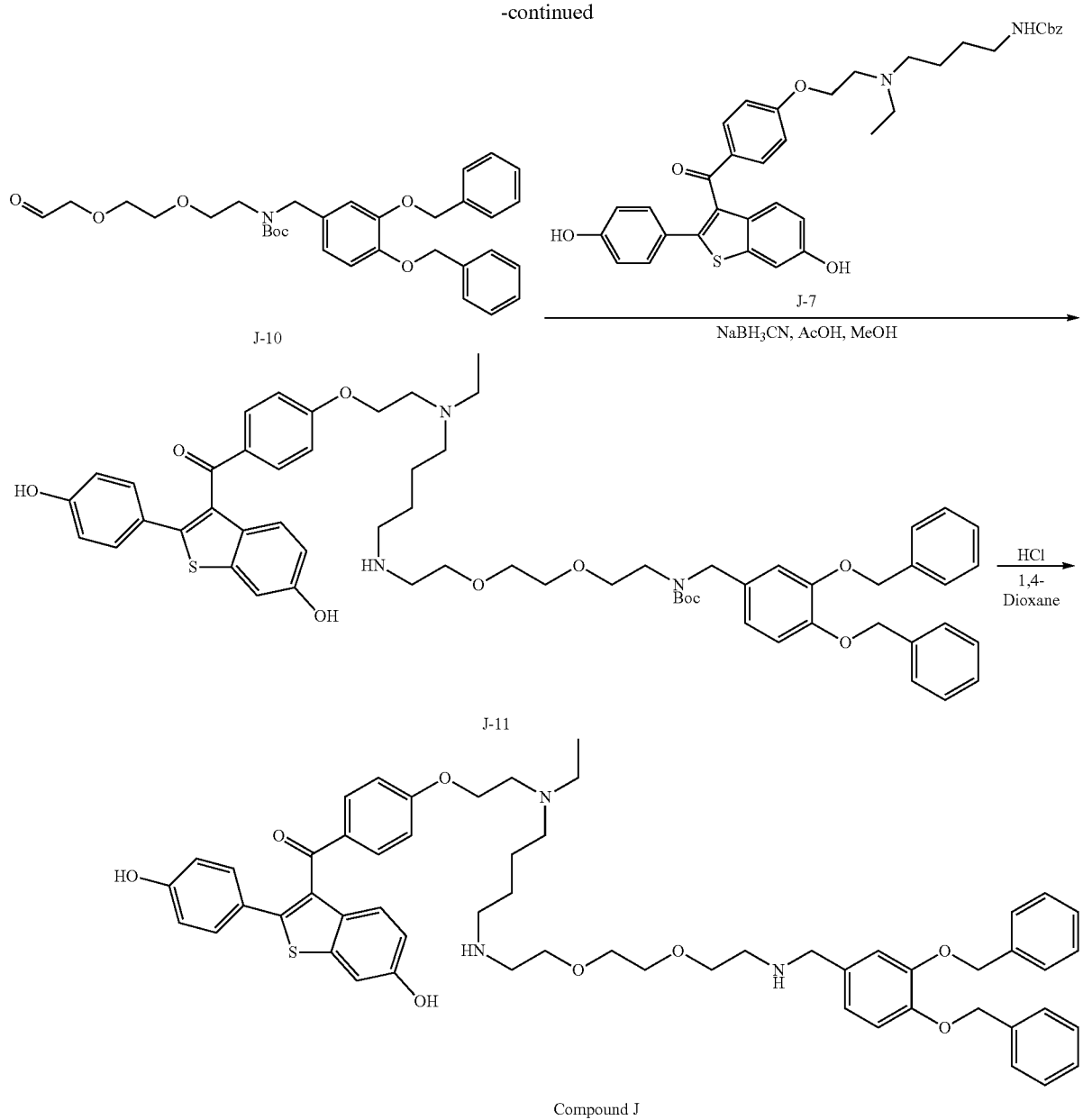

Compound J

Step 1) Synthesis of J-1

To a solution of 4-(((benzyloxy)carbonyl)amino)butanoic acid (50 g, 0.21 mol) in DMF (500 mL) were added $K_2CO_3$ (30 g, 0.22 mol) and MeI (60 g, 0.42 mol) at 0° C. The reaction mixture was stirred at r.t overnight. The mixture was poured into water and extracted with EA. The combined organic layers was dried over $Na_2SO_4$ and concentrated to give J-1 (methyl 4-(((benzyloxy)carbonyl)amino)butanoate, 50 g) as colorless oil.

$^1$H-NMR (DMSO_$d_6$, 400 MHz): δ (ppm) 7.39-7.28 (m, 5H), 5.01 (s, 2H), 3.59 (s, 3H), 3.02 (q, J=6.4 Hz, 2H) 2.32 (t, J=7.2 Hz, 2H), 1.68-1.65 (m, 2H);

Step 2) Synthesis of J-2

To a solution of crude J-1 (50 g, 0.20 mol) in EtOH (500 mL) were added $CaCl_2$ (44.4 g, 0.40 mol) and $NaBH_4$ (30.4 g, 0.80 mol) at 0° C. The reaction mixture was stirred at r.t overnight. The mixture was poured into water and extracted with EA. The combined organic layers was dried over $Na_2SO_4$ and concentrated to give J-2 (benzyl (4-hydroxybutyl)carbamate, 35 g) as white solid.

$^1$H-NMR (DMSO_$d_6$, 400 MHz): δ (ppm) 7.39-7.30 (m, 5H), 7.23 (t, J=4.8 Hz, 1H), 5.01 (s, 2H), 3.40-3.37 (m, 2H) 3.00-2.97 (m, 2H), 1.44-1.41 (m, 4H); ESI-MS Calcd m/z for $C_{12}H_{17}NO_3$ [M+H]$^+$ 224.13 found 224.10.

Step 3) Synthesis of J-3

To a solution of crude J-2 (35 g, 0.16 mol) in DCM (350 mL) were added $Et_3N$ (32.3 g, 0.32 mol) and MsCl (27.4 g, 0.24 mol) at 0° C. The reaction mixture was stirred at r.t overnight. The mixture was poured into water and extracted with EA. The combined organic layers was dried over Na$_2$SO$_4$ and concentrated to give J-3 (4-(((benzyloxy)carbonyl)amino)butyl methanesulfonate, 45 g) as colorless oil.

$^1$H-NMR (DMSO_d$_6$, 400 MHz): δ (ppm) 7.39-7.30 (m, 5H), 5.02 (s, 2H), 4.20 (t, J=6.4 Hz, 2H), 3.16 (s, 3H), 3.06-2.99 (m, 2H), 1.70-1.63 (m, 2H), 1.53-1.41 (m, 2H); ESI-MS Calcd m/z for C$_{13}$H$_{19}$NO$_5$S [M+H]$^+$ 302.11 found 302.10

Step 4) Synthesis of J-4

To a solution of crude J-3 (45 g, 0.15 mol) in acetonitrile (450 mL) were added 2-(ethylamino)ethanol (16 g, 0.18 mol) and K$_2$CO$_3$ (31.7 g, 0.23 mol). The reaction mixture was stirred at 80° C. overnight. The mixture was poured into water and extracted with EA. The combined organic layers was dried over Na$_2$SO$_4$ and concentrated. The residue was purified by column chromatography (DCM/MeOH=10:1) to afford J-4 (benzyl (4-(ethyl(2-hydroxyethyl)amino)butyl)carbamate, 25 g) as colorless oil.

$^1$H-NMR (DMSO_d$_6$, 400 MHz): δ (ppm) 7.39-7.30 (m, 5H), 5.02 (s, 2H), 3.44-3.36 (m, 4H), 3.00-2.97 (m, 2H), 2.47-2.40 (m, 4H), 1.39-1.37 (m, 4H) 0.94 (t, J=6.8 Hz, 3H); ESI-MS Calcd m/z for C$_{16}$H$_{26}$N$_2$O$_3$ [M+H]$^+$ 295.20 found 295.20

Step 5) Synthesis of J-5

To a solution of 6-methoxy-2-(4-methoxyphenyl)benzo[b]thiophene (21 g, 77.8 mmol) in DCM (300 mL) were added AlCl$_3$ (12 g, 93.3 mmol) and 4-(benzyloxy)benzoyl chloride (24 g, 93.3 mmol) at 0° C. The reaction mixture was stirred at r.t overnight. The mixture was poured into water and extracted with DCM. The combined organic layers was dried over Na$_2$SO$_4$ and concentrated. The residue was purified by column chromatography (PE/EA=2:1) to afford J-5 ((4-hydroxyphenyl) (6-methoxy-2-(4-methoxyphenyl)benzo[b]thiophen-3-yl)methanone, 20 g) as yellow solid.

$^1$H-NMR (DMSO_d$_6$, 400 MHz): δ (ppm) 10.48 (brs, 1H), 7.65-7.63 (m, 3H), 7.35-7.26 (m, 3H), 7.03-6.98 (m, 1H), 6.91-6.87 (m, 2H), 6.78-6.73 (m, 2H), 3.85 (s, 3H), 3.73 (s, 3H); EST-MS Calcd m/z for C$_{23}$H$_{18}$O$_4$S [M+H]$^+$ 391.10 found 391.00

Step 6) Synthesis of J-6

To a solution of J-5 (37 g, 94.9 mmol) in THF (400 mL) were added J-4 (28 g, 94.9 mmol), PPh$_3$ (37 g, 142 mmol), then DIAD (28 g, 142 mmol) was slowly added to the solution at 0° C. under N$_2$. The reaction mixture was stirred at r.t overnight. The mixture was poured into water and extracted with EA. The combined organic layers was washed with 0.5N HCl, dried over Na$_2$SO$_4$ and concentrated. The residue was purified by column chromatography (DCM/MeOH=20:1) to afford J-6 (benzyl (4-(ethyl(2-(4-(6-methoxy-2-(4-methoxyphenyl)benzo[b]thiophene-3-carbonyl)phenoxy)ethyl)amino)butyl)carbamate, 30 g) as yellow oil.

$^1$H-NMR (DMSO_d$_6$, 400 MHz): δ (ppm) 7.68-7.55 (m, 5H), 7.34-7.20 (m, 8H), 7.01-6.98 (m, 1H) 6.93-6.88 (m, 3H), 5.01 (s, 2H), 4.06-4.01 (m, 2H), 3.86 (s, 3H), 3.73 (s, 3H), 2.97-2.96 (m, 2H), 2.73 (t, J=5.2 Hz, 2H), 2.49-2.47 (m, 4H), 1.37 (m, 4H), 0.93 (t, J=6.8 Hz, 3H); ESI-MS Calcd m/z for C$_{39}$H$_{42}$N$_2$O$_6$S [M+H]$^+$ 667.29 found 667.30

Step 7) Synthesis of J-7

To a solution of J-6 (25 g, 37.5 mmol) in DCM (300 mL) was added BBr$_3$ (47 g, 187.5 mmol) at 0° C. under N$_2$. The reaction mixture was stirred at r.t overnight. The mixture was poured into water and extracted with DCM. The aqueous layer adjusted pH=8 with saturated sodium bicarbonate aqueous solution and filtered. Filter cake was concentrated to give J-7 ((4-(2-((4-aminobutyl) (ethyl)amino)ethoxy)phenyl) (6-hydroxy-2-(4-hydroxyphenyl)benzo[b]thiophen-3-yl)methanone, 18 g) as yellow solid.

$^1$H-NMR (DMSO d$_6$, 400 MHz): δ (ppm) 8.20 (brs, 2H), 7.66 (d, J=8.8 Hz, 2H), 7.37 (d, J=2.0 Hz, 1H), 7.25 (d, J=8.8 Hz, 1H), 7.17 (d, J=8.8 Hz, 2H), 6.94-6.86 (m, 3H), 6.70 (d, J=8.8 Hz, 2H), 4.10-4.08 (m, 2H), 3.19-3.17 (m, 2H), 3.14-3.12 (m, 2H), 2.78-2.63 (m, 4H), 1.56-1.48 (m, 4H), 0.98 (t, J=4.8 Hz, 3H); ESI-MS Calcd m/z for C$_{29}$H$_{32}$N$_2$O$_4$S [M+H]$^+$ 505.22 found 505.20

Step 8) Synthesis of J-8

To a solution of B-3 (3,4-bis(benzyloxy)benzaldehyde, 40 g, 0.13 mol) in MeOH (400 mL) was added 2-(2-(2-aminoethoxy)ethoxy) ethan-1-ol (18.7 g, 0.13 mol). The reaction mixture was stirred at 60° C. for 3 hrs. under N$_2$. Then the reaction mixture was cooled to 0° C. and NaBH$_4$ (7.4 g, 0.19 mol) was slowly added. The reaction mixture was stirred at r.t overnight. The mixture was poured into water and extracted with DCM. The combined organic layers was dried over Na$_2$SO$_4$ and concentrated to give J-8 (2-(2-(2-((3,4-bis(benzyloxy)benzyl)amino)ethoxy)ethoxy)ethan-1-ol, 53 g) as light yellow oil.

ESI-MS Calcd m/z for C27H$_{33}$NO$_5$ [M+H]+ 452.25 found 452.20

Step 9) Synthesis of J-9

To a solution of crude J-8 (53 g, 0.12 mol) in DCM (530 mL) were added Et$_3$N (24 g, 0.24 mol) and Boc$_2$O (30 g, 0.14 mol) at 0° C. The reaction mixture was stirred at r.t overnight. The mixture was poured into water and extracted with DCM, The combined organic layers was washed with 0.5N HCl, saturated sodium bicarbonate aqueous solution and brine, dried over Na$_2$SO$_4$ and concentrated. The residue was purified by column chromatography (PE/EA=2:1) to afford J-9 (tert-butyl (3,4-bis(benzyloxy)benzyl) (2-(2-(2-hydroxyethoxy)ethoxy)ethyl)carbamate, 40 g) as light yellow oil.

$^1$H-NMR (CDCl$_3$, 400 MHz): δ (ppm) 7.47-7.45 (m, 4H), 7.40-7.30 (m, 6H), 6.90-6.86 (m, 2H), 6.78-6.75 (m, 1H), 5.16 (s, 4H), 4.42-4.39 (m, 2H), 3.75-3.25 (m, 12H), 1.51-1.45 (m, 9H) ESI-MS Calcd m/z for C$_{32}$H$_{41}$NO$_7$ [M+Na]+ 574.28 found 574.20

Step 10) Synthesis of J-10

Oxalyl chloride (10.4 g, 81.6 mmol) was slowly added to DMSO (6.4 g, 81.6 mmol) in DCM (200 mL) at −78° C. under N$_2$, then the reaction mixture was stirred at −78° C. for 1 hr. J-9 (15.0 g, 27.2 mmol) in DCM (100 mL) was slowly added to the stirred solution at −78° C. under N$_2$, then the reaction mixture was stirred at −78° C. for 1 hr. TEA (22.0 g, 217.6 mmol) was added slowly to the stirred solution at −78° C. under N$_2$, then the reaction mixture was stirred at −78° C. for 2 hrs. The mixture was poured into water and extracted with DCM. The combined organic layers was washed with 0.5N HCl, saturated sodium bicarbonate aqueous solution and brine, dried over Na$_2$SO$_4$ and concentrated to give J-10 (tert-butyl (3,4-bis(benzyloxy)benzyl) (2-(2-(2-oxoethoxy)ethoxy)ethyl)carbamate, 15 g) as light yellow oil.

¹H-NMR (CDCl₃, 400 MHz): δ (ppm) 9.72 (s, 1H), 7.47-7.45 (m, 4H), 7.39-7.30 (m, 6H), 6.91-6.86 (m, 2H), 6.78-6.76 (m, 1H), 5.16 (s, 4H), 4.41 (s, 2H), 3.70-3.26 (m, 10H), 1.51-1.45 (m, 9H);

Step 11) Synthesis of J-11

To a solution of J-7 ((4-(2-((4-aminobutyl) (ethyl)amino) ethoxy)phenyl) (6-hydroxy-2-(4-hydroxyphenyl)benzo[b] thiophen-3-yl)methanone, 15 g, 29.7 mmol) in MeOH (300 mL) were added J-10 (19.6 g, 35.6 mmol), Sodium cyanoborohydride (3.7 g, 59.4 mmol) and AcOH (356 mg, 5.94 mmol) at 0° C. under N₂. The reaction mixture was stirred at r.t overnight. The mixture was poured into water and extracted with DCM. The combined organic layers was dried over Na₂SO₄ and concentrated. The residue was purified by column chromatography (DCM/MeOH=8:1) to afford J-11 (tert-butyl (3,4-bis(benzyloxy)benzyl) (14-ethyl-16-(4-(6-hydroxy-2-(4-hydroxyphenyl)benzo[b]thiophene-3-carbonyl)phenoxy)-3,6-dioxa-9,14-diazahexadecyl)carbamate, 6 g) as brown solid.

¹H-NMR (DMSO_d₆, 400 MHz): δ (ppm) 8.28 (brs, 2H), 7.65 (d, J=8.4 Hz, 2H), 7.44-7.24 (m, 13H), 7.16 (d, J=8.4 Hz, 2H), 7.01-6.99 (m, 1H), 6.90-6.84 (m, 3H), 6.74-6.72 (m, 1H), 6.67 (d, J=8.4 Hz, 2H), 5.09 (s, 2H), 5.08 (s, 2H), 4.30 (s, 2H), 4.03-4.01 (m, 2H), 3.26-3.15 (m, 10H), 2.90-2.73 (m, 6H), 2.45-2.40 (m, 4H), 1.52-1.48 (m, 4H), 1.41-1.34 (m, 9H), 0.94-0.91 (t, J=6.8 Hz, 3H); ESI-MS Calcd m/z for C₆₁H₇₁N₃O₁₀S [M+H]⁺ 1038.50 found 1038.80

Step 12) Synthesis of Compound J

To a solution of J-11 (2 g, 1.93 mmol) in 1,4-dioxane (60 mL) was slowly added HCl/dioxane (4 mL). The reaction mixture was stirred at r.t overnight. The mixture was filtered. The filter cake was dissolved in MeOH (30 mL), adjusted pH=8 with saturated sodium bicarbonate and concentrated. The residue was purified by prep-HPLC to give Compound J ((4-((1-(3,4-bis(benzyloxy)phenyl)-16-ethyl-5,8-dioxa-2,11,16-triazaoctadecan-18-yl)oxy)phenyl) (6-hydroxy-2-(4-hydroxyphenyl)benzo[b]thiophen-3-yl)methanone, 1.2 g) as yellow solid.

¹H-NMR (CD₃OD, 400 MHz): δ (ppm) 8.49 (s, 2H), 7.73 (d, J=8.4 Hz, 2H), 7.45-7.41 (m, 5H), 7.37-7.28 (m, 7H), 7.21-7.17 (m, 3H), 7.09-7.03 (m, 2H), 6.92-6.88 (m, 3H), 6.65 (d, J=8.4 Hz, 2H), 5.15 (s, 2H), 5.14 (s, 2H), 4.22-4.20 (m, 2H), 4.12 (s, 2H), 3.73-3.66 (m, 8H), 3.27-3.26 (m, 2H), 3.12 (s, 4H), 3.05-2.94 (m, 6H), 1.71 (s, 4H), 1.20 (t, J=6.8 Hz 3H); ESI-MS Calcd m/z for C₅₆H₆₃N₃O₈S [M+H]⁺ 938.44 found 938.80

Example 24. Preparation of Compound L (((R)-5-((3-((21-(3,4-bis((4-fluorobenzyl)oxy)phenoxy)-20-hydroxy-3,6,9,12,15-pentaoxa-18-azahenicosyl) amino)-5-chlorophenyl)amino)benzo[c][2,6] naphthyridine-8-carboxylic acid)

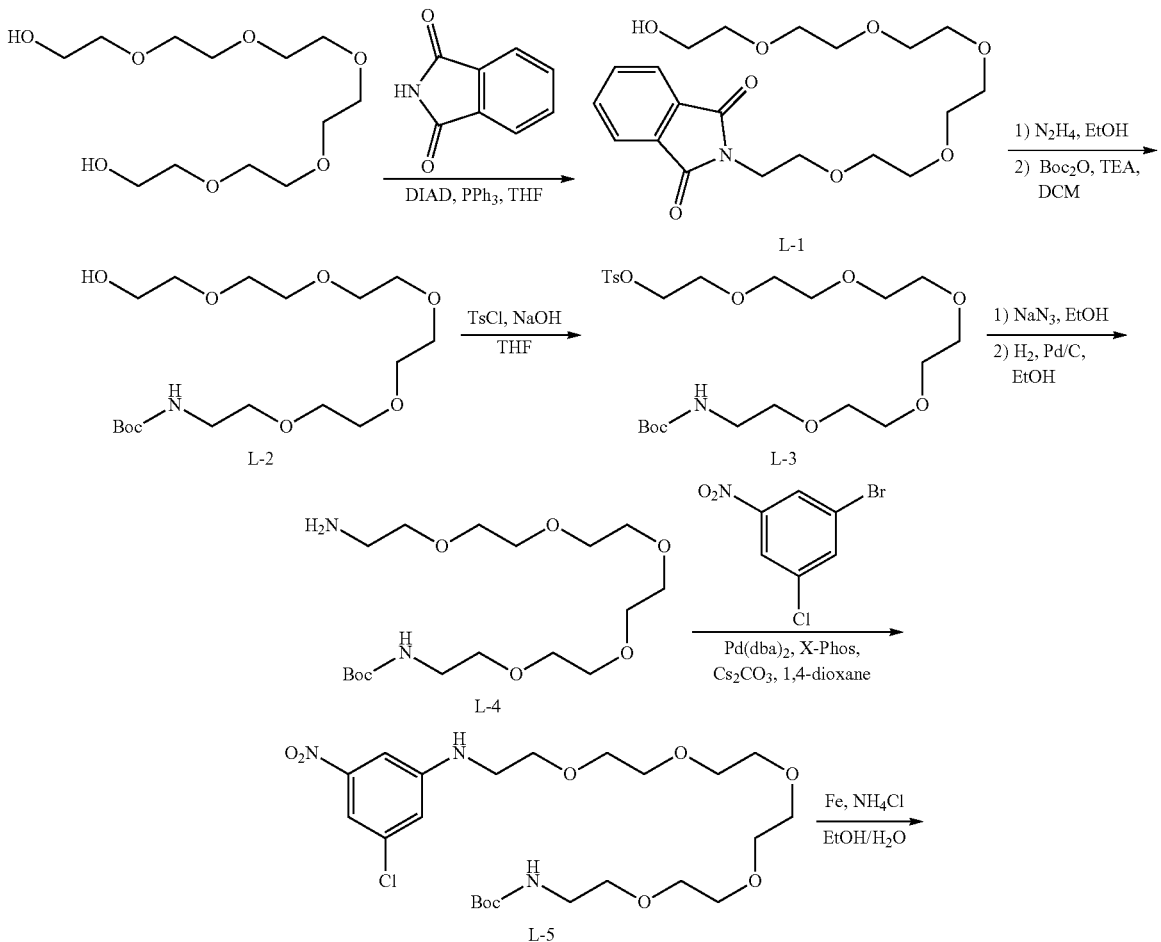

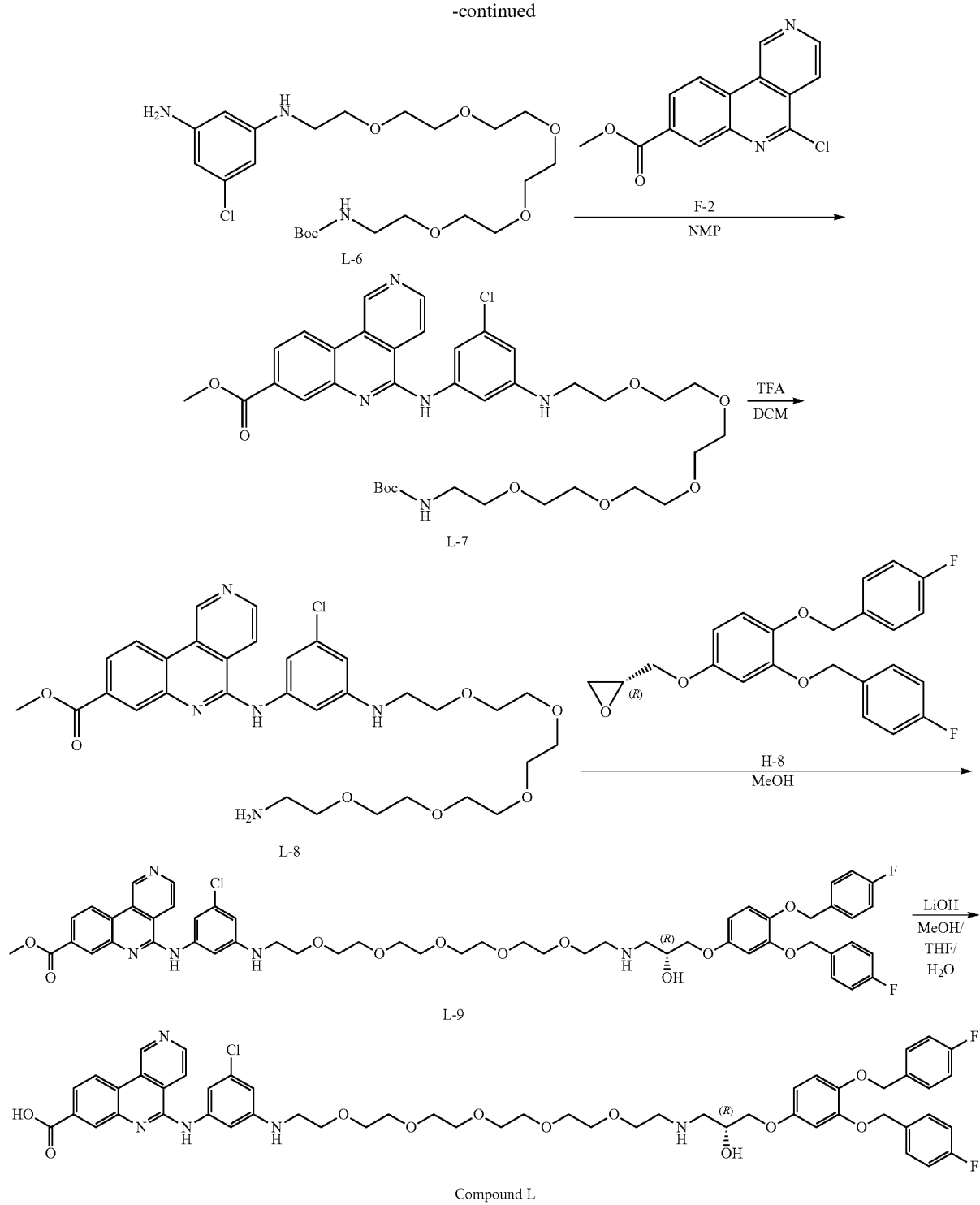

Step 1) Synthesis of L-1

To a solution of 3,6,9,12,15-pentaoxaheptadecane-1,17-diol (10 g, 35.5 mmol), PPh$_3$ (13.9 g, 53.2 mmol) and phthalimide (7.82 g, 53.2 mmol) in THF (150 mL) was added DIAD (10.7 g, 53.2 mmol) in THF (20 mL) at 0-5° C. in a drop-wise manner. The reaction mixture was stirred at r.t overnight. The mixture was poured into water and extracted with EA. The combined organic layers was dried over Na$_2$SO$_4$ and concentrated. The residue was purified by column chromatography (PE/EA=100/1-20/1) to give L-1 (2-(17-hydroxy-3,6,9,12,15-pentaoxaheptadecyl)isoindoline-1,3-dione, 3.00 g, 21.4%) as yellow oil.

ESI-MS Calcd m/z for C$_{20}$H$_{29}$NO$_8$ [M+H]$^+$ 412.20 found 411.90

Step 2) Synthesis of L-2

To a solution of L-1 (3 g, 7.3 mmol) in EtOH (30 mL) was added hydrazine (0.7 g, 21.9 mmol). The reaction mixture was stirred at 50° C. for 2 hrs. The mixture was collected by filtration and concentrated to give the crude amine intermediate (2.5 g). To a solution of the crude intermediate (2.5 g, 6.10 mmol) and Et$_3$N (1.23 g, 12.2 mmol) in DCM (5 mL) was added (Boc)$_2$O (2.66 g, 12.2 mmol) in DCM (5 mL) at 0-5° C. in a drop-wise manner. The reaction mixture was stirred at r.t overnight. The mixture was poured into water and extracted with EA. The combined organic layers was dried over Na$_2$SO$_4$ and concentrated. The residue was purified by column chromatography (PE/EA=100/1-5/1) to give L-2 (tert-butyl (17-hydroxy-3,6,9,12,15-pentaoxaheptadecyl)carbamate, 3 g, 91%) as yellow solid.

$^1$H-NMR (CDCl$_3$, 400 MHz): δ (ppm) 3.74-3.54 (m, 22H), 3.33-3.31 (m, 2H), 1.45 (s, 9H); ESI-MS Calcd m/z for C$_{17}$H$_{35}$NO$_8$ [M+H]$^+$ 382.25 found 382.20

Step 3) Synthesis of L-3

To a solution of L-2 (1.5 g, 3.94 mmol) and NaOH (0.32 g, 7.88 mmol) in THF (20 mL) and H$_2$O (15 mL) was added TsCl (1.13 g, 5.91 mmol) in THF (5 mL) at 0-5° C. in a drop-wise manner. The mixture was stirred at r.t overnight. The mixture was poured into water and extracted with EA. The combined organic layers was dried over Na$_2$SO$_4$ and concentrated. The residue was purified by column chromatography (PE/EA=100/1~20/1) to give L-3 (2,2-dimethyl-4-oxo-3,8,11,14,17,20-hexaoxa-5-azadocosan-22-yl 4-methylbenzenesulfonate, 1.50 g, 71.4%) as yellow oil.

$^1$H-NMR (CDCl$_3$, 400 MHz): δ (ppm) 7.81 (d, J=8.0 Hz, 2H), 7.36 (d, J=8.0 Hz, 2H) 4.18-4.16 (m, 2H) 3.71-3.54 (m, 20H), 3.33-3.31 (m, 2H), 2.46 (s, 3H) 1.45 (s, 9H); ESI-MS Calcd m/z for C$_{24}$H$_{41}$NO$_{10}$S [M+Na]$^+$ 558.24 found 558.20

Step 4) Synthesis of L-4

To a solution of L-3 (1.5 g, 2.80 mmol) in EtOH (500 mL) was added NaN$_3$ (0.77 g, 11.2 mmol). The reaction mixture was stirred at 60° C. overnight. The solids were collected by filtration. The mixture was quenched with water and extracted with EA. The combined organic layers was dried over Na$_2$SO$_4$ and concentrated to give the crude azide intermediate. A mixture of the crude intermediate (1.13 g, 2.80 mmol) and 5% Pd/C (500 mg, 50% in water) in EtOH (30 mL) was stirred at 10° C. for 4 hrs with a H$_2$ balloon. The mixture was filtered and the filtrate was concentrated to give crude L-4 (tert-butyl (17-amino-3,6,9,12,15-pentaoxaheptadecyl)carbamate, 0.85 g, 85%) as yellow oil.

$^1$H-NMR (CDCl$_3$, 400 MHz): δ (ppm) 3.67-3.48 (m, 22H), 2.89-2.87 (m, 2H), 1.45 (s, 9H); ESI-MS Calcd m/z for C$_{17}$H$_{36}$N$_2$O$_7$ [M+H]$^+$ 381.26 found 381.00

Step 5) Synthesis of L-5

The mixture of L-4 (0.85 g, 2.23 mmol), 1-bromo-3-chloro-5-nitrobenzene (5.81 g, 26.3 mmol), Cs$_2$CO$_3$ (5.81 g, 26.3 mmol), X-Phos (0.34 g) and Pd(dba)$_2$ (0.17 g) in dioxane (30 mL) was stirred at 100° C. for 16 hrs. The mixture was poured into water and extracted with EA. The combined organic layers was dried over Na$_2$SO$_4$ and concentrated. The residue was purified by column chromatography (PE/EA=100/1-20/1) to give L-5 (tert-butyl (17-((3-chloro-5-nitrophenyl)amino)-3,6,9,12,15-pentaoxaheptadecyl)carbamate, 0.9 g, 75.0%) as yellow oil.

$^1$H-NMR (CDCl$_3$, 400 MHz): δ (ppm) 7.50 (s, 1H), 7.37 (s, 1H), 6.94 (s, 1H), 3.75-3.52 (m, 22H), 3.35-3.30 (m, 2H), 1.45 (s, 9H); ESI-MS Calcd m/z for C$_{23}$H$_{38}$ClN$_3$O$_9$[M+H]$^+$ 536.24 found 535.90

Step 6) Synthesis of L-6

The mixture of L-5 (1.0 g, 1.86 mmol), NH$_4$Cl (0.52 g, 9.32 mmol) and Fe (0.52 g, 9.32 mmol) in EtOH (10 mL) and H$_2$O (10 mL) was stirred at 80° C. for 4 hrs. The mixture was poured into water and extracted with EA. The combined organic layers was dried over Na$_2$SO$_4$ and concentrated. The residue was purified by column chromatography (PE/EA=100/1-20/1) to give L-6 (tert-butyl (17-((3-amino-5-chlorophenyl)amino)-3,6,9,12,15-pentaoxaheptadecyl)carbamate, 0.9 g, 95.0%) as yellow oil.

$^1$H-NMR (CDCl$_3$, 400 MHz): δ (ppm) 6.10-6.07 (m, 2H), 5.91 (s, 1H), 3.69-3.52 (m, 22H), 3.32-3.22 (m, 2H), 1.45 (s, 9H) ESI-MS Calcd m/z for C$_{23}$H$_{40}$ClN$_3$O$_7$[M+H]$^+$ 506.27 found 505.90

Step 7) Synthesis of L-7

The mixture of F-2 (methyl 5-chlorobenzo[c][2,6]naphthyridine-8-carboxylate, 0.5 g, 1.8 mmol) and L-6 (0.9 g, 1.8 mmol) in NMP (20 mL) was stirred at 80° C. overnight. The mixture was poured into water and extracted with EA. The combined organic layers was dried over Na$_2$SO$_4$ and concentrated to give L-7 (methyl 5-((3-chloro-5-((2,2-dimethyl-4-oxo-3,8,11,14,17,20-hexaoxa-5-azadocosan-22-yl)amino)phenyl)amino)benzo[c][2,6]naphthyridine-8-carboxylate, 0.5 g, crude).

Step 8) Synthesis of L-8

To a solution of L-7 (0.5 g, 0.7 mmol) in DCM (4 mL) was slowly added TFA (4 mL) at 0° C. The reaction mixture was stirred at r.t for 1 hr. The mixture was poured into saturated aqueous NaHCO$_3$ solution and extracted with EA. The combined organic layers was dried over Na$_2$SO$_4$ and concentrated to give L-8 (methyl 5-((3-((17-amino-3,6,9,12,15-pentaoxaheptadecyl)amino)-5-chlorophenyl)amino)benzo[c][2,6]naphthyridine-8-carboxylate, 400 mg, 92.6%).

LC-MS Calcd m/z for C$_{32}$H$_{40}$ClN$_5$O$_7$ [M+H]$^+$ 643.1 found 643.4

Step 9) Synthesis of L-9

The mixture of L-8 (400.0 mg, 0.6 mmol) and H-8 ((R)-2-((3,4-bis((4-fluorobenzyl)oxy)phenoxy)methyl)oxirane, 248.4 mg, 0.6 mmol) in MeOH (10 mL) was stirred at 50° C. overnight. The reaction mixture was concentrated and purified by prep-TLC (DCM/MeOH=10/1) to give the L-9 (methyl (R)-5-((3-((21-(3,4-bis((4-fluorobenzyl)oxy)phenoxy)-20-hydroxy-3,6,9,12,15-pentaoxa-18-azahenicosyl)amino)-5-chlorophenyl)amino)benzo[c][2,6]naphthyridine-8-carboxylate, 150.0 mg, 23.1%).

LC-MS Calcd m/z for C$_{55}$H$_{60}$ClF$_2$N$_5$O$_{11}$ [M+H]$^+$ 1041.5 found 1041.1.

Step 10) Synthesis of Compound L

To a solution of L-9 (150.0 mg, 0.1 mmol) in MeOH/THF/H$_2$O (3/3/2 mL) was added LiOH·H$_2$O (12.0 mg, 0.3 mmol). The mixture was stirred at r.t for 1 hr. The mixture was added 1N HCl to pH=5. The mixture was concentrated and purified by prep-TLC (DCM/MeOH=10/1) to give Compound L ((R)-5-((3-((21-(3,4-bis((4-fluorobenzyl)oxy)phenoxy)-20-hydroxy-3,6,9,12,15-pentaoxa-18-azahenicosyl)amino)-5-chlorophenyl)amino)benzo[c][2,6]naphthyridine-8-carboxylic acid, 30 mg, 20.2%) as yellow solid.

$^1$H-NMR (CDCl$_3$, 400 MHz): δ (ppm) 9.91 (s, 1H), 8.83 (s, 1H), 8.50-8.41 (m, 2H), 8.14 (s, 1H), 7.90 (s, 1H), 7.80 (s, 1H), 7.43 (s, 1H), 7.38-7.30 (m, 4H), 7.02-6.98 (m, 4H), 6.78-6.73 (m, 2H), 6.55-6.54 (m, 1H), 6.36-6.31 (m, 2H), 4.95 (s, 2H), 4.93 (s, 2H), 4.56 (s, 1H), 4.07-4.04 (m, 1H), 3.95-3.88 (m, 3H), 3.76-3.54 (m, 18H), 3.40-3.17 (m, 6H);

LC-MS Calcd m/z for C$_{54}$H$_{58}$ClF$_2$N$_5$O$_{11}$ [M+H]$^+$ 1026.39 found 1025.70

Example 25. Preparation of Compound M ((S)-3-(6-(3-((4-(1-(4-(benzyloxy)-3-phenethoxyphenyl)-5,8,11,14-tetraoxa-2-azahexadecan-16-yl)piperazin-1-yl)methyl)-1,2,3,4-tetrahydroisoquinoline-2-carbonyl)benzo[d][1,3]dioxol-5-yl)-N-(4-hydroxyphenyl)-N-phenyl-5,6,7,8-tetrahydroindolizine-1-carboxamide)

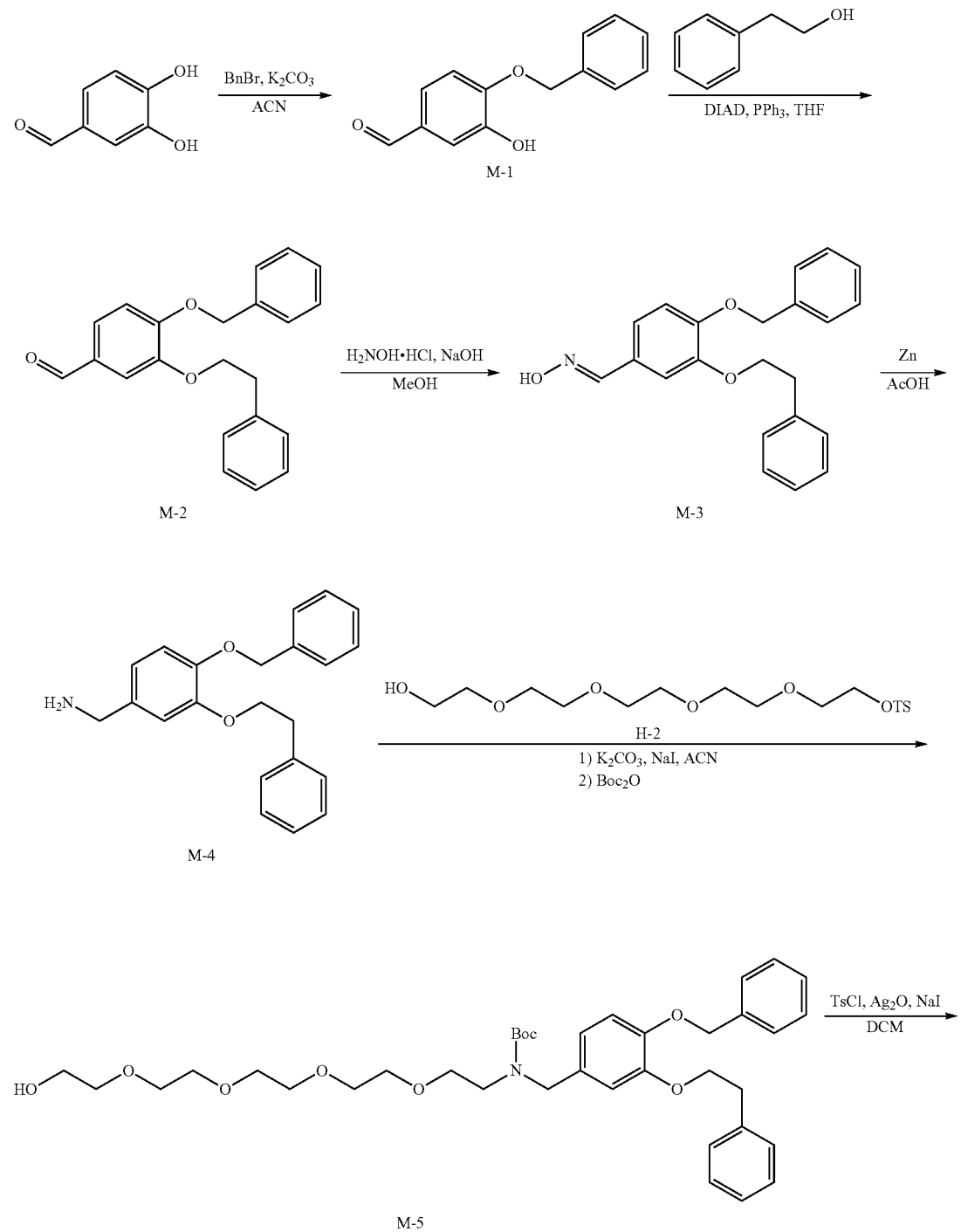

-continued
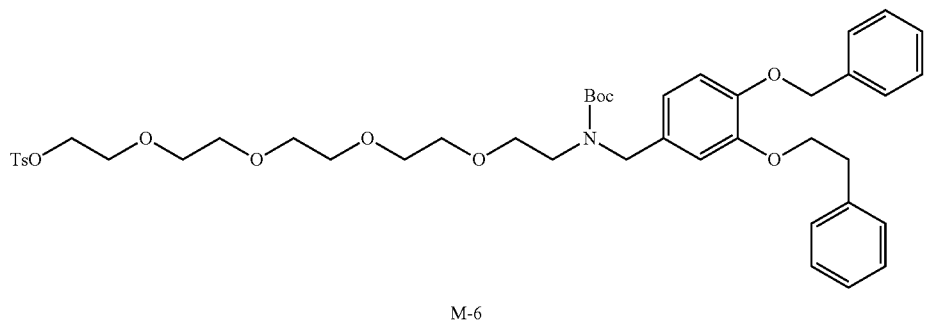
M-6
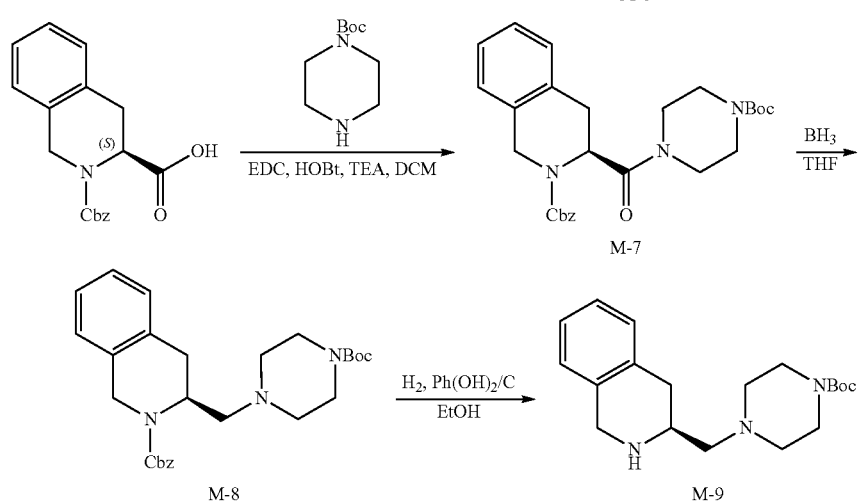
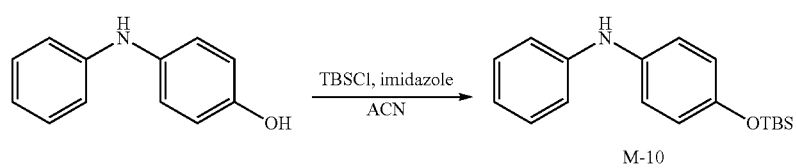
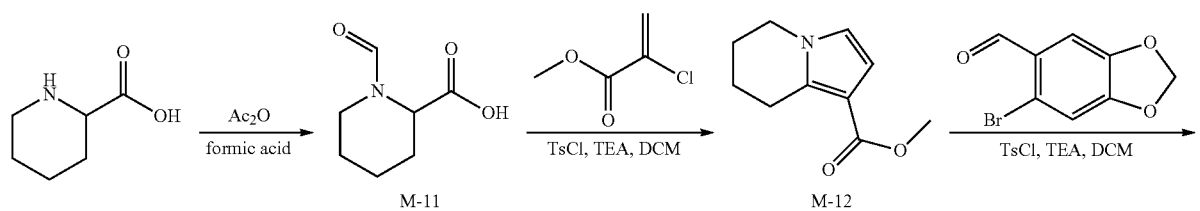
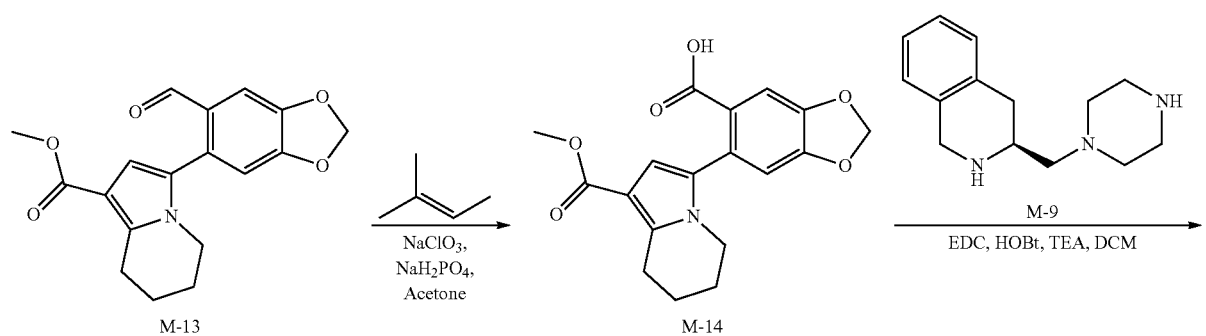

-continued
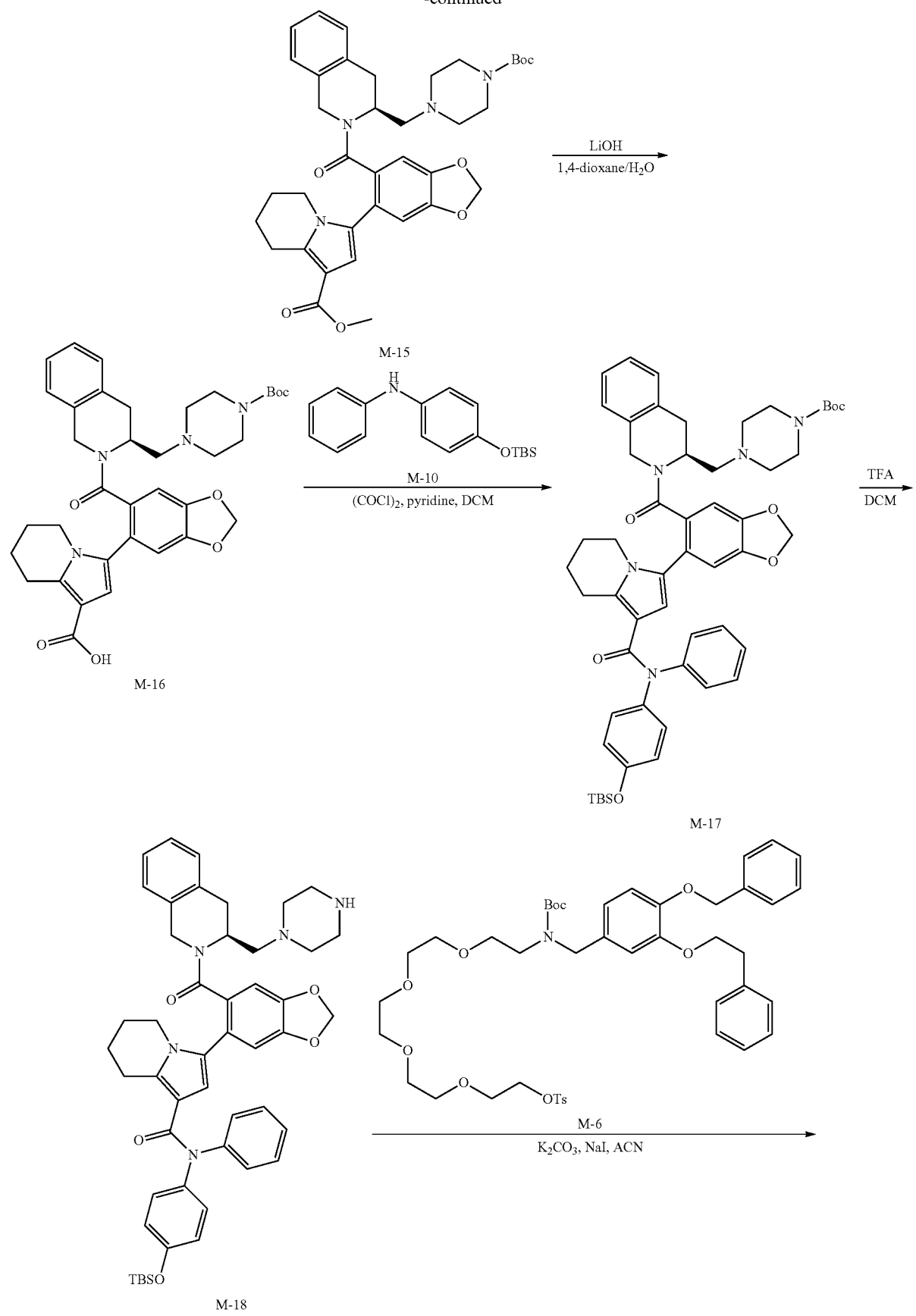

-continued

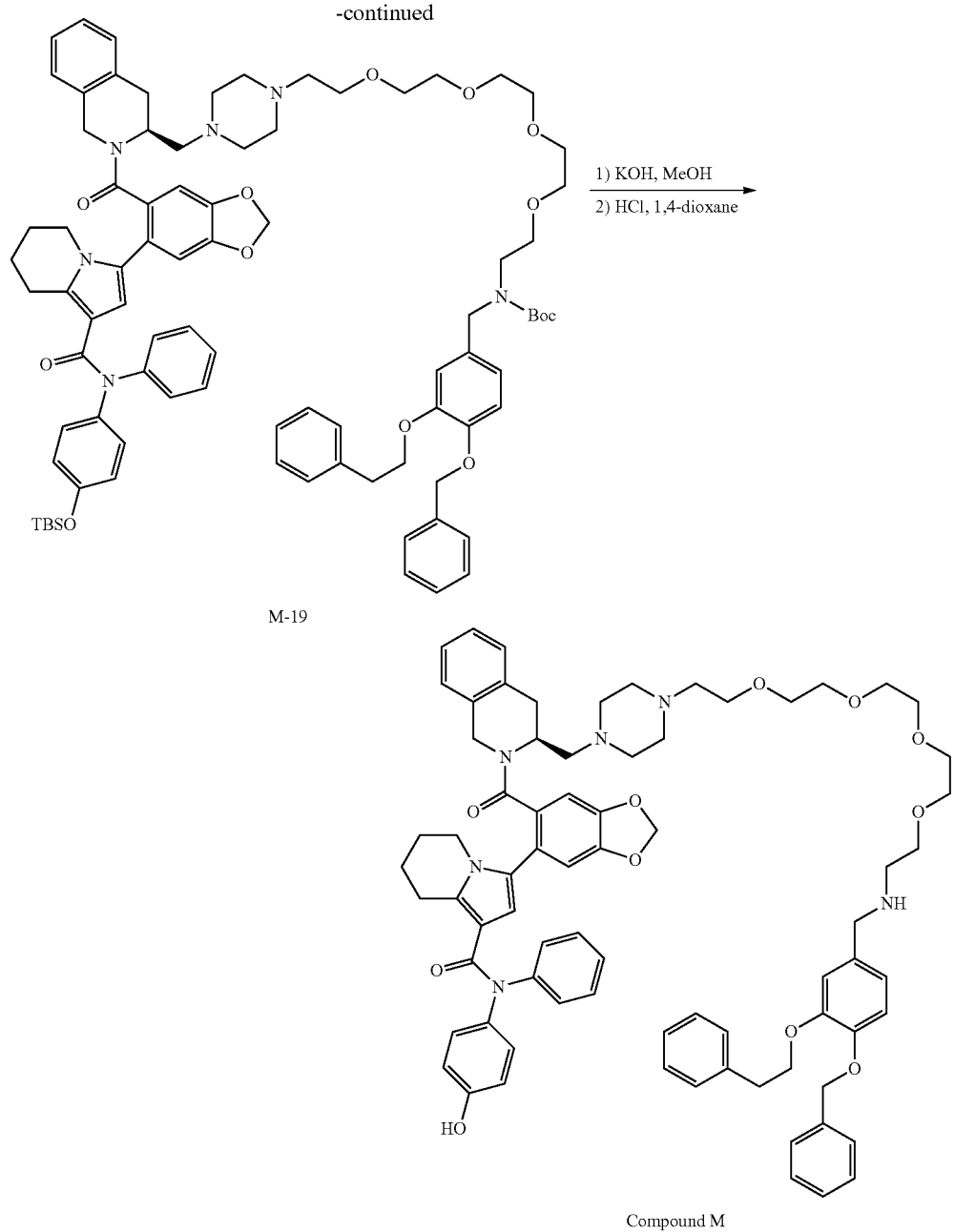

M-19

Compound M

Step 1) Synthesis of M-1

To a solution of 3,4-dihydroxybenzaldehyde (50.0 g, 362.3 mmol) in ACN (700 mL) were added $K_2CO_3$ (39.6 g, 471.0 mmol) and benzyl bromide (61.6 g, 362.3 mmol). The reaction mixture was stirred at 80° C. for 16 hrs. The mixture was concentrated, quenched with HCl (300 mL, 1N) and extracted with EA. The combined organic layers was dried over $Na_2SO_4$ and concentrated. The residue was purified by column chromatography to afford M-1 (4-(benzyloxy)-3-hydroxybenzaldehyde, 25.0 g, 30.3%) as white solid.

ESI-MS Calcd m/z for $C_{14}H_{12}O_3[M+H]^+$ 229.09 found 228.90

Step 2) Synthesis of M-2

To a solution of M-1 (25.0 g, 109.6 mmol) in THF (500 mL) were added 2-phenylethanol (16.1 g, 131.6 mmol), $PPh_3$ (43.1 g, 164.4 mmol) and DIAD (33.2 g, 164.4 mmol). The reaction mixture was stirred at 65° C. for 16 hrs. The mixture was concentrated and purified by column chromatography to afford M-2 (4-(benzyloxy)-3-phenethoxybenzaldehyde, 30.0 g, 82.4%) as white solid.

ESI-MS Calcd m/z for $C_{22}H_{20}O_3[M+H]^+$ 333.15 found 332.90

Step 3) Synthesis of M-3

To a solution of hydroxyl ammonium hydrochloride (17.0 g, 0241.0 mmol) and NaOH (152 mL, 1.6 M in $H_2O$) in MeOH (152 mL) was added M-2 (40.0 g, 120.5 mmol). The reaction mixture was stirred at 70° C. for 1 hr. The mixture was evaporated to remove MeOH and extracted with EA. The combined organic layers was dried over $Na_2SO_4$ and concentrated to give M-3 (crude) as white solid.

Step 4) Synthesis of M-4

To a stirred solution of M-3 (crude) in acetic acid (425 mL) was added zinc powder (55.1 g, 847.7 mmol) in 6 portions under 70° C. The reaction mixture was stirred at 70° C. for 1 hr. The mixture was filtered and the most solvent was evaporated in a vacuum. Excess of ammonia was added to the solution and the solution was extracted with EA. The combined organic layers was washed with water, dried over $Na_2SO_4$ and concentrated. The residue was purified by column chromatography to give M-4 ((4-(benzyloxy)-3-phenethoxyphenyl)methanamine, 22.9 g, 57.1%) as colorless oil.

ESI-MS Calcd m/z for $C_{22}H_{23}NO_2$ $[M+H]^+$ 334.43 found 334.1.

Step 5) Synthesis of M-5

The mixture of M-4 (20.0 g, 51.0 mmol), H-2 (14-hydroxy-3,6,9,12-tetraoxatetradecyl 4-methylbenzenesulfonate, 22.9 g, 68.8 mmol), $K_2CO_3$ (14.1 g, 102.2 mmol) and NaI (3.2 g, 21.3 mmol) in ACN (1.0 L) was stirred at 90° C. for 15 hrs and cooled to r.t. The mixture was added $Boc_{20}$ (27.7 g, 127.1 mmol) and stirred at r.t for 5 hrs. After concentrated in vacuum, the residue was purified by column chromatography to give M-5 (tert-butyl (4-(benzyloxy)-3-phenethoxybenzyl) (14-hydroxy-3,6,9,12-tetraoxatetradecyl)carbamate, 12.5 g, 27.8%) as yellow oil.

ESI-MS Calcd m/z for $C_{37}H_{51}NO_9$ $[M+H]^+$ 654.81 found [M-100]+554.9

Step 6) Synthesis of M-6

To a solution of M-5 (12.5 g, 19.1 mmol) in DCM (125 mL) were added $Ag_2O$ (6.66 g, 28.7 mmol), NaI (3.2 g, 21.0 mmol) and TsCl (3.6 g, 19.1 mmol) at 0° C. The reaction mixture was stirred at r.t for 1 hr. The mixture was filtered through celite and the filtrate was washed with 10% $NaHCO_3$ aqueous solution. The organic layers was dried over $Na_2SO_4$ and concentrated. The residue was purified by column chromatography to give M-6 (5-(4-(benzyloxy)-3-phenethoxybenzyl)-2,2-dimethyl-4-oxo-3,8,11,14,17-pentaoxa-5-azanonadecan-19-yl 4-methylbenzenesulfonate, 13.0 g, 84.2%) as yellow oil. (TLC: EA/PE=1/5, Rf=0.4)

ESI-MS Calcd m/z for $C_{44}H_{57}NO_{11}S$ $[M+H]^+$ 808.9 found [M-100]+708.8

Step 7) Synthesis of M-7

To a solution of (S)-2-((benzyloxy)carbonyl)-1,2,3,4-tetrahydroisoquinoline-3-carboxylic acid (15.0 g, 48.2 mmol) in dry DCM (500 mL) were added tert-butyl piperazine-1-carboxylate (9.86 g, 53.0 mmol), $Et_3N$ (27 mL, 192.8 mmol), HOBt (7.80 g, 57.8 mmol) and EDCI (9.90 g, 57.8 mmol). The reaction mixture was stirred at r.t overnight. The mixture was diluted with DCM and aqueous $NH_4Cl$. The organic layers was washed with brine, dried over $Na_2SO_4$ and concentrated. The residue was purified by column chromatography to afford M-7 (benzyl (S)-3-(4-(tert-butoxycarbonyl)piperazine-1-carbonyl)-3,4-dihydroisoquinoline-2 (1H)-carboxylate, 18.0 g, 77.9%) as white solid. (TLC: PE/EA=3:1, Rf=0.5).

ESI-MS Calcd m/z for $C_{27}H_{33}N_3O_5$ $[M+1]^+$480.5 found [M-100]+380.9

Step 8) Synthesis of M-8

To a solution of M-7 (18.0 g, 37.6 mmol) in dry THF (800 mL) was added borane-THF complex (2 M solution in $Me_2S$, 56.4 mL) at r.t under $N_2$ in a drop-wise manner. The reaction mixture was refluxed for 1 hr and cooled to r.t. The mixture was quenched by slow addition of methanol and aqueous $NH_4Cl$, and extracted with EA. The combined organic layers was dried over $Na_2SO_4$ and concentrated to give M-8 (benzyl (S)-3-((4-(tert-butoxycarbonyl)piperazin-1-yl)methyl)-3,4-dihydroisoquinoline-2 (1H)-carboxylate, 15.0 g, 85.8%) as white solid.

ESI-MS Calcd m/z for $C_{27}H_{35}N_3O_4$ $[M+H]^+$ 466.27 found 465.90

Step 9) Synthesis of M-9

To a solution of M-8 (15.0 g, 32.3 mmol) in EtOH (200 mL) was added $Pd(OH)_2/C$ (3.0 g, 61.0 mmol). The reaction mixture was stirred under $H_2$ gas (1 atm) at r.t overnight. The mixture was filtered and concentrated. The residue was purified by column chromatography to afford M-9 (tert-butyl (S)-4-((1,2,3,4-tetrahydroisoquinolin-3-yl)methyl)piperazine-1-carboxylate, 8.0 g, 74.9%) as white solid. (TLC: EA/PE=2:1, Rf=0.4).

ESI-MS Calcd m/z for $C_{19}H_{29}N_3O_2$ $[M+H]^+$ 332.24 found 332.00

Step 10) Synthesis of M-10

To a solution of 4-(phenylamino)phenol (10.0 g, 54.1 mmol) in ACN (300 mL) were added imidazole (5.5 g, 81.2 mmol) and TBSCl (12.2 g, 81.2 mmol). The reaction mixture was refluxed for 1 hr. The mixture was diluted with water, extracted with EA. The combined organic layers was dried over $Na_2SO_4$ and concentrated. The residue was purified by column chromatography to afford M-10 (4-((tert-butyldimethylsilyl)oxy)-N-phenylaniline, 12.0 g, 74.2%) as yellow solid.

ESI-MS Calcd m/z for $C_{18}H_{25}NOSi$ $[M+H]^+$ 300.18 found 299.90

Step 11) Synthesis of M-11

To a solution of piperidine-2-carboxylic acid (20.0 g, 155.0 mmol) in formic acid (150.0 mL) was added $Ac_2O$ (100.0 mL) in a drop-wise manner. The reaction was stirred at r.t overnight and added water (125.0 mL) at 0° C. The mixture was stirred at 0° C. for 2 hrs and concentrated. The residue was taken up in MeOH (100.0 mL) and concentrated to give the crude M-11 (1-formylpiperidine-2-carboxylic acid, 21 g) as brown oil.

ESI-MS Calcd m/z for $C_7H_{11}NO_3$ $[M+H]^+$ 158.08 found 158.00

Step 12) Synthesis of M-12

To a solution of M-11 (10.0 g, 63.6 mmol) in dichloroethane (65 mL) were added TsCl (13.4 g, 70.4 mmol), methyl 2-chloroacrylate (16.5 mL, 162.4 mmol) and $Et_3N$ (26.8 mL, 191.2 mmol) in a drop-wise manner. The reaction mixture was refluxed overnight. The mixture was diluted with DCM, wash with 1M HCl and aqueous NaHCO$_3$. The organic layer was washed with brine, dried over Na$_2$SO$_4$ and concentrated. The residue was purified by column chromatography to afford M-12 (methyl 5,6,7,8-tetrahydroindolizine-1-carboxylate, 5.0 g, 43.9%) as yellow oil. (TLC: EA/PE=3:1, Rf=0.6).

ESI-MS Calcd m/z for C$_{10}$H$_{13}$NO$_2$ [M+H]$^+$ 180.10 found 180.00

Step 13) Synthesis of M-13

To a solution of M-12 (6.4 g, 35.7 mmol) in DMAC (50 mL) were added KOAc (7.0 g, 71.4 mmol), 6-bromobenzo[d][1,3]dioxole-5-carbaldehyde (12.3 g, 53.6 mmol) and Pd(PPh$_3$)$_2$Cl$_2$ (1.3 g, 1.8 mmol). The reaction mixture was stirred at 130° C. for 1 hr and added water (0.139 mL). Then the reaction mixture was stirred at 130° C. overnight. The mixture was diluted with EA, washed with brine, dried over Na$_2$SO$_4$ and concentrated. The residue was purified by column chromatography to afford M-13 (4 g, 34.5%) as yellow solid. (TLC: EA/PE=3:1, Rf=0.8).

ESI-MS Calcd m/z for C$_{18}$H$_{17}$NO$_5$ [M+H]$^+$ 328.12 found 327.80

Step 14) Synthesis of M-14

To a solution of M-13 (3.37 g, 10.3 mmol) in acetone (20 mL) were added 2-methylbut-2-ene (8.8 mL, 80.24 mmol) and a solution of NaClO$_2$ (3.3 g, 36.05 mmol) and NaH$_2$PO$_4$ (3.6 g, 25.75 mmol) in water (9.3 mL) at 0° C. The reaction mixture was stirred at r.t for 7 hrs. The mixture was concentrated to remove the acetone and the residue was filtered to give M-14 (6-(1-(methoxycarbonyl)-5,6,7,8-tetrahydroindolizin-3-yl)benzo[d][1,3]dioxole-5-carboxylic acid, 2.4 g, 67.9%) as yellow oil. (TLC: EA/PE=1/2, Rf=0.3).

ESI-MS Calcd m/z for C$_{18}$H$_{17}$NO$_6$ [M+H]$^+$ 344.12 found 343.80

Step 15) Synthesis of M-15

To a solution of M-14 (2.0 g, 5.83 mmol) in dry DCM (500 mL) were added M-9 (tert-butyl (S)-4-((1,2,3,4-tetrahydroisoquinolin-3-yl)methyl)piperazine-1-carboxylate, 2 g, 9.06 mmol), Et$_3$N (5.5 mL, 39.6 mmol), HOBt (0.94 g, 6.96 mmol) and EDCI (1.34 g, 6.96 mmol). The reaction mixture was stirred at r.t overnight. The mixture was diluted with DCM and aqueous NH$_4$Cl. The combined organic layers was washed with brine, dried over Na$_2$SO$_4$ and concentrated. The residue was purified by column chromatography to afford M-15 (methyl (S)-3-(6-(3-((4-(tert-butoxycarbonyl)piperazin-1-yl)methyl)-1,2,3,4-tetrahydroisoquinoline-2-carbonyl)benzo[d][1,3]dioxol-5-yl)-5,6,7,8-tetrahydroindolizine-1-carboxylate, 2.7 g, 70.6%) as yellow solid. (TLC: PE/EA=3:1, Rf=0.5).

ESI-MS Calcd m/z for C$_{37}$H$_{44}$N$_4$O$_7$ [M+H]$^+$ 657.33 found 656.80

Step 16) Synthesis of M-16

The mixture of M-15 (4 g, 6.1 mmol) and LiOH·H$_2$O (0.77 g, 18.3 mmol) in dioxane (24 mL) and water (12 mL) was refluxed overnight. The mixture was acidified with 1N HCl aqueous solution and concentrated. The residue was purified by column chromatography to afford M-16 ((S)-3-(6-(3-((4-(tert-butoxycarbonyl)piperazin-1-yl)methyl)-1,2,3,4-tetrahydroisoquinoline-2-carbonyl)benzo[d][1,3]dioxol-5-yl)-5,6,7,8-tetrahydroindolizine-1-carboxylic acid, 3 g, 74.1%) as yellow solid. (TLC: MeOH/DCM=1/15, Rf=0.2) ESI-MS Calcd m/z for C$_{36}$H$_{42}$N$_4$O$_7$ [M+H]$^+$ 643.32 found 642.80

Step 17) Synthesis of M-17

To a solution of M-16 (0.26 g, 0.47 mmol) in dry DCM (5 mL) was added oxalyl dichloride (0.12 mL, 1.42 mmol) at 0° C. The reaction mixture was stirred at r.t for 20 min. The mixture was concentrated and diluted with DCM (3.5 mL). To the solution was added a solution of M-10 (4-((tert-butyldimethylsilyl)oxy)-N-phenylaniline, 0.21 g, 0.71 mmol) and pyridine (0.12 mL, 1.42 mmol) in DCM (1.5 mL). The reaction mixture was stirred at r.t overnight and concentrated. The residue was purified by column chromatography to give M-17 (tert-butyl (S)-4-((2-(6-(1-(((4-((tert-butyldimethylsilyl)oxy)phenyl) (phenyl)carbamoyl)-5,6,7,8-tetrahydroindolizin-3-yl)benzo[d][1,3]dioxole-5-carbonyl)-1,2,3,4-tetrahydroisoquinolin-3-yl)methyl) piperazine-1-carboxylate, 0.23 g, 60.9%) as yellow solid. (TLC: EA/PE=1/1, Rf=0.5) ESI-MS Calcd m/z for C$_{54}$H$_{65}$N$_5$O$_7$Si [M+H]$^+$ 924.22 found 923.80

Step 18) Synthesis of M-18

To a solution of M-17 (3.5 g, 3.79 mmol) in DCM (50 mL) was added TFA (10 mL) at 0° C. The reaction mixture was stirred at 0° C. for 4 hrs. The mixture was acidified with 10% K$_2$CO$_3$ solution and extracted with DCM. The organic layer was dried over Na$_2$SO$_4$ and concentrated to give crude M-18 ((S)—N-(4-((tert-butyldimethylsilyl)oxy)phenyl)-N-phenyl-3-(6-(3-(piperazin-1-ylmethyl)-1,2,3,4-tetrahydroisoquinoline-2-carbonyl)benzo[d][1,3]dioxol-5-yl)-5,6,7,8-tetrahydroindolizine-1-carboxamide, 3.5 g) as yellow solid. (TLC: EA/PE=1/1, Rf=0.3) ESI-MS Calcd m/z for C$_{49}$H$_{57}$N$_5$O$_5$Si [M+H]$^+$ 824.11 found 823.80

Step 19) Synthesis of M-19

The mixture of M-18 (3.5 g, 4.25 mmol), M-6 (4.1 g, 5.1 mmol), K$_2$CO$_3$ (1.5 g, 10.63 mmol) and NaI (0.26 g, 1.7 mmol, 0.4 eq) in ACN (80 mL) was stirred at 90° C. overnight and concentrated. The residue was purified by column chromatography to give M-19 (tert-butyl (S)-(4-(benzyloxy)-3-phenethoxybenzyl) (14-(4-((2-(6-(1-(((4-(((tert-butyldimethylsilyl)oxy)phenyl) (phenyl)carbamoyl)-5,6,7,8-tetrahydroindolizin-3-yl)benzo[d][1,3]dioxole-5-carbonyl)-1,2,3,4-tetrahydroisoquinolin-3-yl)methyl) piperazin-1-yl)-3,6,9,12-tetraoxatetradecyl)carbamate 4.0 g, 64.5%) as yellow solid. (TLC: EA/PE=I/O, Rf=0.6) ESI-MS Calcd m/z for C$_{86}$H$_{106}$N$_6$O$_{13}$Si [M+H]$^+$ 1459.77 found 1459.90

Step 20) Synthesis of Compound M

To a solution of M-19 (2.2 g, 1.50 mmol) in MeOH (40 mL) was added KOH (0.34 g, 6.0 mmol) and stirred at r.t for 3 hrs. Then the reaction mixture was added HCl/dioxane (4M, 18 mL) and stirred at r.t for another 2 hrs. The mixture was basified with aqueous NaHCO$_3$ solution and extracted with DCM. The organic layer was dried over Na$_2$SO$_4$ and concentrated. The residue was purified by column chromatography to give Compound M ((S)-3-(6-(3-((4-(1-(4-(benzyloxy)-3-phenethoxyphenyl)-5,8,11,14-tetraoxa-2-azahexadecan-16-yl)piperazin-1-yl)methyl)-1,2,3,4- tetrahydroisoquinoline-2-carbonyl)benzo[d][1,3]dioxol-5-yl)-N-(4-hydroxyphenyl)-N-phenyl-5,6,7,8-tetrahydroindolizine-1-carboxamide, 1.1 g, 59%) as white solid. (TLC: MeOH/DCM=1/10, Rf=0.4)

$^1$H-NMR (CDCl$_3$, 400 MHz): δ (ppm) 9.56 (brs, 1H), 7.43-7.40 (m, 8H), 7.36-7.06 (m, 15H), 6.97-6.83 (m, 5H), 6.53 (s, 1H), 6.03-5.99 (m, 2H), 5.72 (brs, 1H), 5.12-4.90 (m, 3H), 4.54-4.46 (m, 2H), 4.24-4.16 (m, 4H), 3.84-3.60 (m, 28H), 3.30-3.09 (m, 6H), 2.68-2.52 (m, 3H), 2.28-2.20 (m, 1H), 1.53-1.49 (m, 2H), 1.15-1.06 (m, 1H), 0.93-0.86 (m, 1H); ESI-MS Calcd m/z for C$_{75}$H$_{84}$N$_6$O$_{11}$ [M+H]$^+$ 1245.63 found 1245.90.

Example 26. Preparation of Compound P ((R)-1-((4-(benzo[d]thiazol-5-ylamino)-6-(tert-butylsulfonyl)quinazolin-7-yl)oxy)-24-(3,4-bis((4-fluorobenzyl)oxy)phenoxy)-6,9,12,15,18-pentaoxa-3,21-diazatetracosan-23-ol)

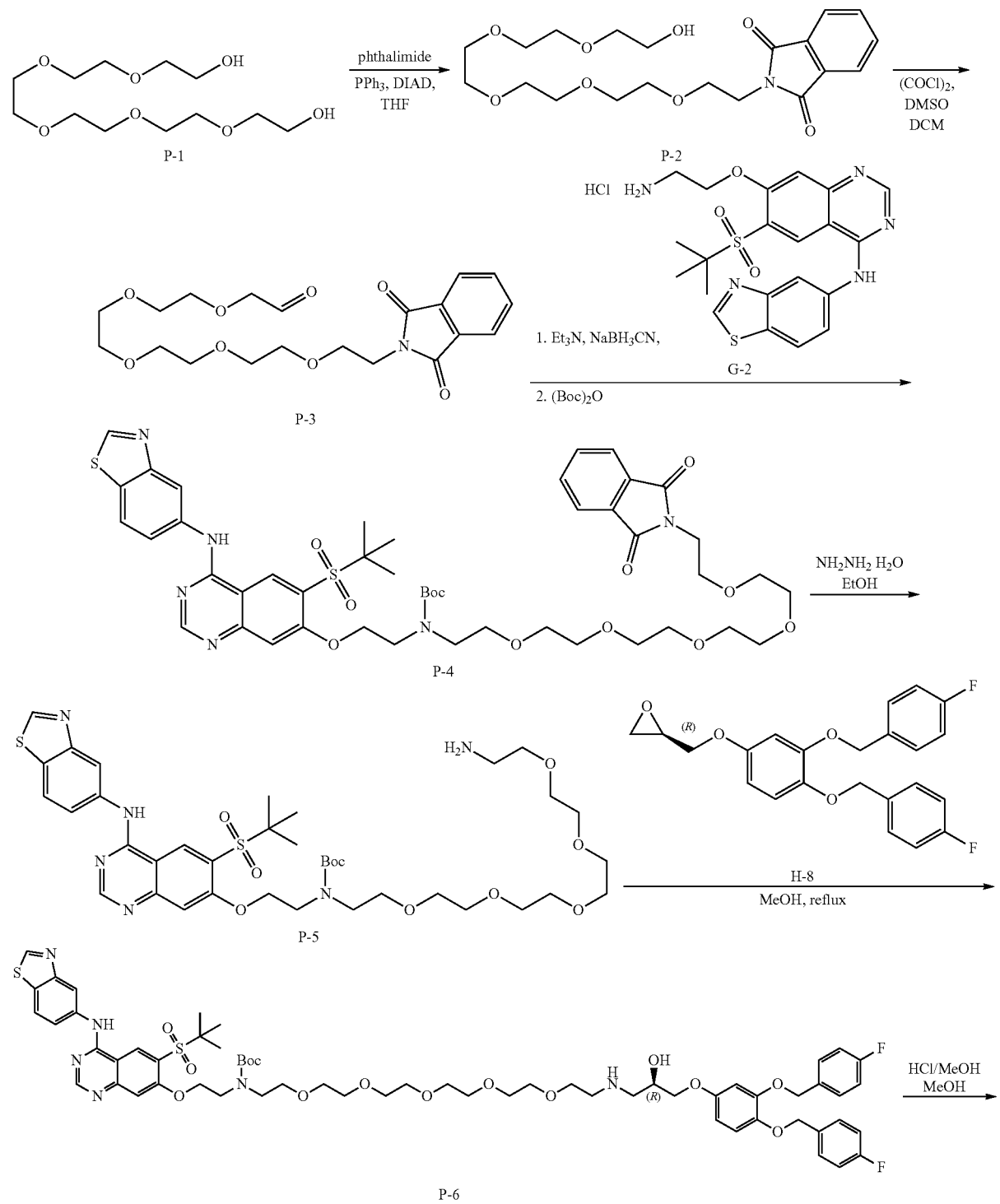

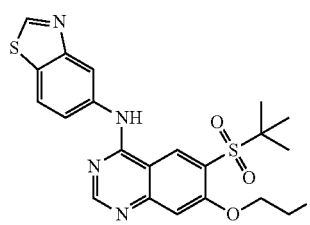

Compound P

Step 1) Synthesis of P-2

To a solution of P-1 (3,6,9,12,15-pentaoxaheptadecane-1,17-diol, CAS No.: 2615-15-8, 20.0 g, 70.9 mmol, 1 eq), phthalimide (CAS No.: 85-41-6, 12.6 g, 85.7 mmol, 1.2 eq), $PPh_3$ (24.0 g, 91.5 mmol, 1.3 eq) in THF (200 mL) was added DIAD (diisopropyl azodicarboxylate, 16.0 g, 79.2 mmol, 1.1 eq) at 0° C. and stirred at room temperature for overnight. The mixture was poured into ice/water (200 mL). The mixture was extracted with ethyl acetate (EA). The organic layer was concentrated to give the crude. The crude was purified by silica column (DCM/MeOH=200/1~70/1) to give P-2 (2-(17-hydroxy-3,6,9,12,15-pentaoxaheptadecyl) isoindoline-1,3-dione, 10.0 g, yield: 34.3%) as yellow oil. (TLC: DCM/MeOH=10/1, Rf=0.3) LC-MS Calcd m/z for $C_{20}H_{29}NO_8$ [M]411.45 found 411.9

Step 2) Synthesis of P-3

To a solution of DMSO (2.38 g, 30.5 mmol, 2.5 eq) in DCM (40 mL), oxalyl chloride (3.10 g, 14.6 mmol, 2 eq) was added dropwise at −70° C. and stirred for 30 min under $N_2$. A solution of P-2 (5.00 g, 12.2 mmol, 1 eq) in DCM (10 mL) was added dropwise to reaction mixture and stirred at −70° C. for 2 h, triethylamine (4.95 g, 48.8 mmol, 4.0 eq) was added dropwise at −70° C. and stirred at room temperature for overnight. The mixture was poured into ice/water (200 mL) and extracted with EA. The organic layer was dried over $Na_2SO_4$ and concentrated to give P-3 (17-(1,3-dioxoisoindolin-2-yl)-3,6,9,12,15-pentaoxaheptadecanal, 3.0 g, yield: 60.3%) as yellow solid.

LC-MS Calcd m/z for $C_{20}H_{27}NO_8$ [M]409.44 found 409.9.

Step 3) Synthesis of P-4

To a solution of P-3 (1.80 g, 3.94 mmol, 1 eq), G-2 (N-(7-(2-aminoethoxy)-6-(tert-butylsulfonyl)quinazolin-4-yl)benzo[d]thiazol-5-amine hydrochloride, 1.93 g, 4.73 mmol, 1.2 eq), triethylamine (0.96 g, 9.46 mmol, 2.4 eq) in MeOH (40 mL) was added sodium cyanoborohydride (0.50 g, 7.88 mmol, 2 eq) and stirred at room temperature for overnight. $(Boc)_2O$ (1.72 g, 7.88 mmol, 2.0 eq) was added at 0° C. and stirred at room temperature for 3 h. The mixture was poured into ice/water (50 mL). The mixture was extracted with EA. The organic layer was concentrated to give the crude of P-4 (tert-butyl (2-((4-(benzo[d]thiazol-5-ylamino)-6-(tert-butylsulfonyl)quinazolin-7-yl)oxy)ethyl) (17-(1,3-dioxoisoindolin-2-yl)-3,6,9,12,15-pentaoxaheptadecyl)carbamate, 1.10 g, crude) as yellow oil.

LC-MS Calcd m/z for $C_{46}H_{58}N_6O_{12}S_2$[M]951.12 found 951.7.

Step 4) Synthesis of P-5

To a solution of P-4 (1.10 g, 1.16 mmol, 1 eq) in EtOH (15 mL) was added hydrazine hydrate 80% (0.4 mL, 5.80 mmol, 5 eq) stirred at 50° C. for 2 hrs. The solvent was removed in vacuo, and the residue was purified by silica column (DCM/MeOH=150/1~50/1) to give the crude which was purified by prep-HPLC and lyophilized to give P-5 (tert-butyl (17-amino-3,6,9,12,15-pentaoxaheptadecyl) (2-((4-(benzo[d]thiazol-5-ylamino)-6-(tert-butylsulfonyl)quinazolin-7-yl) oxy)ethyl)carbamate, 290.0 mg) as yellow solid. (TLC: DCM/MeOH=10/1, Rf=0.3); LC-MS Calcd m/z for $C_{39}H_{58}N_6O_9S_2$ [M]819.05 found 820.8.

Step 5) Synthesis of P-6

To a solution of P-5 (160.0 mg, 0.195 mmol, 1 eq) in MeOH (1 mL) and acetonitrile (1 mL) was added H-8 ((R)-2-((3,4-bis((4-fluorobenzyl)oxy)phenoxy)methyl)oxirane, 99.7 mg, 0.24 mmol, 1.25 eq). The reaction mixture was stirred at 80° C. for 48 hrs. The solvent was removed in vacuo, and the residue was purified by prepare TLC to give P-6 (tert-butyl (R)-(2-((4-(benzo[d]thiazol-5-ylamino)-6-(tert-butylsulfonyl)quinazolin-7-yl)oxy)ethyl) (21-(3,4-bis ((4-fluorobenzyl)oxy)phenoxy)-20-hydroxy-3,6,9,12,15-pentaoxa-18-azahenicosyl)carbamate, 50.0 mg, yield: 21.0%) as yellow oil. (TLC: DCM/MeOH=10/1, Rf=0.5); LC-MS Calcd m/z for $C_{61}H_{76}F_2N_6O_{14}S_2$ [M]1219.4 found 1219.8.

Step 6) Synthesis of Compound P

To a solution of P-6 (80.0 mg, 0.066 mmol) and MeOH (0.5 mL) was added HCl/MeOH (1 mL, 3.0 mol/L) and stirred at room temperature for 3 hrs. The mixture was concentrated and the residue was purified by prep-HPLC and lyophilized to give a white solid which was dissolved in MeOH (2 mL) was added AMBERLYST® A-21 (CAS No.: 9049-93-8) and stirred at room temperature for 30 min. The mixture was filtered and the filtrate was concentrated to give Compound P ((R)-1-((4-(benzo[d]thiazol-5-ylamino)-6-(tert-butylsulfonyl)quinazolin-7-yl)oxy)-24-(3,4-bis((4-fluorobenzyl)oxy)phenoxy)-6,9,12,15,18-pentaoxa-3,21-diazatetracosan-23-ol, 36.0 mg, yield 49.0%) as white solid.

$^1H$ NMR (CDCl$_3$, 400 MHz): δ 8.99-9.02 (d, J=11.6 Hz, 2H), 8.69 (s, 1H), 8.57-8.64 (d, J=26.8 Hz, 2H), 7.93-7.96 (d, J=8.4 Hz, 1H), 7.85-7.87 (d, J=8.8 Hz, 1H), 7.33-7.40

(m, 5H), 7.00-7.06 (m, 4H), 6.77-6.80 (d, J=8.8 Hz, 1H), 6.49-6.50 (s, 1H), 6.27-6.30 (m, 1H), 4.99-5.01 (d, J=7.2 Hz, 4H), 4.46 (s, 2H), 3.73-3.94 (m, 12H), 3.53-3.65 (m, 14H), 3.24-3.31 (m, 6H), 3.08-3.17 (m, 2H), 1.407 (s, 9H); LC-MS Calcd m/z for $C_{56}H_{68}F_2N_6O_{12}S_2$ [MS]1119.3; MS Found: 1121.7 [MS+2].

Example 27. Preparation of Compound Q (N-(1-(3, 4-bis(benzyloxy)phenyl)-5,8,11,14,17-pentaoxa-2-azanonadecan-19-yl)-4-phenylbutanamide)

Step 2) Synthesis of Compound Q

To a solution of Q-2 (250 mg, 0.59 mmol) in MeOH (10 mL) was added B-3 (3,4-bis(benzyloxy)benzaldehyde, 209 mg, 0.657 mmol). The mixture was stirred for 6 hours at 65° C. NaBH$_4$ (26.6 mg, 0.710 mmol) was added at rt. The reaction mixture was stirred overnight at 50° C. The above solution was poured into water. The solution was extracted and the residue was purified by pre-HPLC to afford Compound Q (N-(1-(3,4-bis(benzyloxy)phenyl)-5,8,11,14,17-pentaoxa-2-azanonadecan-19-yl)-4-phenylbutanamide, 15 mg) as yellow oil.

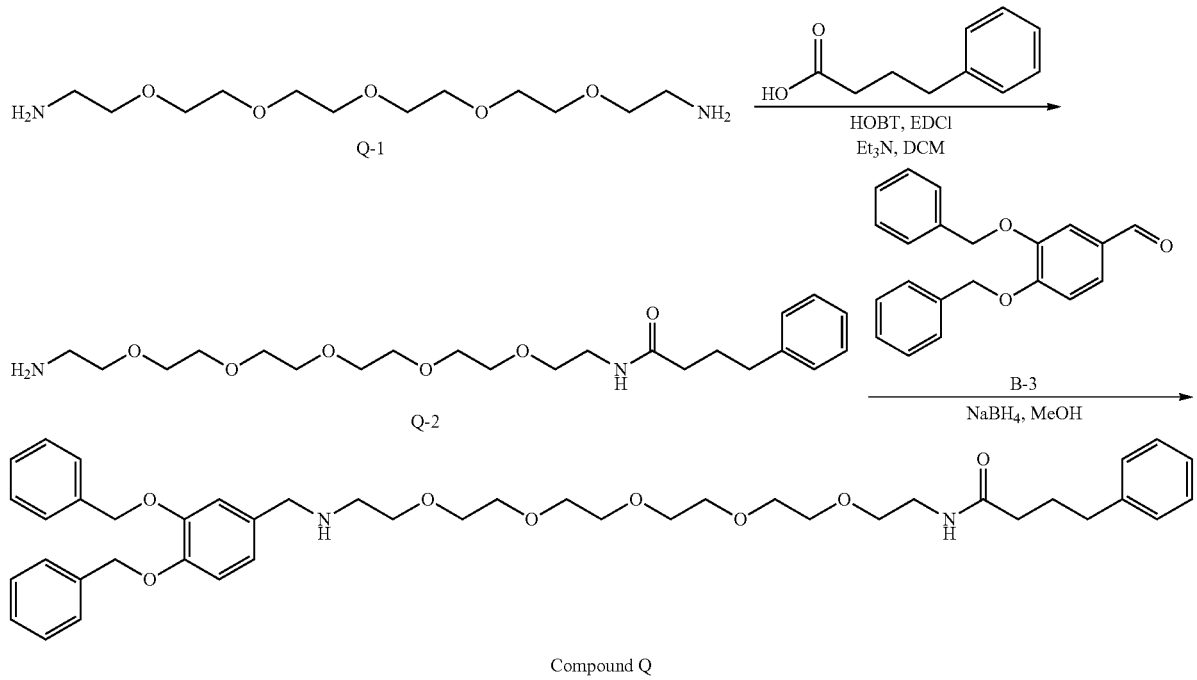

Compound Q

Step 1) Synthesis of Q-2

To a solution of Q-1 (198 mg, 0.708 mmol) in DCM (10 mL) was added HOBT (123 mg, 0.920 mmol), EDCI (176 mg, 0.920 mmol) and Et$_3$N (119 mg, 1.18 mmol). The solution of 4-phenylbutanoic acid (97 mg, 0.59 mmol) in DCM (10 mL) was added at 0° C. The mixture was stirred at room temperature overnight. The above solution was poured into water and extracted with DCM (10 mL×3). The combined organic layers were washed with brine, dried over Na$_2$SO$_4$ and concentrated to give Q-2 (N-(17-amino-3,6,9, 12,15-pentaoxaheptadecyl)-4-phenylbutanamide, 250 mg) as yellow oil. The crude Q-2 was used for the next step reaction without further purification.

$^1$H-NMR (CD$_3$OD, 400 MHz) δ (ppm) 7.48-7.44 (m, 4H), 7.38-7.16 (m, 11H), 7.09 (s, 1H), 7.00 (d, 1H), 6.90 (d, 1H), 5.16 (s, 2H), 5.13 (s, 2H), 3.74 (s, 2H), 3.62-3.58 (m, 18H), 3.53-3.50 (m, 2H), 3.35-3.32 (m, 2H), 2.75 (t, 2H), 2.62 (t, 2H), 2.21 (t, 2H), 1.91 (q, 2H); ESI-MS Calcd m/z for $C_{43}H_{56}N_2O_8$ [M+H]$^+$ 729.9 Found 729.0, 730.0.

Example 28. Preparation of Compound R (N-(1-(3, 4-bis(benzyloxy)phenyl)-5,8,11,14,17,20,23-heptaoxa-2-azapentacosan-25-yl)-4-phenylbutanamide)

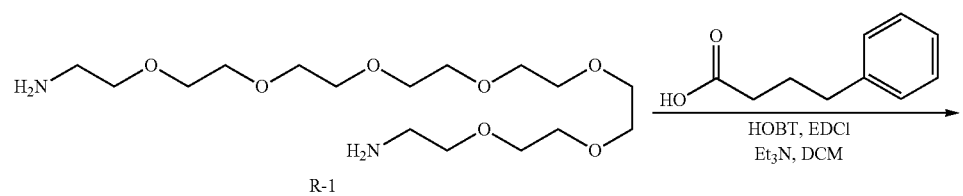

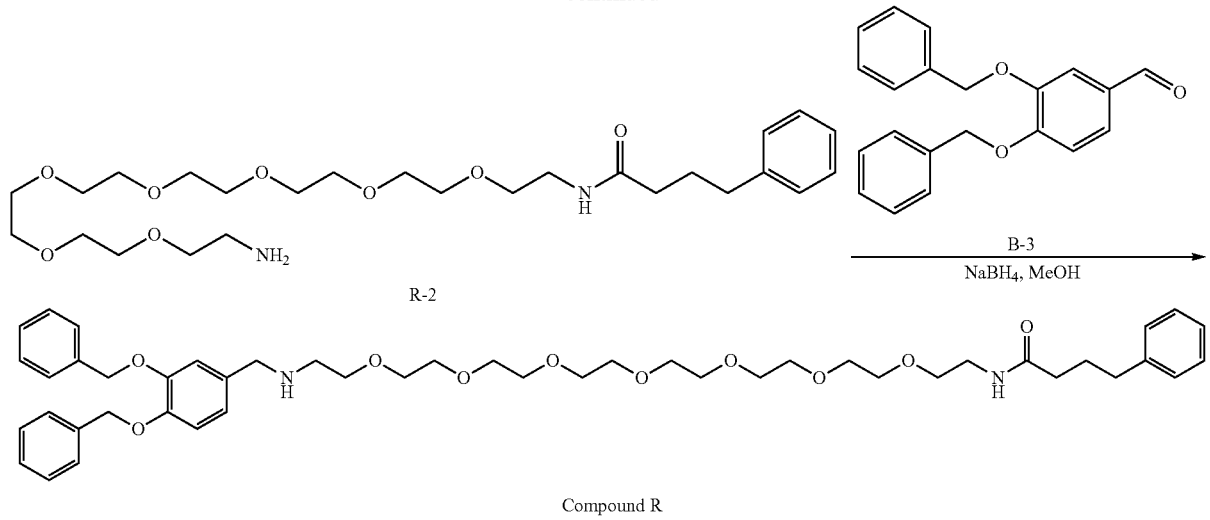

Step 1) Synthesis of R-2

To a solution of R-1 (262 mg, 0.71 mmol) in DCM (10 mL) was added HOBT (123 mg, 0.91 mmol), EDCI (176 mg, 0.91 mmol) and Et$_3$N (184 mg, 1.82 mmol). The solution of 4-phenylbutanoic acid (99.2 mg, 0.60 mmol) in DCM (10 mL) was added at 0° C. The mixture was stirred at room temperature overnight. The above solution was poured into water and extracted with DCM (10 mL×3). The combined organic layers were washed with brine, dried over Na$_2$SO$_4$ and concentrated to give R-2 (N-(23-amino-3,6,9,12,15,18,21-heptaoxatricosyl)-4-phenylbutanamide, 310 mg) as yellow oil. The crude R-2 was used for the next step reaction without further purification.

Step 2) Synthesis of Compound R

To a solution of R-2 (310 mg, 0.60 mmol) in MeOH (10 mL) was added B-3 (3,4-bis(benzyloxy)benzaldehyde, 209 mg, 0.66 mmol). The mixture was stirred for 6 hours at 65° C. NaBH$_4$ (28 mg, 0.72 mmol) was added at rt. The reaction mixture was stirred overnight at 50° C. The above solution was poured into water. The solution was extracted and the residue was purified by pre-HPLC to afford Compound R (N-(1-(3,4-bis(benzyloxy)phenyl)-5, 8, 11, 14, 17, 20, 23-heptaoxa-2-azapentacosan-25-yl)-4-phenylbutanamide, 25 mg) as yellow oil.

$^1$H-NMR (CD$_3$OD, 400 MHz) δ (ppm) 7.48-7.44 (m, 4H), 7.38-7.16 (m, 11H), 7.10 (s, 1H), 7.02-7.00 (m, 1H), 6.91 (m, 1H), 5.16 (s, 2H), 5.13 (s, 2H), 3.77 (s, 2H), 3.62-3.57 (m, 26H), 3.52 (t, 2H), 3.36-3.32 (m, 2H), 2.78 (t, 2H), 2.62 (t, 2H), 2.21 (t, 2H), 1.91 (q, 1H), 1.29 (m, 2H); ESI-MS Calcd m/z for C$_{47}$H$_{64}$N$_2$O$_{10}$ [M+H]$^+$ 818.03 Found 818.1.

Example 29. Preparation of Compound S ((R)—N-(15-(3,4-bis((4-fluorobenzyl)oxy)phenoxy)-14-hydroxy-3,6,9-trioxa-12-azapentadecyl)-4-phenylbutanamide)

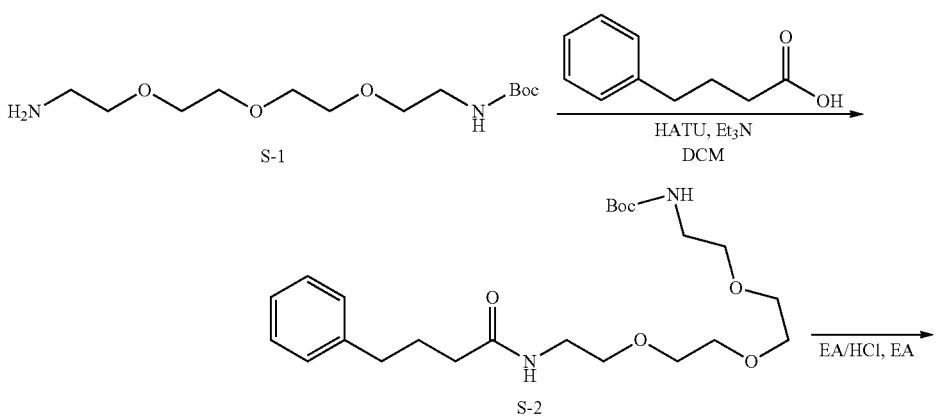

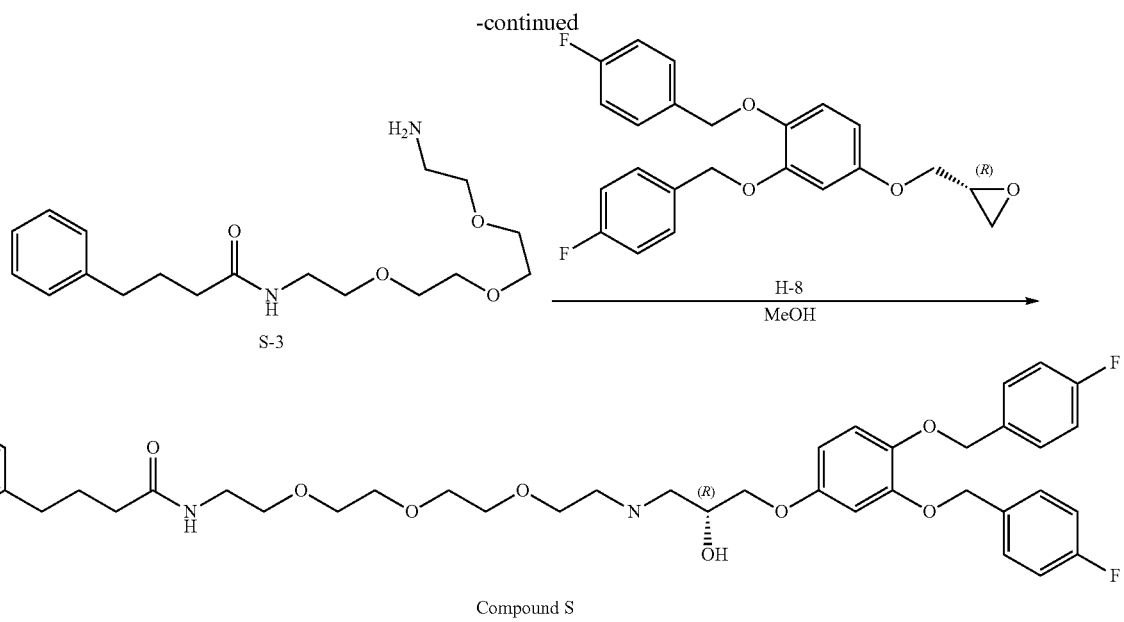

Step 1) Synthesis of S-2

To a solution of S-1 (tert-butyl (2-(2-(2-(2-aminoethoxy)ethoxy)ethoxy)ethyl)carbamate, 40.0 g, 137 mmol, 1.00 eq) in dichloromethane (400 mL) was added triethylamine (27.6 g, 274 mmol, 2.00 eq), 4-Phenylbutyric acid (26.7 g, 164 mmol, 1.20 eq) and HATU (78.0 g, 205 mmol, 1.50 eq). Another batch was carried out as the above procedure. The mixture was stirred at 20° C. for overnight, washed with saturated sodium bicarbonate solution (500 mL) and sodium chloride saturated solution (500 mL). The combined organic layers were dried over Sodium sulphate, filtered, and concentrated. The crude was purified by column chromatography (DCM/MeOH=50/1-5/1) to give the S-2 (tert-butyl (13-oxo-16-phenyl-3,6,9-trioxa-12-azahexadecyl)carbamate, 120 g, 100%) as yellow oil. (TLC: DCM/MeOH=20/1, $R_f$=0.4); $^1$H-NMR (CDCl$_3$, 400 MHz): δ 7.29 (m, 2H), 7.19 (m, 3H), 3.65 (m, 6H), 3.48 (m, 4H), 2.69 (t, 2H), 2.32 (m, 2H), 2.00 (m, 2H), 1.98 (s, 9H).

Step 2) Synthesis of S-3

To a solution of S-2 (tert-butyl (13-oxo-16-phenyl-3,6,9-trioxa-12-azahexadecyl)carbamate, 60.0 g, 137 mmol, 1.00 eq) and in ethyl acetate (300 mL) was add EA/HCl (4N, 300 ml) slowly at 0° C. Another batch was carried out as the above procedure. The mixture was stirred at 20° C. for 3 hours. The reaction was concentrated to give the S-3 (N-(2-(2-(2-(2-aminoethoxy)ethoxy)ethoxy)ethyl)-4-phenylbutanamide, 60.0 g, 65.0%). (TLC: DCM/MeOH=10/1, $R_f$=0.5); $^1$H-NMR (CDCl$_3$, 400 MHz): δ 7.30 (m, 2H), 7.20 (m, 3H), 6.42 (s, 1H), 5.97 (s, 2H), 3.66 (m, 12H), 3.44 (t, 2H), 3.14 (m, 2H), 2.62 (t, 2H), 2.22 (t, 2H), 1.95 (m, 2H).

Step 3) Synthesis of Compound S

To a solution of S-3 (N-(2-(2-(2-(2-aminoethoxy)ethoxy)ethoxy)ethyl)-4-phenylbutanamide, 10.0 g, 29.4 mmol, 1.00 eq) and H-8 ((R)-2-((3,4-bis((4-fluorobenzyl)oxy)phenoxy)methyl)oxirane, 11.8 g, 29.4 mmol, 1.00 eq) in methanol (300 mL) was stirred overnight at 50° C. Another 2 batches and 7.5 g of compound 9 batch were carried out as the above procedure. The reaction was concentrated and purified by column chromatography (DCM/MeOH=50/1-20/1) to give the Compound S ((R)—N-(15-(3,4-bis((4-fluorobenzyl)oxy)phenoxy)-14-hydroxy-3,6,9-trioxa-12-azapentadecyl)-4-phenylbutanamide, 10.0 g, 12.3%).

$^1$H-NMR (CDCl$_3$, 400 MHz): δ 7.42-7.36 (m, 4H), 7.30-7.26 (m, 2H), 7.20-7.18 (m, 3H), 7.08-7.03 (m, 4H), 6.86-6.83 (d, 1H), 6.59 (d, 1H), 6.49 (s, 1H), 6.39 (m, 1H), 5.06 (s, 2H), 5.01 (s, 2H), 4.11-4.08 (m, 1H), 3.92-3.89 (m, 2H), 3.64-3.57 (m, 12H), 3.48-3.46 (m, 2H), 2.94-2.78 (m, 4H), 2.63 (t, 2H), 2.02 (t, 2H), 1.99 (m, 2H); ESI-MS Calcd m/z for $C_{41}H_{50}F_2N_2O_8$ [M+H]$^+$ 737.8 Found 737.9.

Example 30. Preparation of Compound T ((R)—N-(15-(3-((4-fluorobenzyl)oxy)phenoxy)-14-hydroxy-3,6,9-trioxa-12-azapentadecyl)-4-phenylbutanamide)

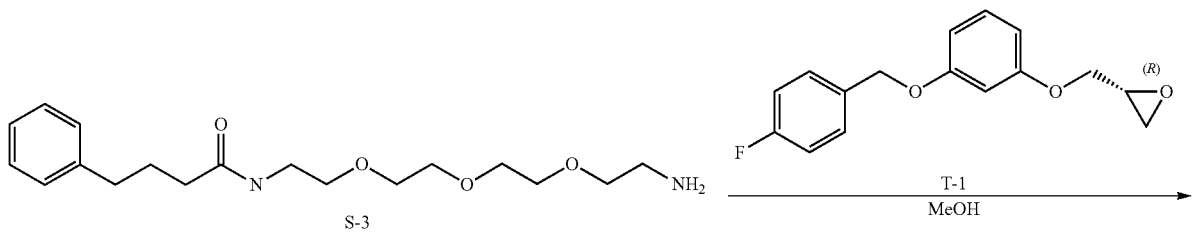

-continued

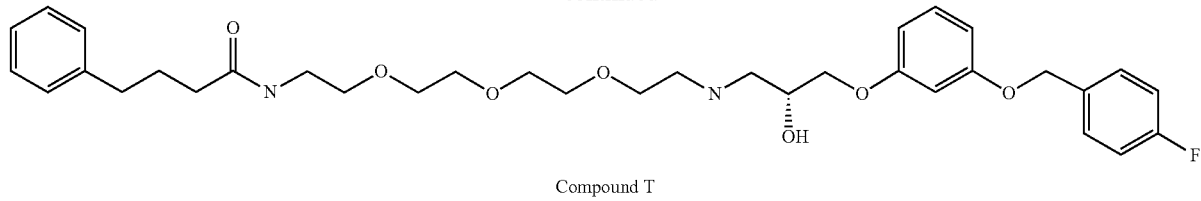

Compound T

To a solution of S-3 (N-(2-(2-(2-(2-aminoethoxy)ethoxy)ethoxy)ethyl)-4-phenylbutanamide, 30.0 g, 88.2 mmol, 1.00 eq) and T-1 ((R)-2-((3-((4-fluorobenzyl)oxy)phenoxy)methyl)oxirane, 24.3 g, 88.2 mmol, 1.00 eq) in methanol (600 mL) was stirred overnight at 50° C. The reaction was concentrated and purified by column chromatography (DCM/MeOH=50/1~20/1) to give the Compound T ((R)—N-(15-(3-((4-fluorobenzyl)oxy)phenoxy)-14-hydroxy-3,6,9-trioxa-12-azapentadecyl)-4-phenylbutanamide, 10.0 g, 18.4%).

$^1$H-NMR (CDCl$_3$, 400 MHz): δ 7.42-7.39 (m, 2H), 7.30-7.26 (m, 2H), 7.21-7.19 (m, 4H), 7.10-7.06 (m, 2H), 6.60-6.52 (m, 3H), 6.46 (m, 1H), 5.00 (s, 2H), 4.17-4.15 (m, 1H), 4.01-3.93 (m, 4H), 3.67-3.57 (m, 10H), 3.48-3.44 (m, 2H), 2.98-2.83 (m, 4H), 2.66 (t, 2H), 2.17 (t, 2H), 2.01 (m, 2H); ESI-MS Calcd m/z for C$_{34}$H$_{45}$FN$_2$O$_7$[M+H]$^+$ 613.7 Found 613.9.

Example 31. Preparation of Compound U (N-(7-((1-(3,4-bis(benzyloxy)phenyl)-5,8,11-trioxa-2-aza-tridecan-13-yl) (methyl)amino)-3H-phenothiazin-3-ylidene)-N-methylmethanaminium 2,2,2-trifluoroacetate)

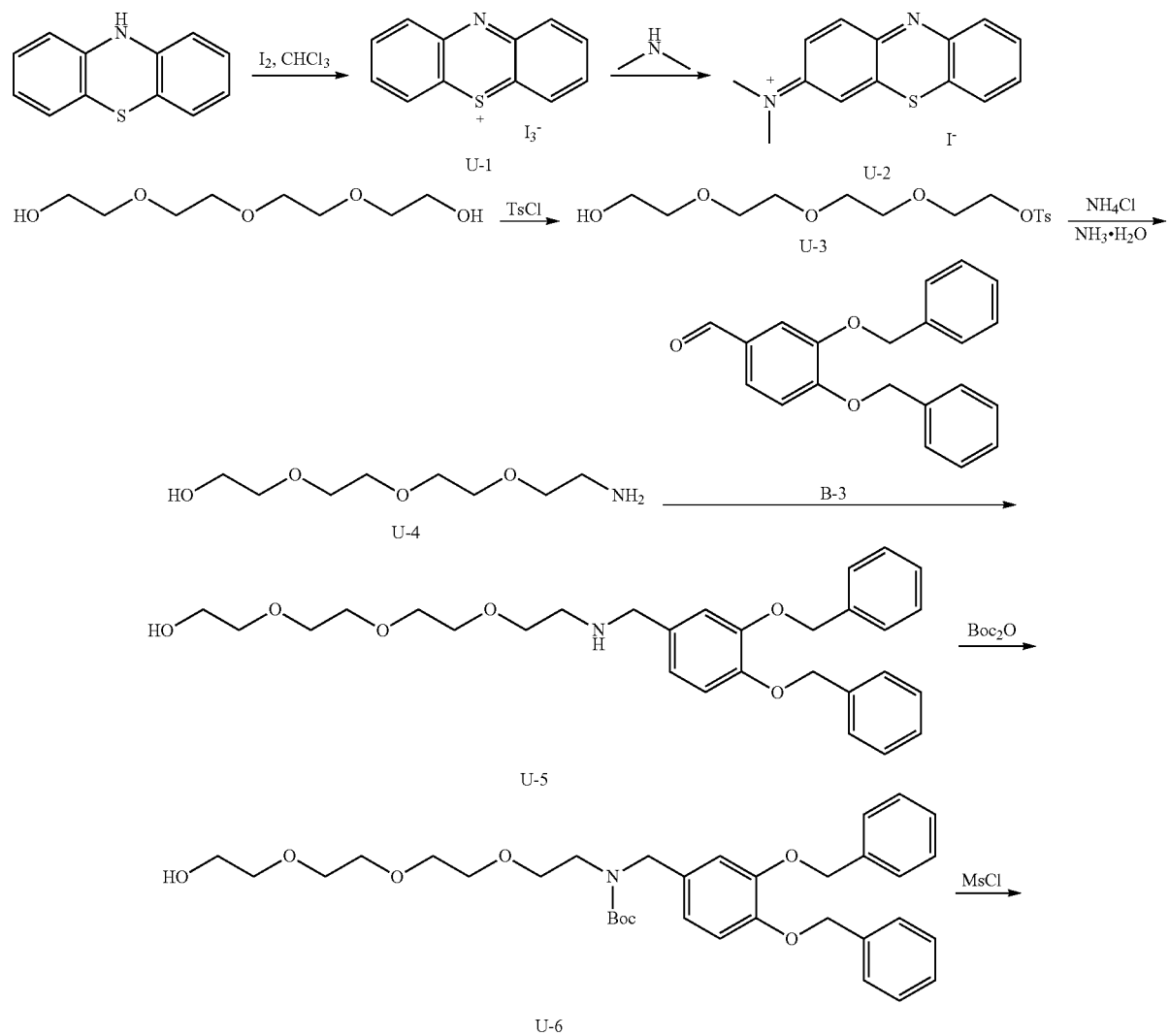

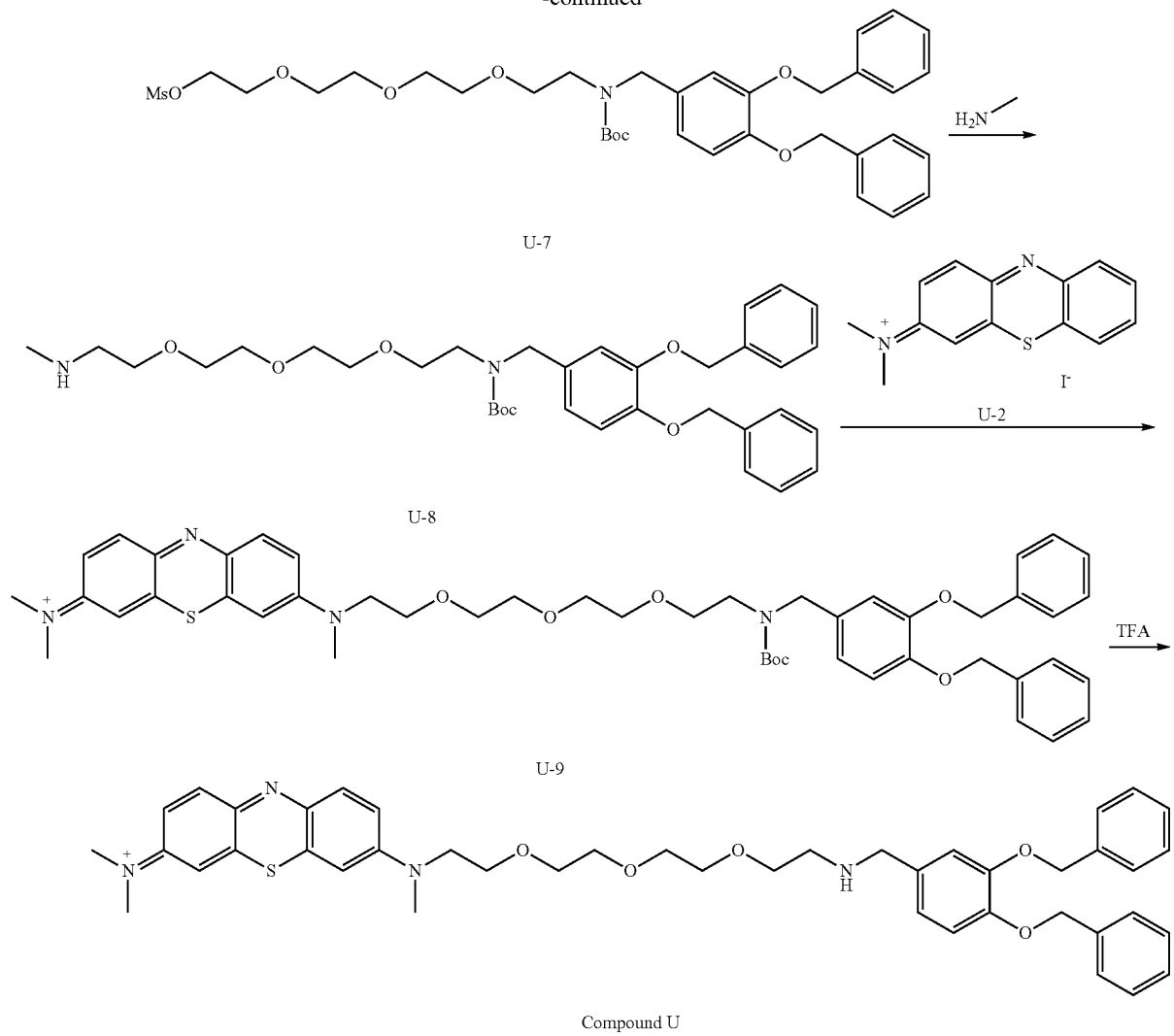

Compound U

Step 1) Synthesis of U-1

To a mixture of 10H-phenothiazine (40.0 g, 0.20 mol, 1.0 eq) in CHCl$_3$ (1.2 L) was added dropwise a solution of I$_2$ (153 g, 0.60 mol, 3.0 eq) in CHCl$_3$ (500 mL) at 0° C. Then the mixture was stirred at 0° C. for 7 hrs. The mixture was filtered. The filter cake was dried in vacuo to give U-1 (160 g, crude) as a black solid. (TLC: N/A); ESI-MS Calcd m/z for C$_{12}$H$_8$I$_3$NS [M−I$_3$]$^+$ 198.26 Found 198.9.

Step 2) Synthesis of U-2

To a mixture of U-1 (160 g, 0.28 mol, 1.0 eq) in DCM (1.6 L) was added dimethylamine (276 mL, 0.55 mol, 2.0 eq, 2M in THF) at r.t. Then the mixture was stirred at r.t. for 4 hrs. The mixture was filtered. The filter cake was dried in vacuo to give U-2 (N-methyl-N-(3H-phenothiazin-3-ylidene)methanaminium iodide, 40.0 g, yield 54% for 2 steps) as a black solid. (TLC: N/A); ESI-MS Calcd m/z for C$_{14}$H$_{13}$IN$_2$S [M−I+H]$^+$ 241.33 Found 242.9.

Step 3) Synthesis of U-3

To a stirred solution of 2,2'-((oxybis(ethane-2,1-diyl))bis(oxy))bis(ethan-1-ol) (500 g, 2.58 mol, 1.0 eq) and NaOH (113 g, 2.84 mol, 1.1 eq) in THF/H$_2$O (5 L, v/v=1:1) was added a solution of TsCl (246 g, 1.29 mol, 0.5 eq) in THF (2.5 L) at 0° C. over 5 hrs. The solution was stirred for 2 hrs at 0° C. The mixture was treated with water and extracted with EA (3 L×3). The combined organic layers were washed with brine, dried, and concentrated. The residue was purified by chromatography column (PE/EA=10:1-1:2) to give U-3 (2-(2-(2-(2-hydroxyethoxy)ethoxy)ethoxy)ethyl 4-methylbenzenesulfonate, 300 g, yield 70%) as yellow oil. (TLC: EA, Rf=0.4); $^1$H-NMR (CDCl$_3$, 400 MHz): δ 7.81-7.83 (m, 2H), 7.36 (d, J=8.0 Hz, 2H), 4.18 (t, J=4.8 Hz, 2H), 3.58-3.74 (m, 14H), 2.46 (s, 3H).

Step 4) Synthesis of U-4

To a mixture of U-3 (2-(2-(2-(2-hydroxyethoxy)ethoxy)ethoxy)ethyl 4-methylbenzenesulfonate, 300 g, 0.86 mol, 1.0 eq) in NH$_3$—H$_2$O (3 L) was added NH$_4$Cl (47.5 g, 0.91 mol, 1.05 eq) at r.t. Then the mixture was stirred at r.t. for 16 hrs. The mixture was concentrated. The residue was dissolved in DCM. The mixture was filtered. The filtrate was concentrated to give U-4 (2-(2-(2-(2-aminoethoxy)ethoxy)ethoxy)ethan-1-ol, 170 g, crude) as yellow oil. (TLC: N/A);

$^1$H-NMR (CDCl$_3$, 400 MHz): δ 3.73-3.75 (m, 2H), 3.65-3.69 (m, 9H), 3.58-3.63 (m, 3H), 3.48-3.49 (m, 3H).

Step 5) Synthesis of U-5

A mixture of U-4 (2-(2-(2-(2-aminoethoxy)ethoxy)ethoxy)ethan-1-ol, 170 g, 0.88 mol, 1.0 eq) and B-3 (3,4-bis(benzyloxy)benzaldehyde, 308 g, 0.97 mol, 1.1 eq) in MeOH (1.7 L) was stirred at 60° C. for 5 hrs. The above solution was cooled to r.t. NaBH$_4$ (66.9 g, 1.76 mol, 2.0 eq) was added portion wise. The mixture was stirred for 3 hrs at r.t. The mixture was treated with water and extracted with EA (2 L×3). The combined organic layers were washed with brine, dried, and concentrated. The residue was purified by chromatography column (DCM/MeOH=100:1-15:1) to give U-5 (1-(3,4-bis(benzyloxy)phenyl)-5,8,11-trioxa-2-azatridecan-13-ol, 130 g, yield 29.8% for 2 steps) as yellow oil. (TLC: DCM/MeOH=10/1, Rf=0.5); $^1$H-NMR (CDCl$_3$, 400 MHz): δ 7.44-7.48 (m, 4H), 7.31-7.38 (m, 6H), 7.14 (s, 1H), 6.89 (s, 2H), 5.15 (d, J=2.8 Hz, 4H), 3.88 (s, 2H), 3.53-3.73 (m, 15H), 2.89 (t, J=4.8 Hz, 2H).

Step 6) Synthesis of U-6

To a mixture of U-5 (1-(3,4-bis(benzyloxy)phenyl)-5,8,11-trioxa-2-azatridecan-13-ol, 130 g, 0.26 mol, 1.0 eq) and TEA (31.8 g, 0.032 mol, 1.2 eq) in DCM (1.3 L) was added Boc$_2$O (60.1 g, 0.28 mol, 1.05 eq) at 0° C. Then the mixture was stirred at r.t. for 5 hrs. The mixture was treated with water and extracted with DCM (2 L×3). The combined organic layers were washed with brine, dried, and concentrated to give U-6 (tert-butyl (3,4-bis(benzyloxy)benzyl) (2-(2-(2-(2-hydroxyethoxy)ethoxy)ethoxy)ethyl)carbamate, 140 g, yield 89.7%) as yellow oil. (TLC: DCM/MeOH=10/1, Rf=0.7); $^1$H-NMR (CDCl$_3$, 400 MHz): δ 7.46 (d, J=7.6 Hz, 4H), 7.30-7.39 (m, 6H), 6.88-6.92 (m, 2H), 6.77 (br s, 1H), 5.16 (d, J=2.8 Hz, 4H), 4.41 (d, J=4.8 Hz, 2H), 3.49-3.79 (m, 15H), 3.25-3.35 (m, 2H), 1.44-1.50 (m, 9H).

Step 7) Synthesis of U-7

To a mixture of U-6 (tert-butyl (3,4-bis(benzyloxy)benzyl) (2-(2-(2-(2-hydroxyethoxy)ethoxy)ethoxy)ethyl)carbamate, 200 g, 0.34 mol, 1.0 eq) and TEA (50.9 g, 0.50 mol, 1.5 eq) in DCM (2 L) was added methane sulfonyl chloride (46.0 g, 0.40 mol, 1.2 eq) at 0° C. Then the mixture was stirred at r.t. for 6 hrs. The mixture was treated with water and extracted with DCM (2 L×3). The combined organic layers were washed with brine, dried, and concentrated to give U-7 (5-(3,4-bis(benzyloxy)benzyl)-2,2-dimethyl-4-oxo-3,8,11,14-tetraoxa-5-azahexadecan-16-yl methanesulfonate, 200 g, yield 88.4%) as yellow oil. (TLC: N/A); $^1$H-NMR (CDCl$_3$, 400 MHz): δ 7.46 (d, J=7.6 Hz, 4H), 7.30-7.40 (m, 6H), 6.86-6.90 (m, 2H), 6.75-6.77 (m, 1H), 5.16 (d, J=2.8 Hz, 4H), 4.36-4.38 (m, 2H), 3.24-3.80 (m, 16H), 3.05 (s, 3H), 1.45-1.50 (m, 9H).

Step 8) Synthesis of U-8

To a mixture of U-7 (5-(3,4-bis(benzyloxy)benzyl)-2,2-dimethyl-4-oxo-3,8,11,14-tetraoxa-5-azahexadecan-16-yl methanesulfonate, 200 g, 0.30 mol, 1.0 eq) and Na$_2$CO$_3$ (63.0 g, 0.59 mol, 2.0 eq) in EtOH (2 L) was added methylamine ethyl alcohol solution (61.4 g, 0.59 mol, 2.0 eq, 30%) at r.t. Then the mixture was stirred at 60° C. for 16 hrs. The mixture was filtered. The filtrate was concentrated and purified by chromatography column (DCM/MeOH=100:1-10:1) to give U-8 (tert-butyl (3,4-bis(benzyloxy)benzyl) (5,8,11-trioxa-2-azatridecan-13-yl)carbamate, 100 g, yield 55.6%) as yellow oil. (TLC: DCM/MeOH=10/1, Rf=0.4); $^1$H-NMR (CDCl$_3$, 400 MHz): δ 7.30-7.47 (m, 10H), 6.86-6.91 (m, 2H), 6.76 (br s, 1H), 5.16 (s, 4H), 4.41 (d, J=7.6 Hz, 2H), 3.48-3.67 (m, 12H), 3.24-3.34 (m, 2H), 2.79 (s, 2H), 2.46 (s, 3H), 1.47 (d, J=23.2 Hz, 9H).

Step 9) Synthesis of U-9

A mixture of U-8 (tert-butyl (3,4-bis(benzyloxy)benzyl) (5,8,11-trioxa-2-azatridecan-13-yl)carbamate, 5.00 g, 8.22 mmol, 1.0 eq) and U-2 (N-methyl-N-(3H-phenothiazin-3-ylidene)methanaminium iodide, 3.00 g, 8.22 mmol, 1.0 eq) in DCM (150 mL) was stirred at r.t for 16 hrs. The mixture was filtered. Another 19 batches were carried out as the above procedure. (TLC: N/A); ESI-MS Calcd m/z for C$_{49}$H$_{59}$N$_4$O$_7$S$^+$[M+H]$^+$ 848.09 Found 849.8.

Step 10) Synthesis of Compound U

To the solution of U-9 in DCM (150 mL) was added TFA (30 mL) at r.t. Then the mixture was stirred at r.t. for 2 hrs. The mixture was concentrated. Another 19 batches were carried out as the above procedure. The residue was purified by prep-HPLC to give Compound U (N-(7-((1-(3,4-bis(benzyloxy)phenyl)-5,8,11-trioxa-2-azatridecan-13-yl)(methyl)amino)-3H-phenothiazin-3-ylidene)-N-methylmethanaminium 2,2,2-trifluoroacetate, 9.0 g, yield 6.3% for 2 steps) as a blue solid. (TLC: N/A); $^1$H-NMR (CDCl$_3$, 400 MHz): δ 10.19 (br s, 2H), 7.82-7.85 (m, 2H), 7.28-7.43 (m, 12H), 7.24-7.27 (m, 1H), 7.09-7.11 (m, 2H), 7.01-7.03 (m, 1H), 6.79-6.81 (m, 1H), 5.07 (s, 2H), 4.99 (s, 2H), 4.17 (s, 2H), 3.81-3.86 (m, 6H), 3.55-3.57 (m, 8H), 3.33 (s, 3H), 3.17 (s, 8H).; ESI-MS Calcd m/z for C$_{46}$H$_{51}$F$_3$N$_4$O$_7$S [M-CF$_3$COO-]$^+$747.97 Found 747.9.

Example 32. Preparation of Compound V ((R)—N-(7-((15-(3,4-bis((4-fluorobenzyl)oxy)phenoxy)-14-hydroxy-3,6,9-trioxa-12-azapentadecyl) (methyl)amino)-3H-phenothiazin-3-ylidene)-N-methylmethanaminium 2,2,2-trifluoroacetate)

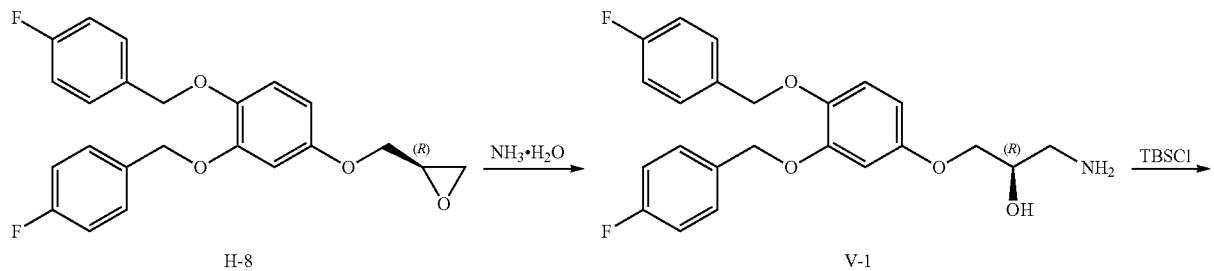

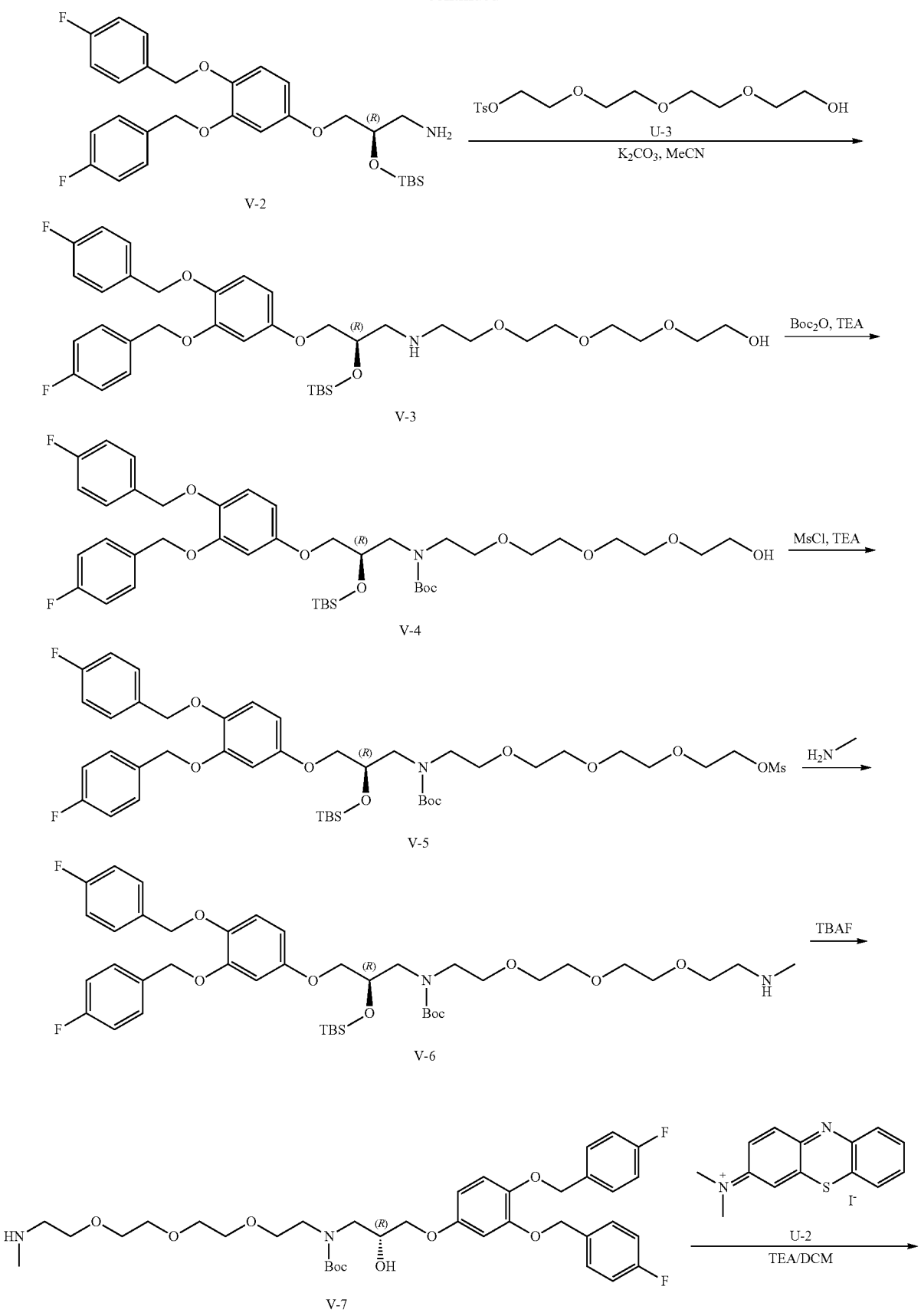

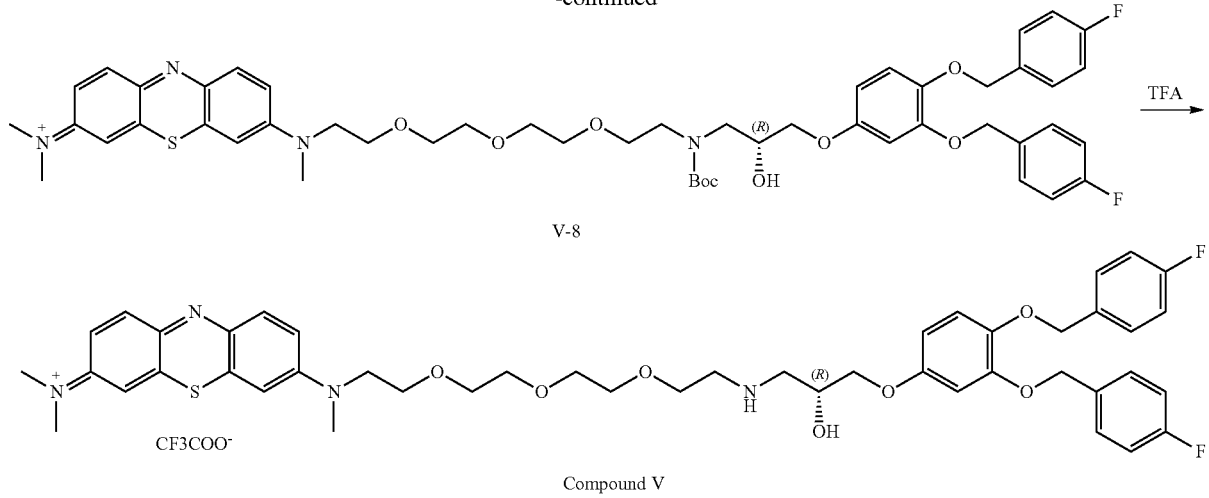

Step 1) Synthesis of V-1

To a solution of H-8 ((R)-2-((3,4-bis((4-fluorobenzyl)oxy)phenoxy)methyl)oxirane, 56.6 g, 142 mmol, 1.0 eq) in MeOH (1.1 L) was added NH$_3$·H$_2$O (560 mL). The mixture was stirred at 50° C. for 2 hours. Then the mixture was concentrated under reduced pressure to give V-1 ((R)-1-amino-3-(3,4-bis((4-fluorobenzyl)oxy)phenoxy)propan-2-ol, 50 g, 84.7%) as white solid. (TLC: DCM/MeOH=10/1, R$_f$=0.3). Another 5 batches were carried out as the above procedure.; $^1$H-NMR (CDCl$_3$, 400 MHz): β 7.36-7.43 (m, 4H), 7.01-7.09 (m, 4H), 6.85-6.87 (m, 1H), 6.60 (d, J=2.8 Hz, 1H), 6.42 (dd, J=8.8 Hz, 1H), 5.00-5.08 (m, 4H), 3.90-3.95 (m, 3H), 2.82-2.99 (m, 2H), 2.00 (s, 3H).

Step 2) Synthesis of V-2

To a solution of V-1 ((R)-1-amino-3-(3,4-bis((4-fluorobenzyl)oxy)phenoxy)propan-2-ol, 300 g, 723 mmol, 1.0 eq) in DCM (3 L) was added 1H-imidazole (59.0 g, 867 mol, 1.2 eq) and TBSCl (109 g, 723 mol, 1.0 eq) at 0° C. The mixture was stirred at rt for 3 hours. The mixture was washed with water and brine, then concentrated. The residue was purified by column chromatography (DCM/MeOH=100:1-10:1) to give V-2 ((R)-3-(3,4-bis((4-fluorobenzyl)oxy)phenoxy)-2-((tert-butyldimethylsilyl)oxy)propan-1-amine, 256 g, yield 67.0%) as white solid. (TLC: DCM/MeOH=15/1, Rf=0.5).; $^1$H-NMR (CDCl$_3$, 400 MHz): δ 7.37-7.43 (m, 4H), 7.01-7.09 (m, 4H), 6.86 (d, J=8.0 Hz, 1H), 6.55 (d, J=2.4 Hz, 1H), 6.40 (dd, J=8.8 Hz, 1H), 5.02-5.08 (m, 4H), 3.98-4.00 (m, 1H), 3.81-3.89 (m, 1H), 2.80-2.93 (m, 2H), 0.93 (s, 9H), 0.11-0.14 (m, 6H).

Step 3) Synthesis of V-3

To a mixture of V-2 (256 g, 0.48 mol, 1.0 eq) in MeCN (6 L) was added U-3 (2-(2-(2-(2-hydroxyethoxy)ethoxy)ethoxy)ethyl 4-methylbenzenesulfonate, 168 g, 0.48 mol, 1.0 eq), K$_2$CO$_3$ (133 g, 0.97 mol, 2.0 eq) and KI (19.9 g, 0.12 mol, 0.4 eq) at rt. Then the mixture was stirred at 70° C. for 16 hrs. The mixture was concentrated to give V-3 ((R)-5-((3,4-bis((4-fluorobenzyl)oxy)phenoxy)methyl)-2,2,3,3-tetramethyl-4,10,13,16-tetraoxa-7-aza-3-silaoctadecan-18-ol, 384 g, crude) as yellow oil. (TLC: DCM/MeOH=15/1, Rf=0.6). The residue was used into next step directly.; ESI-MS Calcd m/z for C37H$_{53}$F2NO$_8$Si [M+H]$^+$ 705.92 Found 707.3.

Step 4) Synthesis of V-4

To a solution of V-3 ((R)-5-((3,4-bis((4-fluorobenzyl)oxy)phenoxy)methyl)-2,2,3,3-tetramethyl-4,10,13,16-tetraoxa-7-aza-3-silaoctadecan-18-ol, 384 g, 543 mmol, 1.0 eq) in DCM (3 L) was added TEA (110 g, 1.09 mol, 2.0 eq) and Boc$_2$O (176 g, 814 mol, 1.5 eq) at 0° C. The mixture was stirred at rt for 1 hours. The mixture was washed with water and brine, then concentrated. The residue was purified by column chromatography (DCM/MeOH=100:1-40:1) to give V-4 (tert-butyl (R)-(3-(3,4-bis((4-fluorobenzyl)oxy)phenoxy)-2-((tert-butyldimethylsilyl)oxy)propyl) (2-(2-(2-(2-hydroxyethoxy)ethoxy)ethoxy)ethyl)carbamate, 129 g, yield 33.1% for 2 steps) as yellow oil. (TLC: DCM/MeOH=20/1, Rf=0.6).; $^1$H-NMR (CDCl$_3$, 400 MHz): δ 7.40-7.43 (m, 2H), 7.16-7.20 (m, 1H), 7.08 (t, J=8.6 Hz, 2H), 6.51-6.58 (m, 3H), 5.01 (s, 2H), 5.21-5.35 (m, 1H), 3.80-3.89 (m, 2H), 3.52-3.74 (m, 16H), 3.20-3.44 (m, 2H), 2.55 (s, 1H), 1.49 (s, 9H), 0.90 (s, 9H), 0.11 (s, 6H)

Step 5) Synthesis of V-5

To a mixture of V-4 (tert-butyl (R)-(3-(3,4-bis((4-fluorobenzyl)oxy)phenoxy)-2-((tert-butyldimethylsilyl)oxy)propyl) (2-(2-(2-(2-hydroxyethoxy)ethoxy)ethoxy)ethyl)carbamate, 129 g, 160 mmol, 1.0 eq) and TEA (24.2 g, 240 mmol, 1.5 eq) in DCM (1.5 L) was added methane sulfonyl chloride (21.9 g, 192 mmol, 1.2 eq) at 0° C. Then the mixture was stirred at r.t. for 3 hrs. The mixture was treated with water and extracted with DCM (500 mL×2). The combined organic layers were washed with brine, dried and concentrated to give V-5 ((R)-5-((3,4-bis((4-fluorobenzyl)oxy)phenoxy)methyl)-7-(tert-butoxycarbonyl)-2,2,3,3-tetramethyl-4,10,13,16-tetraoxa-7-aza-3-silaoctadecan-18-yl methanesulfonate, 141 g, crude) as yellow oil. (TLC: DCM/MeOH=20/1, Rf=0.8).; $^1$H-NMR (CDCl$_3$, 400 MHz): δ 7.37-7.44 (m, 4H), 7.02-7.09 (m, 4H), 6.85 (d, J=8.8 Hz, 1H), 6.53-6.57 (m, 1H), 63.6-6.39 (m, 1H), 5.02-5.08 (m, 4H), 4.37-4.39 (m, 2H), 4.21-4.30 (m, 1H), 3.75-3.81 (m, 4H), 3.56-3.70 (m, 19H), 3.34-3.43 (m, 1H), 3.16-3.30 (m, 1H), 3.07 (s, 3H), 1.48 (s, 9H), 0.90 (s, 9H), 0.08-0.10 (m, 6H).

Step 6) Synthesis of V-6

To a mixture of V-5 ((R)-5-((3,4-bis((4-fluorobenzyl)oxy)phenoxy)methyl)-7-(tert-butoxycarbonyl)-2,2,3,3-tetramethyl-4,10,13,16-tetraoxa-7-aza-3-silaoctadecan-18-yl methanesulfonate, 141 g, 160 mmol, 1.0 eq) and Na$_2$CO$_3$ (33.9 g, 320 mmol, 2.0 eq) in EtOH (1.5 L) was added methylamine ethyl alcohol solution (32.0 g, 320 mmol, 2.0 eq, 30%) at r.t. Then the mixture was stirred at 60° C. overnight. The mixture was filtered. The filtrate was concentrated and purified by column chromatography (DCM/MeOH=100:1-10:1) to give V-6 (tert-butyl (R)-(3-(3,4-bis((4-fluorobenzyl)oxy)phenoxy)-2-((tert-butyldimethylsilyl)oxy)propyl) (5,8,11-trioxa-2-azatridecan-13-yl)carbamate, 83 g, yield 63.8%) as yellow oil. (TLC: DCM/MeOH=15/1, Rf=0.5).; $^1$H-NMR (CDCl$_3$, 400 MHz): δ 7.37-7.43 (m, 4H), 7.02-7.09 (m, 4H), 6.85 (d, J=8.8 Hz, 1H), 6.53-6.56 (m, 1H), 6.36-6.40 (m, 1H), 5.02-5.08 (m, 4H), 4.21-4.29 (m, 1H), 3.32-3.83 (m, 19H), 3.20-3.25 (m, 1H), 3.07-3.10 (m, 2H), 2.66-2.68 (m, 2H), 1.47 (s, 9H), 0.90 (s, 9H), 0.10 (s, 6H).

Step 7) Synthesis of V-7

To a solution of V-6 (tert-butyl (R)-(3-(3,4-bis((4-fluorobenzyl)oxy)phenoxy)-2-((tert-butyldimethylsilyl)oxy)propyl) (5,8,11-trioxa-2-azatridecan-13-yl)carbamate, 83 g, 101 mmol, 1.0 eq) in THF (500 mL) was added TBAF (39.7 g, 152 mmol, 1.5 eq) at 0° C. The mixture was stirred at rt for 6 hours. The mixture was diluted with water and extracted with DCM (500 mL×2). The organic layer was washed with water and brine, then concentrated to give V-7 (tert-butyl (R)-(3-(3,4-bis((4-fluorobenzyl)oxy)phenoxy)-2-hydroxypropyl) (5,8,11-trioxa-2-azatridecan-13-yl)carbamate, 48.0 g, yield 67.3%) as yellow oil. (TLC: DCM/MeOH=10/1, Rf=0.3).; $^1$H-NMR (CDCl$_3$, 400 MHz): δ 7.36-7.43 (m, 4H), 7.00-7.08 (m, 4H), 6.85 (d, J=8.4 Hz, 1H), 6.62 (d, J=6.8 Hz, 1H), 6.41-6.43 (m, 1H), 5.08 (s, 2H), 5.02 (s, 1H), 4.18 (s, 1H), 3.90-3.91 (m, 2H), 3.63-3.66 (m, 13H), 3.45-3.58 (m, 3H), 2.83-2.84 (m, 2H), 2.48-2.51 (m, 3H), 1.46-1.48 (m, 9H).

Step 8) Synthesis of V-8

To a solution of V-7 (tert-butyl (R)-(3-(3,4-bis((4-fluorobenzyl)oxy)phenoxy)-2-hydroxypropyl) (5,8,11-trioxa-2-azatridecan-13-yl)carbamate, 42.0 g, 59.6 mmol, 1.0 eq) in DCM (1 L) was added TEA (12.1 g, 119 mmol, 2.0 eq) and U-2 (N-methyl-N-(3H-phenothiazin-3-ylidene)methanaminium iodide, 21.9 g, 59.6 mmol, 1.0 eq) at rt. The mixture was stirred at rt overnight. The mixture was concentrated to give V-8 ((R)—N-(7-((5-(3-(3,4-bis((4-fluorobenzyl)oxy)phenoxy)-2-hydroxypropyl)-2,2-dimethyl-4-oxo-3,8,11,14-tetraoxa-5-azahexadecan-16-yl) (methyl)amino)-3H-phenothiazin-3-ylidene)-N-methylmethanaminium, 50 g, crude) as dark blue oil. (TLC: N/A). The residue was used into next step directly.; ESI-MS Calcd m/z for $C_{51}H_{61}F_2N_4O_9S^+$[M-Boc]$^+$944.12 Found 844.8.

Step 9) Synthesis of Compound V

To the solution of V-8 (((R)—N-(7-((5-(3-(3,4-bis((4-fluorobenzyl)oxy)phenoxy)-2-hydroxypropyl)-2,2-dimethyl-4-oxo-3,8,11,14-tetraoxa-5-azahexadecan-16-yl) (methyl)amino)-3H-phenothiazin-3-ylidene)-N-methylmethanaminium, 50 g, crude) in DCM (300 mL) was added TFA (30 mL) at 0° C. Then the mixture was stirred at rt for 3 hrs. The mixture was concentrated. The residue was purified by prep-HPLC to give Compound V ((R)—N-(7-((15-(3,4-bis((4-fluorobenzyl)oxy)phenoxy)-14-hydroxy-3,6,9-trioxa-12-azapentadecyl) (methyl)amino)-3H-phenothiazin-3-ylidene)-N-methylmethanaminium 2,2,2-trifluoroacetate, 10 g, yield 20.0% for 2 steps) as dark blue solid. (TLC: N/A); $^1$H-NMR (DMSO-d$_6$, 400 MHz): δ 8.67 (s, 1H), 8.57 (s, 1H), 7.90-7.94 (m, 2H), 7.42-7.52 (m, 8H), 7.16-7.24 (m, 4H), 6.94 (d, J=9.2 Hz, 1H), 6.67 (d, J=2.8 Hz, 1H), 6.67 (dd, J=4.8 Hz, 1H), 5.07 (s, 2H), 5.00 (s, 2H), 4.13-4.16 (m, 1H), 3.84-3.94 (m, 4H), 3.49-3.56 (m, 8H), 3.34-3.37 (m, 8H), 3.00-3.17 (m, 5H); ESI-MS Calcd m/z for $C_{48}H_{53}F_5N_4O_9S$ [M-CF$_3$COO-]$^+$844.00 Found 844.8.

Example 33. Preparation of Compound W (R)—N-(7-((15-(3-((4-fluorobenzyl)oxy)phenoxy)-14-hydroxy-3,6,9-trioxa-12-azapentadecyl) (methyl)amino)-3H-phenothiazin-3-ylidene)-N-methylmethanaminium 2,2,2-trifluoroacetate)

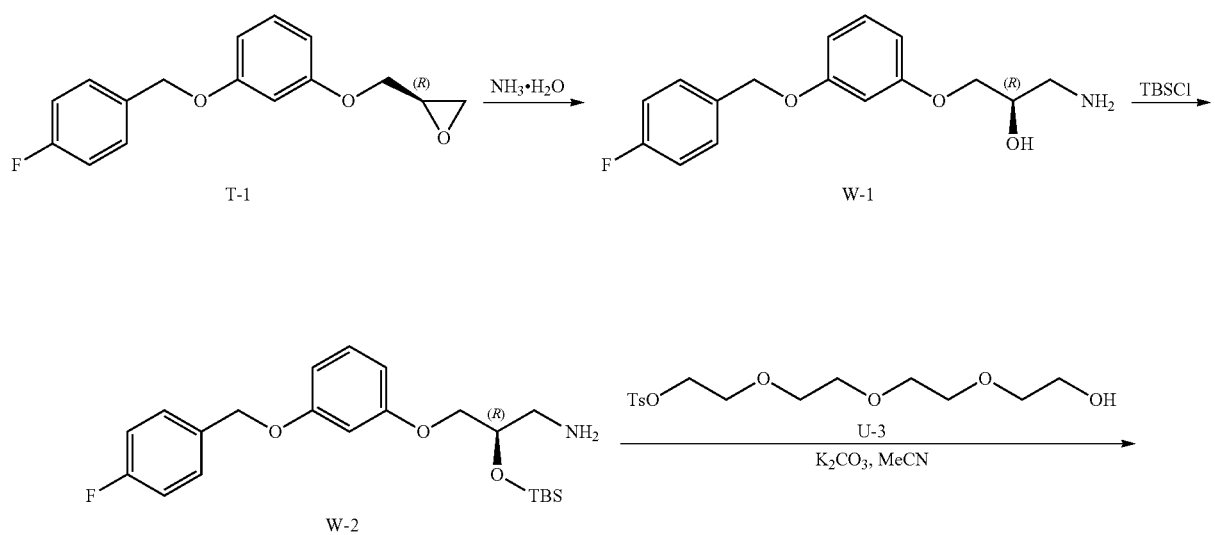

-continued

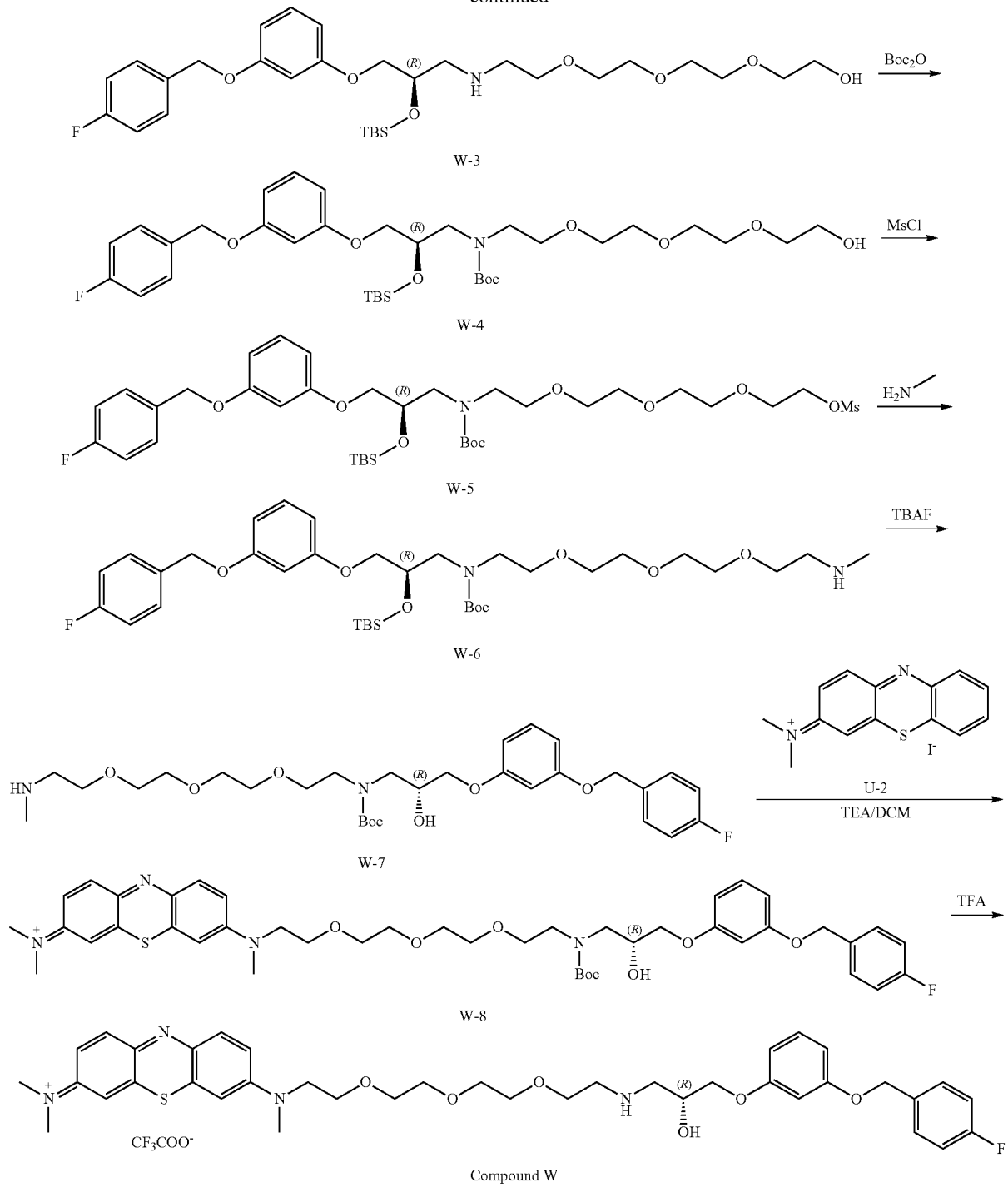

Step 1) Synthesis of W-1

To a solution of T-1 ((R)-2-((3-((4-fluorobenzyl)oxy)phenoxy)methyl)oxirane, 450 g, 1.64 mol, 1.0 eq) in MeOH (3 L) was added NH$_3$·H$_2$O (3 L). The mixture was stirred at 50° C. for 5 hours. Then the mixture was concentrated under reduced pressure to give W-1 ((R)-1-amino-3-(3-((4-fluorobenzyl)oxy)phenoxy)propan-2-ol, 300 g, 62.7%) as yellowish oil. (TLC: DCM/MeOH=10/1, R$_f$=0.3); $^1$H-NMR (CDCl$_3$, 400 MHz): δ 7.39-7.43 (m, 2H), 7.20 (t, J=8.0 Hz, 1H), 7.08 (t, J=8.6 Hz, 2H), 6.54-6.60 (m, 3H), 5.01 (s, 2H), 3.97 (s, 3H), 2.78-3.03 (m, 2H), 1.18-2.49 (br s, 2H).

Step 2) Synthesis of W-2

To a solution of W-1 ((R)-1-amino-3-(3-((4-fluorobenzyl)oxy)phenoxy)propan-2-ol, 300 g, 1.03 mol, 1.0 eq) in DCM (3 L) was added 1H-imidazole (84.1 g, 1.23 mol, 1.2 eq) and TBSCl (155 g, 1.03 mol, 1.0 eq) at 0° C. The mixture was stirred at rt for 3 hours. The mixture was washed with water and brine, then concentrated. The residue was purified by column chromatography (DCM/MeOH=100:1-10:1) to give W-2 ((R)-2-((tert-butyldimethylsilyl)oxy)-3-(3-((4-fluorobenzyl)oxy)phenoxy)propan-1-amine, 260 g, yield 62.2%) as yellowish oil. (TLC: DCM/MeOH=15/1, Rf=0.5).; $^1$H-NMR (CDCl$_3$, 400 MHz): δ 7.40-7.44 (m, 2H), 7.20 (t, J=8.6 Hz, 1H), 7.07-7.11 (m, 2H), 6.53-6.60 (m, 3H), 5.02 (s, 2H), 4.01-4.04 (m, 1H), 3.89-3.92 (m, 2H), 2.84-2.91 (m, 2H), 0.93 (s, 9H), 0.15 (s, 3H), 0.13 (s, 3H).

Step 3) Synthesis of W-3

To a mixture of W-2 ((R)-2-((tert-butyldimethylsilyl)oxy)-3-(3-((4-fluorobenzyl)oxy)phenoxy)propan-1-amine, 260 g, 0.64 mol, 1.0 eq) in MeCN (6 L) was added U-3 (2-(2-(2-(2-hydroxyethoxy)ethoxy)ethoxy)ethyl 4-methylbenzenesulfonate, 223 g, 0.64 mol, 1.0 eq), K$_2$CO$_3$ (177 g, 1.28 mol, 2.0 eq) and KI (42.6 g, 0.25 mol, 0.4 eq) at rt. Then the mixture was stirred at 70° C. for 16 hrs. The mixture was filtered. The filtrate was concentrated to give W-3 ((R)-5-((3-((4-fluorobenzyl)oxy)phenoxy)methyl)-2,2,3,3-tetramethyl-4,10,13,16-tetraoxa-7-aza-3-silaoctadecan-18-ol, 390 g, crude) as yellow oil. (TLC: DCM/MeOH=15/1, Rf=0.6). The residue was used into next step directly.; ESI-MS Calcd m/z for C$_{30}$H$_{48}$FNO$_7$Si [M+H]$^+$ 582.80 Found 582.9.

Step 4) Synthesis of W-4

To a solution of W-3 (((R)-5-((3-((4-fluorobenzyl)oxy)phenoxy)methyl)-2,2,3,3-tetramethyl-4,10,13,16-tetraoxa-7-aza-3-silaoctadecan-18-ol, 390 g, 671 mmol, 1.0 eq) in DCM (3 L) was added TEA (81.3 g, 805 mol, 1.2 eq) and Boc$_{2}$O (175 g, 805 mol, 1.2 eq) at 0° C. The mixture was stirred at rt for 3 hours. The mixture was washed with water and brine, then concentrated. The residue was purified by column chromatography (DCM/MeOH=100:1-40:1) to give W-4 (tert-butyl (R)-(2-((tert-butyldimethylsilyl)oxy)-3-(3-((4-fluorobenzyl)oxy)phenoxy)propyl) (2-(2-(2-(2-hydroxyethoxy)ethoxy)ethoxy)ethyl)carbamate, 130 g, yield 29.7% for 2 steps) as yellowish oil. (TLC: DCM/MeOH=20/1, Rf=0.6).; $^1$H-NMR (CDCl$_3$, 400 MHz): δ 7.40-7.43 (m, 2H), 7.16-7.20 (m, 1H), 7.08 (t, J=8.6 Hz, 2H), 6.51-6.58 (m, 3H), 5.01 (s, 2H), 5.21-5.35 (m, 1H), 3.80-3.89 (m, 2H), 3.52-3.74 (m, 16H), 3.20-3.44 (m, 2H), 2.55 (s, 1H), 1.49 (s, 9H), 0.90 (s, 9H), 0.11 (s, 6H).

Step 5) Synthesis of W-5

To a mixture of W-4 (tert-butyl (R)-(2-((tert-butyldimethylsilyl)oxy)-3-(3-((4-fluorobenzyl)oxy)phenoxy)propyl) (2-(2-(2-(2-hydroxyethoxy)ethoxy)ethoxy)ethyl)carbamate, 130 g, 191 mmol, 1.0 eq) and TEA (28.9 g, 286 mmol, 1.5 eq) in DCM (1.5 L) was added methane sufonyl chloride (26.1 g, 229 mmol, 1.2 eq) at 0° C. Then the mixture was stirred at r.t. for 3 hrs. The mixture was treated with water and extracted with DCM (500 mL×2). The combined organic layers were washed with brine, dried and concentrated to give W-5 ((R)-7-(tert-butoxycarbonyl)-5-((3-((4-fluorobenzyl)oxy)phenoxy)methyl)-2,2,3,3-tetramethyl-4,10,13,16-tetraoxa-7-aza-3-silaoctadecan-18-yl methanesulfonate, 120 g, yield 82.8%) as yellow oil. (TLC: DCM/MeOH=20/1, Rf=0.8).; ESI-MS Calcd m/z for C$_{36}$H$_{58}$FNO$_{11}$SSi [M-Boc]$^+$ 659.99 Found 659.9.

Step 6) Synthesis of W-6

To a mixture of W-5 ((R)-7-(tert-butoxycarbonyl)-5-((3-((4-fluorobenzyl)oxy)phenoxy)methyl)-2,2,3,3-tetramethyl-4,10,13,16-tetraoxa-7-aza-3-silaoctadecan-18-yl methanesulfonate, 120 g, 158 mmol, 1.0 eq) and Na$_2$CO$_3$ (33.5 g, 316 mmol, 2.0 eq) in EtOH (1.5 L) was added methylamine ethyl alcohol solution (32.6 g, 316 mmol, 2.0 eq, 30%) at r.t. Then the mixture was stirred at 60° C. overnight. The mixture was filtered. The filtrate was concentrated and purified by column chromatography (DCM/MeOH=100:1-10:1) to give W-6 (tert-butyl (R)-(2-((tert-butyldimethylsilyl)oxy)-3-(3-((4-fluorobenzyl)oxy)phenoxy)propyl) (5,8,11-trioxa-2-azatridecan-13-yl)carbamate, 42 g, yield 38.3%) as yellow oil. (TLC: DCM/MeOH=15/1, Rf=0.5).; $^1$H-NMR (CDCl$_3$, 400 MHz): δ 7.40-7.43 (m, 2H), 7.17-7.19 (m, 1H), 7.08 (t, J=8.8 Hz, 2H), 6.51-6.58 (m, 3H), 5.01 (s, 2H), 4.22-4.35 (m, 2H), 3.80-3.88 (m, 2H), 3.70-3.77 (m, 2H), 3.54-3.66 (m, 12H), 3.33-3.43 (m, 1H), 3.20-3.26 (m, 1H), 2.97-3.06 (m, 2H), 2.61-2.67 (m, 3H), 1.47 (s, 9H), 0.90 (s, 9H), 0.10 (s, 6H).

Step 7) Synthesis of W-7

To a solution of W-6 (tert-butyl (R)-(2-((tert-butyldimethylsilyl)oxy)-3-(3-((4-fluorobenzyl)oxy)phenoxy)propyl) (5,8,11-trioxa-2-azatridecan-13-yl)carbamate, 42 g, 60.5 mmol, 1.0 eq) in THF (500 mL) was added TBAF (23.7 g, 90.8 mmol, 1.5 eq) at 0° C. The mixture was stirred at rt for 6 hours. The mixture was diluted with water and extracted with DCM (500 mL×2). The organic layer was washed with water and brine, then concentrated to give W-7 (tert-butyl (R)-(3-(3-((4-fluorobenzyl)oxy)phenoxy)-2-hydroxypropyl) (5,8,11-trioxa-2-azatridecan-13-yl)carbamate, 20.5 g, yield 58.4%) as yellowish oil. (TLC: DCM/MeOH=10/1, Rf=0.3).; $^1$H-NMR (CDCl$_3$, 400 MHz): δ 7.40-7.43 (m, 2H), 7.19 (t, J=8.0 Hz, 1H), 7.08 (t, J=8.6 Hz, 2H), 6.54-6.59 (m, 3H), 5.01 (s, 2H), 4.20 (s, 1H), 3.89-3.98 (m, 2H), 3.56-3.80 (m, 14H), 3.22-3.51 (m, 3H), 2.76 (t, J=5.0 Hz, 2H), 2.44 (s, 3H), 1.48 (s, 9H).

Step 8) Synthesis of W-8

To a solution of W-7 (tert-butyl (R)-(3-(3-((4-fluorobenzyl)oxy)phenoxy)-2-hydroxypropyl) (5,8,11-trioxa-2-azatridecan-13-yl)carbamate, 20.5 g, 35.3 mmol, 1.0 eq) in DCM (1 L) was added TEA (7.14 g, 70.6 mmol, 2.0 eq) and U-2 (N-methyl-N-(3H-phenothiazin-3-ylidene)methanaminium iodide, 13.0 g, 35.3 mmol, 1.0 eq) at rt. The mixture was stirred at rt overnight. The mixture was concentrated to give W-8 ((R)—N-(7-((5-(3-(3-((4-fluorobenzyl)oxy)phenoxy)-2-hydroxypropyl)-2,2-dimethyl-4-oxo-3,8,11,14-tetraoxa-5-azahexadecan-16-yl) (methyl)amino)-3H-phenothiazin-3-ylidene)-N-methylmethanaminium, 24 g, crude) as dark blue oil. (TLC: N/A). The residue was used into next step directly.; ESI-MS Calcd m/z for C$_{44}$H$_{56}$FN$_4$O$_8$S$^+$[M+H]$^+$ 821.01 Found 821.7.

Step 9) Synthesis of Compound W

To the solution of W-8 ((R)—N-(7-((5-(3-(3-((4-fluorobenzyl)oxy)phenoxy)-2-hydroxypropyl)-2,2-dimethyl-4-oxo-3,8,11,14-tetraoxa-5-azahexadecan-16-yl) (methyl)amino)-3H-phenothiazin-3-ylidene)-N-methylmethanaminium, 24 g, crude) in DCM (300 mL) was added TFA (30 mL) at 0° C. Then the mixture was stirred at rt for 3 hrs. The mixture was concentrated. The residue was purified by prep-HPLC to give Compound W ((R)—N-(7-((15-((4-fluorobenzyl)oxy)phenoxy)-14-hydroxy-3,6,9-trioxa-12-azapentadecyl) (methyl)amino)-3H-phenothiazin-3-ylidene)-N-methylmethanaminium 2,2,2-trifluoroacetate, 10 g, yield 34.0% for 2 steps) as dark blue solid. (TLC: N/A); $^1$H-NMR (DMSO-$d_6$, 400 MHz): δ 8.71 (s, 1H), 8.59 (s, 1H), 7.09-7.94 (m, 2H), 7.46-7.52 (m, 5H), 7.17-7.24 (m, 3H), 6.52-6.63 (m, 3H), 5.05 (s, 2H), 3.89-4.18 (m, 6H), 3.63-3.73 (m, 4H), 3.46-3.56 (m, 8H), 3.31-3.38 (m, 8H), 2.94-3.22 (m, 5H).; ESI-MS Calcd m/z for $C_{41}H_{48}F_4N_4O_8S$ [M-CF$_3$COO-]$^+$719.89 Found 719.8.

In the following experimental examples, it was confirmed through experiments that the cargo delivery system according to the disclosure could selectively degrade the target by specifically binding to the target in cultured cells and activating autophagy. Specifically, cell lines primarily expressing the target protein (MCF7, NTERA-2, ACHN, U87-MG, LNCaP, HEK293T) or gene recombinant cell lines (SH-SY5Y-tau, HeLa-HttQ97, PC12-α-synA30P) were treated with the examples of the disclosure prepared above and cultured, and then target protein degradation activity in cultured cells was confirmed by immunoblotting and immunofluorescence staining.

Experimental Example 1. Evaluation of Oligomerization Activity of p62 Protein in Cultured Cells by Immunoblotting In order to evaluate the oligomerization activity efficacy of p62 protein according to examples of the disclosure, HEK293 cell line, which is human embryonic kidney-derived cell, was collected. The cell lines were treated with Example 3 (PBA 1104), Example 4 (PBA 1105), Example 5 (Anle F105), Example 8 (PHTPP 1304), Example 11 (BTA-1 1104), Example 12 (Curcumin 1204), Example 1 (ATC 1105), Example 2 (ATC 1104), Example 10 (Resv 1105), Example 13 (Rilu 204) according to the examples, YTK-1105 compound, which is an autophagy targeting ligand compound as a comparative example, and DMSO as a control at 2 mM, 2 hr, respectively.

In order to measure intracellular p62 protein activation and oligomerization in cells according to the treatment with these compounds, the respective cells were dispensed into a 100 pi dish. The cells were collected after further culturing for 24 hours so that the cells were completely attached to the surface of the plate. 100 μl of lysis buffer (20 mM Tris (pH 7.4), 150 mM NaCl, 1% Triton X-100, 2 mM NaF, 2 mM EDTA, 2 mM beta-glycerophosphate, 5 mM sodium orthovanadate, 1 mM PMSF, leupeptin, aproteinin) were injected into each sample and the cells were lysed. Based on the measured total protein concentration, each sample was treated with test compounds at room temperature for 2 hours, and then a sample buffer was added and allowed to react at 95° C. for 10 minutes. 25 μl was taken from the samples after the reaction, and dispensed into each well of acrylamide gel, and then immunoblotting was performed. Immunoblotting showed representative results from three or more independent experiments. The results are shown in FIGS. 2A to 2C.

As seen in FIGS. 2A to 2C, it was confirmed that when treated with the example compounds according to the disclosure as well as the autophagy targeting ligand compound YTK-1105, it resulted in a decrease of the monomer of p62 proteins and simultaneously an increase in oligomers and high-molecular aggregates, unlike when treated with DMSO as a control.

Experimental Example 2. Evaluation of Target Protein Degradation in Cultured Cells by Immunoblotting In order to evaluate the target protein degradation efficacy by the example compounds according to the disclosure, cell lines primarily expressing target proteins (MCF7, NTERA-2, ACHN, U87-MG, LNCaP, HEK293T) or gene recombinant cell lines (SH-SY5Y-tau, HeLa-HttQ97, PC12-α-synA30P) were cultured in a 12-well plate, and treated with Example 1 (ATC 1104), Example 2 (ATC 1105), Example 3 (ATCPBA 1104), Example 4 (ATCPBA 1105), Example 5 (Anle138b F105), Example 6 (Fumagilin 105), Example 7 (Vinclozolin 2204), Example 8 (PHTPP 1304), Example 9 (Baicalein 2204), Example 10 (Resveratrol 1105), Example 11 (BTA-1 1104) and Example 13 (Riluzole 204) according to the disclosure according to respective concentrations, and then immunoblotting was performed as in Experimental Example 1. Immunoblotting showed representative results from three or more independent experiments. The results are shown in FIGS. 3A to 3C.

As seen in FIGS. 3A to 3C, when treated with the example compounds according to the disclosure, it was confirmed that an amount of the target protein gradually increased according to the concentration of the compounds.

Experimental Example 3. Evaluation of Target Protein Degradation Mechanism in Cultured Cells by Immunoblotting In order to evaluate whether the target protein degradation mechanism of examples of the disclosure was mediated by autophagy, cell lines primarily expressing target proteins or gene recombinant cell lines were cultured in 12-well plates, and treated with 2.5 μM of Example 1 (ATC 1104), Example 2 (ATC 1105), Example 4 (ATCPBA 1105), Example 5 (Anle138b F105), Example 6 (Fumagilin 105), Example 8 (PHTPP 1304), Example 10 (Resveratrol 1105), Example 11 (BTA-1 1104), Example 12 (Curcumin 1204), Example 13 (Riluzole 204) according to the disclosure alone, or treated in combination with 10 μM of hydrxhoychloroquine (HCQ), an inhibitor of the autophagy-lysosomal pathway, and then immunoblotting was performed as in Experimental Example 1. Immunoblotting showed representative results from three or more independent experiments. The results are shown in FIGS. 4A and 4B.

As seen in FIGS. 4A and 4B, it was confirmed that when treated with the example compounds according to the disclosure alone, an amount of target protein decreased, and that when treated in combination with HCQ, an inhibitor of the autophagy-lysosomal pathway, the decreased amount of target protein again increased.

Experimental Example 4. Comparison Evaluation of Target Protein Degradation Efficacy in Cultured Cells by Immunoblotting In order to evaluate whether the target protein degradation efficacy of the example compounds of the disclosure is superior to the target protein degradation efficacy of the autophagy targeting ligand or target-binding ligand alone, cell lines primarily expressing target proteins or gene recombinant cell lines were cultured in 12-well plates, and treated with Example 1 (ATC 1104), Example 3 (ATCPBA 1104), Example 4 (PBA-1105), Example 6 (Fumagilin 105), Example 7 (Vinclozolin 2204), Example 8 (PHTPP 1304), Example 9 (Baicalein 2204), Example 10 (Resveratrol 1105), Example 11 (BTA-1 1104) according to the disclosure, the autophagy targeting ligand or target-binding ligand comprised in each example as a comparative example at 2.5 μM, 24 hr, respectively, and then immunoblotting was performed as in Experimental Example 1. Immunoblotting showed representative results from three or more independent experiments. The results are shown in FIGS. 5A to 5C.

As seen in FIGS. 5A to 5C, it was confirmed that after treatment with the example compounds of the disclosure, an amount of target protein was significantly decreased as compared with that after treatment with the autophagy targeting ligand or target-binding ligand.

Experimental Example 5. Evaluation of the Activity of P62-Mediated Delivery of Target Proteins in Cultured Cells to Autophagy by Immunofluorescence Staining and Confocal Microscopy In order to confirm the efficacy of P62-mediated delivery of target proteins to autophagy after treatment with the example compounds of the disclosure, immunofluorescence staining was performed by using p62 and each target protein as markers. The cover glass was placed on a 24-well plate for immunofluorescence staining, cell lines primarily expressing the target protein or gene recombinant cell lines were cultured. The cells were dispensed and cultured 24 hours, and then treated with Example 1 (ATCRET-1104), Example 5 (Anle138b F105), Example 7 (Vinclozolin 2204), Example 8 (PHTPP 1304), Example 9 (Baicalein 2204), Example 10 (Resveratrol 1105), Example Example 11 (BTA-1 1104), Example 30 (Compound T) according to the disclosure, respectively. The cells were further cultured for 24 hours for the action of the compounds, the medium was removed, and the cells were fixed using formaldehyde at room temperature. In order to prevent non-specific staining, the cells were reacted with the blocking solution at room temperature for 1 hour, and then the p62 antibody and target protein antibody diluted at a certain ratio were treated using the block solution, and then reacted at room temperature for 1 hour. After the antibody-treated cells were washed three times with PBS, the goat-derived secondary antibody was diluted to a certain ratio using a blocking solution, and then reacted at room temperature for 30 minutes. The cells were washed again with PBS three times, and subjected to DAPI staining for intracellular nuclear staining, and then the level of expression of p62 and LC3, intracellular puncta formation and intracellular coexistence level were observed by confocal microscopy. The results are shown in FIGS. 6A to 6C and FIG. 23B. Immunofluorescence staining showed representative results from three or more independent experiments.

As shown in FIGS. 6A to 6C and FIG. 23B, it was confirmed that after treatment with the example compounds according to the disclosure, intracellular puncta formation of p62 proteins, intracellular puncta formation of target proteins, and the local co-existence thereof were increased.

Experimental Example 6. Evaluation of Target Proteion Degradation in Cultured Cells by Immunoblotting In order to evaluate the target proteion degradation efficacy by Examples 14 to 33 according the disclosure, the following experiment was conducted.

First, as cell lines primarily expressing the target protein, Human kidney-derived cancer cells, HEK293T (ATCC, CRL-3216), human prostate-derived cancer cells, LNcap (Korean Cell Line Bank, Korean Cell Line Research Foundation, KCLB No. 80018), mouse embryonic fibroblast, MEF (ATCC, SCRC-1008), human cervical cancer cells, HeLa (Korean Cell Line Bank, Korean Cell Line Research Foundation, KCLB No. 10002), human blood-derived cells, K562 (Korean Cell Line Bank, Korean Cell Line Research Foundation, KCLB No. 10243), human blood-derived cells, THP-1 (Korean Cell Line Bank, Korean Cell Line Research Foundation, KCLB No. 40202), human lung-derived cancer cells, A549 (Korean Cell Line Bank, Korean Cell Line Research Foundation, KCLB No. 10185), human breast-derived cancer cells, MCF7 (Korean Cell Line Bank, Korean Cell Line Research Foundation, KCLB No. 30022), human neuroblastoma, SH-SY5Y cell lines (Korean Cell Line Bank, Korean Cell Line Research Foundation, KCLB No. 22266), human pancreatic cancer cells, PANC-1 (Korean Cell Line Bank, Korean Cell Line Research Foundation, KCLB No. 21469) were cultured, respectively, in an incubator maintained at 5% carbon dioxide, using DMEM containing 10% FBS and 1% streptomycin/penicillin, RPMI1640, or MEM medium, and then the respective cells were dispensed in 12-well plate. Additional incubation was performed for 24 hours to ensure that each cell completely fixed to the surface of the plate.

In order to confirm whether Compounds A to W of Examples 14 to 33 degrade the target protein respectively, the cultured cells were treated with the compound of each example for 24 hours and then collected.

In this case, HEK293T, which is human kidney-derived cancer cells, LNcap, which is human prostate-derived cancer cells, and MEF cell line, which is mouse embryonic fibroblasts, were treated with Example 14 (Compound A). HEK293T, which is human kidney-derived cancer cells, was treated with Example 15 (Compound B). HEK293T cell line, which is human kidney-derived cancer cells, and HeLa cell line, which is cervical-derived cancer cells, were treated with Example 16 (Compound C). HEK293T cell line, which is human kidney-derived cancer cells, was treated with Example 17 (Compound D). K562 cell line, which is human blood-derived cells, was treated with Example 18 (Compound E). HEK293T cell line, which is human kidney-derived cancer cells, was treated with Example 19 (Compound F). THP-1 cell line, which is human blood-derived cells, was treated with Example 20 (Compound G). A549 cell line, which is human lung-derived cancer cells, was treated with Example 21 (Compound H). A549 cell line, which is human lung-derived cancer cells, was treated with Example 22 (Compound I). MCF7 cell line, which is human breast-derived cancer cells, was treated with Example 23 (Compound J). HEK293T cell line, which is human blood-derived cells, was treated with Example 24 (Compound L). SH-SY5Y, which is human neuroblastoma, and HeLa cell line, which is cervical-derived cancer cells, were treated with Example 25 (Compound M). THP-1 cell line, which is human blood-derived cells, was treated with Example 26 (Compound P). SH-SY5Y, which is human neuroblastoma, and HeLa cell line, which is cervical-derived cancer cells, were treated with Example 27 (Compound Q). SH-SY5Y, which is human neuroblastoma, and HeLa cell line, which is cervical-derived cancer cells, were treated with Example 28 (Compound R). HeLa cell line, a human cervical-derived cancer cell, was treated with Example 29 (Compound S). SH-SY5Y cell line, which is human neuroblastoma, was treated with Example 30 (Compound T). SH-SY5Y cell line, which is human neuroblastoma, was treated with Example 31 (Compound U). PANC-1 cell line, which is human pancreatic-derived cancer cells, was treated with Example 32 (Compound V). PANC-1 cell line, which is human pancreatic-derived cancer cells, was treated with Example 33 (Compound W).

In order to extract proteins from each collected cell, 50 μL of lysis buffer (20 mM Tris, pH 7.4, 150 mM NaCl, 1% triton-X-100, 2 mM NaF, 2 mM EDTA, 2 mM b-glycerophosphate, 5 mM sodium orthovanadate, 1 mM PMSF, leupeptin, aprotenin) were injected into each sample and the cells were lysed. Based on the measured total protein concentration, a sample buffer was added to each sample and allowed to react at 100° C. for 5 minutes. 5 µL was taken from the samples after the reaction, and dispensed into each well of acrylamide gel, and then immunoblotting was performed. Immunoblotting showed representative results from three or more independent experiments. The results are shown in FIGS. 7 to 26.

As shown in FIG. 7, the decrease in the level of the target proteins BRD2, BRD3 and BRD4 by Example 14 (Compound A) was greater than the decrease in the level by Control, and thus, it can confirm that BDR2, BDR3, and BDR4 can be degraded by Example 14 (Compound A).

As shown in FIG. 8, the decrease in the level of the target protein PDE4 by Example 15 (Compound B) was greater than the decrease in the level by Control, and thus, it can confirm that PDE4 can be degraded by Example 15 (Compound B).

As shown in FIG. 9, the decrease in the level of the target protein ACVR1 by Example 16 (Compound C) was greater than the decrease in the level by Control, and thus, it can confirm that ACVR1 can be degraded by Example 16 (Compound C).

As shown in FIG. 10, the decrease in the level of the target protein Chk1 by Example 17 (Compound D) was greater than the decrease in the level by Control, and thus, it can confirm that Chk1 can be degraded by Example 17 (Compound D).

As shown in FIG. 11, the decrease in the level of the target proteins c-Abl and BCR-Abl by Example 18 (Compound E) was greater than the decrease in the level by Control, and thus, it can confirm that c-Abl and BCR-Abl can be degraded by Example 18 (Compound E).

As shown in FIG. 12, the decrease in the level of the target protein CK2 by Example 19 (Compound F) was greater than the decrease in the level by Control, and thus, it can confirm that CK2 can be degraded by Example 19 (Compound F).

As shown in FIG. 13, the decrease in the level of the target protein RIPK2 by Example 20 (Compound G) was greater than the decrease in the level by Control, and thus, it can confirm that RIPK2 can be degraded by Example 20 (Compound G).

As shown in FIG. 14, the decrease in the level of the target proteins Cyclin D1, STAT3 and p-STAT3 by Example 21 (Compound H) was greater than the decrease in the level by Control, and thus, it can confirm that Cyclin D1, STAT3 and p-STAT3 can be degraded by Example 21 (Compound H).

As shown in FIG. 15, the decrease in the level of the target proteins Cyclin D1, STAT3 and p-STAT3 by Example 22 (Compound I) was greater than the decrease in the level by Control, and thus, it can confirm that Cyclin D1, STAT3 and p-STAT3 can be degraded by Example 22 (Compound I).

As shown in FIG. 16, the decrease in the level of the target protein ERα by Example 23 (Compound J) was greater than the decrease in the level by Control, and thus, it can confirm that ERα can be degraded by Example 23 (Compound J).

As shown in FIG. 17, the decrease in the level of the target protein Bcl-2 by Example 24 (Compound L) was greater than the decrease in the level by Control, and thus, it can confirm that Bcl-2 can be degraded by Example 24 (Compound L).

As shown in FIG. 18, the decrease in the level of the target proteins Desmin Mut(L385P), α-synuclein(A53T) and Tau by Example 25 (Compound M) was greater than the decrease in the level by Control, and thus, it can confirm that Desmin Mut (L385P), α-synuclein(A53T) and Tau can be degraded by Example 25 (Compound M).

As shown in FIG. 19, the decrease in the level of the target protein RIPK2 by Example 26 (Compound P) was greater than the decrease in the level by Control, and thus, it can confirm that RIPK2 can be degraded by Example 26 (Compound P).

As shown in FIG. 20, the decrease in the level of the target proteins Tau and Desmin Mut(L385P) by Example 27 (Compound Q) was greater than the decrease in the level by Control, and thus, it can confirm that Tau and Desmin Mut(L385P) can be degraded by Example 27 (Compound Q).

As shown in FIG. 21, the decrease in the level of the target proteins Tau and Desmin Mut(L385P) by Example 28 (Compound R) was greater than the decrease in the level by Control, and thus, it can confirm that Tau and Desmin Mut(L385P) can be degraded by Example 28 (Compound R).

As shown in FIG. 22, the decrease in the level of the target protein Desmin Mut(L385P) by Example 29 (Compound S) was greater than the decrease in the level by Control, and thus, it can confirm that Desmin Mut(L385P) can be degraded by Example 29 (Compound S).

As shown in FIG. 23A, the decrease in the level of the target protein Tau by Example 30 (Compound T) was greater than the decrease in the level by Control, and thus, it can confirm that Tau can be degraded by Example 30 (Compound T).

As shown in FIG. 24, the decrease in the level of the target proteins Tau and α-syn. Mut(A53T) by Example 31 (Compound U) was greater than the decrease in the level by Control, and thus, it can confirm that Tau and α-syn. Mut(A53T) can be degraded by Example 31 (Compound U).

As shown in FIG. 25, the decrease in the level of the target protein p-53 by Example 32 (Compound V) was greater than the decrease in the level by Control, and thus, it can confirm that p-53 can be degraded by Example 32 (Compound V).

As shown in FIG. 26, the decrease in the level of the target protein p-53 by Example 33 (Compound W) was greater than the decrease in the level by Control, and thus, it can confirm that p-53 can be degraded by Example 33 (Compound W).

As such, when the cargo delivery system according to the disclosure is used, each target protein can be selectively degraded while activating autophagy, and it can confirm that the degradation efficiency is significantly increased, compared to when only one of the autophagy targeting ligand and the target-binding ligand is treated.

The present invention can provide the following embodiments as an example.

According to the first embodiment, there may be provided a cargo delivery system comprising an autophagy targeting ligand and a target-binding ligand, which is cargo, carried by the autophagy targeting ligand, wherein the autophagy targeting ligand is a compound having a structure of the following Chemical Formula 1, or a pharmaceutically acceptable salt, stereoisomer, solvate or hydrate thereof:

[Chemical Formula 1]

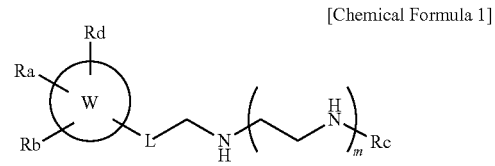

wherein,

W is C6-C10 aryl;

L is —$(CH_2)_{n1}$— or —O—$(CH_2)_{n2}$—CH(OH)—, provided that —O— in the —O—$(CH_2)_{n2}$—CH(OH)— is bonded to any one of carbones of W, where n1 is an integer of 1 to 4;

n2 is an integer of 1 to 4;

m is an integer of 0 to 2;

$R_a$ is $R_1$ or —$OR_1$, where $R_1$ is hydrogen or —$(CH_2)_{n3}$—$R'_1$, $R'_1$ is phenyl which is unsubstituted or substituted by hydroxy, halogen, $C_{1-4}$ alkyl, $C_{1-4}$ alkoxy, nitro, amino, (C1-4 alkyl)amino, or di ($C_{1-4}$ alkyl)amino, n3 is an integer of 1 to 6;

$R_b$ is —$OR_2$, where $R_2$ is hydrogen or —$(CH_2)_{n4}$—$R'_2$, $R'_2$ is phenyl which is unsubstituted or substituted by hydroxy, halogen, $C_{1-4}$ alkyl, $C_{1-4}$ alkoxy, nitro, amino, ($C_{1-4}$ alkyl)amino, or di ($C_{1-4}$ alkyl)amino, n4 is an integer of 1 to 6;

$R_c$ is —$(CH_2)_{n5}$—OH, —$(CH_2)_{n5}$—NH—C(=NH)$NH_2$, —C(=NH)$NH_2$, —CH($R_3$)—COOH, —CH(COO—$R_4$)—$CH_2CH_2CH_2$—NH—C(=NH)$NH_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH($NH_2$)—COOH, or —$(CH_2)_{n6}$—$CONH_2$, n5 is an integer of 2 to 4, n6 is an integer of 1 to 4, $R_3$ is hydrogen or $C_{1-4}$ alkyl, $R_4$ is $C_{1-4}$ alkyl, and $R_d$ is hydrogen, halogen, $C_{1-4}$ alkoxy or $C_{1-4}$ alkyl.

According to the second embodiment, there may be provided the cargo delivery system as defined in the first embodiment, wherein the autophagy targeting ligand is directly connected to the target-binding ligand or connected to the target-binding ligand by a linker.

According to the third embodiment, there may be provided the cargo delivery system as defined in the first or second embodiment, wherein in the Chemical Compound 1, W is phenyl;

L is —$(CH_2)_n$r- or —O—$(CH_2)_{n2}$—CH(OH)—, provided that —O— in the —O—$(CH_2)_{n2}$—CH(OH)— is bonded to a benzene ring, where n1 is an integer of 0 to 1, n2 is an integer of 1 to 2;

m is an integer of 0 to 2;

$R_a$ is hydrogen or —O—$(CH_2)_{n3}$—R', where $R'_1$ is phenyl which is unsubstituted or substituted by hydroxy, fluoro, chloro, bromo, methyl, ethyl, methoxy, ethoxy, nitro, amino or dimethylamino, n3 is an integer of 1 to 4;

$R_b$ is hydroxy or —O—$(CH_2)_{n4}$—$R'_2$, where $R'_2$ is phenyl which is unsubstituted or substituted by hydroxy, fluoro, chloro, bromo, methyl, ethyl, methoxy, ethoxy, nitro, amino or dimethylamino, n4 is an integer of 1 to 4;

R is —$(CH_2)_{n5}$—OH, —$(CH_2)_{n5}$—NH—C(=NH)$NH_2$, —C(=NH)$NH_2$, —$(CH_2)_{n5}$—O—$(CH_2)_{n5}$—OH, —CONH$(CH_2)_{n5}$—OH, —CO$(CH_2)_{n6}$—OH, —$(CH_2)_{n6}$—CH($NH_2$)—COOH or —$(CH_2)_{n6}$—$CONH_2$, where n5 is an integer of 2 to 3, n6 is an integer of 1 to 2;

$R_d$ is hydrogen, halogen, $C_{1-2}$ alkoxy or $C_{1-2}$ alkyl.

According to the fourth embodiment, there may be provided the cargo delivery system as defined in any one of the first to third embodiments, wherein the linker has a structure of -Q-$(CH_2CH_2O)_x$—$(CH_2)_y$—P—, -Q-$(CH_2CH_2CH_2O)_x$—$(CH_2)_y$—P—, -Q-$(CH_2CH_2NH)_x$—$(CH_2)_y$—P—, or -Q-$(CH_2CH_2CONH)_x$—$(CH_2)_y$—P—, where Q comprises —NH—, —O—, =N— or —N($CH_3$)—, which is a moiety modified by binding to the target-binding ligand, P comprises —NH—, —O—, —$CH_2$— or —C(=O)—, which is a moiety modified by binding to the autophagy targeting ligand, x is an integer from 0 to 4, y is an integer from 0 to 3.

According to the fifth embodiment, there may be provided the cargo delivery system as defined in any one of the first to fourth embodiments, wherein a bond between the P and the autophagy targeting ligand is —CONH—, —O—, —NH—, —NHCO— or —COO—.

According to the sixth embodiment, there may be provided the cargo delivery system as defined in any one of the first to fifth embodiments, wherein the target-binding ligand is a compound that specifically binds to a pathological protein, organelle, or aggregate thereof.

According to the seventh embodiment, there may be provided the cargo delivery system as defined in any one of the first to sixth embodiments, wherein the pathological protein is a causative protein that induces cancer, proteinophagy, rare or intractable disease, or genetic disease.

According to the eighth embodiment, there may be provided the cargo delivery system as defined in any one of the first to seventh embodiments, wherein the proteinopathy is neurodegenerative disease, alpha-1 antitrypsin deficiency, keratopathy, retinitis pigmentosa, type 2 diabetes, or cystic fibrosis.

According to the ninth embodiment, there may be provided the cargo delivery system as defined in any one of the first to eighth embodiments, wherein the neurodegenerative disease is at least one selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

According to the tenth embodiment, there may be provided a pharmaceutical composition comprising the cargo delivery system as defined in any one of the first to ninth embodiments, as an active ingredient.

According to the eleventh embodiment, there may be provided a food composition comprising the cargo delivery system as defined in any one of the first to tenth embodiments.

According to the twelfth embodiment, there may be provided a method for activating autophagy of a target, comprising administering to a subject a composition comprising the cargo delivery system as defined in any one of the first to eleventh embodiments in an effective amount.

It should be understood that the above-described embodiments are given by way of illustration only and the scope of the present disclosure is not limited to the above detailed description. In addition, various changes, modifications and substitutions within the scope of the present disclosure will become apparent to those skilled in the art.

What is claimed is:

1. A cargo delivery system, comprising an autophagy targeting ligand; and a target-binding ligand, which is cargo, carried by the autophagy targeting ligand, wherein the autophagy targeting ligand is connected to the target-binding ligand by a linker, wherein the autophagy targeting ligand connected to the target-binding ligand by a linker is selected from the group consisting of compounds shown in the following table:

| No. | Name of Compound |
|---|---|
| 1 | (2E,4E,6E,8E)-N-(2-(2-(2-(((R)-3-(3,4-bis(benzyloxy)phenoxy)-2-hydroxypropyl)amino)ethoxy)ethoxy)ethyl)-3,7-dimethyl-9-(2,6,6-trimethylcyclohex-1-en-1-yl)nona-2,4,6,8-tetraenamide |
| 2 | (2E,4E,6E,8E)-N-(2-(2-(2-((3,4-bis(benzyloxy)benzyl)amino)ethoxy)ethoxy)ethyl)-3,7-dimethyl-9-(2,6,6-trimethylcyclohex-1-en-1-yl)nona-2,4,6,8-tetraenamide |
| 3 | (R)-N-(15-(3,4-bis(benzyloxy)phenoxy)-14-hydroxy-3,6,9-trioxa-12-azapentadecyl)-4-phenylbutaneamide |
| 4 | N-(1-(3,4-bis(benzyloxy)phenyl)-5,8,11-trioxa-2-azatridecan-13-yl)-4-phenylbutanamide |
| 5 | 3-(3-(benzo[d][1,3]dioxol-5-yl)-1H-pyrazol-5-yl)-N-(2-(2-(2-((3-((4-fluorobenzyl)oxy))benzyl)amino)ethoxy)ethoxy)ethyl)aniline |
| 6 | (3R,4S,5S,6R)-5-methoxy-4-((2R,3R)-2-methyl-3-(3-methylbut-2-en-1-yl)oxirane-2-yl)-1-oxaspiro[2.5]octan-6-yl(13E,15E,17E,19E)-1-(3-(benzyloxy)phenyl)-12-oxo-5,8-dioxa-2,11-diazahenicosa-13,15,17,19-tetraene-21-oate |
| 7 | 3-(3,5-dichlorophenyl)-5-((R)-15-(3,4-diphenethoxyphenoxy)-14-hydroxy-6,9-dioxa-3,12-diazapentadecyl)-5-methyloxazolidine-2,4-dione |
| 8 | (R)-1-(4-(benzyloxy)-3-(3-phenylpropoxy)phenoxy)-3-((2-(2-(2-(4-(2-phenyl-5,7-bis(trifluoromethyl)pyrazolo[1,5-a]pyrimidin-3-yl)phenoxy)ethoxy)ethoxy)ethyl)amino)propan-2-ol |
| 9 | (R,Z)-4-((2-(2-(2-((3-(3,4-diphenethoxyphenoxy)-2-hydroxypropyl)amino)ethoxy)ethoxy)ethyl)imino)-2-phenyl-4H-chromene-5,6,7-triol |
| 10 | (E)-5-(4-(2-(2-(2-((3,4-bis(benzyloxy)benzyl)amino)ethoxy)ethoxy)ethoxy)styryl)benzene-1,3-diol |
| 11 | (R)-2-(4-(benzo[d]thiazol-2-yl)phenyl)-14-(3,4-bis(benzyloxy)phenoxy)-5,8-dioxa-2,11-diazatetradecane-13-ol |
| 12 | (1E,6E)-1-(4-(2-(2-(2-(((R)-3-(3-(benzyloxy)-4-phenethoxyphenoxy)-2-hydroxypropyl)amino)ethoxy)ethoxy)ethoxy)-3-methoxyphenyl)-7-(4-hydroxy-3-methoxyphenyl)hepta-1,6-diene-3,5-dione |
| 13 | (R)-1-(3-phenethoxyphenoxy)-3-((2-(2-(2-((6-(trifluoromethoxy))benzo[d]thiazol-2-yl)amino)ethoxy)ethoxy)ethyl)amino)propan-2-ol |
| 14 | N-(2-(2-(2-(((R)-3-(3,4-bis(benzyloxy)phenoxy)-2-hydroxypropyl)amino)ethoxy)ethoxy)ethyl)-2-((S)-4-(4-chlorophenyl)-2,3,9-trimethyl-6H-thieno[3,2-f][1,2,4]triazolo[4,3-a][1,4]diazepin-6-yl)acetamide |
| 15 | (1s,4s)-N-(2-(2-(2-((3,4-bis(benzyloxy)benzyl)amino)ethoxy)ethoxy)ethyl)-4-cyano-4-(3-(cyclopentyloxy)-4-methoxyphenyl)cyclohexane-1-carboxamide |
| 16 | (R)-1-(3-phenethoxyphenoxy)-3-((2-(2-(2-(4-(4-(3-(quinolin-5-yl)pyrazolo[1,5-a]pyrimidin-6-yl)phenyl)piperazin-1-yl)ethoxy)ethoxy)ethyl)amino)propan-2-ol |
| 17 | 5-(3-fluorophenyl)-N-((S)-1-(2-(2-(2-(((R)-2-hydroxy-3-(3-phenethoxyphenoxy)propyl)amino)ethoxy)ethoxy)ethyl)piperidin-3-yl)-3-ureidothiophene-2-carboxamide |
| 18 | (R)-2-((6-(4-(15-(4-(benzyloxy)-3-(3-phenylpropoxy)phenoxy)-14-hydroxy-6,9-dioxa-3,12-diazapentadecyl)piperazin-1-yl)-2-methylpyrimidin-4-yl)amino)-N-(2-chloro-6-methylphenyl)thiazole-5-carboxamide |
| 19 | (R)-5-((3-((2-(2-(2-((3-(4-(benzyloxy)-3-phenethoxyphenoxy)-2-hydroxypropyl)amino)ethoxy)ethoxy)ethyl)amino)phenyl)amino)benzo[c][2,6]naphthyridine-8-carboxylic acid |
| 20 | N-(7-((1-(3-(benzyloxy)phenyl)-5,8-dioxa-2,11-diazatridecan-13-yl)oxy)-6-(tert-butylsulfonyl)quinazolin-4-yl)benzo[d]thiazol-5-amine |
| 21 | ((2-(((5S,8S,10aR)-8-(((S)-5-amino-1-(benzhydrylamino)-1,5-dioxopentan-2-yl)carbamoyl)-3-((R)-1-(3,4-bis((4-fluorobenzyl)oxy)phenoxy)-2-hydroxy-7,10,13,16-tetraoxa-4-azaicosan-20-oyl)-6-oxodecahydropyrrolo[1,2-a][1,5]diazocin-5-yl)carbamoyl)-1H-indol-5-yl)difluoromethyl)phosphonic acid |
| 22 | ((2-(((5S,8S,10aR)-8-(((S)-5-amino-1-(benzhydrylamino)-1,5-dioxopentan-2-yl)carbamoyl)-3-(1-(3,4-bis(benzyloxy)phenyl)-5,8,11,14-tetraoxa-2-azaoctadecan-18-oyl)-6-oxodecahydropyrrolo[1,2-a][1,5]diazocin-5-yl)carbamoyl)-1H-indol-5-yl)difluoromethyl)phosphonic acid |
| 23 | (4-((1-(3,4-bis(benzyloxy)phenoxy)-16-ethyl-5,8-dioxa-2,11,16-triazaoctadecan-18-yl)oxy)phenyl)(6-hydroxy-2-(4-hydroxyphenyl)benzo[b]thiophen-3-yl)methanone |
| 24 | (R)-5-((3-((21-(3,4-bis((4-fluorobenzyl)oxy)phenoxy)-20-hydroxy-3,6,9,12,15-pentaoxa-18-azahenicosyl)amino)-5-chlorophenyl)amino)benzo[c][2,6]naphthyridine-8-carboxylic acid |
| 25 | (S)-3-(6-(3-((4-(1-(4-(benzyloxy)-3-phenethoxyphenyl)-5,8,11,14-tetraoxa-2-azahexadecan-16-yl)piperazin-1-yl)methyl)-1,2,3,4-tetrahydroisoquinoline-2-carbonyl)benzo[d][1,3]dioxol-5-yl)-N-(4-hydroxyphenyl)-N-phenyl-5,6,7,8-tetrahydroindolizine-1-carboxamide |
| 26 | (R)-1-((4-(benzo[d]thiazol-5-ylamino)-6-(tert-butylsulfonyl)quinazolin-7-yl)oxy)-24-(3,4-bis((4-fluorobenzyl)oxy)phenoxy)-6,9,12,15,18-pentaoxa-3,21-diazatetracosan-23-ol |
| 27 | N-(1-(3,4-bis(benzyloxy)phenyl)-5,8,11,14,17-pentaoxa-2-azanonadecan-19-yl)-4-phenylbutanamide |
| 28 | N-(1-(3,4-bis(benzyloxy)phenyl)-5,8,11,14,17,20,23-heptaoxa-2-azapentacosan-25-yl)-4-phenylbutanamide |
| 29 | (R)-N-(15-(3,4-bis((4-fluorobenzyl)oxy)phenoxy)-14-hydroxy-3,6,9-trioxa-12-azapentadecyl)-4-phenylbutanamide |
| 30 | (R)-N-(15-(3-((4-fluorobenzyl)oxy)phenoxy)-14-hydroxy-3,6,9-trioxa-12-azapentadecyl)-4-phenylbutanamide |
| 31 | N-(7-((1-(3,4-bis(benzyloxy)phenyl)-5,8,11-trioxa-2-azatridecan-13-yl)(methyl)amino)-3H-phenothiazin-3-ylidene)-N-methylmethanaminium 2,2,2-trifluoroacetate |
| 32 | (R)-N-(7-((15-(3,4-bis((4-fluorobenzyl)oxy)phenoxy)-14-hydroxy-3,6,9-trioxa-12-azapentadecyl)(methyl)amino)-3H-phenothiazin-3-ylidene)-N-methylmethanaminium 2,2,2-trifluoroacetate |
| 33 | (R)-N-(7-((15-(3-((4-fluorobenzyl)oxy)phenoxy)-14-hydroxy-3,6,9-trioxa-12-azapentadecyl)(methyl)amino)-3H-phenothiazin-3-ylidene)-N-methylmethanaminium 2,2,2-trifluoroacetate. |

2. The cargo delivery system of claim 1, wherein the target-binding ligand is a compound that specifically binds to a pathological protein, organelle, foreign invader or aggregate thereof.

3. The cargo delivery system of claim 2, wherein the pathological protein is a causative protein that induces cancer, proteinophagy, rare or intractable disease, or genetic disease.

4. The cargo delivery system of claim 3, wherein the proteinopathy is neurodegenerative disease, alpha-1 antitrypsin deficiency, keratopathy, retinitis pigmentosa, type 2 diabetes, or cystic fibrosis.

5. The cargo delivery system of claim 4, wherein the neurodegenerative disease is at least one selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

6. A pharmaceutical composition comprising the cargo delivery system of claim 1 as an active ingredient.

7. A food composition comprising the cargo delivery system of claim 1 as an active ingredient.

8. A method for activating autophagy of a target in a subject, comprising administering to the subject a composition comprising the cargo delivery system of claim 1 in an effective amount.

* * * * *